(12) United States Patent
Maynard et al.

(10) Patent No.: US 8,129,395 B2
(45) Date of Patent: Mar. 6, 2012

(54) 4,5-DISUBSTITUTED-2-ARYL PYRIMIDINES

(75) Inventors: George D. Maynard, Clinton, CT (US);
Manuka Ghosh, Madison, CT (US);
Jun Yuan, Guilford, CT (US); Kevin S. Currie, North Branford, CT (US); Scott Mitchell, East Haven, CT (US); Qin Guo, Waterford, CT (US); He Zhao, Branford, CT (US)

(73) Assignee: Novartis International Pharmaceutical Ltd., Hamilton (BM)

( * ) Notice: Subject to any disclaimer, the term of this patent is extended or adjusted under 35 U.S.C. 154(b) by 368 days.

(21) Appl. No.: 12/320,539

(22) Filed: Jan. 26, 2009

(65) Prior Publication Data
US 2010/0022516 A1    Jan. 28, 2010

Related U.S. Application Data

(63) Continuation of application No. 11/123,755, filed on May 6, 2005, now Pat. No. 7,482,350.

(60) Provisional application No. 60/569,222, filed on May 8, 2004, provisional application No. 60/649,973, filed on Feb. 4, 2005.

(51) Int. Cl.
*A01N 43/54* (2006.01)
*C07D 239/42* (2006.01)
*C07D 401/04* (2006.01)
*C07D 403/00* (2006.01)

(52) U.S. Cl. ........................ 514/256; 544/295
(58) Field of Classification Search .................. 514/256; 544/295
See application file for complete search history.

(56) References Cited

U.S. PATENT DOCUMENTS

| | | | |
|---|---|---|---|
| 3,479,357 A * | 11/1969 | Wagner | 544/324 |
| 3,944,581 A | 3/1976 | Schwan | |
| 3,969,355 A | 7/1976 | Schwan | |
| 4,648,896 A | 3/1987 | Brunner | |
| 5,022,915 A | 6/1991 | Prisbylla | |
| 6,121,202 A | 9/2000 | Karp et al. | |
| 2002/0072521 A1 | 6/2002 | Yoon et al. | |
| 2002/0099207 A1 | 7/2002 | Stadler | |
| 2003/0216382 A1 | 11/2003 | Boehringer et al. | |
| 2004/0158067 A1 | 8/2004 | Hutchison et al. | |

FOREIGN PATENT DOCUMENTS

| | | |
|---|---|---|
| EP | 0 640 599 | 3/1995 |
| GB | 2 115 809 A | 9/1983 |
| JP | 2-22266 | 1/1990 |
| JP | 2-275865 | 11/1990 |
| JP | 10-130150 A | 5/1998 |
| JP | 2003-527377 A | 9/2003 |
| WO | 01/49288 A1 | 7/2001 |
| WO | 01/60805 A1 | 8/2001 |
| WO | 01/68614 A2 | 9/2001 |
| WO | 02/06242 A2 | 1/2002 |
| WO | 02/18350 A1 | 3/2002 |
| WO | 02/42280 A2 | 5/2002 |
| WO | 03/068757 A1 | 8/2003 |
| WO | WO-03/082829 | 10/2003 |
| WO | WO-03/091246 | 11/2003 |
| WO | WO-2005/049572 | 6/2005 |
| WO | WO-2005/049573 | 6/2005 |
| WO | WO-2005/049606 | 6/2005 |

OTHER PUBLICATIONS

Supplementary Partial European Search Report for Corresponding European Application No. 05746687.2 dated Jul. 27, 2009.
J. Cieplik et al., Synthesis and Immunomodulatory Activity of 6-Methyl-2-Phenyl-5-Substituted Pyrimidines, Il Farmaco, 50 (2), 131-136 (1995).
H. Bredereck et al., Synthese und Reaktionen von 1,2-Bis(dialkylamino)athylenen, Chem. Ber. 107, 1545-1554 (1974).
A. Kuno et al., Studies on Cerebral Protective Agents. III.1a) Novel 4-Arylpyrimidine Derivatives with Anti-anoxic and Anti-lipid Peroxidation Activities. (3), Chem. Pharm. Bull. 41(1) 139-147 (1993).

* cited by examiner

*Primary Examiner* — Andrew D Kosar
*Assistant Examiner* — Erich A Leeser
(74) *Attorney, Agent, or Firm* — Peter F. Corless; Dwight K. Kim; Edwards Wildman Palmer LLP

(57) ABSTRACT

4,5-disubstituted-2-arypyrimidines of Formula I and Formula II are provided:

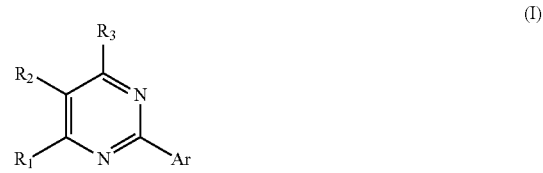

wherein $R_1$, $R_2$, $R_3$, $R_8$, $R_9$, A and Ar are defined herein. Such compounds are ligands of C5a receptors. Preferred compounds of Formula I and II bind to C5a receptors with high affinity and exhibit neutral antagonist or inverse agonist activity at C5a receptors. The present invention also relates to pharmaceutical compositions comprising such compounds, and to the use of such compounds in treating a variety of inflammatory, cardiovascular, and immune system disorders. In addition, the present invention provides labeled 4,5-disubstituted-2-arylpyrimidines, which are useful as probes for the localization of C5a receptors.

5 Claims, No Drawings

4,5-DISUBSTITUTED-2-ARYL PYRIMIDINES

CROSS-REFERENCE TO RELATED APPLICATION(S)

This application is a continuation of U.S. patent application 11/123,755, filed May 6, 2005 (now U.S. Pat. No. 7,482, 350), which claims priority from U.S. Provisional Application Ser. No.60/569,222 filed May 8, 2004 and of U.S. Provisional Application Ser. No.60/649,973 filed Feb. 4, 2005, each of which is incorporated by reference.

FIELD OF THE INVENTION

This invention relates generally to 4,5-disubstituted-2-arylpyrimidines that that have useful pharmacological properties. The invention further relates to the use of such compounds for treating a variety of inflammatory and immune system disorders and as probes for the localization of C5a receptors.

BACKGROUND OF THE INVENTION

C5a, a 74 amino acid peptide, is generated in the complement cascade by the cleavage of the complement protein C5 by the complement C5 convertase enzyme. C5a has both anaphylatoxic (e.g., bronchoconstricting and vascular spasmogenic) and chemotactic effects. Therefore, it is active in engendering both the vascular and cellular phases of inflammatory responses. Because it is a plasma protein and, therefore, generally almost instantly available at a site of an inciting stimulus, it is a key mediator in terms of initiating the complex series of events that results in augmentation and amplification of an initial inflammatory stimulus. The anaphylatoxic and chemotactic effects of the C5a peptide are believed to be mediated through its interaction with C5a receptor (CD88 antigen), a 52 kD membrane bound G-protein coupled receptor (GPCR). C5a is a potent chemoattractant for polymorphonuclear leukocytes, bringing neutrophils, basophils, eosinophils and monocytes to sites of inflammation and/or cellular injury. C5a is one of the most potent chemotactic agents known for a wide variety of inflammatory cell types. C5a also "primes" or prepares neutrophils for various antibacterial functions (e.g., phagocytosis). Additionally, C5a stimulates the release of inflammatory mediators (e.g., histamines, TNF-α, IL-1, IL-6, IL-8, prostaglandins, and leukotrienes) and the release of lysosomal enzymes and other cytotoxic components from granulocytes. Among its other actions, C5a also promotes the production of activated oxygen radicals and the contraction of smooth muscle.

Considerable experimental evidence implicates increased levels of C5a in a number of autoimmune diseases and inflammatory and related disorders. Agents that block the binding of C5a to its receptor other agents, including inverse agonists, which modulate signal transduction associated with C5a-receptor interactions, can inhibit the pathogenic events, including chemotaxis, associated with anaphylatoxin activity contributing to such inflammatory and autoimmune conditions. The present invention provides such agents, and has further related advantages.

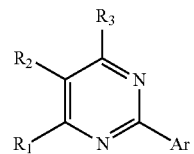

(I)

or a pharmaceutically acceptable salt thereof, wherein:

$R_1$ is selected from hydrogen, optionally substituted alkyl, optionally substituted alkenyl, optionally substituted alkynyl, optionally substituted cycloalkyl, optionally substituted cycloalkenyl, optionally substituted alkoxy, optionally substituted cycloalkoxy, optionally substituted (cycloalkyl)alkoxy, or optionally substituted heterocycloalkyl;

$R_2$ is selected from —$XR_A$, —$(CR_AR_B)OR_A$, —$CR_AR_BNR_4R_5$ and —$CR_AR_BQ$;

$R_3$ is selected from optionally substituted aryl, optionally substituted cycloalkyl, optionally substituted arylalkyl, optionally substituted aryloxy, optionally substituted arylalkoxy, optionally substituted heterocycle, optionally substituted heterocycle-oxy, —O—$(CR_AR_B)_m$—Y, —$N(R_B)$—$(CR_AR_B)_m$—$XR_A$, or —$N(R_B)$—$(CR_AR_B)_m$—Y, wherein said heterocycle is saturated, unsaturated or aromatic and has from 1 to 3 rings and 3 to 7 ring members in each ring;

$R_4$ is:
  (i) $C_2$-$C_8$alkyl, $C_2$-$C_8$alkenyl, $C_2$-$C_8$alkynyl, ($C_3$-$C_7$cycloalkyl)$C_0$-$C_4$alkyl, mono- or di-($C_1$-$C_4$alkylamino)$C_2$-$C_4$alkyl, (3- to 7-membered heterocycloalkyl)$C_0$-$C_4$alkyl, aryl$C_0$-$C_4$alkyl, or heteroaryl$C_{0-4}$alkyl, each of which is optionally substituted; or
  (ii) joined to $R_5$ to form, with the nitrogen to which $R_4$ and $R_5$ are bound, a heterocycle having from 1 to 3 rings, 5 to 7 ring members in each ring, and is optionally substituted;

$R_5$ is:
  (i) hydrogen;
  (ii) $C_1$-$C_6$alkyl, $C_2$-$C_6$alkenyl, $C_2$-$C_6$alkynyl, ($C_3$-$C_7$carbocycle)$C_0$-$C_4$alkyl, each of which is optionally substituted; or
  (iii) joined to $R_4$ to form an optionally substituted heterocycle;

Ar is mono-, di-, or tri-substituted phenyl, optionally substituted naphthyl, or optionally substituted heteroaryl having from 1 to 3 rings, 5 to 7 ring members in each ring;

$R_A$ and $R_B$, which may be the same or different, are independently selected at each occurrence from:
  (i) hydrogen and hydroxy, and (ii) alkyl groups, cycloalkyl groups, and (cycloalkyl)alkyl groups, each of which is optionally further substituted with one or more substituent(s) independently selected from oxo, hydroxy, halogen, cyano, amino, $C_{1-6}$alkoxy, mono- or di-($C_{1-6}$-alkyl)amino, —NHC(=O)($C_{1-6}$alkyl), —N($C_{1-6}$alkyl)C(=O)($C_{1-6}$alkyl), —NHS(O)$_n$($C_{1-6}$alkyl), —S(O)$_n$($C_{1-6}$alkyl), —S(O)$_n$NH($C_{1-6}$alkyl), —S(O)$_n$N($C_{1-6}$alkyl)($C_{1-6}$alkyl), and Z;

X is independently selected at each occurrence from —$CHR_B$—, —O—, —C(=O)—, —C(=O)O—, —S(O)$_n$—, —NR$_B$—, —C(=O)NR$_B$—, —S(O)$_n$NR$_B$—, —NR$_B$C(=O)—, and —NR$_B$S(O)$_n$—;

Y and Z are independently selected at each occurrence from 3- to 7-membered carbocyclic or heterocyclic groups which are saturated, unsaturated, or aromatic, which are optionally substituted with one or more substituents independently selected from halogen, oxo, hydroxy, amino, cyano, C$_{1-4}$alkyl, C$_{1-4}$alkoxy, mono- or di(C$_{1-4}$alkyl)amino, and —S(O)$_n$(alkyl);

Q is an optionally substituted carbocyclic or optionally substituted heterocyclic group which are saturated, unsaturated or aromatic and comprises between 3 and 18 ring atoms arranged in 1, 2, or 3 rings which are fused, spiro or coupled by a bond;

m is independently selected at each occurrence from integers ranging from 0 to 8; and n is an integer independently selected at each occurrence from 0, 1, and 2.

Within certain other aspects, compounds provided herein are 4,5-disubstituted-2-arylpyrimidines of Formula II:

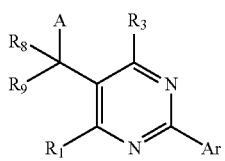

(II)

or a pharmaceutically acceptable form thereof, wherein:

Ar is mono-, di-, or tri-substituted phenyl, optionally substituted naphthyl, or optionally substituted heteroaryl having from 1 to 3 rings and 5 to 7 ring members in each ring;

A is OR$_4$, NR$_4$R$_5$, or CR$_4$(XR$_y$)$_2$;

R$_1$ is selected from hydrogen, optionally substituted alkyl, optionally substituted alkenyl, optionally substituted alkynyl, optionally substituted cycloalkyl, optionally substituted cycloalkenyl, optionally substituted alkoxy, optionally substituted cycloalkoxy, optionally substituted (cycloalkyl)alkoxy, or optionally substituted heterocycloalkyl;

R$_3$ is selected from halogen, amino, cyano, optionally substituted alkyl, optionally substituted alkenyl, optionally substituted alkynyl, optionally substituted cycloalkyl, optionally substituted alkoxy, optionally substituted cycloalkyloxy, optionally substituted aryl, optionally substituted arylalkyl, optionally substituted aryloxy, optionally substituted arylalkoxy, optionally substituted heterocycle, optionally substituted heterocycle-oxy, -E-(CR$_C$R$_D$)$_m$-Z, or -E-(CR$_C$R$_D$)$_m$—XR$_4$, wherein said heterocycle has from 1 to 3 rings and between 3 and 7 ring members in each ring;

R$_4$ is:
(i) C$_2$-C$_8$alkyl, C$_2$-C$_8$alkenyl, C$_2$-C$_8$alkynyl, (C$_3$-C$_7$cycloalkyl)C$_0$-C$_4$alkyl, mono- or di-(C$_1$-C$_4$alkylamino)C$_2$-C$_4$alkyl, (3- to 7-membered heterocycloalkyl)C$_0$-C$_4$alkyl, arylC$_0$-C$_4$alkyl, or heteroaryl C$_{0-4}$alkyl, each of which is substituted with from 0 to 4 substituents independently chosen from R$_x$, C$_2$-C$_4$alkanoyl, mono- and di-(C$_1$-C$_4$alkyl)aminoC$_1$-C$_4$alkyl, mono- and di-(C$_1$-C$_4$alkyl)aminoC$_1$-C$_4$alkoxy, (3- to 7-membered heterocycloalkyl)C$_0$-C$_4$alkyl and XR$_y$; or
(ii) joined to R$_5$ to form, with the nitrogen to which R$_4$ and R$_5$ are bound, a heterocycle having from 1 to 3 rings, 5 to 7 ring members in each ring, wherein the heterocycle is substituted with from 0 to 4 substituents independently chosen from R$_x$, oxo and W-Z;

R$_5$ is:
(i) hydrogen;
(ii) C$_1$-C$_6$alkyl, C$_2$-C$_6$alkenyl, C$_2$-C$_6$alkynyl, (C$_3$-C$_7$carbocycle)C$_0$-C$_4$alkyl, each of which is substituted with from 0 to 3 substituents independently chosen from halogen, hydroxy, amino, cyano, C$_1$-C$_4$alkyl, C$_1$-C$_4$alkoxy, methylamino, dimethylamino, trifluoromethyl and trifluoromethoxy; or
(iii) joined to R$_4$ to form an optionally substituted heterocycle;

R$_8$ and R$_9$ are independently selected from hydrogen, halogen, hydroxy, C$_1$-C$_6$alkyl, C$_2$-C$_6$alkenyl, C$_2$-C$_6$alkynyl, C$_1$-C$_6$alkoxy, C$_1$-C$_6$alkylamino and (C$_3$-C$_7$cycloalkyl)C$_0$-C$_4$alkyl;

E is a single covalent bond, oxygen, or NR$_4$;

X is a single covalent bond, —CR$_A$R$_B$—, —O—, —C(=O)—, —C(=O)O—, —S(O)$_n$— or —NR$_B$—; and R$_y$ is:
(i) hydrogen; or
(ii) C$_1$-C$_{10}$alkyl, C$_2$-C$_{10}$alkenyl, C$_2$-C$_{10}$alkynyl, (C$_3$-C$_{10}$carbocycle)C$_0$-C$_4$alkyl or (3- to 10-membered heterocycle)C$_0$-C$_4$alkyl, each of which is substituted with from 0 to 6 substituents independently selected from R$_x$, oxo, —NH(C$_1$-C$_6$alkanoyl), —N(C$_1$-C$_6$alkyl)(C$_1$-C$_6$alkanoyl), —NHS(O$_n$)(C$_1$-C$_6$alkyl), —N(S(O$_n$)(C$_1$-C$_6$alkyl)$_2$, —S(O$_n$)NH(C$_1$-C$_6$alkyl) and —S(O$_n$)N(C$_1$-C$_6$alkyl)$_2$;

W is a single covalent bond, —CR$_A$R$_B$—, —NR$_B$— or —O—;

Z is independently selected at each occurrence from 3- to 7-membered carbocycles and heterocycles, each of which is substituted with from 0 to 4 substituents independently selected from halogen, oxo, —COOH, hydroxy, amino, cyano, C$_1$-C$_6$alkyl, C$_1$-C$_6$alkoxy, C$_1$-C$_6$haloalkyl, C$_1$-C$_6$haloalkoxy, mono- and di-(C$_1$-C$_6$alkyl)amino, (C$_1$-C$_6$alkyl)(2-acetamide)amino and —S(O$_n$)(C$_1$-C$_6$alkyl);

R$_A$ and R$_B$ are independently selected at each occurrence from:
(i) hydrogen; and
(ii) C$_1$-C$_{10}$alkyl, C$_2$-C$_{10}$alkenyl, C$_2$-C$_{10}$alkynyl, saturated or partially saturated (C$_3$-C$_{10}$carbocycle)C$_0$-C$_4$alkyl and saturated or partially saturated (3- to 10-membered heterocycle)C$_0$-C$_4$alkyl, each of which is substituted with from 0 to 6 substituents independently selected from oxo, hydroxy, halogen, cyano, amino, C$_1$-C$_6$alkoxy, mono- and di-(C$_1$-C$_4$alkyl)amino, —COOH, —C(=O)NH$_2$, —NHC(=O)(C$_1$-C$_6$alkyl), —N(C$_1$-C$_6$alkyl)C(=O)(C$_1$-C$_6$alkyl), —NHS(O$_n$)(C$_1$-C$_6$alkyl), SO$_3$H, —SO$_2$NH$_2$, —S(O$_n$)(C$_1$-C$_6$alkyl), —S(O$_n$)NH(C$_1$-C$_6$alkyl), —S(O$_n$)N(C$_1$-C$_6$alkyl)(C$_1$-C$_6$alkyl) and Z;

R$_C$ and R$_D$ are independently selected from R$_A$, hydroxy, C$_{1-6}$alkoxy, and oxo;

R$_x$ is independently chosen at each occurrence from halogen, hydroxy, amino, cyano, nitro, —COOH, —C(=O)NH$_2$, C$_1$-C$_6$alkoxycarbonyl, mono- and di-(C$_{1-6}$alkyl)aminocarbonyl, C$_1$-C$_6$alkyl, C$_2$-C$_6$alkenyl, C$_2$-C$_6$alkynyl, mono- and di-(C$_1$-C$_6$alkyl)amino, C$_1$-C$_6$alkoxy, C$_1$-C$_2$hydroxyalkyl, C$_1$-C$_2$haloalkyl, C$_1$-C$_2$haloalkoxy, (C$_3$-C$_7$cycloalkyl)C$_0$-C$_4$alkyl, and —S(O$_n$)(C$_1$-C$_6$alkyl);

m is an integer independently selected at each occurrence from 0-8; and n is an integer independently selected at each occurrence from 0, 1 and 2.

Within certain other aspects, compounds provided herein are 4,5-disubstituted-2-arylpyrimidines of Formula IX:

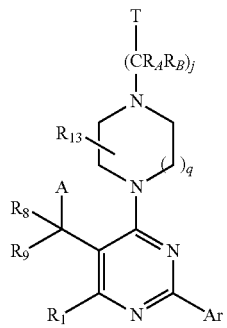

(IX)

wherein:
Ar is mono-, di-, or tri-substituted phenyl, optionally substituted naphthyl, or optionally substituted heteroaryl, said heteroaryl having from 1 to 3 rings, 5 to 7 ring members in each ring and, in at least one of said rings, from 1 to about 3 heteroatoms selected from N, O and S;

q is 0, 1 or 2;

A is $OR_4$, $NR_4R_5$, or $CR_4R_5XR_y$;

$R_1$ is selected from hydrogen, optionally substituted alkyl, optionally substituted alkenyl, optionally substituted alkynyl, optionally substituted cycloalkyl, optionally substituted cycloalkenyl, optionally substituted alkoxy, optionally substituted cycloalkoxy, or optionally substituted (cycloalkyl)alkoxy;

$R_4$ is:
(i) $C_2$-$C_8$alkyl, $C_2$-$C_8$alkenyl, $C_2$-$C_8$alkynyl, ($C_3$-$C_7$cycloalkyl)$C_0$-$C_4$alkyl, mono- or di-$C_1$-$C_4$alkylamino)$C_2$-$C_4$alkyl, (3- to 7-membered heterocycloalkyl)$C_0$-$C_4$alkyl, phenyl$C_0$-$C_4$alkyl, or heteroaryl$C_{0-4}$alkyl, each of which is substituted with from 0.0 to 4 substituents independently chosen from $R_x$, $C_2$-$C_4$alkanoyl, mono- and di-($C_1$-$C_4$alkyl)amino$C_1$-$C_4$alkyl, mono- and di-($C_1$-$C_4$alkyl)amino$C_1$-$C_4$alkoxy, (3- to 7-membered heterocycloalkyl)$C_0$-$C_4$alkyl and $XR_y$; or
(ii) joined to $R_5$ to form, with the nitrogen to which $R_4$ and $R_5$ are bound, a heterocycle having from 1 to 3 rings, 5 to 7 ring members in each ring, and is substituted with from 0 to 4 substituents independently chosen from $R_x$, oxo and W-Z;

$R_5$ is:
(i) hydrogen;
(ii) $C_1$-$C_6$alkyl, $C_2$-$C_6$alkenyl, $C_2$-$C_6$alkynyl, ($C_3$-$C_7$carbocycle)$C_0$-$C_4$alkyl, each of which is substituted with from 0 to 3 substituents independently chosen from halogen, hydroxy, amino, cyano, $C_1$-$C_4$alkyl, $C_1$-$C_4$alkoxy, methylamino, dimethylamino, trifluoromethyl and trifluoromethoxy; or
(iii) joined to $R_4$ to form an optionally substituted heterocycle;

$R_8$ and $R_9$ are independently selected from hydrogen, halogen, hydroxy, $C_1$-$C_6$alkyl, $C_2$-$C_6$alkenyl, $C_2$-$C_6$alkynyl, $C_1$-$C_6$alkoxy, $C_1$-$C_6$alkylamino and ($C_3$-$C_7$cycloalkyl)$C_0$-$C_4$alkyl;

$R_{13}$ represents from 0 to 3 substituents independently chosen from:
(i) $R_x$; and (ii) phenyl and pyridyl, each of which is substituted with from 0 to 4 substituents independently chosen from halogen, hydroxy, amino, cyano, $C_1$-$C_4$alkyl, $C_1$-$C_4$alkoxy, ($C_3$-$C_7$cycloalkyl)$C_0$-$C_4$alkyl, $C_1$-$C_2$haloalkyl, $C_1$-$C_2$haloalkoxy and mono- and di-($C_1$-$C_4$alkyl)amino; and X is a single covalent bond, $-CR_4R_B-$, $-O-$, $-C(=O)-$, $-C(=O)O-$, $-S(O)_n-$ or $-NR_B-$; and $R_y$ is:
(i) hydrogen; or
(ii) $C_1$-$C_{10}$alkyl, $C_2$-$C_{10}$alkenyl, $C_2$-$C_{10}$alkynyl, $C_3$-$C_{10}$carbocycle$C_0$-$C_4$alkyl or (3- to 10-membered heterocycle)$C_0$-$C_4$alkyl, each of which is substituted with from 0 to 6 substituents independently selected from $R_x$, oxo, $-NH(C_1$-$C_6$alkanoyl), $-N(C_1$-$C_6$alkyl)($C_1$-$C_6$alkanoyl), $-NHS(O_n)(C_1$-$C_6$alkyl), $-N(S(O_n))(C_1$-$C_6$alkyl)$_2$, $-S(O_n)NH(C_1$-$C_6$alkyl) and $-S(O_n)N(C_1$-$C_6$alkyl)$_2$;

W is a single covalent bond, $-CR_4R_B-$, $-NR_B-$ or $-O-$;

Z is independently selected at each occurrence from 3- to 7-membered carbocycles and heterocycles, each of which is substituted with from 0 to 4 substituents independently selected from halogen, oxo, $-COOH$, hydroxy, amino, cyano, $C_1$-$C_6$alkyl, $C_1$-$C_6$alkoxy, $C_1$-$C_6$haloalkyl, $C_1$-$C_6$haloalkoxy, mono- and di-($C_1$-$C_6$alkyl)amino and $-S(O_n)(C_1$-$C_6$alkyl); and $R_A$ and $R_B$ are independently selected at each occurrence from:
(i) hydrogen; and
(ii) $C_1$-$C_{10}$alkyl, $C_2$-$C_{10}$alkenyl, $C_2$-$C_{10}$alkynyl, saturated or partially saturated ($C_3$-$C_{10}$carbocycle)$C_0$-$C_4$alkyl and saturated or partially saturated (3- to 10-membered heterocycle)$C_0$-$C_4$alkyl, each of which is substituted with from 0 to 6 substituents independently selected from oxo, hydroxy, halogen, cyano, amino, $C_1$-$C_6$alkoxy, mono- and di-($C_1$-$C_4$alkyl)amino, $-COOH$, $-C(=O)NH_2$, $-SO_2NH_2$, $-NHC(=O)(C_1$-$C_6$alkyl), $-N(C_1$-$C_6$alkyl)C(=O)(C_1$-$C_6$alkyl), $-NHS(O_n)(C_1$-$C_6$alkyl), $-S(O_n)(C_1$-$C_6$alkyl), $-S(O_n)NH(C_1$-$C_6$alkyl), $-S(O_n)N(C_1$-$C_6$alkyl)($C_1$-$C_6$alkyl) and Z;

$R_C$ and $R_D$ are independently selected from $R_A$, hydroxy, $C_{1-6}$alkoxy, and oxo;

$R_x$ is independently chosen at each occurrence from halogen, hydroxy, amino, cyano, nitro, $-COOH$, $-C(=O)NH_2$, $C_1$-$C_6$alkoxycarbonyl, mono- and di-($C_{1-6}$alkyl)aminocarbonyl, $C_1$-$C_6$alkyl, $C_2$-$C_6$alkenyl, $C_2$-$C_6$alkynyl, mono- and di-($C_1$-$C_6$alkyl)amino, $C_1$-$C_6$alkoxy, $C_1$-$C_2$hydroxyalkyl, $C_1$-$C_2$haloalkyl, $C_1$-$C_2$haloalkoxy, ($C_3$-$C_7$cycloalkyl)$C_0$-$C_4$alkyl, and $-S(O_n)(C_1$-$C_6$alkyl);

T is $CO_2H$, $CONH_2$, $C_{1-6}$alkoxycarbonyl, mono- or di-($C_{1-6}$alkyl)aminocarbonyl, $SO_3H$, $-SO_2NH_2$, or $SO_2(C_{1-6}$alkyl); and n is an integer independently selected at each occurrence from 0, 1 and 2.

In certain embodiments, C5a receptor modulators provided herein exhibit high affinity for C5a receptor (i.e., an affinity constant for binding to C5a receptor of less than 1 micromolar) or very high affinity for C5a receptor (i.e., an affinity constant for binding to C5a receptor of less than 100 nanomolar). In certain embodiments, such modulators exhibit an affinity for human C5a receptor that is higher than for rat or mouse C5a receptor, preferably at least five times higher, more preferably ten times higher. Affinity of a compound for C5a receptor may be determined, for example, via a radioligand binding assay, such as the assay provided in Example 23.

Within certain aspects, modulators as described herein are C5a receptor antagonists, such as inverse agonists. Certain such compounds exhibit an $EC_{50}$ of 1 micromolar or less, 500 nM or less, 100 nM or less, or 25 nM or less, in a standard in vitro C5a receptor-mediated chemotaxis assay (such as the assay provided in Example 18) or a calcium mobilization assay (as described in Example 25).

Within further aspects, C5a receptor antagonists are essentially free of C5a receptor agonist activity (i.e., exhibit less than 5% agonist activity in a GTP binding assay as described in Example 24).

The present invention further provides, within other aspects, pharmaceutical compositions comprising at least one C5a receptor modulator as described herein, in combination with a physiologically acceptable carrier or excipient. Processes for preparing such pharmaceutical compositions are also provided. Such compositions are particularly useful in the treatment of C5a-mediated inflammation, such as inflammation associated with various inflammatory and immune system disorders.

Within further aspects, methods are provided for inhibiting signal-transducing activity of a cellular C5a receptor, comprising contacting a cell expressing a C5a receptor with at least one C5a receptor modulator as described herein, and thereby reducing signal transduction by the C5a receptor.

Methods are further provided for inhibiting binding of C5a to C5a receptor in vitro, comprising contacting C5a receptor with at least one C5a receptor modulator as described herein, under conditions and in an amount sufficient to detectably inhibit C5a binding to C5a receptor.

The present invention further provides methods for inhibiting binding of C5a to C5a receptor in a human patient, comprising contacting cells expressing C5a receptor with at least one C5a receptor modulator as described herein.

Within further aspects, the present invention provides methods for treating a patient in need of anti-inflammatory treatment or immunomodulatory treatment. Such methods generally comprise administering to the patient a therapeutically effective amount of a C5a receptor modulator as described herein. Treatment of humans, domesticated companion animals (pets) or livestock animals suffering such conditions is contemplated by the present invention. In certain such aspects, methods are provided for treating a patient suffering from cystic fibrosis, rheumatoid arthritis, psoriasis, cardiovascular disease, reperfusion injury, or bronchial asthma comprising administering to the patient a therapeutically effective amount of a C5a receptor modulator as described herein. In further such aspects, methods are provided for treating a patient suffering from stroke, myocardial infarction, atherosclerosis, ischemic heart disease, or ischemia-reperfusion injury comprising administering to the patient a therapeutically effective amount of a C5a receptor modulator as described herein.

The present invention further provides methods for inhibiting C5a receptor-mediated cellular chemotaxis (preferably leukocyte (e.g., neutrophil) chemotaxis), comprising contacting mammalian white blood cells with a therapeutically effective amount of a C5a receptor modulator as described herein. In certain embodiments, the white blood cells are primate white blood cells, such as human white blood cells.

Within further aspects, the present invention provides methods for using a C5a receptor modulator as described herein as a probe for the localization of receptors, particularly C5a receptors. Such localization may be achieved, for example, in tissue sections (e.g., via autoradiography) or in vivo (e.g., via positron emission tomography, PET, or single positron emission computed tomography, SPECT, scanning and imaging). Within certain such aspects, the present invention provides methods for localizing C5a receptors in a tissue sample, comprising: (a) contacting the tissue sample containing C5a receptors with a detectably labeled compound as described herein under conditions that permit binding of the compound to C5a receptors; and (b) detecting the bound compound. Such methods may, optionally, further comprise a step of washing the contacted tissue sample, prior to detection. Suitable detectable labels include, for example, radiolabels such as $^{125}I$, tritium, $^{14}C$, $^{32}P$ and $^{99}Tc$.

The present invention also provides packaged pharmaceutical preparations, comprising: (a) a pharmaceutical composition as described herein in a container; and (b) instructions for using the composition to treat a patient suffering from one or more conditions responsive to C5a receptor modulation, such as rheumatoid arthritis, psoriasis, cardiovascular disease, reperfusion injury, bronchial asthma, stroke, myocardial infarction, atherosclerosis, ischemic heart disease, or ischemia-reperfusion injury.

In yet another aspect, the present invention provides methods for preparing the compounds disclosed herein, including the intermediates.

These and other aspects of the present invention will become apparent upon reference to the following detailed description.

DETAILED DESCRIPTION OF THE INVENTION

As noted above, the present invention provides 4,5-disubstituted-2-arylpyrimidines that modulate C5a receptor activation and/or C5a receptor-mediated signal transduction. Such compounds may be used in vitro or in vivo to modulate (preferably inhibit) C5a receptor activity in a variety of contexts.

Chemical Description and Terminology

Compounds are generally described herein using standard nomenclature. For compounds having asymmetric centers, it should be understood that (unless otherwise specified) all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope (i.e., an atom having the same atomic number but a different mass number). By way of general example, and without limitation, isotopes of hydrogen include tritium and deuterium and isotopes of carbon include $^{11}C$, $^{13}C$, and $^{14}C$.

Certain compounds are described herein using a general formula that includes variables (e.g., R, $R_1$-$R_6$, Ar). Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted or substituted with up to two R* groups and R* at each occurrence is selected independently from the definition of R*. Also, combinations of substituents and/or variables are permissible only if such combinations result in stable compounds.

The term "4,5-disubstituted-2-arylpyrimidine," as used herein, refers to compounds of Formula I, Formula II and/or other Formula(s) provided herein, as well as pharmaceutically acceptable salts thereof. It will be apparent that such compounds may be further substituted as indicated (e.g., 4,5,6-trisubstituted-2-arylpryimidines are encompassed by the term "4,5-disubstituted-2-arylpyrimidine").

A "pharmaceutically acceptable salt" of a compound recited herein is an acid or base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences,* 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred.

It will be apparent that each compound of Formula I or Formula II (and/or other Formula(s) provided herein) may, but need not, be formulated as a hydrate, solvate or noncovalent complex. In addition, the various crystal forms and polymorphs are within the scope of the present invention, as are prodrugs of the compounds of the Formulas provided herein. A "prodrug" is a compound that may not fully satisfy the structural requirements of the compounds provided herein, but is modified in vivo, following administration to a patient, to produce a compound of Formula I, Formula II or other formula provided herein. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

A "therapeutically effective amount" (or dose) is an amount that, upon administration to a patient, results in a discernible patient benefit (e.g., provides detectable relief from a condition being treated). Such relief may be detected using any appropriate criteria, including alleviation of one or more symptoms. A therapeutically effective amount or dose generally results in a concentration of compound in a body fluid (such as blood, plasma, serum, CSF, synovial fluid, lymph, cellular interstitial fluid, tears or urine) that is sufficient to inhibit chemotaxis of white blood cells in an in vitro assay and/or alter C5a receptor activity or activation as measured by an in vitro calcium mobilization assay. It will be apparent that the discernible patient benefit may be apparent after administration of a single dose, or may become apparent following repeated administration of the therapeutically effective dose according to a predetermined regimen, depending upon the indication for which the compound is administered.

A "substituent," as used herein, refers to a molecular moiety that is covalently bonded to an atom within a molecule of interest. For example, a "ring substituent" may be a moiety such as a halogen, alkyl group, haloalkyl group or other substituent described herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound (i.e., a compound that can be isolated, characterized and tested for biological activity). When a substituent is oxo (i.e., =O), then 2 hydrogens on the atom are replaced. An oxo group that is a substituent of an aromatic carbon atom results in a conversion of —CH— to —C(=O)— and a loss of aromaticity. For example a pyridyl group substituted by oxo is a pyridone.

The phrase "optionally substituted" indicates that a group may either be unsubstituted or substituted at one or more of any of the available positions, typically 1, 2, 3, 4, or 5 positions, by one or more suitable substituents such as those disclosed herein. Optional substitution may also be indicated by the phrase "substituted with from 0 to X substituents," in which X is the maximum number of substituents.

Suitable substituents include, for example, halogen, cyano, amino, hydroxy, nitro, azido, $CONH_2$, COOH, $SO_2NH_2$, alkyl (e.g., $C_1$-$C_8$alkyl), alkenyl (e.g., $C_2$-$C_8$alkenyl), alkynyl (e.g., $C_2$-$C_8$alkynyl), alkoxy (e.g., $C_1$-$C_8$alkoxy), alkyl ether (e.g., $C_2$-$C_8$alkyl ether), alkylthio (e.g., $C_1$-$C_8$alkylthio), haloalkyl (e.g., $C_1$-$C_8$haloalkyl), hydroxyalkyl (e.g., $C_1$-$C_8$hydroxyalkyl), aminoalkyl (e.g., $C_1$-$C_8$aminoalkyl), haloalkoxy (e.g., $C_1$-$C_8$haloalkoxy), alkanoyl (e.g., $C_1$-$C_8$alkanoyl), alkanone (e.g., $C_1$-$C_8$alkanone), alkanoyloxy (e.g., $C_1$-$C_8$alkanoyloxy), alkoxycarbonyl (e.g., $C_1$-$C_8$alkoxycarbonyl), mono- and di-($C_1$-$C_8$alkyl)amino, mono- and di-($C_1$-$C_8$alkyl)amino$C_1$-$C_8$alkyl, mono- and di-($C_1$-$C_8$alkyl)aminocarbonyl, mono- and di-($C_1$-$C_8$alkyl)sulfonamido, alkylsulfinyl (e.g., $C_1$-$C_8$alkylsulfinyl), alkylsulfonyl (e.g., $C_1$-$C_8$alkylsulfonyl), aryl (e.g., phenyl), arylalkyl (e.g., ($C_6$-$C_{18}$aryl)$C_1$-$C_8$alkyl, such as benyl and phenethyl), aryloxy (e.g., $C_6$-$C_{18}$aryloxy such as phenoxy), arylalkoxy (e.g., ($C_6$-$C_{18}$aryl)$C_1$-$C_8$alkoxy) and/or 3- to 8-membered heterocyclic groups such as coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino or pyrrolidinyl. Certain groups within the formulas provided herein are optionally substituted with from 1 to 3, 1 to 4 or 1 to 5 independently selected substituents.

A dash ("—") that is not between two letters or symbols is used to indicate a point of attachment for a substituent. For example, —CONH$_2$ is attached through the carbon atom.

As used herein, "alkyl" is intended to include both branched and straight-chain saturated aliphatic hydrocarbon groups, and where specified, having the specified number of carbon atoms. Thus, the term "C$_1$-C$_6$alkyl" (or "C$_{1-6}$alkyl"), as used herein, indicates an alkyl group having from 1 to 6 carbon atoms. "C$_0$-C$_4$alkyl" refers to a single covalent bond (e.g., a C$_0$alkyl) or a C$_1$-C$_4$alkyl group. Alkyl groups include groups having from 1 to 8 carbon atoms (C$_1$-C$_8$alkyl), from 1 to 6 carbon atoms (C$_1$-C$_6$alkyl) and from 1 to 4 carbon atoms (C$_1$-C$_4$alkyl), such as methyl, ethyl, n-propyl, isopropyl, n-butyl, sec-butyl, tert-butyl, pentyl, 2-pentyl, isopentyl, neopentyl, hexyl, 2-hexyl, 3-hexyl, and 3-methylpentyl. In certain embodiments, preferred alkyl groups are methyl, ethyl, propyl, butyl, and 3-pentyl. "Aminoalkyl" is an alkyl group as defined herein substituted with one or more —NH$_2$ substituents. "Hydroxyalkyl" is an alkyl group as defined herein substituted with one or more —OH substituents. "Carboxyalkyl" is an alkyl group as defined herein substituted with one or more —COOH substituents.

"Alkylene" refers to a divalent alkyl group, as defined above. C$_0$-C$_4$alkylene is a single covalent bond or an alkylene group having from 1 to 4 carbon atoms.

"Alkenyl" refers to a straight or branched hydrocarbon chain comprising one or more unsaturated carbon-carbon bonds, such as ethenyl and propenyl. Alkenyl groups include C$_2$-C$_8$alkenyl, C$_2$-C$_6$alkenyl and C$_2$-C$_4$alkenyl groups (which have from 2 to 8, 2 to 6 or 2 to 4 carbon atoms, respectively), such as ethenyl, allyl or isopropenyl.

"Alkynyl" refers to straight or branched hydrocarbon chains comprising one or more triple carbon-carbon bonds. Alkynyl groups include C$_2$-C$_8$alkynyl, C$_2$-C$_6$alkynyl and C$_2$-C$_4$alkynyl groups, which have from 2 to 8, 2 to 6 or 2 to 4 carbon atoms, respectively. Alkynyl groups include for example groups such as ethynyl and propynyl.

By "alkoxy," as used herein, is meant an alkyl group as described above attached via an oxygen bridge. Alkoxy groups include C$_1$-C$_6$alkoxy and C$_1$-C$_4$alkoxy groups, which have from 1 to 6 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups. Similarly "alkylthio" refers to an alkyl group as described above attached via a sulfur bridge.

The term "alkanoyl" refers to an alkyl group as defined above attached through a carbonyl bridge. Alkanoyl groups include C$_2$-C$_8$alkanoyl, C$_2$-C$_6$alkanoyl and C$_2$-C$_4$alkanoyl groups, which have from 2 to 8, 2 to 6 or 2 to 4 carbon atoms, respectively. "C$_1$alkanoyl" refers to —(C=O)—H, which (along with C$_2$-C$_8$alkanoyl) is encompassed by the term "C$_1$-C$_8$alkanoyl." Ethanoyl is C$_2$alkanoyl.

An "alkanone" is an alkyl group as defined above with the indicated number of carbon atoms substituted at least one position with an oxo group. "C$_3$-C$_8$alkanone," "C$_3$-C$_6$alkanone" and "C$_3$-C$_4$alkanone" refer to an alkanone having from 3 to 8, 6 or 4 carbon atoms, respectively. By way of example, a C$_3$ alkanone group has the structure —CH$_2$—(C=O)—CH$_3$.

Similarly, "alkyl ether" refers to a linear or branched ether substituent linked via a carbon-carbon bond. Alkyl ether groups include C$_2$-C$_8$alkyl ether, C$_2$-C$_6$alkyl ether and C$_2$-C$_4$alkyl ether groups, which have 2 to 8, 6 or 4 carbon atoms, respectively. By way of example, a C$_2$ alkyl ether group has the structure —CH$_2$—O—CH$_3$.

The term "alkoxycarbonyl" refers to an alkoxy group attached through a keto (—(C=O)—) bridge (i.e., a group having the general structure —C(=O)—O-alkyl). Alkoxycarbonyl groups include C$_1$-C$_8$, C$_1$-C$_6$ and C$_1$-C$_4$alkoxycarbonyl groups, which have from 1 to 8, 6 or 4 carbon atoms, respectively, in the alkyl portion of the group (i.e., the carbon of the keto bridge is not included in the indicated number of carbon atoms). "C$_1$alkoxycarbonyl" refers to —C(=O)—O—CH$_3$; C$_3$alkoxycarbonyl indicates —C(=O)—O—(CH$_2$)$_2$CH$_3$ or —C(=O)—O—(CH)(CH$_3$)$_2$.

"Alkanoyloxy," as used herein, refers to an alkanoyl group linked via an oxygen bridge (e.g., a group having the general structure —C—(=O)-alkyl). Alkanoyloxy groups include C$_1$-C$_8$, C$_1$-C$_6$ and C$_1$-C$_4$alkanoyloxy groups, which have from 1 to 8, 6 or 4 carbon atoms, respectively, in the alkyl portion of the group.

"Alkylamino" refers to a secondary or tertiary amine having the general structure —NH-alkyl or —N(alkyl)(alkyl), wherein each alkyl may be the same or different. Such groups include, for example, mono- and di-(C$_1$-C$_8$alkyl)amino groups, in which each alkyl may be the same or different and may contain from 1 to 8 carbon atoms, as well as mono- and di-(C$_1$-C$_6$alkyl)amino groups and mono- and di-(C$_1$-C$_4$alkyl) amino groups. "Mono- or di-(C$_1$-C$_4$alkylamino)C$_0$-C$_4$alkyl" refers to a mono- and di-(C$_1$-C$_4$alkyl)amino group that is linked via a single covalent bond (C$_0$alkyl) or a C$_1$-C$_4$alkylene group (i.e., a group having the general structure —C$_0$-C$_4$alkyl—NH—(C$_1$-C$_4$alkyl) or —C$_0$-C$_4$alkyl-N (C$_1$-C$_4$alkyl)$_2$, in which each alkyl may be the same or different. Similarly, "mono- or di-(C$_1$-C$_4$alkyl)aminoC$_1$-C$_4$alkoxy" refers to an alkylamino group linked via an alkoxy group (i.e., a group of the formula —O—(C$_1$-C$_4$alkyl)-NH(C$_1$-C$_4$alkyl) or —O—(C$_1$-C$_4$alkyl)-N(C$_1$-C$_4$alkyl)$_2$.

The term "aminocarbonyl" refers to an amide group (i.e., —(C=O)NH$_2$). "Mono- or di-(C$_1$-C$_6$alkyl)aminocarbonyl" refers to an amide group in which one or both of the hydrogen atoms is replaced with an independently chosen C$_1$-C$_6$alkyl. Such groups may also be indicated by "—C(=O)NH(alkyl) or —C(=O)N(alkyl)(alkyl)."

"(C$_1$-C$_6$alkyl)(2-acetamide)amino" refers to an amino group in which one hydrogen is replaced with C$_1$-C$_6$alkyl and the other hydrogen is replaced with a 2-acetamide group.

The term "halogen" refers to fluorine, chlorine, bromine and iodine.

A "haloalkyl" is a branched or straight-chain alkyl group, substituted with 1 or more halogen atoms (e.g., "haloC$_1$-C$_8$alkyl" groups have from 1 to 8 carbon atoms; "haloC$_1$-C$_6$alkyl" groups have from 1 to 6 carbon atoms). Examples of haloalkyl groups-include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. Within certain compounds provided herein, not more than 5 or 3 haloalkyl groups are present. The term "haloalkoxy" refers to a haloalkyl group as defined above attached via an oxygen bridge. "HaloC$_1$-C$_8$alkoxy" groups have 1 to 8 carbon atoms.

A "carbocycle" is any saturated, partially saturated, or aromatic group having 1 or 2 fused, pendant or spiro rings, with 3 to 8 atoms in each ring, and with all ring members being carbon. The term "carbocycle" encompasses aromatic groups such as phenyl and naphthyl, as well as groups that comprise both aromatic and nonaromatic rings (e.g., tetrahydronaphthyl), and groups with saturated and partially saturated rings (such as cyclohexyl and cyclohexenyl). When substitutions are indicated, carbocycles may be substituted on any ring atom where such substitution results in a stable compound. The term "$C_3$-$C_{10}$carbocycle" refers to such groups having from 3 to 10 ring members. A "$C_3$-$C_{10}$carbocycle$C_0$-$C_4$alkyl" group is a $C_3$-$C_{10}$carbocycle that is linked via a single covalent bond or a $C_1$-$C_4$alkylene group.

Certain carbocycles are "cycloalkyl" (i.e., a saturated or partially saturated carbocycle). Such groups typically contain from 3 to about 8 ring carbon atoms; in certain embodiments, such groups have from 3 to 7 ring carbon atoms. Examples of cycloalkyl groups include cyclopropyl, cyclobutyl, cyclopentyl and cyclohexyl, as well as such groups modified by the presence of one or more double or triple bonds (e.g., cyclohexenyl) and bridged or caged saturated ring groups such as norbornane or adamantane. If substituted, any ring carbon atom may be bonded to any indicated substituent.

In the term "(cycloalkyl)alkyl", "cycloalkyl" and "alkyl" are as defined above, and the point of attachment is on the alkyl group. This term encompasses, but is not limited to, cyclopropylmethyl, cyclohexylmethyl and cyclohexylethyl. "($C_3$-$C_7$cycloalkyl)$C_0$-$C_4$alkyl" refers to 3- to 7-membered cycloalkyl rings that are linked via a single covalent bond or a $C_1$-$C_4$alkylene.

Similarly, "(cycloalkyl)alkoxy" refers to a cycloalkyl group linked via an alkoxy group (i.e., a group of the formula O-alkyl-cycloalkyl).

"Cycloalkoxy" refers to a cycloalkyl as described above linked via an oxygen bridge (e.g., cyclopentyloxy or cyclohexyloxy)

Other carbocycles are "aryl" (i.e., carbocycles that comprise at least one aromatic ring). In addition to the aromatic ring(s), additional non-aromatic ring(s) may be present in an aryl group. Representative aryl groups include phenyl, naphthyl (e.g., 1-naphthyl and 2-naphthyl), biphenyl, tetrahydronaphthyl and indanyl.

The term "arylalkyl" refers to an aryl group that is linked via an alkylene group. Certain arylalkyl groups are aryl$C_0$-$C_2$alkyl, in which an aryl group is linked via a single covalent bond or a methylene or ethylene moiety. Such groups include, for example, groups in which phenyl or naphthyl is linked via a single covalent bond or $C_1$-$C_2$alkylene, such as benzyl, 1-phenyl-ethyl and 2-phenyl-ethyl.

The term "aryloxy" refers to an aryl group linked via an oxygen (i.e., a group having the general structure —O-aryl). Phenoxy is a representative aryloxy group.

The term "arylalkoxy" refers to an aryl group linked via an alkoxy group (i.e., a group having the general structure —O-alkyl-aryl).

A "heteroatom" is an atom other than carbon, such as oxygen, sulfur or nitrogen.

The term "heterocycle" or "heterocyclic group" is used to indicate saturated, partially unsaturated, or aromatic groups having 1 or 2 fused, pendent or spiro rings, with 3 to 8 atoms in each ring, and in at least one ring from 1 to 4 heteroatoms independently selected from N, O and S, with remaining atoms being carbon. Certain heterocycles are 3- to 10-membered monocyclic or bicyclic groups; other are 4-to 6-membered monocyclic groups. The heterocyclic ring may be attached at any heteroatom or carbon atom that results in a stable structure, and may be substituted on carbon and/or nitrogen atom(s) if the resulting compound is stable. Any nitrogen and/or sulfur heteroatoms may optionally be oxidized, and any nitrogen may optionally be quaternized.

Variations on the term "(heterocycle)alkyl" refer to a heterocycle that is linked via a single covalent bond or alkylene group. Such groups include, for example, (3- to 10-membered heterocycle)$C_0$-$C_4$alkyl groups, in which the heterocycle contains from 3 to 10 ring members and is linked via a single covalent bond or $C_1$-$C_4$alkylene. Unless otherwise specified, the heterocycle portion of such groups may be saturated, partially saturated or aromatic. "(4- to 6-membered heterocycloalkyl)$C_0$-$C_4$alkyl" refers to a heterocycloalkyl group of from 4 to 6 ring members that is linked via a single covalent bond or a $C_1$-$C_4$alkylene.

Certain heterocycles are "heteroaryl" (i.e., groups that comprise at least one aromatic ring having from 1 to 4 heteroatoms). When the total number of S and O atoms in a heteroaryl group exceeds 1, then these heteroatoms are not adjacent to one another; preferably the total number of S and O atoms in a heteroaryl is not more than 1, 2 or 3, more preferably 1 or 2 and most preferably not more than 1. Examples of heteroaryl groups include pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, and 5,6,7,8-tetrahydroisoquinoline.

Other heterocycles are referred to herein as "heterocycloalkyl" (i.e., saturated or partially saturated heterocycles). Heterocycloalkyl groups have 1 or 2 rings, each with from 3 to about 8 ring atoms, and more typically from 5 to 7 ring atoms. Examples of heterocycloalkyl groups include morpholinyl, piperazinyl, piperidinyl and pyrrolidinyl.

Additional examples of heterocyclic groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3, 4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "C5a receptor" is a G-protein coupled receptor that specifically binds C5a peptide. Certain preferred C5a receptors are human, such as the protein product of the sequence that produces the human C5a receptor PCR product described by Gerard and Gerard (1991) *Nature* 349:614-17. The human C5a receptor may also be that described by Boulay (1991) *Biochemistry* 30(12):2993-99 (nucleotide sequence encoding the receptor is available at GENBANK Accession No. M62505). Non-primate C5a receptors include the rat C5a receptor (encoded by the nucleotide sequence having GENBANK Accession No. X65862, Y09613 or AB003042), canine C5a receptor (encoded by the nucleotide sequence having GENBANK Accession No. X65860), and guinea pig C5a receptor (encoded by the nucleotide sequence having GENBANK Accession No. U86103).

A "C5a receptor modulator" (also referred to herein as a "modulator") is any compound that modulates C5a receptor activation and/or activity (i.e., C5a receptor-mediated signal transduction, as measured using a C5a receptor-mediated chemotaxis assay or calcium mobilization assay as provided herein). In certain embodiments, such a modulator may exhibit an affinity constant for binding to a C5a receptor of less than 1 micromolar in a standard C5a receptor radioligand binding assay; and/or an $EC_{50}$ of less than 1 micromolar in a standard C5a receptor-mediated chemotaxis assay or calcium mobilization assay. In other embodiments the a C5a receptor modulator may exhibit an affinity constant or $EC_{50}$ of less than 500 nM, 200 nM, 100 nM, 50 nM, 25 nM, 10 nM or 5 nM in such an assay. A modulator may be a C5a receptor agonist or antagonist, although, for certain purposes described herein, a modulator preferably inhibits C5a activation resulting from binding of C5a (i.e., the modulator is an antagonist). In addition, or alternatively, a modulator may act as an inverse agonist of C5a receptor. In certain embodiments, modulators provided herein modulate activation and/or activity of a primate C5a receptor, such as human C5a receptor, which may be a cloned, recombinantly expressed receptor or a naturally expressed receptor. For treating non-human animals of any particular species, a compound exhibiting high affinity for C5a receptor of that particular species is preferred.

Certain C5a receptor modulators exhibit high activity in a standard in vitro C5a receptor mediated chemotaxis assay, as specified in Example 18, herein. Such compounds exhibit an $EC_{50}$ of 4 μM or less in such a standard C5a mediated chemotaxis assay, preferably an $EC_{50}$ of 1 μM or less in such an assay, more preferably an $EC_{50}$ of 0.1 μM or less in such an assay, and even more preferably and $EC_{50}$ of 10 nM or less in such an assay.

An "inverse agonist" of a C5a receptor is a compound that reduces the activity of C5a receptor below its basal activity level in the absence of added C5a. Inverse agonists may also inhibit the activity of C5a at C5a receptor, and/or may inhibit binding of C5a to C5a receptor. The ability of a compound to inhibit the binding of C5a to C5a receptor may be measured by a binding assay, such as the radioligand binding assay given in Example 23. The basal activity of C5a receptor may be determined from a GTP binding assay, such as the assay of Example 24. The reduction of C5a receptor activity may also be determined from a GTP binding assay or a calcium mobilization assay such as the assay of Example 25.

A "neutral antagonist of C5a receptor is a compound which inhibits the activity of C5a at C5a receptor, but does not significantly change the basal activity of C5a receptor. Neutral antagonists of C5a receptor may inhibit the binding of C5a to C5a receptor.

A "partial agonist" of C5a receptor elevates the activity of C5a receptor above the basal activity level of the receptor in the absence of C5a, but does not elevate the activity of C5a receptor to the level brought about by saturating levels of the natural agonist, C5a Partial agonist compounds may inhibit the binding of C5a to C5a receptor. Partial agonists of C5a receptor usually elevate the activity of C5a receptor, producing a level of elevation ranging from 5% to 90% of the activity level brought about by receptor-saturating concentrations of the natural agonist, C5a.

4,5-disubstituted-2-arylpyrimidines

As noted above, the present invention provides 4,5-disubstituted-2-arylpyrimidines of Formulas I, II, IX and other formulas provided herein. Such compounds may be used to alter C5a receptor activity in a variety of contexts, including in the treatment of patients suffering from diseases or disorders responsive to C5a receptor modulation, such as autoimmune disorders and inflammatory conditions. C5a receptor modulators may also be used within a variety of in vitro assays (e.g., assays for receptor activity), as probes for detection and localization of C5a receptor and as standards in assays of ligand binding and C5a receptor-mediated signal transduction.

Certain compounds of Formulas I, II and IX include those in which $R_1$ is hydrogen, $C_1$-$C_6$alkyl, $C_2$-$C_6$alkenyl, $C_2$-$C_6$alkynyl, $C_1$-$C_6$alkoxy, $C_1$-$C_6$haloalkyl, $C_1$-$C_6$haloalkoxy, or ($C_3$-$C_7$cycloalkyl)$C_0$-$C_4$alkyl. In certain other compounds, $R_1$ is not hydrogen. Other compounds of Formula II include those compounds in which $R_1$ is $C_1$-$C_4$alkyl or $C_1$-$C_4$alkoxy, or in which $R_1$ is methyl, ethyl or methoxy.

Yet other compounds of Formulas I, II and IX include those in which:

$R_4$ is:
(i) $C_2$-$C_8$alkyl, $C_2$-$C_8$alkenyl, $C_2$-$C_8$alkynyl, ($C_3$-$C_7$Cycloalkyl)$C_0$-$C_4$alkyl, mono- or di-($C_1$-$C_4$alkylamino)$C_2$-$C_4$alkyl, (3- to 7-membered heterocycloalkyl)$C_0$-$C_4$alkyl, phenyl$C_0$-$C_4$alkyl, pyridyl$C_0$-$C_4$alkyl, pyrimidinyl$C_0$-$C_4$alkyl, thienyl$C_0$-$C_4$alkyl, imidazolyl$C_0$-$C_4$alkyl, pyrrolyl$C_0$-$C_4$alkyl, pyrazolyl$C_0$-$C_4$alkyl, benzoisothiazolyl or tetrahydronapthyl, each of which is substituted with from 0 to 4 substituents independently chosen from $R_x$, $C_2$-$C_4$alkanoyl, mono- and di-($C_1$-$C_4$alkyl)amino$C_1$-$C_4$alkyl, mono- and di-($C_1$-$C_4$alkyl)amino$C_1$-$C_4$alkoxy, (3- to 7-membered heterocycloalkyl)$C_0$-$C_4$alkyl and $XR_y$; or
(ii) joined to $R_5$ to form, with the nitrogen to which $R_4$ and $R_5$ are bound, a heterocycle having from 1 to 3 rings, 5 to 7 ring members in each ring, wherein the heterocycle is substituted with from 0 to 4 substituents independently chosen from $R_x$, oxo and W-Z; and $R_5$ is:
(i) hydrogen;
(ii) $C_1$-$C_6$alkyl, $C_2$-$C_6$alkenyl, $C_2$-$C_6$alkynyl, or ($C_3$-$C_7$carbocycle)$C_0$-$C_4$alkyl, each of which is substituted with from 0 to 3 substituents independently chosen from halogen, hydroxy, amino, cyano, $C_1$-$C_4$alkyl, $C_1$-$C_4$alkoxy, methylamino, dimethylamino, trifluoromethyl and trifluoromethoxy; or
(iii) joined to $R_4$ to form an optionally substituted heterocycle.

Certain compounds of Formula II include those in which A is $NR_4R_5$; such compounds are referred to herein as compounds of Formula II-a. Certain compounds of Formula II-a include those compounds in which:

$R_4$ is chosen from ($C_3$-$C_7$cycloalkyl)$C_0$-$C_4$alkyl, phenyl$C_0$-$C_4$alkyl, pyridyl$C_0$-$C_4$alkyl, pyrimidinyl$C_0$-$C_4$alkyl, thienyl$C_0$-$C_4$alkyl, imidazolyl$C_0$-$C_4$alkyl, pyrrolyl$C_0$-$C_4$alkyl, pyrazolyl$C_0$-$C_4$alkyl, indolyl$C_0$-$C_4$alkyl, indazolyl$C_0$-$C_4$alkyl, benzocycloalkenyl$C_0$-$C_4$alkyl, decahydronaphthyl$C_0$-$C_4$alkyl, benzoisothiazolyl$C_0$-$C_4$alkyl, tetrahydroquinolinyl$C_0$-$C_4$alkyl and tetrahydronaphthyl$C_0$-$C_4$alkyl, each of which is substituted with from 0 to 4 groups independently chosen from $R_x$, mono- and di-($C_1$-$C_4$alkyl)amino$C_1$-$C_4$alkyl, mono- and di-($C_1$-$C_4$alkyl)amino$C_1$-$C_4$alkoxy, (3- to 7-membered heterocycloalkyl)$C_0$-$C_4$alkyl, $C_2$-$C_4$alkanoyl and $C_2$-$C_4$alkanoyloxy; and $R_5$ is $C_1$-$C_6$alkyl, $C_2$-$C_6$alkenyl or ($C_3$-$C_7$carbocycle)$C_0$-$C_4$alkyl.

Other compounds of Formula II-a provided herein include those in which $R_4$ and $R_5$ are joined to form a saturated or partially saturated heterocycle containing 1 or 2 fused or spiro rings; wherein the heterocycle is substituted with from 0 to 4 substituents independently chosen from halogen, hydroxy, amino, cyano, —COOH, —CH$_2$COOH, C$_{1-6}$alkoxycarbonyl, —CH$_2$CO$_2$—C$_{1-6}$alkyl, —C(=)NH$_2$, C$_1$-C$_6$alkyl, C$_2$-C$_6$alkenyl, C$_2$-C$_6$alkynyl, mono- and di-(C$_1$-C$_6$alkyl)amino, C$_1$-C$_6$alkoxy, C$_1$-C$_2$haloalkyl, C$_1$-C$_2$haloalkoxy, (C$_3$-C$_7$cycloalkyl)C$_0$-C$_4$alkyl, —S(O$_n$)(C$_1$-C$_6$alkyl), SO$_3$H, SO$_2$NH$_2$ and phenyl. In certain such compounds, R$_4$ and R$_5$ are joined to form a saturated 4- to 7-membered heterocyclic ring that is substituted with from 0 to 3 substituents independently chosen from halogen, hydroxy, amino, cyano, C$_1$-C$_2$alkyl, C$_1$-C$_2$alkoxy, trifluoromethyl, difluoromethyl, trifluoromethoxy difluoromethoxy, —COOH, —CH$_2$COOH, C$_{1-2}$alkoxycarbonyl, and —CH$_2$CO$_2$—C$_{1-2}$alkyl. Within certain compounds of Formula II-a in which R$_4$ and R$_5$ are combined to form a 4 to 7-membered heterocyclic ring, the heterocycle is selected from azepanyl, morpholinyl, homomorpholinyl, pyrrolidinyl, piperazinyl, homopiperazinyl, piperidinyl, homopiperidinyl, and the like.

In certain other compounds of Formula II-a, R$_4$ and R$_5$ are combined to form a heterocycle that comprises 2 rings; wherein each ring is substituted with from 0 to 3 substituents independently selected from halogen, hydroxy, amino, cyano, C$_1$-C$_2$alkyl, C$_1$-C$_2$alkoxy, trifluoromethyl, difluoromethyl, trifluoromethoxy, and difluoromethoxy. Certain compounds of Formula II-a in which R$_4$ and R$_5$ are combined to form a bicyclic heterocycle include those in which the heterocycle is tetrahydroquinolinyl, tetrahydroisoquinolinyl, decahydroquinolinyl, decahydroisoquinolinyl, indazolyl, indolinyl, phenylimidazolyl, pyridooxazinyl, benzoxazinyl, or the like.

Also provided are compounds of Formula II that further satisfy Formula III:

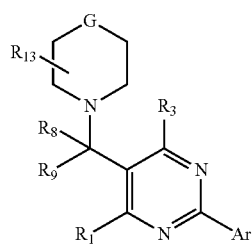

(III)

wherein:
R$_{13}$ represents from 0 to 3 substituents independently chosen from:
(i) R$_x$; and
(ii) phenyl and pyridyl, each of which is substituted with from 0 to 4 substituents independently chosen from halogen, hydroxy, amino, cyano, C$_1$-C$_4$alkyl, C$_1$-C$_4$alkoxy, (C$_3$-C$_7$cycloalkyl)C$_0$-C$_4$alkyl, C$_1$-C$_2$haloalkyl, C$_1$-C$_2$haloalkoxy and mono- and di-(C$_1$-C$_4$alkyl)amino;
G is CH$_2$, sulfur, oxygen or NR$_E$; wherein R$_E$ is:
(i) hydrogen; or
(ii) C$_1$-C$_6$alkyl, (C$_3$-C$_7$cycloalkyl)C$_0$-C$_4$alkyl, phenyl or a 5- or 6-membered heteroaryl ring, each of which is substituted with from 0 to 3 substituents independently chosen from R$_x$;
and the remaining variables are as described for Formula II.
In certain compounds of Formula III, G is oxygen.
In certain compounds of Formula III, R$_{13}$ represents from 0 to 2 substitiuents independently chosen from halogen, methyl, methoxy, ethyl, phenyl, and phenoxy, wherein each phenyl or phenoxy group is substituted with between 0 and 3 substituents independently chosen from R$_x$.

Certain compounds of Formula II-a further satisfy Formula IV:

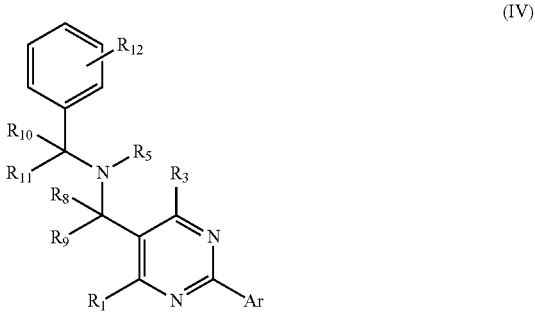

(IV)

wherein:
R$_{10}$ and R$_{11}$ are independently chosen from hydrogen, C$_1$-C$_6$alkyl, C$_1$-C$_2$haloalkyl and (C$_3$-C$_7$cycloalkyl)C$_0$-C$_2$alkyl;
R$_{12}$ represents from 0 to 3 substituents independently chosen from R$_x$, mono- and di-(C$_1$-C$_4$alkyl)aminoC$_1$-C$_4$alkyl, mono- and di-(C$_1$-C$_4$alkyl)aminoC$_1$-C$_4$alkoxy and YZ; or two adjacent R$_{12}$ groups are joined to form a fused 5- to 7-membered carbocyclic or heterocyclic ring; and the remaining variables are as described for Formula II-a.

The invention further provides certain compounds of Formula IV in which R$_{12}$ represents from 0 to 3 substituents independently chosen from halogen, hydroxy, amino, cyano, C$_1$-C$_4$alkyl, mono- and di-(C$_1$-C$_2$alkyl)amino, C$_1$-C$_4$alkoxy, C$_1$-C$_2$haloalkyl, C$_1$-C$_2$haloalkoxy and (C$_3$-C$_7$cycloalkyl)C$_0$-C$_2$alkyl.

Other compounds of Formula IV include those compounds in which:
R$_1$ is hydrogen, C$_1$-C$_6$alkyl, C$_2$-C$_6$alkenyl, C$_2$-C$_6$alkynyl, C$_1$-C$_6$alkoxy, C$_1$-C$_6$haloalkyl, C$_1$-C$_6$haloalkoxy, (C$_3$-C$_7$cycloalkyl)C$_0$-C$_4$alkyl;
R$_3$ is selected from alkoxy, cycloalkoxy, phenyl, 4- to 7-membered heterocycles, —O(CH$_2$)$_n$phenyl, —O(CH$_2$)$_n$pyridyl, -E-(CR$_C$R$_D$)$_m$-Q, and Q, each of which is substituted with between 0 and 3 substituents selected from halogen, cyano, hydroxy, oxo, (CR$_A$R$_B$)$_j$-T, C$_{1-6}$alkyl, C$_{1-6}$alkoxy, C$_{1-6}$haloalkyl, C$_{1-6}$haloalkoxy, (C$_{1-6}$alkyl)((CR$_A$R$_B$)$_j$-T) amino, mono- and di-(C$_{1-6}$alkyl)amino, benzyl, S(O)$_n$C$_{1-6}$alkyl, α,ω-C$_{1-4}$alkylene, α,ω-C$_{1-4}$alkyleneoxy, α,ω-C$_{1-4}$alkylenedioxy, -E-(CH$_2$)$_m$-Q, and Q;
T is CO$_2$H, CONH$_2$, C$_{1-6}$alkoxycarbonyl, mono- or di-(C$_{1-6}$alkyl)aminocarbonyl, SO$_3$H, SO$_2$NH$_2$ or SO$_2$(C$_{1-6}$alkyl);
j is an integer ranging from 0 to 6;
Q is a saturated heterocyclic ring comprising between 4 and 7 ring members, in which the point of attachment is a carbon or nitrogen atom;
R$_8$ and R$_9$ are independently chosen from hydrogen, halogen, hydroxy, C$_1$-C$_6$alkyl, C$_1$-C$_6$alkenyl, (C$_3$-C$_6$cycloalkyl)C$_0$-C$_4$alkyl and C$_1$-C$_6$alkoxy; and
Ar is phenyl, 1-naphthyl, 2-naphthyl, pyridyl, pyrimidinyl, pyrazinyl, pyridizinyl, thienyl, thiazolyl, pyrazolyl, imidazolyl, tetrazolyl, oxazolyl, isoxazolyl, indazolyl, indolyl, pyrrolyl, furanyl, or triazolyl, each of which is optionally mono-, di-, or tri-substituted.

Other compounds of Formula II-a include compounds of Formula V:

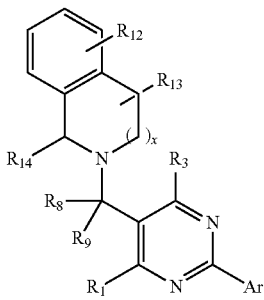

(V)

wherein:

R$_{12}$ and R$_{13}$ independently represent from 0 to 3 substituents independently chosen from R$_x$;

R$_{14}$ is hydrogen, C$_1$-C$_6$alkyl, C$_2$-C$_6$alkenyl, C$_2$-C$_6$alkynyl, C$_1$-C$_2$haloalkyl or (C$_3$-C$_7$cycloalkyl)C$_0$-C$_2$alkyl, COOH, CONH$_2$, CH$_2$COOH, CH$_2$CONH$_2$, C$_{1-6}$alkoxycarbonyl, CH$_2$CO$_2$—C$_{1-6}$alkyl, or SO$_3$H;

x is an integer selected from 0, 1 and 2 (in certain compounds x is 1);

and the remaining variables are as described for Formula II-a.

Certain compounds of Formula V include those compounds in which R$_{12}$ and R$_{13}$ independently represent from 0 to 2 substituents independently chosen from halogen, methyl, methoxy and ethyl; and R$_{14}$ is hydrogen, C$_1$-C$_6$alkyl, C$_2$-C$_6$alkenyl or (C$_3$-C$_7$cycloalkyl)C$_0$-C$_2$alkyl.

Also provided herein are compounds of Formula V in which:

R$_1$ is hydrogen, C$_1$-C$_6$alkyl, C$_2$-C$_6$alkenyl, C$_2$-C$_6$alkynyl, C$_1$-C$_6$alkoxy, C$_1$-C$_6$haloalkyl, C$_1$-C$_6$haloalkoxy, or (C$_3$-C$_7$cycloalkyl)C$_0$-C$_4$alkyl;

R$_3$ is selected from alkoxy, cycloalkoxy, phenyl, 4- to 7-membered heterocycles, —O(CH$_2$)$_n$phenyl, —O(CH$_2$)$_n$pyridyl, -E-(CR$_C$R$_D$)$_m$-Q, and Q, each of which is substituted with between 0 and 3 substituents selected from halogen, cyano, hydroxy, oxo, (CR$_4$R$_B$)$_j$-T, C$_{1-6}$alkyl, C$_{1-6}$alkoxy, C$_{1-6}$haloalkyl, C$_{1-6}$-haloalkoxy, mono- and di-(C$_{1-6}$-alkyl) amino, benzyl, S(O)$_n$(C$_{1-6}$alkyl), α,ω-C$_{1-4}$alkylene, α,ω-C$_{1-4}$alkyleneoxy, α,ω-C$_{1-4}$alkylenedioxy, -E-(CH$_2$)$_m$-Q, and Q;

R$_C$ and R$_D$ are the same or different and are independently selected at each occurrence from hydrogen, oxo, C$_{1-4}$alkyl, hydroxy, and C$_{1-4}$alkoxy;

T is CO$_2$H, CONH$_2$, C$_{1-6}$alkoxycarbonyl, mono- or di-(C$_{1-6}$alkyl)aminocarbonyl, SO$_3$H, SO$_2$NH$_2$ or SO$_2$(C$_{1-6}$alkyl);

j is an integer ranging from 0 to 6;

Q is a saturated heterocyclic ring comprising between 4 and 7 ring members, in which the point of attachment is a carbon or nitrogen atom;

R$_8$ and R$_9$ are independently chosen from hydrogen, halogen, hydroxy, C$_1$-C$_6$alkyl, C$_1$-C$_6$alkenyl, (C$_3$-C$_6$cycloalkyl)C$_0$-C$_4$alkyl and C$_1$-C$_6$alkoxy; and Ar is phenyl which is mono-, di-, or tri-substituted, or 1-naphthyl, 2-naphthyl, pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, indolyl, indazolyl, and triazolyl, each of which is optionally mono-, di-, or tri-substituted.

Yet other compounds of Formula II-a include compounds of Formula VI:

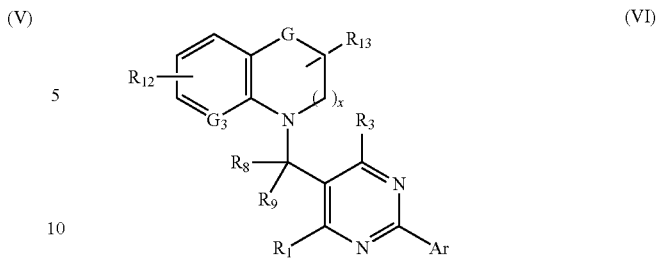

(VI)

wherein:

R$_{12}$ and R$_{13}$ represent from 0 to 3 substituents independently chosen from R$_x$;

G is CH$_2$, NH, sulfur or oxygen;

G$_3$ is N, CH, or CR$_x$;

x is an integer selected from 0, 1 and 2 (in certain compounds x is 1);

and the remaining variables are as described for Formula II-a.

Other compounds of Formula II-a provided herein include those compounds that satisfy Formula VII:

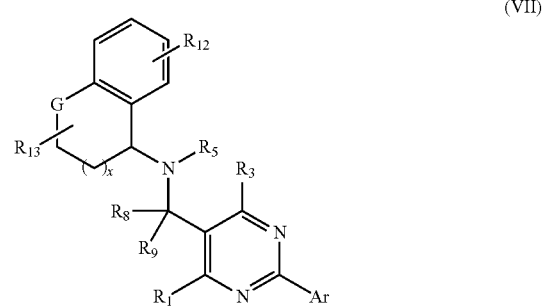

(VII)

wherein:

R$_{12}$ and R$_{13}$ independently represent from 0 to 3 substituents independently chosen from R$_x$;

G is CH$_2$, NH or oxygen (in certain compounds G is CH$_2$); and x is an integer selected from 0, 1 and 2 (in certain compounds x is 1);

and the remaining variables are as described for Formula II-a.

In certain compounds of Formula VI or Formula VII, R$_{12}$ and R$_{13}$ independently represent from 0 to 3 substituents independently chosen from halogen, hydroxy, amino, cyano, C$_1$-C$_4$alkyl, mono- and di-(C$_1$-C$_2$alkyl)amino, C$_1$-C$_4$alkoxy, C$_1$-C$_2$haloalkyl, C$_1$-C$_2$haloalkoxy, and (C$_3$-C$_7$cycloalkyl)C$_0$-C$_2$alkyl. Other compounds of Formula VI and Formula VII include those in which R$_{12}$ and R$_{13}$ independently represent from 0 to 2 substituents independently chosen from halogen, C$_1$-C$_2$alkyl and C$_1$-C$_2$alkoxy (e.g., halogen, methyl, methoxy and ethyl).

Other compounds of Formula VII include those in which R$_5$ is C$_1$-C$_6$alkyl; and R$_{12}$ and R$_{13}$ each represent from 0 to 2 substituents independently chosen from halogen, methyl, methoxy and ethyl.

Other compounds of Formula II provided herein include those compounds, which are herein defined as compounds of Formula II-b, in which:

A is OR$_4$; and

R$_4$ is C$_2$-C$_6$alkyl, C$_2$-C$_6$alkenyl, phenylC$_0$-C$_4$alkyl, naphthylC$_0$-C$_4$alkyl, pyridylC$_0$-C$_4$alkyl, pyrimidinylC$_0$-C$_4$alkyl, thienylC$_0$-C$_4$alkyl, imidazolylC$_0$-C$_4$alkyl or pyrrolylC$_0$-

$C_4$alkyl, each of which is substituted with from 0 to 4 substituents independently chosen from $R_x$, mono- and di-($C_1$-$C_4$alkyl)amino$C_1$-$C_4$alkyl, mono- and di-($C_1$-$C_4$alkyl)amino$C_1$-$C_4$alkoxy, (3- to 7-membered heterocycloalkyl)$C_0$-$C_4$alkyl and $C_2$-$C_4$alkanoyl.

Certain compounds of Formula II-b include those compounds in which $R_4$ is phenyl, benzyl, pyridyl or pyridylmethyl, each of which is substituted with from 0 to 4 substituents independently chosen from $R_x$, mono- and di-$C_1$-$C_4$alkyl)amino$C_0$-$C_4$alkyl, mono- and di-($C_1$-$C_4$alkyl) amino$C_1$-$C_4$alkoxy, (3- to 7-membered heterocycloalkyl)$C_0$-$C_4$alkyl and $C_2$-$C_4$alkanoyl.

Yet other compounds provided herein include those compounds of Formula II-b that further satisfy Formula VIII:

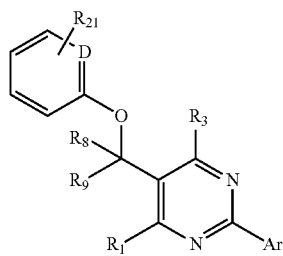

(VIII)

wherein:

D is CH or N;

$R_{21}$, represents from 0 to 3 substituents independently chosen from $R_x$ and $LR_d$; or two adjacent $R_{21}$ groups are joined to form a fused 5- to 7-membered carbocyclic or heterocyclic ring that is substituted with from 0 to 3 substituents independently chosen from $R_x$;

L is a single covalent bond or —$CH_2$—;

$R_d$ is piperazinyl, morpholinyl, piperidinyl or pyrrolidinyl;

and the remaining variables are as described for Formula II-b.

Certain compounds according to Formula VIII include those compounds in which:

$R_{21}$ represents from 0 to 3 substituents independently chosen from $R_x$ and $LR_d$;

$R_1$ is hydrogen, $C_1$-$C_6$alkyl, $C_2$-$C_6$alkenyl, $C_2$-$C_6$alkynyl, $C_1$-$C_6$alkoxy, $C_1$-$C_6$haloalkyl, $C_1$-$C_6$haloalkoxy, ($C_3$-$C_7$cycloalkyl)$C_0$-$C_4$alkyl;

$R_3$ is selected from alkoxy, cycloalkoxy, phenyl, 4- to 7-membered heterocycles, —O($CH_2$)$_n$phenyl, —O($CH_2$)$_n$pyridyl, -E-($CR_CR_D$)$_m$-Q, and Q, each of which is substituted with between 0 and 3 substituents selected from halogen, cyano, hydroxy, oxo, ($CR_AR_B$)$_j$-T, $C_{1-6}$alkyl, $C_{1-6}$alkoxy, $C_{1-6}$haloalkyl, $C_{1-6}$haloalkoxy, mono- and di-($C_{1-6}$alkyl) amino, ($C_{1-6}$alkyl)(($CR_AR_B$)$_j$-T)amino, benzyl, $S(O)_n$ ($C_{1-6}$-alkyl), α,ω-$C_{1-4}$alkylene, α,ω-$C_{1-4}$alkyleneoxy,α,ω-$C_{1-4}$alkylenedioxy, -E-($CH_2$)$_m$-Q, and Q;

T is $CO_2H$, $CONH_2$, $C_{1-6}$alkoxycarbonyl, mono- or di-($C_{1-6}$alkyl)aminocarbonyl, $SO_3H$, $SO_2NH_2$ or $SO_2$ ($C_{1-6}$alkyl);

j is an integer ranging from 0 to 6;

Q is a saturated heterocyclic ring comprising between 4 and 7 ring members, in which the point of attachment is a carbon or nitrogen atom;

E is O, $NR_D$, or a single covalent bond;

$R_8$ and $R_9$ are independently chosen from hydrogen, halogen, hydroxy, $C_1$-$C_6$alkyl, $C_1$-$C_6$alkenyl, ($C_3$-$C_6$cycloalkyl)$C_0$-$C_4$alkyl and $C_1$-$C_6$alkoxy; and Ar is phenyl which is mono-, di-, or tri-substituted; or 1-naphthyl, 2-naphthyl, pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, indolyl, indazolyl, or triazolyl, each of which is optionally mono-, di-, or tri-substituted.

Yet other compounds of Formula VIII include those compounds in which the group designated:

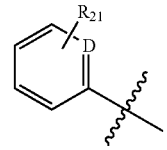

is chosen from naphthyl, tetrahydronaphthyl, benzofuranyl, benzodioxolyl, indanyl, indolyl, indazolyl, benzodioxolyl, benzo[1,4]dioxanyl and benzoxazolyl, each of which is substituted with from 0 to 3 substituents independently chosen from $R_x$.

Certain compounds of Formula IX include those in which

Ar is mono-, di-, or tri-substituted phenyl, which phenyl group is substituted with one to three substituents independently chosen from hydroxy, halogen, cyano, amino, nitro, —COOH, aminocarbonyl, —$SO_2NH_2$, $C_{1-6}$alkyl, $C_{1-6}$alkenyl, $C_{1-6}$alkynyl, $C_{1-6}$haloalkyl, $C_{1-6}$aminoalkyl, $C_{1-6}$hydroxyalkyl, $C_{1-6}$carboxyalkyl, $C_{1-6}$alkoxy, $C_{1-6}$haloalkoxy, $C_{1-6}$alkylthio, $C_{1-6}$alkanoyl, $C_{1-6}$alkanoyloxy, $C_{3-6}$alkanone, $C_{1-6}$alkyl ether, mono- or di-($C_{1-6}$alkyl)amino$C_{0-6}$alkyl, —NHC(=O)($C_{1-6}$alkyl), —N($C_{1-6}$alkyl)C(=O)($C_{1-6}$alkyl), —NHS(O)$_n$($C_{1-6}$alkyl), ($C_{1-6}$alkyl)C(=O)$NH_2$, —($C_{1-6}$alkyl)C(=O)NH($C_{1-6}$alkyl), —($C_{1-6}$alkyl)C(=O)NH($C_{1-6}$alkyl)($C_{1-6}$alkyl), —S(O)$_n$($C_{1-6}$alkyl), —S(O)$_n$NH($C_{1-6}$alkyl), —S(O)$_n$N($C_{1-6}$alkyl)($C_{1-6}$alkyl) and Z; or Ar is selected from naphthyl or heteroaryl, each of which is substituted with 0 to 4 substituents independently chosen from hydroxy, halogen, cyano, amino, nitro, —COOH, aminocarbonyl, —$SO_2NH_2$, $C_{1-6}$alkyl, $C_{1-6}$alkenyl, $C_{1-6}$alkynyl, $C_{1-6}$haloalkyl, $C_{1-6}$aminoalkyl, $C_{1-6}$hydroxyalkyl, $C_{1-6}$carboxyalkyl, $C_{1-6}$alkoxy, $C_{1-6}$haloalkoxy, $C_{1-6}$alkylthio, $C_{1-6}$alkanoyl, $C_{1-6}$alkanoyloxy, $C_{3-6}$alkanone, $C_{1-6}$alkyl ether, mono- or di-($C_{1-6}$alkyl)amino$C_{0-6}$alkyl, —NHC(=O) ($C_{1-6}$alkyl), —N($C_{1-6}$-alkyl)C(=O)($C_{1-6}$alkyl), —NHS(O)$_n$ ($C_{1-6}$alkyl), —($C_{1-6}$alkyl)C(=O)$NH_2$, —($C_{1-6}$alkyl)C(=O) NH($C_{1-6}$alkyl), —($C_{1-6}$alkyl)C(=O)NH($C_{1-6}$alkyl)($C_{1-6}$alkyl), —S(O)$_n$($C_{1-6}$alkyl), —S(O)$_n$NH($C_{1-6}$alkyl), —S(O)$_n$ N($C_{1-6}$alkyl)($C_{1-6}$alkyl) and Z; and $R_1$ is selected from hydrogen, alkyl, alkenyl, alkynyl, cycloalkyl, cycloalkenyl, alkoxy, cycloalkoxy, and (cycloalkyl)alkoxy, each of which is substituted with 0 to 4 groups independently selected from which phenyl group is substituted with one to three substituents independently chosen from hydroxy, halogen, cyano, amino, nitro, —COOH, aminocarbonyl, —$SO_2NH_2$, $C_{1-6}$alkyl, $C_{1-6}$alkenyl, $C_{1-6}$alkynyl, $C_{1-6}$haloalkyl, $C_{1-6}$aminoalkyl, $C_{1-6}$hydroxyalkyl, $C_{1-6}$carboxyalkyl, $C_{1-6}$alkoxy, $C_{1-6}$haloalkoxy, $C_{1-6}$alkylthio, $C_{1-6}$alkanoyl, $C_{1-6}$alkanoyloxy, $C_{3-6}$alkanone, $C_{1-6}$alkyl ether, mono- or di-($C_{1-6}$alkyl)amino$C_{0-6}$alkyl, —NHC(=O)($C_{1-6}$alkyl), —N($C_{1-6}$alkyl)C(=O)($C_{1-6}$alkyl), —NHS(O)$_n$($C_{1-6}$alkyl), —($C_{1-6}$alkyl)C(=O)$NH_2$, —($C_{1-6}$alkyl)C(=O)NH($C_{1-6}$alkyl), —($C_{1-6}$alkyl)C(=O)NH($C_{1-6}$alkyl)($C_{1-6}$alkyl), —S(O)$_n$($C_{1-6}$alkyl), —S(O)$_n$NH($C_{1-6}$alkyl), —S(O)$_n$N($C_{1-6}$alkyl)($C_{1-6}$alkyl) and Z.

Within certain compounds of Formula IX, described above:

Ar is phenyl, pyridyl or pyrimidyl, each of which is substituted with from 0 to 4 substituents independently chosen from halogen, hydroxy, cyano, amino, nitro, $C_1$-$C_6$alkyl, $C_2$-$C_6$alkenyl, $C_2$-$C_6$alkynyl, $C_1$-$C_2$haloalkyl, $C_1$-$C_6$alkoxy and $C_1$-$C_2$haloalkoxy;

q is 1;

A is $OR_4$;

$R_1$ is hydrogen, methyl or ethyl;

$R_4$ is ($C_3$-$C_7$cycloalkyl)$C_0$-$C_4$alkyl, (3- to 7-membered heterocycloalkyl)$C_0$-$C_4$alkyl, phenyl$C_0$-$C_4$alkyl, or heteroaryl$C_{0-4}$alkyl, each of which is substituted with from 0 to 4 substituents independently chosen from $R_x$;

$R_8$ and $R_9$ are independently selected from hydrogen, and $C_1$-$C_6$alkyl;

$R_{13}$ represents from 0 to 3 substituents independently chosen from $R_x$;

$R_A$ and $R_B$ are independently selected at each occurrence from hydrogen, methyl and ethyl;

$R_x$ is independently chosen at each occurrence from halogen, hydroxy, amino, cyano, nitro, —COOH, —C(=O)$NH_2$, $C_1$-$C_6$alkoxycarbonyl, mono- and di-($C_1$-alkyl)aminocarbonyl, $C_1$-$C_6$alkyl, $C_2$-$C_6$alkenyl, $C_2$-$C_6$alkynyl, mono- and di-($C_1$-$C_6$alkyl)amino, $C_1$-$C_6$alkoxy, $C_1$-$C_2$hydroxyalkyl, $C_1$-$C_2$haloalkyl, $C_1$-$C_2$haloalkoxy, ($C_3$-$C_7$cycloalkyl)$C_0$-$C_4$alkyl, and —$S(O_n)$($C_1$-$C_6$alkyl); and T is $CONH_2$, $C_{1-6}$alkoxycarbonyl, mono- or di-($C_{1-6}$alkyl)aminocarbonyl, $SO_2NH_2$, (C=O)$CH_2NH_2$, or $SO_2$($C_{1-6}$alkyl).

Certain compounds of Formula V provided herein further satisfy Formula X:

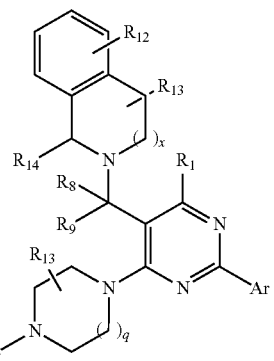

(X)

wherein:

$R_{12}$ and $R_{13}$ independently represent from 0 to 3 substituents independently chosen from $R_x$;

$R_{14}$ is hydrogen, $C_1$-$C_6$alkyl, $C_2$-$C_6$alkenyl, $C_2$-$C_6$alkynyl, $C_1$-$C_2$haloalkyl or ($C_3$-$C_7$cycloalkyl)$C_0$-$C_2$alkyl, COOH, $CONH_2$, $CH_2COOH$, $CH_2CONH_2$, $C_{1-6}$alkoxycarbonyl, and $CH_2CO_2$-$C_{1-6}$alkyl; and x is 0, 1 or 2.

Other compounds of Formula II-b provided herein further satisfy Formula XI:

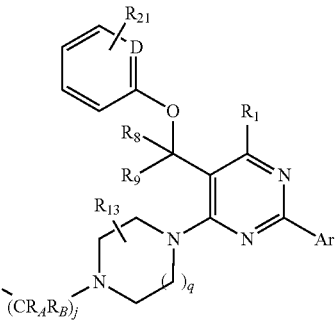

(XI)

wherein:

D is CH or N;

$R_{13}$ represents from 0 to 3 substituents independently chosen from hydroxy, methyl, and ethyl;

$R_{21}$ represents from 0 to 3 substituents independently chosen from $R_x$ and $LR_F$; or two adjacent $R_{21}$ groups are joined to form a fused 5- to 7-membered carbocyclic or heterocyclic ring that is substituted with from 0 to 3 substituents independently chosen from $R_x$;

L is a single covalent bond or —$CH_2$—;

$R_F$ is piperazinyl, morpholinyl, piperidinyl or pyrrolidinyl;

and the remaining variables are as described for Formula II-b.

Yet other compounds according to any one of Formulas II, II-a, II-b, III, IV, V, VI, VII, VIII, IX, X, or XI include those compounds in which:

$R_3$ is selected from alkoxy, cycloalkoxy, phenyl, 4- to 7-membered heterocycles, —O($CH_2$)$_n$phenyl, —O($CH_2$)$_n$pyridyl, -E-($CR_CR$)$_m$-Q, and Q, each of which is substituted with between 0 and 3 substituents selected from halogen, cyano, hydroxy, oxo, ($CR_AR_B$)$_j$-T, $C_{1-6}$alkyl, $C_{1-6}$alkoxy, $C_{1-6}$haloalkyl, $C_{1-6}$haloalkoxy, mono- and di-($C_{1-6}$alkyl) amino, benzyl, $S(O)_n C_{1-6}$alkyl, $\alpha,\omega$-$C_{1-4}$alkylene, $\alpha,\omega$-$C_{1-4}$alkyleneoxy, $\alpha,\omega$-$C_{1-4}$alkylenedioxy, -E-($CH_2$)$_m$-Q, and Q;

$R_C$ and $R_D$ are the same or different and are independently selected at each occurrence from hydrogen, oxo, $C_{1-4}$alkyl, hydroxy, and $C_{1-4}$alkoxy;

T is $CO_2H$, $CONH_2$, $C_{1-6}$alkoxycarbonyl, mono- or di-($C_{1-6}$alkyl)aminocarbonyl, $SO_3H$, $SO_2NH_2$ or $SO_2$($C_{1-6}$alkyl);

j is an integer ranging from 0 to 6;

Q is a saturated heterocyclic ring comprising between 4 and 7 ring members, and wherein the point of attachment is a carbon or nitrogen atom; and $R_8$ and $R_9$ are independently chosen from hydrogen, halogen, hydroxy, $C_1$-$C_6$alkyl, $C_1$-$C_6$alkenyl, ($C_3$-$C_6$cycloalkyl)$C_0$-$C_4$alkyl and $C_1$-$C_6$alkoxy.

Within certain such compounds:

$R_1$ is hydrogen, $C_1$-$C_6$alkyl, $C_2$-$C_6$alkenyl, $C_2$-$C_6$alkynyl, $C_1$-$C_6$alkoxy, $C_1$-$C_6$haloalkyl, $C_1$-$C_6$haloalkoxy, or ($C_3$-$C_7$cycloalkyl)$C_0$-$C_4$alkyl; and Ar is phenyl, 1-naphthyl, 2-naphthyl, pyridyl, pyrimidinyl, pyrazinyl, pyridizinyl, thienyl, thiazolyl, pyrazolyl, imidazolyl, tetrazolyl, oxazolyl, isoxazolyl, indazolyl, indolyl, pyrrolyl, furanyl, or triazolyl, each of which is optionally mono-, di-, or tri-substituted.

Within further such compounds, $R_3$ is pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, triazolyl, piperidinyl, piperazinyl, pyrrolidinyl, azetidinyl, azepanyl, or diazepanyl, each of which is substituted with between 0 and 3 substituents selected from halogen, cyano, hydroxy, oxo, $(CR_AR_B)_j$-T, $C_{1-6}$alkyl, $C_{1-6}$alkoxy, $C_{1-6}$haloalkyl, $C_{1-6}$haloalkoxy, mono- and di-($C_{1-6}$alkyl)amino, benzyl, $S(O)_nC_{1-6}$alkyl, $\alpha,\omega$-$C_{1-4}$alkylene, $\alpha,\omega$-$C_{1-4}$alkyleneoxy, $\alpha,\omega$-$C_{1-4}$alkylenedioxy, -E-$(CH_2)_m$-Q, and Q. Other compounds of Formula III include those in which $R_3$ is selected from $C_{1-6}$alkoxy, $C_{3-8}$cycloalkoxy, carboxylic acid substituted $C_{1-6}$alkoxy, E-$(CH_2)_m$-Q, wherein E is absent, O, NH, or N($C_{1-6}$alkyl), and Q is a saturated 4- to 7-membered heterocyclic ring, and in which the point of attachment is a carbon or nitrogen atom.

Certain compounds of any one of Formula II, II-a, II-b, III, IV, V, VI, VII, VIII, IX, X, or XI include those compounds in which:
$R_3$ is $C_{1-6}$alkoxy, carboxylic acid substituted $C_{1-6}$alkoxy, $C_{3-7}$cycloalkyloxy, or a residue according to the formula:

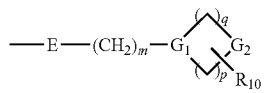

wherein E is O, $NR_D$, or a single covalent bond;
m is an integer ranging from 0 to 4;
p and q are independently selected integers from the range of 0-5 such that $2 \leq p+q \leq 5$;
$G_1$ is CH, $CR_{10}$, or N;
$G_2$ is CH, $CR_{10}$, NH, $NR_E$, O, or S;
$R_{10}$ represents one or two substituents selected from halogen, cyano, hydroxy, oxo, $(CH_2)_j$-T, N(methyl)$(CH_2)_j$-T, methyl, ethyl, methoxy, ethoxy, monofluoromethyl, difluoromethyl, trifluoromethyl, monofluoromethoxy, difluoromethoxy, and trifluoromethoxy;
$R_E$ is selected from $R_D$, T, and $CH_2T$;
T is $CO_2H$, $CONH_2$, $C_{1-6}$alkoxycarbonyl, mono- or di-($C_{1-6}$alkyl)aminocarbonyl, $SO_3H$, $SO_2NH_2$ or $SO_2(C_{1-6}$alkyl); and
j is an integer ranging from 0 to 6.

Certain other compounds of any one of Formula II, II-a, II-b, III, IV, V, VI, VII, VIII, IX, X, or XI include those compounds in which $R_3$ has the formula:

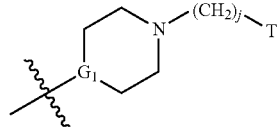

wherein T is $CO_2H$, $CONH_2$, $C_{1-6}$alkoxycarbonyl, mono- or di-($C_{1-6}$alkyl)aminocarbonyl, $SO_3H$, $SO_2NH_2$ or $SO_2(C_{1-6}$alkyl);
$G_1$ is N or CH; and
J is 0, 1, 2, or 3.

Other compounds of Formula III include those compounds in which:
$R_3$ is selected from phenyl, phenoxy, benzyloxy, each of which is substituted with 0-2 groups selected from halogen, cyano, hydroxy, —COOH, $C_{1-4}$alkyl, $C_{1-4}$haloalkyl, $C_{1-4}$alkoxy, $C_{1-4}$haloalkoxy, $\alpha,\omega$-$C_{1-3}$alkylenedioxy, $C_{1-4}$alkylthio, —SO($C_{1-4}$alkyl), and —SO$_2$($C_{1-4}$alkyl); or
$R_3$ is selected from E-$(CH_2)_m$-Q, wherein E is absent, O, NH, or N($C_{1-6}$alkyl), and Q is a saturated 4- to 7-membered heterocyclic ring in which the point of attachment is a carbon or nitrogen atom.

Other compounds of the invention include compounds of Formula XII:

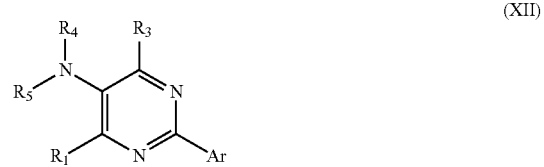

wherein:
$R_1$ is selected from hydrogen, optionally substituted alkyl, optionally substituted alkenyl, optionally substituted alkynyl, optionally substituted cycloalkyl, optionally substituted cycloalkenyl, optionally substituted alkoxy, optionally substituted cycloalkoxy, and optionally substituted (cycloalkyl)alkoxy;
$R_3$ is selected from optionally substituted aryl, optionally substituted arylalkyl, optionally substituted aryloxy, optionally substituted arylalkoxy, optionally substituted heterocyclic, optionally substituted heterocyclic-oxy, —O—$(CR_AR_B)_m$—Y, —N($R_B$)—$(CR_AR_B)_m$—$XR_A$, and —N($R_B$)—$(CR_AR_B)_m$—Y, wherein said heterocyclic residue is saturated, unsaturated or aromatic having from 1 to 3 rings and 3 to 7 ring members in each ring;
$R_4$ and $R_5$ are independently selected from: (i) hydrogen and hydroxy; and (ii) alkyl groups, cycloalkyl groups, and (cycloalkyl)alkyl groups consisting of 1 to 8 carbon atoms, each of which is optionally substituted and optionally comprises one or more double or triple bonds;
Ar is mono-, di-, or tri-substituted phenyl, optionally substituted naphthyl, or optionally substituted heteroaryl;
$R_A$ and $R_B$, which may be the same or different, are independently selected at each occurrence from: (i) hydrogen and hydroxy; and (ii) alkyl groups, cycloalkyl groups, and (cycloalkyl)alkyl groups, each of which is optionally further substituted with one or more substituent(s) independently selected from oxo, hydroxy, halogen, cyano, amino, $C_{1-6}$alkoxy, mono- or di-($C_{1-6}$alkyl)amino, —NHC(=O)($C_{1-6}$alkyl), —N($C_{1-6}$alkyl)C(=O)($C_{1-6}$alkyl), —NHS(O)$_n$($C_{1-6}$alkyl), —S(O)$_n$($C_{1-6}$alkyl), —S(O)$_n$NH($C_{1-6}$alkyl), —S(O)$_n$N($C_{1-6}$alkyl)($C_{1-6}$alkyl), and Z;
X is independently selected at each occurrence from —CHR$_B$—, —O—, —C(=O)—, —C(=O)O—, —S(O)$_n$—, —NR$_B$—, —C(=O)NR$_B$—, —S(O)$_n$NR$_B$—, —OC(=S)S—, —NR$_B$C(=O)—, —OSiH$_n$(C$_{1-4}$alkyl)$_{2-n}$-, and —NR$_B$S(O)$_n$—;
Y and Z are independently selected at each occurrence from 3- to 7-membered carbocyclic or heterocyclic groups which are saturated, unsaturated, or aromatic, each of which is optionally substituted with one or more substituents independently selected from halogen, oxo, hydroxy, amino, cyano, $C_{1-4}$alkyl, $C_{1-4}$alkoxy, mono- or di($C_{1-4}$alkyl)amino, and —S(O)$_n$(alkyl), said 3- to 7-membered heterocyclic groups containing one or more heteroatom(s) independently selected from N, O and S, with the point of attachment being either carbon or nitrogen;
m is independently selected at each occurrence from integers ranging from 0 to 8; and
n is independently selected at each occurrence from 0, 1, and 2.

Certain compounds of Formula XII include those compounds in which $R_1$ is hydrogen, $C_{1-6}$alkyl, $C_{1-6}$-alkoxy, halogen, $C_{1-6}$haloalkyl, $C_{1-6}$haloalkoxy or ($C_{3-8}$cycloalkyl)$C_{0-6}$alkyl.

Yet other compounds of Formula XII include those compounds in which $R_3$ is phenyl, pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, triazolyl, piperidinyl, piperazinyl, pyrrolidinyl, azetidinyl, azepanyl, diazepanyl, —O(CH$_2$)$_n$phenyl, —O(CH$_2$)$_n$pyridyl, -E-(CH$_2$)$_m$-Q, and Q, each of which is substituted with from 0 to 3 substituents selected from halogen, cyano, hydroxy, $C_{1-6}$alkyl, $C_{1-6}$alkoxy, $C_{1-6}$haloalkyl, $C_{1-6}$haloalkoxy, mono- and di-($C_{1-6}$alkyl)amino, benzyl, S(O)$_n$$C_{1-6}$alkyl, $\alpha,\omega$-$C_{1-4}$alkylene, $\alpha,\omega$-$C_{1-4}$alkyleneoxy, $\alpha,\omega$-$C_{1-4}$alkylenedioxy, -E-(CH$_2$)$_m$-Q, and Q; wherein Q is a saturated heterocyclic ring comprising between 4 and 7 ring members in which the point of attachment is a carbon or nitrogen atom.

In yet other compounds of Formula XII, $R_3$ is selected from phenyl, phenoxy, benzyloxy, each of which is substituted with 0-2 groups selected from halogen, cyano, hydroxy, —COOH, $C_{1-4}$alkyl, $C_{1-4}$haloalkyl, $C_{1-4}$alkoxy, $C_{1-4}$haloalkoxy, $\alpha,\omega$-$C_{1-3}$alkylenedioxy, $C_{1-4}$alkylthio, —SO($C_{1-4}$alkyl), and —SO$_2$($C_{1-4}$alkyl); or $R_3$ is selected from E-(CH$_2$)$_m$-Q, wherein E is O, NH, or N($C_{1-6}$alkyl), wherein Q is a saturated 4- to 7-membered heterocyclic ring in which the point of attachment is a carbon or nitrogen atom.

Certain other compounds of Formula XII include those compounds that further satisfy Formula XIII:

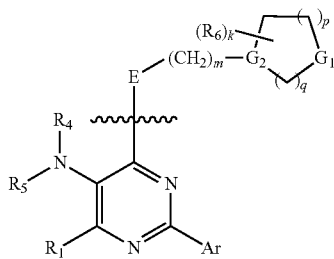

(XIII)

wherein

Ar is mono-, di-, or tri-substituted phenyl, optionally substituted naphthyl, or optionally substituted heteroaryl;

$R_1$ is selected from hydrogen, optionally substituted alkyl, optionally substituted alkenyl, optionally substituted alkynyl, optionally substituted cycloalkyl, optionally substituted cycloalkenyl, optionally substituted alkoxy, optionally substituted alkoxy, optionally substituted alkoxy, optionally substituted cycloalkoxy, or optionally substituted (cycloalkyl)alkoxy;

$R_4$ and $R_5$ are independently selected from (i) hydrogen and hydroxy; and (ii) alkyl groups, cycloalkyl groups, and (cycloalkyl)alkyl groups consisting of 1 to 8 carbon atoms, each of which optionally comprises one or more double or triple bonds, and each of which is optionally further substituted with one or more substituent(s) independently selected from oxo, hydroxy, halogen, cyano, amino, $C_{1-6}$alkoxy, —NH($C_{1-6}$alkyl), —N($C_{1-6}$alkyl)($C_{1-6}$alkyl), —NHC(=O)($C_{1-6}$alkyl), —N($C_{1-6}$alkyl)C(=O)($C_{1-6}$alkyl), —NHS(O)$_n$($C_{1-6}$alkyl), —S(O)$_n$($C_{1-6}$alkyl), —S(O)$_n$NH($C_{1-6}$alkyl), —S(O)$_n$N($C_{1-6}$alkyl)($C_{1-6}$alkyl), and Z;

E is O, NH, or N($C_{1-6}$alkyl);

$G_1$ is oxygen, sulfur, nitrogen, or carbon;

$G_2$ is nitrogen or carbon, wherein at least one of $G_1$ and $G_2$ is not carbon;

p is 0, 1, or 2;

q is 0, 1, or 2, wherein the sum of p and q is at least 1;

$R_6$ is independently selected at each occurrence from hydrogen, halogen, hydroxy, $C_{1-4}$alkyl, $C_{1-4}$alkoxy, $C_{1-4}$fluoroalkyl, $C_{1-4}$fluoroalkoxy, —COOH, C(O)NH$_2$, —CH$_2$COOH, and —CH$_2$C(O)NH$_2$;

k is an integer ranging from 0 to 3; and m is an integer ranging from 0 to 4.

Certain compounds of Formula XIII include those compounds in which the residue

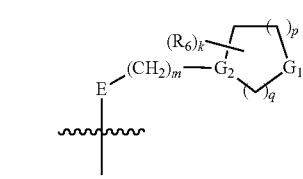

is a piperazinyl or piperidinyl ring substituted with from 0 to 2 $R_6$.

Yet other compounds of Formula XII include those compounds according to Formula XIV:

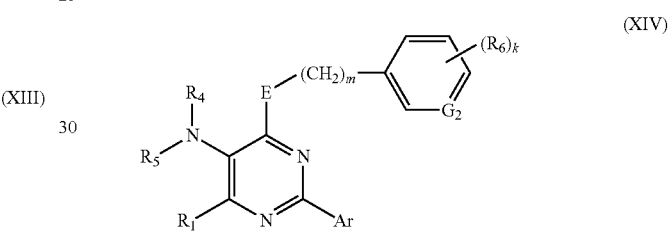

(XIV)

wherein

Ar is mono-, di-, or tri-substituted phenyl, optionally substituted naphthyl, or optionally substituted heteroaryl;

$R_1$ is selected from hydrogen, optionally substituted alkyl, optionally substituted alkenyl, optionally substituted alkynyl, optionally substituted cycloalkyl, optionally substituted cycloalkenyl, optionally substituted alkoxy, optionally substituted alkoxy, optionally substituted alkoxy, optionally substituted cycloalkoxy, and optionally substituted (cycloalkyl)alkoxy;

$R_4$ and $R_5$ are independently selected from: (i) hydrogen and hydroxy, and (ii) alkyl groups, cycloalkyl groups, and (cycloalkyl)alkyl groups consisting of 1 to 8 carbon atoms, each of which optionally comprises one or more double or triple bonds, and each of which is optionally further substituted with one or more substituent(s) independently selected from oxo, hydroxy, halogen, cyano, amino, $C_{1-6}$alkoxy, mono- or di-($C_{1-6}$alkyl)amin, —NHC(=O)($C_{1-6}$alkyl), —N($C_{1-6}$alkyl)C(=O)($C_{1-6}$alkyl), —NHS(O)$_n$($C_{1-6}$alkyl), —S(O)$_n$($C_{1-6}$alkyl), —S(O)$_n$NH($C_{1-6}$alkyl), S(O)$_n$N($C_{1-6}$alkyl)($C_{1-6}$alkyl), and Z;

E is a single covalent bond, O, NH, or N($C_{1-6}$alkyl);

$G_2$ is nitrogen, CH, or CR$_6$;

$R_6$ is independently selected at each occurrence from hydrogen, halogen, hydroxy, cyano, —COOH, $C_{1-4}$alkyl, $C_{1-4}$alkoxy, $C_{1-4}$fluoroalkyl, $C_{1-4}$fluoroalkoxy, $C_{1-4}$alkylthio, —SO($C_{1-4}$alkyl), and —SO$_2$($C_{1-4}$alkyl);

k is an integer ranging from 0 to 3; and m is an integer ranging from 0 to 4.

In certain compounds of Formula I, II, IX and the other Formulas described above, "optionally substituted" residues are substituted with from 0 to 4 substituents independently selected from oxo, hydroxy, halogen, cyano, amino, nitro, —COOH, aminocarbonyl, —SO$_2$NH$_2$, C$_{1-6}$alkyl, C$_{1-6}$alkenyl, C$_{1-6}$alkynyl, C$_{1-6}$haloalkyl, C$_{1-6}$aminoalkyl, C$_{1-6}$hydroxyalkyl, C$_{1-6}$carboxyalkyl, C$_{1-6}$alkoxy, C$_{1-6}$haloalkoxy, C$_{1-6}$alkylthio, C$_{1-6}$alkanoyl, C$_{1-6}$alkanoyloxy, C$_{3-6}$alkanone, C$_{1-6}$alkyl ether, mono- or di-(C$_{1-6}$alkyl)aminoC$_{0-6}$alkyl, —NHC(=O)(C$_{1-6}$alkyl), —N(C$_{1-6}$alkyl)C(=O)(C$_{1-6}$alkyl), —NHS(O)$_n$(C$_{1-6}$alkyl), —(C$_{1-6}$alkyl)C(=O)NH$_2$, —(C$_{1-6}$alkyl)C(=O)NH(C$_{1-6}$alkyl), —(C$_{1-6}$alkyl)C(=O)NH(C$_{1-6}$alkyl)(C$_{1-6}$alkyl), —S(O)$_n$(C$_{1-6}$alkyl), —S(O)$_n$NH(C$_{1-6}$alkyl), —S(O)$_n$N(C$_{1-6}$alkyl)(C$_{1-6}$alkyl) and Z, in which n and Z are as described above. In other compounds of Formula I and the other Formulas described above, "optionally substituted" residues are substituted with from 0 to 4 substituents independently selected from hydroxy, halogen, cyano, amino, —COOH, aminocarbonyl, —SO$_2$NH$_2$, C$_{1-4}$alkyl, C$_{1-4}$haloalkyl, C$_{1-4}$alkoxy, C$_{1-4}$haloalkoxy, and mono- or di-(C$_{1-4}$alkyl)aminoC$_{0-4}$alkyl. Similarly, in certain compounds, "mono-, di- or tri-substituted" residues are substituted with 1, 2 or 3 substituents independently chosen from the groups indicated above.

Certain compounds according to the Formulas provided herein, which have two or more stereogenic centers, have a diastereomeric excess of at least 50%. For example, such compounds may have a diastereomeric excess of at least 60%, 70%, 80%, 85%, 90%, 95%, or 98%. Certain such compounds have a diastereomeric excess of at least 99%.

Certain compounds according to the Formulas provided herein, which have one or more stereogenic center, have an enantiomeric excess of at least 50%. For example, such compounds may have an enantiomeric excess of at least 60%, 70%, 80%, 85%, 90%, 95%, or 98%. Certain such compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

4,5-disubstituted-2-arylpyrimidines provided herein detectably alter (modulate) C5a receptor activity and/or ligand binding, as. determined using a standard in vitro C5 receptor-mediated chemotaxis assay (described in Example 18), radioligand binding (described in Example 23), or C5a receptor-mediated calcium mobilization assay (described in Example 25). Preferred compounds exhibit an EC$_{50}$ of about 500 nM or less in such a standard C5a receptor-mediated chemotaxis, radioligand binding, and/or calcium mobilization assay, more preferably an EC$_{50}$ of about 250 nM or less in such an assay, still more preferably an EC$_{50}$ of about 200, 150, 100, 50, 25, 10, or 5 nM or less in such an assay.

Initial characterization of compounds can be conveniently carried out using a C5a receptor binding assay or functional assay, such as set forth in the Examples, and may be expedited by applying such assays in a high throughput screening setting. Additional assays suitable for determining the effects of small molecule compounds on C5a receptor binding and receptor modulatory activity, as well as assays suitable for measuring their effects on C5a-induced neutropenia in vivo, can be found in the published literature, for example in U.S. Pat. No. 5,807,824, which is incorporated herein by reference for its disclosure in this regard in Examples 6-9, columns 19-23, as well as for its discussion of complement and inflammation at columns 1-2. Those of skill in the art will recognize that such assays can be readily adapted to the use of cells or animals of different species as deemed appropriate.

In certain embodiments, preferred compounds have favorable pharmacological properties, including oral bioavailability (such that a sub-lethal or preferably a pharmaceutically acceptable oral dose, preferably less than 2 grams, more preferably of less than or equal to one gram, can provide a detectable in vivo effect such as a reduction of C5a-induced neutropenia), ability to inhibit leukocyte chemotaxis at nanomolar concentrations and preferably at sub-nanomolar concentrations, low toxicity (a preferred compound is nontoxic when a therapeutically effective amount is administered to a subject), minimal side effects (a preferred compound produces side effects comparable to placebo when a therapeutically effective amount of the compound is administered to a subject), low serum protein binding, and a suitable in vitro and in vivo half-life (a preferred compound exhibits an in vitro half-life that is equal to an in vivo half-life allowing for Q.I.D. dosing, preferably T.I.D. dosing, more preferably B.I.D. dosing, and most preferably once-a-day dosing). Distribution in the body to sites of complement activity is also desirable (e.g., compounds used to treat CNS disorders will preferably penetrate the blood brain barrier, while low brain levels of compounds used to treat periphereal disorders are typically preferred).

Routine assays that are well known in the art may be used to assess these properties, and identify superior compounds for a particular use. For example, assays used to predict bioavailability include transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcova, et al. (1996) *Journal of Chromatography B* 677:1-27. Compound half-life is inversely proportional to the frequency of dosage of a compound required to achieve a therapeutically effective amount. In vitro half-lives of compounds may be predicted from assays of microsomal half-life as described by Kuhnz and Gieschen (1998) *Drug Metabolism and Disposition* 26:1120-27.

As noted above, preferred compounds provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, and (4) does not cause substantial release of liver enzymes.

As used herein, a compound that "does not substantially inhibit cellular ATP production" is a compound that satisfies the criteria set forth in Example 27, herein. In other words, cells treated as described in Example 27 with 100 µM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that "does not significantly prolong heart QT intervals" is a compound that does not result in a statistically significant prolongation of heart QT intervals (as determined by electrocardiography) in guinea pigs, minipigs or dogs upon administration of twice the minimum dose yielding a therapeutically effective in vivo concentration. In certain preferred embodiments, a dose of 0.01, 0.05, 0.1, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound "does not cause substantial liver enlargement" if daily treatment of laboratory rodents (e.g., mice or rats) for 5-10 days with twice the minimum dose that yields a therapeutically effective in vivo concentration results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a compound "does not promote substantial release of liver enzymes" if administration of twice the minimum dose yielding a therapeutically effective in vivo concentration does not elevate serum levels of ALT, LDH or AST in laboratory rodents by more than 100% over matched mock-treated controls. In more highly preferred embodiments, such doses do not elevate such serum levels by more than 75% or 50% over matched controls. Alternately, a compound "does not promote substantial release of liver enzymes" if, in an in vitro hepatocyte assay, concentrations (in culture media or other such solutions that are contacted and incubated with hepatocytes in vitro) equivalent to two-fold the minimum in vivo therapeutic concentration of the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the minimum in vivo therapeutic concentration of the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity at a concentration equal to the minimum therapeutically effective in vivo concentration.

Certain preferred compounds are not clastogenic or mutagenic (e.g., as determined using standard assays such as the Chinese hamster ovary cell vitro micronucleus assay, the mouse lymphoma assay, the human lymphocyte chromosomal aberration assay, the rodent bone marrow micronucleus assay, the Ames test or the like) at a concentration equal to the minimum therapeutically effective in vivo concentration. In other embodiments, certain preferred compounds do not induce sister chromatid exchange (e.g., in Chinese hamster ovary cells) at such concentrations.

In certain embodiments, preferred compounds exert their receptor-modulatory effects with high specificity. This means that they only bind to, activate, or inhibit the activity of certain receptors other than C5a receptors with affinity constants of greater than 100 nanomolar, preferably greater than 1 micromolar, more preferably greater than 4 micromolar. Also provided herein are highly specific C5a receptor modulatory compounds that exhibit 200-fold greater affinity for C5a receptor than for other cellular receptors. Such receptors include neurotransmitter receptors such as alpha- or beta-adrenergic receptors, muscarinic receptors (particularly m1, m2 or m3 receptors), dopamine receptors, and metabotropic glutamate receptors; as well as histamine receptors and cytokine receptors (e.g., interleukin receptors, particularly IL-8 receptors). Such receptors may also include $GABA_A$ receptors, bioactive peptide receptors (other than C5a receptors and C3a receptors, including NPY or VIP receptors), neurokinin receptors, bradykinin receptors, and hormone receptors (e.g., CRF receptors, thyrotropin releasing hormone receptors or melanin-concentrating hormone receptors). Compounds that act with high specificity generally exhibit fewer undesirable side effects.

Within certain embodiments, modulators provided herein do not bind detectably to receptors that do not mediate inflammatory responses, such as GABA receptors, MCH receptors, NPY receptors, dopamine receptors, serotonin receptors and VR1 receptors, with high or even moderate affinity. In addition, or alternatively, certain preferred C5a receptor modulators exhibit an affinity for C5a receptor that is substantially higher than for receptors that do not mediate inflammatory responses (e.g., at least five times higher, at least ten times higher or at least 100 times higher). Assays for evaluating binding to receptors that do not mediate inflammatory responses include, for example, those described in U.S. Pat. No. 6,310,212, which is incorporated herein by reference for its disclosure of a $GABA_A$ receptor binding assays in Examples 14, columns 16-17, in U.S. patent application Ser. No. 10/152,189 which is incorporated herein by reference for its disclosure of an MCH receptor binding assay in Example 2, pages 104-105, in U.S. Pat. No. 6,362,186, which is incorporated herein by reference for its disclosure of $CRF_1$ and NPY receptor binding assays in Examples 19, columns 45-46, in U.S. Pat. No. 6,355,644, which is incorporated herein by reference for its disclosure of a dopamine receptor binding assay at column 10, and in U.S. Pat. No. 6,482,611, which is incorporated herein by reference for its disclosure of VRI receptor binding assays in Examples 4-5, column 14. It will be apparent that the C5a receptor modulators provided herein may, but need not, bind to one or more other receptors known to mediate inflammatory responses, such as C3a receptors and/or $A_3$ receptors.

Certain preferred compounds are C5a receptor antagonists that do not possess significant (e.g., greater than 5%) agonist activity in any of the C5a receptor-mediated functional assays discussed herein. Specifically, this undesired agonist activity can be evaluated, for example, in the GTP binding assay of Example 24, by measuring small molecule mediated GTP binding in the absence of the natural agonist, C5a. Similarly, in a calcium mobilization assay (e.g., that of Example 25) a small molecule compound can be directly assayed for the ability of the compound to stimulate calcium levels in the absence of the natural agonist, C5a. The preferred extent of C5a agonist activity exhibited by compounds provided herein is less than 10%, 5% or 2% of the response elicited by the natural agonist, C5a.

Also preferred, in certain embodiments, are C5a receptor modulators that inhibit the occurrence of C5a-induced oxidative burst (OB) in inflammatory cells (e.g., neutrophil) as can be conveniently determined using an in vitro neutrophil OB assay.

For detection purposes, compounds provided herein may be isotopically-labeled or radiolabeled. Accordingly, compounds recited in Formula I or Formula II (or any other formula specifically recited herein) may have one or more atoms replaced by an atom of the same element having an atomic mass or mass number different from the atomic mass or mass number usually found in nature. Examples of isotopes that can be present in compounds provided herein include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl. In addition, substitution with heavy isotopes such as deuterium (i.e., $^2$H) can afford certain therapeutic advantages resulting from greater metabolic stability, for example increased in vivo half-life or reduced dosage requirements and, hence, may be preferred in some circumstances.

Pharmaceutical Compositions

The present invention also provides pharmaceutical compositions comprising one or more C5a receptor modulators provided herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

Pharmaceutical compositions may be formulated for any appropriate manner of administration, including, for example, topical (e.g., transdermal or ocular), oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions (e.g., in the treatment of skin conditions such as burns or itch).

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Compounds may be formulated for local or topical administration, such as for topical application to the skin or mucous membranes, such as in the eye. Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquatemiums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifing agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fmgers; application using a physical applicator such as a cloth, tissue, swab, stick or brush; spraying (including mist, aerosol or foam spraying); dropper application; sprinkling; soaking; and rinsing. Controlled release vehicles can also be used, and compositions may be formulated for transdermal administration as a transdermal patch.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

C5a modulators described herein may be formulated as inhaled formulations, including sprays, mists, or aerosols. Such formulations are particularly useful for the treatment of asthma or other respiratory conditions. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations suitable for nasal administration, wherein the carrier is a solid, include a coarse powder having a particle size, for example, in the range of 20 to 500 microns which is administered in the manner in which snuff is administered (i.e., by rapid inhalation through the nasal passage from a container of the powder held close up to the nose). Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Modulators may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Modulators are generally administered in a therapeutically effective amount. Preferred systemic doses range from about 0.1 mg to about 140 mg per kilogram of body weight per day (about 0.5 mg to about 7 g per patient per day), with oral doses generally being about 5-20 fold higher than intravenous doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Packaged pharmaceutical compositions are also provided herein, comprising a therapeutically effective amount of at least one C5a receptor modulator in a container (preferably sealed) and instructions for using the C5a receptor modulator to treat a condition responsive to C5a receptor modulation (e.g., rheumatoid arthritis, psoriasis, cardiovascular disease, reperfusion injury, bronchial asthma, chronic pulmonary obstructive disorder (COPD), cystic fibrosis, Alzheimer's disease, stroke, myocardial infarction, atherosclerosis, ischemic heart disease or ischemia-reperfusion injury). The active agent(s) may be formulated for administration in a single pharmaceutical preparation (e.g., within the same pharmaceutical composition). Alternatively, each of the active agents may be formulated for separate administration, by the same or different routes of administration. Within a packaged pharmaceutical preparation, a therapeutically effective amount may be packaged as a single dose unit; alternatively, multiple doses may be packaged together for convenience. The C5a receptor modulator may be presented in any suitable container including, but not limited to, a plastic, paper, metal or glass package such as an ampoule, bottle, vial, blister package, infusion bag, syringe, inhaler or tube. For example, a packaged pharmaceutical preparation for oral administration of an active agent may comprise a blister package containing rows of tablets. Instructions may be present on a label attached to the container or on exterior packaging, or may be provided as a package insert.

Methods of Use

C5a modulators provided herein may be used as agonists or (preferably) antagonists, such as inverse agonists, of C5a receptors in a variety of contexts, both in vitro and in vivo. Within certain aspects, C5a antagonists may be used to inhibit the binding of C5a receptor ligand (e.g., C5a) to C5a receptor in vitro or in vivo. In general, such methods comprise the step of contacting a C5a receptor with a sufficient concentration of one or more C5a receptor modulators as provided herein, in the presence of C5a receptor ligand in aqueous solution and under conditions otherwise suitable for binding of the ligand to C5a receptor. The C5a receptor may be present in suspension (e.g., in an isolated membrane or cell preparation), or in a cultured or isolated cell. Within certain embodiments, the C5a receptor is expressed by a cell present in a patient, and the aqueous solution is a body fluid. In general, the concentration of C5a receptor modulator contacted with the receptor should be sufficient to inhibit C5a binding to C5a receptor in vitro as measured, for example, using a calcium mobilization assay or chemotaxis assay as described herein.

Also provided herein are methods for modulating, preferably inhibiting, the signal-transducing activity of a C5a receptor. Such modulation may be achieved by contacting a C5a receptor (either in vitro or in vivo) with a therapeutically effective amount of one or more C5a receptor modulators provided herein under conditions suitable for binding of the modulator(s) to the receptor. The receptor may be present in solution or suspension, in a cultured or isolated cell preparation or within a patient. Modulation of signal transducing activity may be assessed by detecting an effect on calcium ion conductance (also referred to as calcium mobilization or flux) or by detecting an effect on C5a receptor-mediated cellular chemotaxis. C5a receptor modulator(s) provided herein are preferably administered to a patient (e.g., a human) orally or topically, and are present within at least one body fluid of the animal while modulating C5a receptor signal-transducing activity.

The present invention further provides methods for treating patients suffering from conditions responsive to C5a receptor modulation. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to C5a receptor modulation" if modulation of C5a receptor activity results in alleviation of the condition or a symptom thereof. Patients may include primates (especially humans), domesticated companion animals (such as dogs, cats, horses) and livestock (such as cattle, pigs, sheep), with dosages as described herein.

Conditions that are responsive to C5a receptor modulation include the following:

Autoimmune disorders—e.g., rheumatoid arthritis, systemic lupus erythematosus (and associated glomerulonephritis), psoriasis, Crohn's disease, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), tissue graft rejection, and hyperacute rejection of transplanted organs.

For asthma therapy, C5a receptor antagonists provided herein may be used to prevent or decrease the severity of both acute early phase asthma attack and the late phase reactions that follow such an asthma attack.

Inflammation, Inflammatory disorders and related conditions—e.g., neutropenia, sepsis, septic shock, Alzheimer's disease, stroke, inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), neonatal-onset multisystem inflammatory disease (NOMID), Muckle-Wells syndrome, lichen planus, familial cold autoinflammatory syndrome (FCAS). inflammatory bowel disease (IBD), colitis, cystic fibrosis, ruptured abdominal aortic aneurysm and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. For example, a therapeutically effective amount of a compound provided herein may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Ocular Disorders—e.g., vascular retinopathies, ocular inflammation, age-related macular degeneration, proliferative vitreoretinopathy, Behcet's disease, vernal keratoconjunctivitis, retinal capillary infarction, retinal hemorrhage, prevention of ocular complications during IFN-a therapy, and uveitis.

Vasculitis—e.g., immunovasculitis, microscopic polyangiitis, Churg-Strauss syndrome, Kawasaki syndrome, Wegener's granulomatosis and urticarial vasculitis.

HIV infection and AIDS—C5a receptor modulators provided herein may be used to inhibit HIV infection, delay AIDS progression or decrease the severity of symptoms of HIV infection and AIDS.

In a further aspect, C5a receptor modulators may be used to perfuse a donor organ prior to transplantation of the organ into a recipient patient. Such perfusion is preferably carried out using a solution (e.g., pharmaceutical composition) comprising a concentration of the modulator that is sufficient to inhibit C5a receptor-mediated effects in vitro and/or in vivo. Such perfusion preferably reduces the severity or frequency of one or more of the inflammatory sequelae following organ transplantation when compared to that occurring in control (including, without restriction, historical control) transplant recipients who have received transplants of donor organs that have not been so perfused.

Within further aspects, C5a antagonists provided herein may be used to treat Alzheimer's disease, multiple sclerosis, and cognitive function decline associated with cardiopulmonary bypass surgery and related procedures. Such methods comprise administration of a therapeutically effective amount of a C5a antagonist provided herein to a patient afflicted with one or more of the above conditions, or who is considered to be at risk for the development of one or more such conditions.

In a further aspect, C5a receptor modulators of the current invention may be used in the treatment of disorders associated with pregnancy including antiphospholipid syndrome.

Suitable patients include those patients suffering from or susceptible to a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient a therapeutically effective amount of one or more compounds provided herein. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex and diet of the patient, the time and route of administration, the rate of excretion, any co-administered drugs and the severity of the particular disease, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Certain treatment methods provided herein further comprise administering to a patient a therapeutically effective amount of one or more compounds or forms thereof provided herein in combination with at least one anti-inflammatory or immunomodulatory pharmaceutical agent.

As noted above, certain compounds and compositions provided herein are useful as inhibitors of C5a receptor-mediated chemotaxis (e.g., they may be used as standards in assays of such chemotaxis). Accordingly, methods are provided herein for inhibiting C5a receptor-mediated cellular chemotaxis, preferably leukocyte (e.g., neutrophil) chemotaxis. Such methods comprise contacting white blood cells (particularly primate white blood cells, especially human white blood cells) with one or more compounds provided herein. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound as described herein has been added.

Dosage levels on the order of from about 0.1 mg to about 140 mg per kilogram of body weight per day are useful in the treatment or prevention of conditions involving pathogenic C5a activity (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 µg (micrograms)/mL serum, more preferably sufficient C5a receptor modulator to achieve a serum concentration of 20 ng-1 µg/mL serum should be administered, most preferably sufficient C5a receptor modulator to achieve a serum concentration of 50 ng/mL-200 ng/mL serum should be administered. For direct injection into the synovium (for the treatment of arthritis) sufficient C5a receptor modulator should be administered to achieve a local concentration of approximately 1 micromolar.

Within separate aspects, the present invention provides a variety of non-pharmaceutical in vitro and in vivo uses for the compounds provided herein. For example, such compounds may be labeled and used as probes for the detection and localization of C5a receptor (in samples such as cell preparations or tissue sections, preparations or fractions thereof). Compounds may also be used as positive controls in assays for C5a receptor activity, as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, C5a receptors (e.g, isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

Preparation of Compounds

Representative methods for preparing 4,5-disubstituted-2-aryl pyrimidines are shown in Schemes 1-7. Those skilled in the art will recognize that the reagents and synthetic transformations in the following Schemes can be readily modified to produce additional compounds of Formula I and Formula II. When a protecting group is required, an optional deprotection step may be employed. Suitable protecting groups and methodology for protection and deprotection such as those described in *Protecting Groups in Organic Synthesis* by T. Greene are well known. Compounds and intermediates requiring protection/deprotection will be readily apparent.

Abbreviations used in the following Schemes and Examples are as follows:
n-BuLi n-butyl lithium
$CDCl_3$ deuterated chloroform
DCM dichloromethane
DIBAL-H diisobutylaluminum hydride
DMA N,N-dimethylacetamide
DMF N,N-dimethylformamide
DPPF 1,1'-bis(diphenylphosphino)ferrocene
Et ethyl
EtOH ethanol
EtOAc ethyl acetate
Eq. Equivalent(s)
h hour(s)
HOAc acetic acid
HPLC high pressure liquid chromatography
$^1$H NMR proton nuclear magnetic resonance
Hz hertz
KOtBu potassium tert-butoxide
LAH lithium aluminum hydride
LC/MS liquid chromatography/mass spectrometry
LiOMe lithium methoxide
MeOH methanol
MHz megahertz
Min minute(s)
MS mass spectrometry
(M+1) mass+1
NaOMe sodium methoxide
δ chemical shift
$Pd(PPh_3)_4$ tetrakis(triphenylphosphine) palladium (0)
Ph phenyl
$POCl_3$ phosphorous oxychloride
rt retention time
sat. saturated
TFA trifluoroacetic acid THF tetrahydrofuran
TLC thin layer chromatography
TMSCN trimethylsilylcyanide
18-C-6 18-crown-6

Scheme 1
Preparation of compounds of Formula II wherein A is OR$_4$ or NR$_4$R$_5$

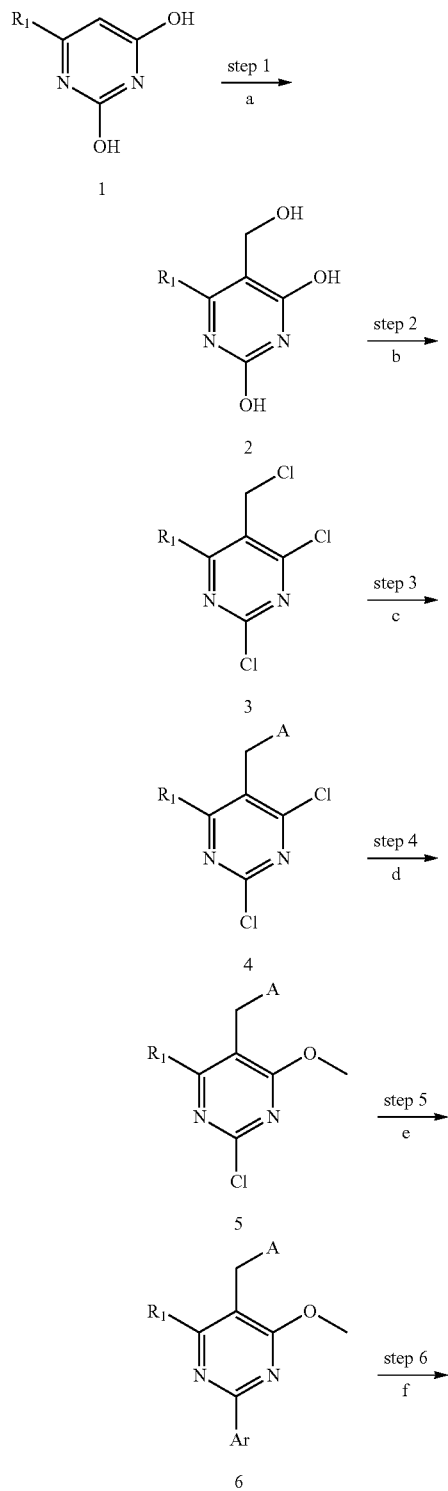

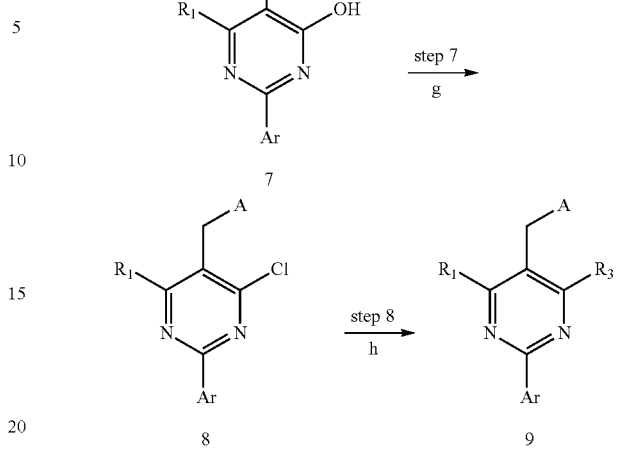

Scheme 1 illustrates a route for preparing compounds of Formula II wherein A is OR$_4$ or NR$_4$R$_5$. In step 1, a suitably 6-substituted-1H-pyrimidine-2,4-dione 1 is reacted with formaldehyde in the presence of sodium hydroxide to obtain the corresponding 5-hydroxymethyl-6-substituted-1H-pyrimidine-2,4-dione 2. In step 2, treatment of 5-hydroxymethyl-6-substituted-1H-pyrimidine-2,4-dione 2 with phosphorous oxychloride in the presence of tri-n-butylamine yields 2,4-dichloro-5-chloromethyl-6-substituted-pyrimidine 3. Step 3 entails reaction of amines, phenols or alcohols with 2,4-dichloro-5-chloromethyl-6-substituted-pyrimidine 3 to obtain, following chromatographic separation from other displacement products, 2,4-dichloropyrinidine 4. Reaction of 2,4-dichloropyrimidine 4 in step 4 with NaOMe yields 2-chloro-4-methoxypyrimidine 5 as a separable mixture with the corresponding isomeric 4-chloro-2-methoxypyrimidine. Suzuki coupling reaction of 5 with various aryl and heteroaryl boronic acids in step 5 provides 2-aryl-4-methoxypyrimidine 6. In step 6, 2-aryl-4-methoxypyrimidine 6 is treated with hydrochloric acid to obtain 2-aryl-4-hydroxypyrimidine 7. Treatment of 7 with phosphorous oxychloride yields 2-aryl-4-chloropyrimidine 8. 2-Aryl-4-chloropyrimidine 8 serves as a versatile electrophile reacting with a variety of amines, alkoxides and other nucleophiles to yield compounds of Formula II (9). Alternatively, 2-aryl-4-chloropyrimidine 8 can be reacted with a variety of boronic acids in the presence of a suitable palladium catalyst (such as Pd(PPh$_3$)$_4$) to obtain compounds of Formula II wherein R$_3$ is attached to the pyrimidine ring via a carbon-carbon bond.

Scheme 2. Preparation of compounds of Formula II wherein A is OR$_4$ or NR$_4$R$_5$

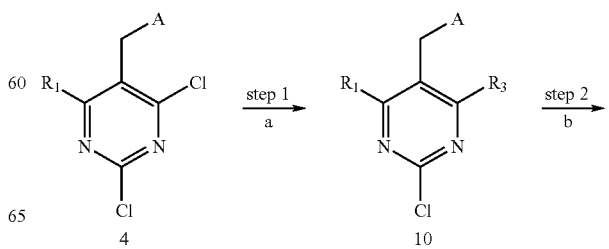

-continued

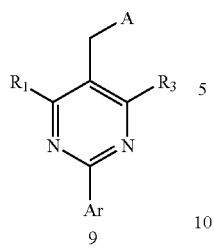
9 a.) Nucleophile;
b.) Arylboronic acid, K$_3$PO$_4$, Pd(PPh$_3$)$_4$.

Scheme 2 illustrates an alternative sequence of transformations wherein R$_3$ is introduced prior to Ar. Step 1 entails reaction of 2,4-dichloropyrimidine 4 with nucleophiles such as amines or alkoxides to provide 2-chloropyrimidine 10. Suzuki coupling of 10 in step 2 provides compounds of Formula II (9). Frequently it is desirable to perform additional synthetic transformations of R$_3$ in compounds 10 and 9 to obtain additional compounds of Formula II.

Scheme 3. Preparation of compounds of Formula II wherein A is OR$_4$ or NR$_4$R$_5$

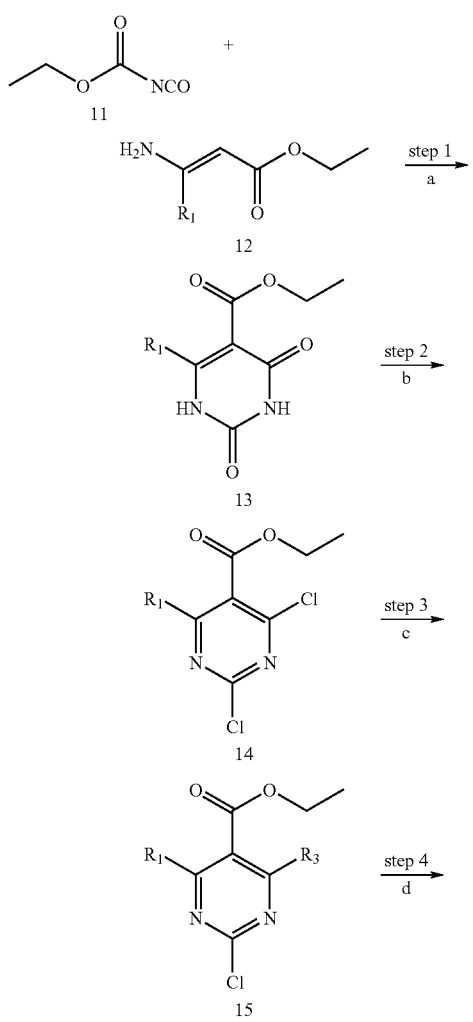

-continued

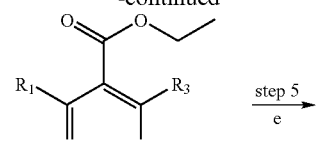
16

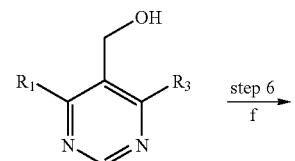
17

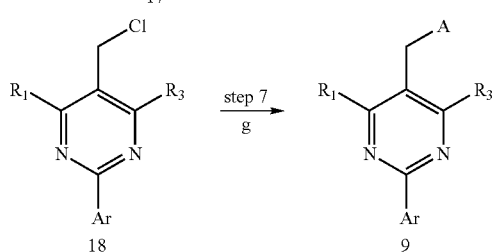
18    9 a.) i) Diethyl ether, 0-5° C.;
    ii) 25% aqueous triethylamine, heat;
b.) POCl$_3$, PhNEt$_2$;
c.) Nucleophile;
d.) Arylboronic acid, K$_3$PO$_4$, Pd(PPh$_3$)$_4$;
e.) DIBAL-H;
f.) SOCl$_2$;
g.) R$_4$R$_5$NH or R$_4$OH/base.

Scheme 3 illustrates another route for preparing compounds of Formula II wherein A is OR$_4$ or NR$_4$R$_5$. Step 1 involves reaction of commercially available ethoxycarbonyl isocyanate 11 with substituted ethyl 3-aminoacrylate 12 to obtain 6-substituted-5-(ethoxycarbonyl)-1H-pyrimidine-2,4-dione 13. In step 2, 6-substituted-5-(ethoxycarbonyl)-1H-pyrimidine-2,4-dione 13 is converted to corresponding 2,4-dichloro-6-substituted-pyrimidine-5-carboxylic acid ethyl ester 14. Step 3 entails reaction of 2,4-dichloro-6-substituted-pyrimidine-5-carboxylic acid ethyl ester 14 with a nucleophile to obtain 2-chloropyrimidine ester 15. In step 3, variable amounts of isomeric substitution product formed by reaction of nucleophile at the 2-position of 14 and bis-substitution may be obtained and are removed by chromatography on silica gel. In step 4, 2-chloropyrimidine 15 is coupled with a suitable metaloaryl derivative with transition metal catalysis (e.g. Suzuki reaction) to obtain 2-arylpyrimidine 16. Step 5 entails reduction of the ester group to form alcohol 17. Suitable reducing agents for use in step 5 include but are not limited to diisobutylaluminum hydride and LAH. Step 6 illustrates conversion of alcohol 17 to the corresponding chloride 18. In step 7, reaction of chloride 18 with a variety of nucleophiles including amines and hydroxyaryls/beteroaryls in the presence of base yields a variety of compounds of Formula II (9).

Scheme 4. Preparation of compounds of Formula I wherein $R_A$ and/or $R_B$ is not hydrogen

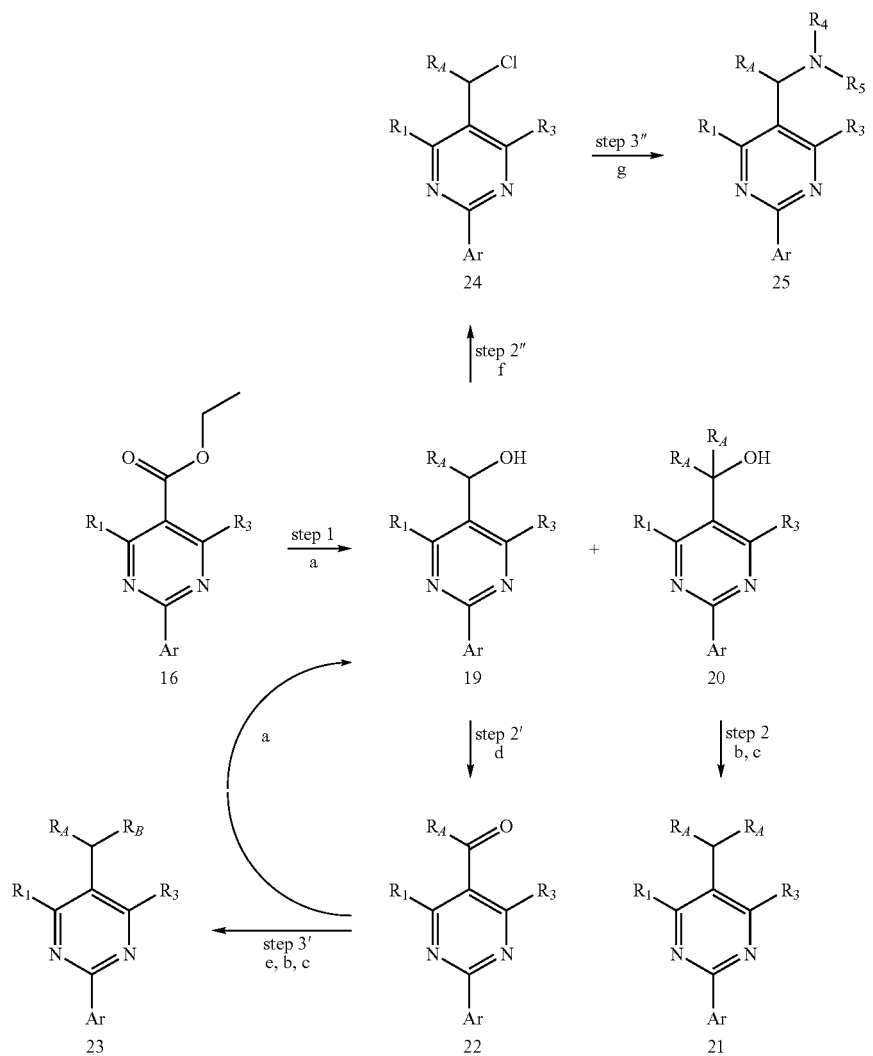

a.) i) $R_A$MgX;
b.) SOCl$_2$, Pyridine;
c.) H$_2$, Pd(C);
d.) PDC;
e.) $R_B$MgX;
f.) SOCl$_2$;
g.) $R_4R_5$NH or $R_4$ OH/base.

Scheme 4 illustrates a route for making compounds of Formula I wherein at least one of the substituents $R_A$ and $R_B$ is alkyl or aryl: In step 1 2-arylpyrimidine ester 16 is treated with a suitable organometallic reagent such as an organomagnesium compound to obtain a mixture of mono-addition/reduction product 19 and bis-addition product 20. When an organomagnesium reagent bearing a hydrogen beta to the carbon-magnesium bond is used, addition/reduction product 19 predominates. When arylmagnesium reagents are used, compound 22 may be obtained along with bis-addition product 20 from step 1. In step 2, bis-addition product 20 is dehydrated and reduced to provide compounds of Formula I (21). Suitable dehydration conditions include but are not limited to thionyl chloride in pyridine. Reduction of the dehydration product may be accomplished via catalytic hydrogenation (e.g. hydrogen, Pd(C)). In step 2', compound 19 is oxidized to the corresponding ketone 22. Ketone 22 can recycled to obtain more 20 by treatment under the same conditions as used in step 1. Alternatively, as illustrated in step 3', ketone 22 can be treated with a suitable organometallic, dehydrated and hydrogenated to obtain compounds of Formula I wherein $R_A$ and $R_B$ are non-equivalent alkyl or aryl substituents (23). In a further variant of Scheme 4, compound 19 can be converted to the corresponding chloride 24 in step 2" and subsequently reacted with amines in step 3" to obtain compounds of Formula I wherein $R_2$ is —$CR_AR_BNR_4R_5$ or —$CR_AR_BOR_4$ (25).

Scheme 5. Preparation of compounds of Formula I wherein $R_2$ is $-NHR_A$ or $-NR_AR_B$

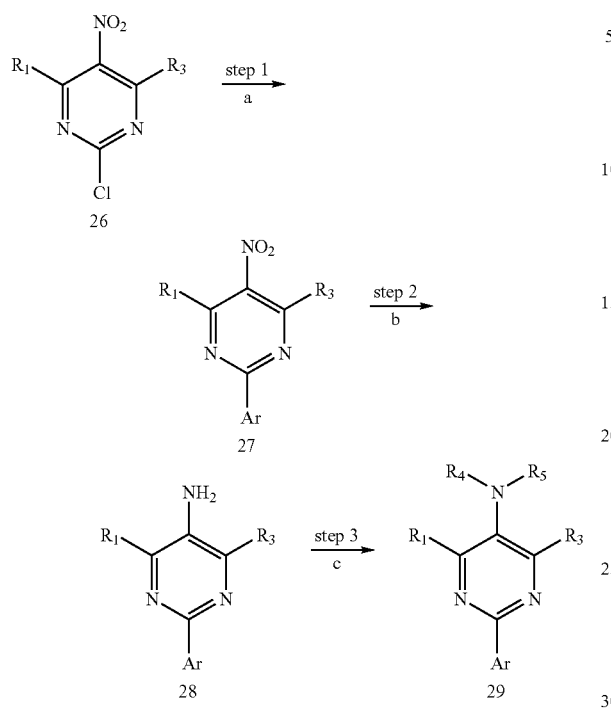

a.) Arylboronic acid, Pd(PPh$_3$)$_4$;
b.) H$_2$, Raney Ni;
c.) Reductive amination.

Scheme 5 illustrates a method for preparing compounds of Formula I wherein is $-NHR_A$ or $-NR_AR_B$. 2-Chloro-5-nitropyrimidines 26 can be prepared by literature procedures (e.g., *Journal of Organic Chemistry* 1983, 48, 1060). In step 1, chloro-5-nitropyrimidine 26 is coupled to an appropriate metaloaryl derivative with transition metal catalysis to obtain 2-aryl-5-nitropyrimidine 27. For example, this may entail coupling of an arylboronic acid in the presence of palladium (0) via the Suzuki reaction (N. Miraura and A. Suzuki *Chemical Reviews* 1995, 95, 2457). In step 2, the nitro substituent in 27 is reduced to obtain 2-aryl-5-aminopyrimidine 28. This transformation may be accomplished via a number of procedures well known in the art including hydrogen and transition metal catalysts or aqueous sodium hydrosulfite. In step 3, reductive amination reaction provides compounds of Formula I (29). Typically, reductive amination is accomplished by reaction of 28 with various aldehydes in the presence of a reducing agent such as sodium triacetoxyborohydride. Those skilled in the art will recognize that alkylation of 28 can also be accomplished by acylation of the 5-amino substituent followed by reduction to obtain mon-substitution. Suitable reducing agents for reduction of the acyl group include diisobutylaluminum hydride in inert solvents such as tetrahydrofuran. Alternatively, acylation followed by treatment with base and alkyl halide and reduction can be employed to obtain unsymmetrical substitution of the 5-amino substituents. Suitable conditions for the aforementioned alkylation reaction include treatment with a strong base including alkali metal hydrides followed by alkylating agents such as alkyl halides including alkyl bromides and alkyl iodides. Finally, 28 can be also be directly alkylated by treatment with a strong base including alkali metal hydrides followed by alkylating agents such as alkyl halides including alkyl bromides and alkyl iodides. Those skilled in the art will recognize that the sequence of transformations in Scheme 4 can be modified. For example, step 2 may be performed on 26 to obtain the corresponding 5-amino-2-chloropyrimidne followed by reductive amination as per step 3 and coupling as described for step 1. Illustrative examples for this method is contained in WO 2001/068614, Examples 1, 7, 21, 26, and 31 which are hereby incorporated by reference.

Scheme 6. Preparation of 3,5-disubstituted indazole 4-boronic acids

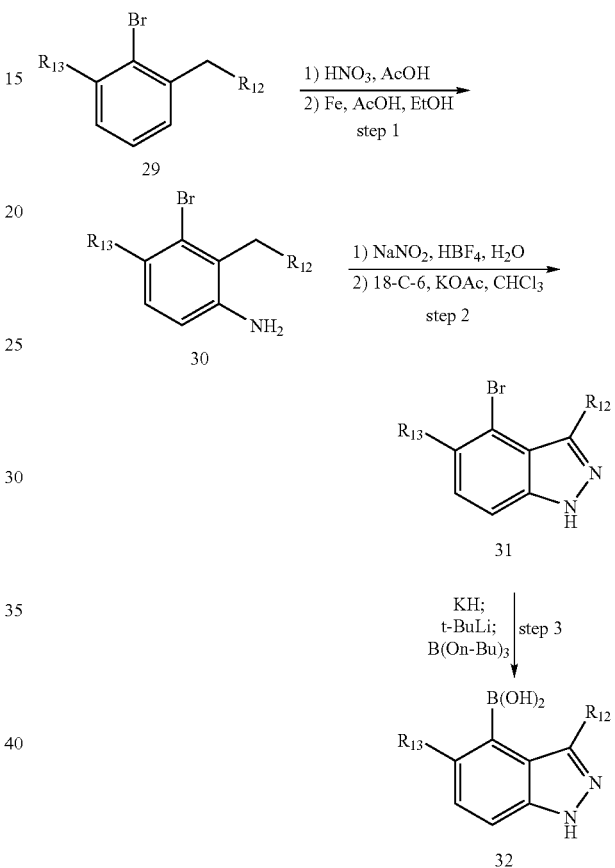

Scheme 6 illustrates a route for preparing 3,5-disubstituted indazole-4-boronic acids. In step 1, substituted bromobenzene 29 is nitrated and then reduced to give the bromoaniline 30 which is converted to the corresponding diazonium salt and cyclized to the bromoindazole 31 in the presence of phase transfer catalyst in step 2. The bromoindazole 31 is converted to the corresponding indazole boronic acid 32 in step 3. In Scheme 9, $R_{12}$ and $R_{13}$ are generally a small alkyl group such as methyl, ethyl, propyl or isopropyl.

Scheme 7. Preparation of 3-alkylindazole-4-boronic acids

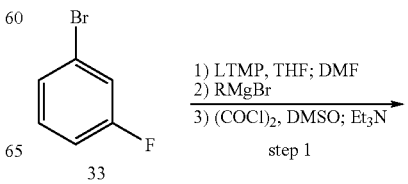

-continued

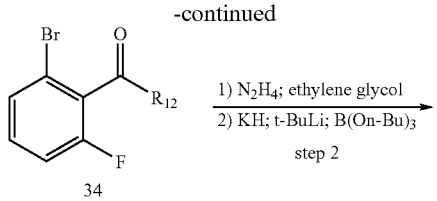

1) N₂H₄; ethylene glycol
2) KH; t-BuLi; B(On-Bu)₃ step 2

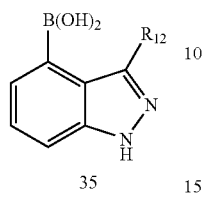

Scheme 7 illustrates a route for preparing 3-alkylindazole-4-boronic acids. In step 1, 3-bromofluorobenzene 33 is lithiated regioselectively and quenched with DMF to yield 2-bromo-6-fluoro-benzaldehyde. The benzaldehyde is reacted with any of various alkyl Grignard reagents to give the corresponding secondary alcohol which is subsequently oxidized to ketone 34. Cyclocondensation with hydrazine yields the corresponding 3-substituted-4-bromoindazole which is converted to the corresponding boronic acid 35 in step 2. In Scheme 7, $R_{12}$ is generally a small alkyl group such as methyl, ethyl, propyl or isopropyl.

Specific examples for the preparation of compounds of Formula I and Formula II (and the other Formulas provided herein) by the methods illustrated in the above Schemes are provided in the following Examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

EXAMPLES

Example 1

Preparation of Certain Starting Materials

A. Synthesis of 2,6-diethylphenylboronic Acid

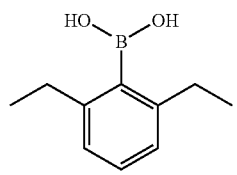

2,6-Diethyl bromobenzene (38.2 g, 180.2 mmol) is added dropwise through an additional funnel over a 1 hour period to a solution of n-BuLi (2.0 M in cyclohexane, 99.1 mL, 198.2 mmol) in THF (380 mL) at −75° C. After addition, the reaction mixture is stirred at −75° C. for 30 min; trimethyl borate (28.1 g, 270.3 mmol) is added slowly over a 40 minute period. The reaction mixture is warmed to room temperature overnight. 2N HCl (250 mL) is added slowly and the resulting mixture is stirred for 1 hour. The organic layer is separated and the aqueous layer is extracted with ether (2×200 mL). The combined organic layers are dried over anhydrous Na₂SO₄ and the solvents are removed in vacuo. Hexane (400 mL) is added to the residue and a white precipitate is formed. Filtration and drying in vacuo give 2,6-diethylphenyl boronic acid as a white solid. ¹H NMR: (CDCl₃) 7.22 (t, 1H), 7.04 (s, 2H), 4.65 (s, 2H), 2.64 (q, 4H), 1.22 (t, 6H).

B. Synthesis of 2,6-dimethyl-3-methoxybenzeneboronic Acid

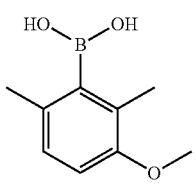

Step 1. Preparation of aldehyde

A solution of 2-bromo-m-xylene (4.2 g, 23 mmol) in DCM (5 mL) at −78° C. is added dropwise to a solution of titanium tetrachloride (5.0 mL, 45 mmol) and dichloromethyl methyl ether (2.3 mL, 25 mmol) in DCM (20 mL). After the addition is complete, the mixture is allowed to warm to room temperature and stirred for and additional 4 h before being poured onto ice water. The reaction is extracted with DCM. The organic fraction is washed with water, dried (Na₂SO₄), and concentrated to give the aldehyde as a pale yellow solid, which is used in the next step without further purification: ¹H NMR (CDCl₃) 10.1 (s, 1H), 7.68 (d, 1H), 7.22 (d, 1H), 2.79 (s, 3H), 2.45 (s, 3H).

Step 2. Preparation of methyl ether

M-chloroperoxybenzoic acid (68%, 8.4 g, 33 mmol) is added to a solution of the above aldehyde (4.7 g) in DCM (120 mL). The mixture is stirred at reflux overnight and concentrated in vacuo. The residue is dissolved in EtOAc and washed successively with sat. NaHCO₃ (3 times), sat. NaHSO₃, and water. The organic fraction is dried (Na₂SO₄) and concentrated to give the crude formate. The formate is treated with potassium carbonate (4 g) in EtOH (80 mL) at room temperature for 20 min, followed by filtration and concentration to give the corresponding alcohol. The crude alcohol is dissolved in acetone (160 mL) and dimethyl sulfate (2.7 mL, 29 mmol), and potassium carbonate (8.0 g, 58 mmol) is added. The mixture is stirred at reflux for 5 h. After cooling to room temperature, filtration, concentration, and flash chromatography provide the desired methyl ether as a colorless oil. ¹H NMR (CDCl₃) 7.02 (d, 1H), 6.73 (d, 1H), 3.80 (s, 3H), 2.37 (s, 3H), 2.35 (s, 3H).

Step 3. Preparation of 2,6-dimethyl-3-methoxybenzeneboronic acid

A solution of 2,4-dimethyl-3-bromoanisole (3.3 g, 15 mmol) in THF (15 mL) is added dropwise at −78° C. to a solution of n-BuLi (11 mL of 1.6M in hexane, 17 mmol) in THF (35 mL). After 30 min, trimethyl borate (2.3 mL, 20 mmol) is added and the mixture is allowed to warm to room temperature overnight. The mixture is poured onto 10% HCl and extracted with EtOAc. The organic fraction is washed with saturated brine, dried (Na₂SO₄), and concentrated to give the desired product as a brownish oil. $^1$H NMR (CDCl$_3$) 6.98 (d, 1H), 6.75 (d, 1H), 4.64 (br s), 3.80 (s, 3 H), 2.27 (s, 3H), 2.22 (s, 3H).

C. Synthesis of (S)-methyl-(1,2,3,4-tetrahydro-naphthalen-1-yl)-amine

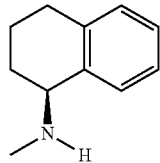

Ethyl chloroformate (7.74 g, 71.3 mmol) is added dropwise to a mixture of (S)-1,2,3,4-tetrahydro-naphthalen-1-ylamine (10.0 g, 67.9 mmol) and K$_2$CO$_3$ (18.8 g, 136 mmol) in CH$_3$CN (100 mL). The resulting mixture is stirred at room temperature overnight. Water (100 mL) is added and the mixture is extracted with ether (2×100 mL). The combined extract is washed with 1 N HCl (2×10 mL), water, dried (Na$_2$SO$_4$), and concentrated in vacuo to give (S)-(1,2,3,4-tetrahydro-naphthalen-1-yl)-carbamic acid ethyl ester as a solid.

(1,2,3,4-Tetrahydro-naphthalen-1-yl)carbamic acid ethyl ester (5.0 g, 22.8 mmol) is added slowly under nitrogen to a suspension of LiAlH (2.6 g, 68 mmol) in THF (50 mL). The resulting mixture is heated at 75° C. with stirring for 2 h. On cooling, Na$_2$SO$_4$.10H$_2$O (15.0 g) and ether (100 mL) are added to the mixture. The resulting mixture is stirred at room temperature for 1 hour, filtered through celite, and concentrated in vacuo. 1 N HCl (20 mL) and ether (20 ML) are added to the residue. The organic layer is separated and discarded. The aqueous layer is basified with 1 N NaOH and extracted with CH$_2$Cl$_2$ (2×25 mL). The combined extract is washed with water (2×), dried (Na$_2$SO$_4$) and concentrated to give (S)-methyl-(1,2,3,4-tetrahydro-naphthalen-1-yl)amine as an oil. [α]$^{RT}$=−10.6 (0.02, EtOH). $^1$H NMR (CDCl$_3$) 7.30 (m, 1H), 7.06-7.20 (m, 3H), 3.66 (t, 1H), 2.78 (m, 2H), 2.50 (s, 3H), 1.70-2.00 (m, 4H).

Similar procedures are applied in the synthesis of the following amines:
(R)-Methyl-(1,2,3,4-tetrahydro-naphthalen-1-yl)amine;
(S)-Ethyl-1,2,3,4-tetrahydro-naphthalen-1-yl)-amine;
(S)-Propyl-(1,2,3,4-tetrahydro-naphthalen-1-yl)amine;
(S)-Indan-1-yl-methyl-amine;
(±)Methyl-(1,2,3,4-tetrahydro-naphthalen-1-yl)-amine; and
(±)Indan-1-yl-methyl-amine.

D. Synthesis of 5-methylindole-4-boronic Acid

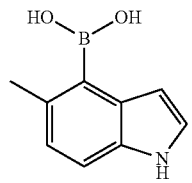

Fuming nitric acid (>90% yellow fuming HNO$_3$) is slowly added to a solution of 2-bromo-m-xylene (20 g, 150 mmol) in HOAc (100 mL) cooled in an ice bath (above freezing point). The resulting mixture is allowed to warm to room temperature, stirred for 1 hour, and heated at 80° C. for 2 h or until the reaction is complete by GC/MS analysis following microscale base work-up. The reaction mixture is cooled to room temperature and poured into ice/water with stirring. The resulting yellow precipitates are collected by suction filtration and air dried to obtain 2,6-dimethyl-3-nitrobromobenzene.

Bredereck's reagent (tert-butoxybis(dimethylamino)methane (16 g, 91 mmol) is added to a solution of 2,6-dimethyl-3-nitrobromobenzene (20 g, 87 mmol) in anhydrous DMF (120 mL) at room temperature. The reaction mixture is heated at 120-125° C. under N$_2$ for 5 h or until starting material is mostly consumed according to TLC. The reaction mixture is allowed to cool to room temperature, poured into water (300 mL), and extracted with DCM (100 mL×3). The combined extracts are dried over anhydrous sodium sulfate, filtered, and concentrated to obtain a mixture of enamines as a dark brown oil. This material is used in the next step without purification.

The crude mixture is dissolved in HOAc/water (250 mL of 4:1), cooled to 0° C. and treated with zinc dust (57 g, 870 mmol) added slowly in portions. After complete addition, the reaction mixture is heated at 110° C. for 4 h. Zinc is removed by filtration through a celite pad and the filtrate is extracted with DCM (100 mL×3). The combined extracts are dried over anhydrous sodium sulfate, concentrated, and purified by flash chromatography on silica gel (EtOAc/Hexane 1:20) to obtain 4-bromo-5-methylindole as a light purple oil.

A solution of 4-bromo-5-methylindole (800 mg, 3.8 mmol) in anhydrous ether (8 mL) is added with stirring to a suspension of potassium hydride (560 mg, 4.2 mmol, 30% dispersion in mineral oil) in anhydrous ether at 0° C. under argon. The resulting mixture is cooled to −78° C. and tert-butyllithium (4.9 mL of 1.7 M in pentane, 8.4 mmol) is slowly added. The resulting cream-colored mixture is stirred at −78° C. for 1 hour. Tributylborate (3.1 mL, 11.4 mmol) is slowly added and the reaction mixture is stirred for 1 hour at −78° C. before being allowed to slowly warm to room temperature. More anhydrous ether is added to facilitate stirring. After stirring for 24 h, the resulting sticky mixture is diluted with ether and transferred in portions with stirring to a precooled solution of 1 M phosphoric acid (50 mL). After stirring for 30 min, the acidic mixture is extracted with diethyl ether (75 mL×3) and the combined extracts are extracted with 1 N sodium hydroxide (20 mL×4). The combined base extracts are cooled with an ice bath, acidified with 1 M phosphoric acid and extracted with EtOAc (20 mL×3). The combined extracts are washed with brine (20 mL), dried over anhydrous sodium sulfate, filtered and concentrated to obtain a beige residue. The residue is triturated with hexane to obtain the desired 5-methylindole-4-boronic acid as a beige gum.

E. Synthesis of 6-isopropyl-2-methyl-3-nitrobenzeneboronic Acid

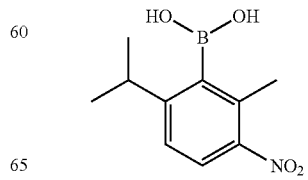

6-Isopropyl-2-methylbenzeneboronic acid (8 g) is added portionwise over 1 hour to 90% HNO₃ (50 mL) at −40° C., maintaining an internal temperature below −30° C. After addition, the mixture is stirred at −40 to −30° C. for 15 min, then poured onto ice, and diluted with water. The solid is collected by filtration, washed with water and dried to give 6-isopropyl-2-methyl-3-nitrobenzeneboronic acid as a white solid. ¹H NMR (DMSO-d6) 7.78 (d, 2H), 7.30 (d, 2H), 2.85 (m, 1H), 2.38 (s, 3H), 1.15 (d, 6H).

F. Synthesis of 4-hydroxy-piperidine-4-carboxylic Acid Amide

Step 1. Synthesis of 1-Benzyl-4-hydroxy-piperidine-4-carboxylic acid amide

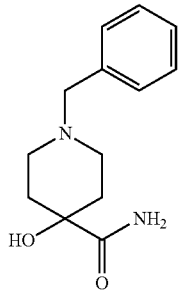

1-Benzyl-4-hydroxy-piperidine-4-carbonitrile (5 g, 23.12 mmol) is dissolved in a mixture of H₂SO₄ (18 mL) and H₂O (2 mL) at 0° C. The mixture is warmed to room temperature for 14 h, transferred into cold 2 N NaOH and adjusted to pH>8. The solid is filtered and washed with H₂O, and dried over sodium sulfate to give the crude product.

Step 2. Synthesis of 4-Hydroxy-piperidine-4-carboxylic acid amide

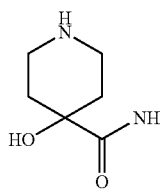

Pd/C (150 mg) and HOAc (2 mL) are added to a solution of 1-benzyl-4-hydroxy-piperidine-4-carboxylic acid amide (2 g, 8.5 mmol) in MeOH. The mixture is shaken under H₂ (40 psi) for 14 h. The catalyst is removed by filtration and the solvent is removed in vacuo to give the title product. ¹H NMR (CD₃OD) 2.96(m, 4H), 2.05(m, 2H), 1.49 (m, 2H).

G. Synthesis of 5-isopropyl-1H-indazole-4-boronic Acid

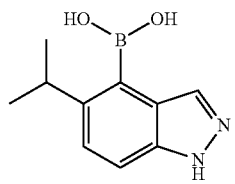

Step 1. Preparation of 4-Bromo-5-isopropyl-1H-indazole

Nitric acid (30 mL, fuming) is added slowly to an ice-cold solution of 2-isopropyl-6-methyl-bromobenzene (10 g, 213 mmol) in HOAc (60 mL). The mixture is heated 1 hour at 90° C. and cooled to room temperature. The reaction mixture is poured into 200 mL ice-water and extracted with CH₂Cl₂ (3×60 mL). The combined extracts are washed with 1 N NaOH (3×40 mL) and then water (40 mL), dried (Na₂SO₄), and concentrated to yield crude 2-isopropyl-6-methyl-5-nitro-bromobenzene which is dissolved in HOAc (75 mL)/EtOH (75 mL). To this is added Fe powder (5.3 g, 95 mmol) and the mixture is refluxed for 2 h. The mixture is cooled to room temperature, diluted with water, and neutralized with solid Na₂CO₃. The mixture is extracted with EtOAc, dried (Na₂SO₄), and concentrated in vacuo. The residue is purified by flash chromatography (elution with Hex/EtOAc 4:1) to yield 3-bromo-4-isopropyl-2-methyl-aniline. A solution of NaNO₂ (798 mg, 12 mmol) in H₂O (10 mL) is added dropwise at 0° C. to a slurry of 3-bromo-4-isopropyl-2-methyl-aniline (2.4 g, 11 mmol) in HBF₄ (15 mL)-H₂O (15 mL), and the mixture is stirred for 1 hour at 0° C. The resulting solid is filtered, washed with cold water and then Et₂O, and dried under reduced pressure to yield the diazonium salt as a beige solid. The diazonium salt is added in one portion to mixture of KOAc (1.5 g, 15 mmol) and 18-C-6 (98 mg, 0.37 mmol) in ethanol-free CHCl₃ (70 mL) at room temperature. The mixture is stirred for 1 hour and the resulting solid is removed by filtration. The filtrate is washed with water, dried (Na₂SO₄), and concentrated in vacuo. The residue is purified by flash chromatography (elution with Hex/EtOAc 4:1) to yield 4-bromo-5-isopropyl-1H-indazole. ¹H NMR (CDCl₃) 8.03 (br s, 1H), 7.41 (d, 1H), 7.35 (d, 1H), 3.55 (m, 1H), 1.24 (d, 6H).

Step 2. Preparation of 5-Isopropyl-1H-indazole-4-boronic acid

A solution of 4-bromo-5-isopropyl-1H-indazole (1.6 g, 6.9 mmol) in Et₂O (4 mL) is added slowly to a suspension of KH (1.0 g of 30% dispersion in mineral oil, 7.7 mmol) in Et₂O (20 mL) at 0° C. and the mixture is stirred for 20 min. After cooling to −78° C., t-BuLi (8.9 mL of 1.7 M in Hex, 15 mmol) is added and the resulting mixture is stirred for 40 min at −78° C. To this is added B(On-Bu)₃ (5.6 mL, 21 mmol) and the mixture is stirred for 24 h at room temperature. The reaction mixture is quenched with 1N H₃PO₄ and extracted with Et₂O. The combined Et₂O layers are back-extracted with 1N NaOH (3×10 mL). The combined NaOH extracts are acidified with 1N H₃PO₄ and extracted with EtOAc. The EtOAc extracts are washed with saturated brine, dried (MgSO₄), and concentrated to yield 5-isopropyl-1H-indazole-4-boronic acid. ¹H NMR (CDCl₃) 7.85 (s, 1H), 7.42 (d, 1H), 7.37 (d, 1H), 3.6 (br s, 2H), 2.88 (m, 1H), 1.32 (d, 6H).

H. Synthesis of 3-isopropyl-1H-indazole-4-boronic Acid

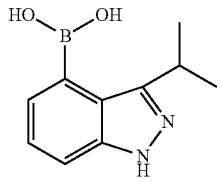

Step 1. Preparation of 1-(2-Bromo-6-fluoro-phenyl)-2-methyl-propan-1-one

To a solution of n-BuLi (25 mL of 1.6 M solution in hexane, 40 mmol) in THF (100 mL) is added 2,2,6,6-teramethylpiperidine (6.8 mL, 40 mmol) at −78° C. and the mixture is stirred for 20 min. To this is added 3-bromofluoroebnzene (7.0 g, 40 mmol). After stirring for 3 h at −78° C., DMF (15 mL, 200 mmol) is added and the mixture is warmed to room temperature and stirred for 1 hour. The mixture is quenched with 1N HCl and extracted with EtOAc. The combined extracts are dried (MgSO₄) and concentrated in vacuo. The residue is purified by flash chromatography (elution with Hex/EtOAc 10:1) to yield 2-bromo-6-fluoro-benzaldehyde. ¹H NMR (CDCl₃) 10.4 (s, 1H), 7.48-7.39 (m, 2H), 7.18-7.14 (m, 1H).

Isopropylmagnesium chloride (18 mL of 2 M in Et₂O, 35 mmol) is added to a solution of 2-bromo-6-fluoro-benzaldehyde (6.0 g, 30 mmol) in THF (40 mL) at −78° C. and the mixture is stirred for 1 hour at 0° C. The mixture is poured into saturated NH₄Cl and extracted with EtOAc. The resulting crude alcohol is oxidized directly by Swern oxidation to yield 1-(2-bromo-6-fluoro-phenyl)-2-methyl-propan-1-one. ¹H NMR (CDCl₃) 7.38 (d, 1H), 7.22 (m, 1H), 7.03 (t, 1H), 3.10 (m, 1H), 1.11 (d, 6H).

Step 2. Preparation of 3-Isopropyl-1H-indazole-4-boronic acid

A mixture of 1-(2-bromo-6-fluoro-phenyl)-2-methyl-propan-1-one (1.1 g, 4.5 mmol) and anhydrous hydrazine (0.17 mL, 5.4 mmol) in ethylene glycol (10 mL) is heated for 16 h at 160° C. Water is added and the mixture is extracted with CH₂Cl₂. The combined extracts are dried (MgSO₄) and concentrated in vacuo. The residue is purified by flash chromatography to yield 4-bromo-3-isopropyl-1H-indazole. ¹H NMR (CDCl₃) 10.1 (br s, 1H), 7.38 (d, 1H), 7.32 (d, 1H), 7.17 (t, 1H), 3.99 (m, 1H), 1.43 (d, 6H).

4-Bromo-3-isopropyl-1H-indazole is converted to the corresponding boronic acid following analogous procedures to that given in the preceding example. ¹H NMR (CD₃OD) 7.44 (d, 1H), 7.32 (t, 1H), 7.05 (d, 1H), 3.56 (m, 1H), 1.38 (d, 6H). LCMS (m/z): 205.45 (MH)⁺.

Example 2

N-{[2-(2,6-diethylphenyl)-4-methoxy-6-methylpyrimidin-5-yl]methyl}-N-methyl-1,2,3,4-tetrahydronaphthalen-1-amine Step 1. Synthesis of 5-hydroxymethyl-6-methyl-pyrimidine-2,4-diol

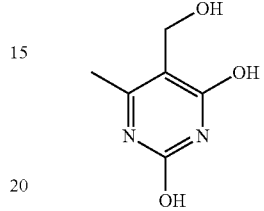

To a flask containing 6-methyl-1H-pyrimidine-2,4-dione (10 g, 79.3 mmol) is added NaOH (1.25 N, 95 mL) and the solution is allowed to stir for 10 min at room temperature. Formaldehyde (37%, 19.60 mL) is added dropwise over 30 min. After 30 min, a thick white precipitate forms and the reaction is allowed to proceed for 150 min. The suspension is then filtered and the filter cake is transferred to an Erlenmeyer flask to which EtOH (absolute, 200 mL) is added. The resulting suspension of white solid is stirred for 30 min. The white solid is collected by filtration, washed with EtOH (50 mL), Et₂O (100 mL) and vacuum dried to provide the title compound as a white solid. [MS mass expected (156.14); mass found (156.02)].

Step 2. Synthesis of 2,4-dichloro-5-chloromethyl-6-methyl-pyrimidine

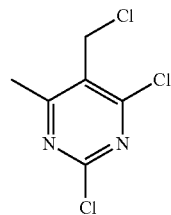

To a flask containing 5-hydroxymethyl6-methyl-pyrimidine-2,4-diol (10 g, 64 mmol) is added tri-n-butylamine (128.2 mL, 2 eq.) and POCl₃ (100 mL) and the solution is refluxed at 90° C. for 7 h. All POCl₃ is then removed on rotovap, and residual is quenched with water (100 mL). The acidic aqueous solution is washed with Et₂O (2×100 mL), then basified using NaOH (1N) and the product is extracted into EtOAc, washed with sat NaHCO₃ (100 mL), brine (100 mL) and dried over Na₂SO₄. The crude solution is filtered, concentrated and purified by SiO₂ flash chromatography using hexanes:Et₂O (10:1) affording the title compound as a waxy solid. [mass expected (211.48); mass found (211.05)].

Step 3. Preparation of (1S)-(2,4-Dichloro-6-methyl-pyrimidin-5-ylmethyl)-methyl-(1,2,3,4-tetrahydro-naphthalen-1-yl)-amine

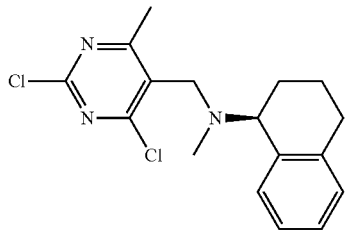

To a flask containing 2,4-dichloro-5-chloromethyl-6-methyl-pyrimidine (107 mg, 0.51 mmol) in absolute ETOH (10 mL) is added $K_2CO_3$ (70 mg, 1.0 eq., 0.51 mmol) and the reaction is cooled to 0° C. with an ice bath. (1S)-Methyl-(1,2,3,4-tetrahydro-naphthalen-1-yl)-amine (82 mg, 1.0 equiv, 0.51 mmol) in 1.0 mL of EtOH is added via syringe in one portion and allowed to warm to ambient temperature over 3 h. Water (50 mL) and EtOAc (50 mL) is added and the EtOAc layer is washed with water (100 mL) and brine (50 mL) and dried over $Na_2SO_4$. Concentration and vacuum drying affords the title compound as a yellow gum. [mass expected (336.26); mass found (336.30)]

Step 4. Preparation of (1S)-(2-Chloro-4-methoxy-6-methyl-pyrimidin-5-ylmethyl)-methyl-(1,2,3,4-tetrahydro-naphthalen-1-yl)-amine

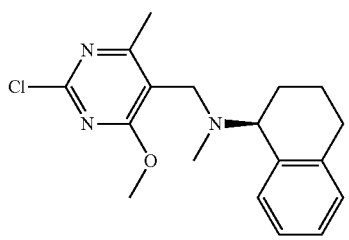

To a flask containing (1S)-(2,4-dichloro-6-methyl-pyrimidin-5-ylmethyl)-methyl-(1,2,3,4-tetrahydro-naphthalen-1-yl)-amine (6.41 g, 19.06 mmol) is added MeOH (100 mL) and the solution is cooled to 0° C. using an ice bath. NaOMe (0.5 M, 38 mL) is added via addition funnel over 20 min. Once addition is complete, the ice bath is removed and the reaction is allowed to proceed overnight warming to room temperature. HOAc (2.0 mL) is added and the reaction mixture is allowed to stir for 10 min, followed by concentration at reduced pressure. The resulting oil is dissolved in EtOAc (100 mL) and washed sat. $NaHCO_3$ (100 mL), brine (100 mL) and dried over $Na_2SO_4$. Flash chromatography on $SiO_2$ using first $CHCl_3$ followed by 20:1 hexanes:$Et_2O$ affords the title compound as a colorless oil. [mass expected (331.84); mass found (331.28)]

Step 5. Preparation of (1S)—N-{[2-(2,6-diethylphenyl)-4-methoxy-6-methylpyrimidin-5-yl]methyl}-N-methyl-1,2,3,4-tetrahydronaphthalen-1-amine

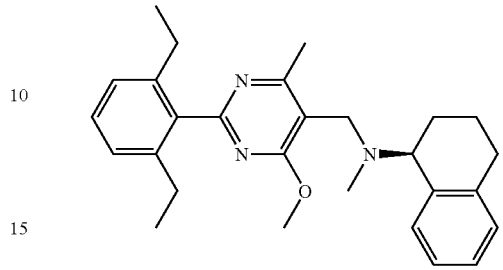

To a sealed tube containing (1S)-(2,4-dichloro-6-methyl-pyrimidin-5-ylmethyl)-methyl-(1,2,3,4-tetrahydro-naphthalen-1-yl)-amine (3.4 g, 10.25 mmol) is added dioxane (40 mL), 2,6-diethylphenylboronic acid (3.65 g, 2.0 eq., 20.5 mmol) and $K_2CO_3$ (5.7 g, 4.0 eq., 41 mmol dissolved in 10 mL water) under a nitrogen atmosphere. $Pd(PPh_3)_4$ (5 mol %, 590 mg) is added and after sealing is allowed to react at 95° C. for 16 h. After cooling to room temperature, EtOAc (100 mL) and water (100 mL) is added and the organic layer is washed with sat. $NaHCO_3$ (100 mL), brine (100 mL) and dried over $Na_2SO_4$. The crude sample is purified by $SiO_2$ flash chromatography using hexanes:$Et_2O$ 5:1 with 1.0% triethylamine to recover the title compound as a colorless oil. [mass expected (429.60); mass found (429.33)]

Example 3

Synthesis of 1-[2-(2,6-diethylphenyl)-6-methyl-5-({methyl[(1S)-1,2,3,4-tetrahydronaphthalen-1-yl]amino}methyl)pyrimidin-4-yl]piperidin-4-one

Step 1. Preparation of 2-(2,6-Diethyl-phenyl)-6-methyl-5-{[methyl-(1S)-(1,2,3,4-tetrahydro-naphthalen-1-yl)-amino]-methyl}-pyrimidin-4-ol

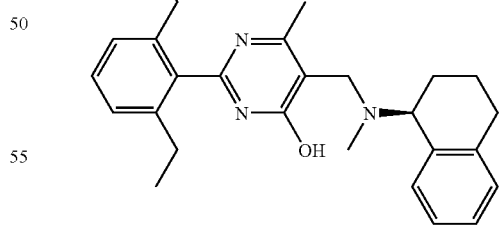

To a flask containing (1S)—N-{[2-(2,6-diethylphenyl)-4-methoxy-6-methylpyrimidin-5-yl]methyl}-N-methyl-1,2,3,4-tetrahydronaphthalen-1-amine (3.5 g, 8.15 mmol) is added EtOH (50 mL) and HCl (12 N, 50 mL) and the solution is heated at 90° C. for 16 h. The solution is cooled to 0° C. and basified using 5N NaOH slowly, followed by addition of EtOAc (100 mL). The organic layer is washed with sat. $NaHCO_3$ (100 mL), brine (100 mL) and dried over $Na_2SO_4$.

Concentration and vacuum drying affords the title compound as a white gummy foam. [mass expected (415.57); mass found (415.33)]

Step 2. Preparation of [4-chloro-2-(2,6-diethyl-phenyl)-6-methyl-pyrimidin-5-ylmethyl]-methyl-(1S)-(1,2,3,4-tetrahydro-naphthalen-1-yl)amine

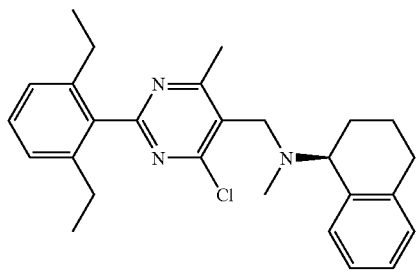

To a flask containing 2-2,6-diethyl-phenyl)-6-methyl-5-{[methyl-(1S)-(1,2,3,4-tetrahydro-naphthalen-1-yl)-amino]-methyl}-pyrimidin-4-ol (3.30 g, 7.94 mmol) is added POCl₃ (30 mL) and heated at 95° C. for 60 min. Once cool, all POCl₃ is removed at reduced pressure and saturated aqueous NaHCO₃ (100 mL) and EtOAc (100 mL) are added. The organic layer is washed with water (100 mL), brine (100 mL) and dried over Na₂SO₄. Filtration, concentration and vacuum drying affords the title compound as a yellow syrup. [mass expected (434.02); mass found (434.28)]

Step 3. Preparation of [2-(2,6-Diethyl-phenyl)-4-(1,4-dioxa-8-aza-spiro[4.5]dec-8-yl)-6-methyl-pyrimidin-5-ylmethyl]-methyl-(1S)-(1,2,3,4-tetrahydro-naphthalen-1-yl)-amine

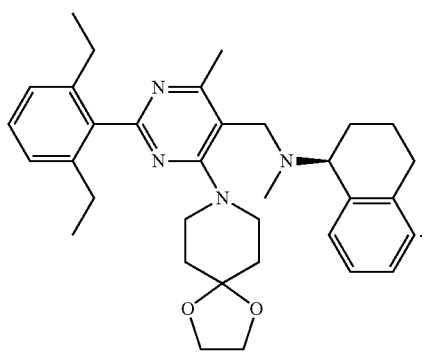

To a vial containing [4-chloro-2-(2,6-diethyl-phenyl)-6-methyl-pyrimidin-5-ylmethyl]-methyl-(1S)-(1,2,3,4-tetrahydro-naphthalen-1-yl)-amine (1.0 mL of a 0.2M DMA solution, 0.2 mmol) is added 1,4-dioxa-8-azaspiro(4,5)decane (1.0 ml of a 1.0M DMA solution, 5.0 eq.) and the resulting solution is vortex heated at 85° C. for 12 h. Once the reaction has cooled to room temperature, EtOAc (1.0 mL) and sat NaHCO₃ (1.0 mL) is added and the organic layer is plated directly onto a SiO2 preparatory chromatography plate and the product is eluted using hexanes:Et₂O 1:1, which affords the title compound as a colorless oil. [mass expected (540.74); mass found (540.43)].

Step 4. Preparation of 1-[2-(2,6-diethylphenyl)-6-methyl-5-({methyl[(1S)-1,2,3,4-tetrahydronaphthalen-1-yl]amino}methyl)pyrimidin-4-yl]piperidin-4-one

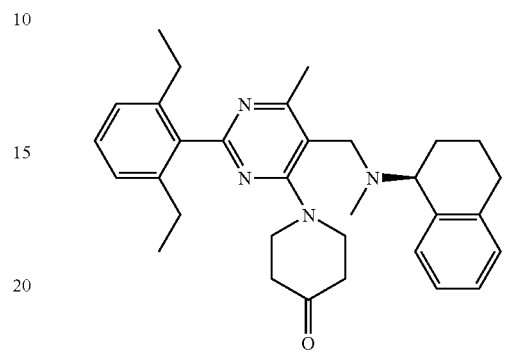

To a flask containing [2-(2,6-diethyl-phenyl)-4-(1,4-dioxa-8-aza-spiro[4.5]dec-8-yl)-6-methyl-pyrimidin-5-ylmethyl]-methyl-(1S)-(1,2,3,4-tetrahydro-naphthalen-1-yl) amine (80 mg, 0.148 mmol) is added HCl (3 M, 20 mL) and the reaction is heated at 60° C. for 4 h. Once cool, the reaction is basified with NaOH (1 N, 100 mL)) and EtOAc (100 mL) is added to extract the product. The organic layer is washed with water (100 mL), brine (100 mL) and dried over Na₂SO₄. Filtration, concentration and vacuum drying yields the title compound as a colorless gum. [mass expected (496.69); mass found (496.32)].

Example 4

Synthesis of 4-(aminomethyl)-1-[2-(2,6-diethylphenyl)-6-methyl-5-({methyl[(1S)-1,2,3,4-tetrahydronaphthalen-1-yl]amino}methyl)pyrimidin-4-yl]piperidin-4-ol Step 1. Preparation of 1-(2-(2,6-diethyl-phenyl)-6-methyl-5-{[methyl-(1S)-(1,2,3,4-tetrahydro-naphthalen-1-yl)-amino]-methyl}-pyrimidin-4-yl)-4-trimethylsilanyloxy-piperidine-4-carbonitrile

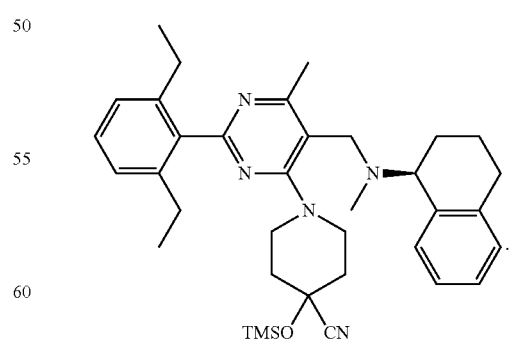

To a flask containing LiOMe (2.55 mg, 0.05 eq., 0.067 mmol) is added anhydrous THF (5 mL) followed by TMSCN (0.213 mL, 1.2 eq., 1.60 mmol) purging the reaction with nitrogen. 1-[2-(2,6-Diethylphenyl)-6-methyl-5-({methyl

[(1S)-1,2,3,4-tetrahydronaphthalen-1-yl]amino}methyl)pyrimidin-4-yl]piperidin-4-one (0.66 g, 1.33 mmol) in THF (5 mL) is then added at room temperature and allowed to react for 1 hour. After reaction is complete, aqueous NaHCO$_3$ (10%, 50 mL) is added along with EtOAc (50 mL) and the organic layer is collected and washed with water (50 mL), brine (50 mL) and dried over Na$_2$SO$_4$. Filtration, concentration and vacuum drying yields the title compound as a yellow syrup. [mass expected (595.89); mass found (595.27)]

Step 2. Preparation of 4-(aminomethyl)-1-[2-(2,6-diethylphenyl)-6-methyl-5-({methyl[(1S)-1,2,3,4-tetrahydronaphthalen-1-yl]amino}methyl)pyrimidin-4-yl]piperidin-4-ol

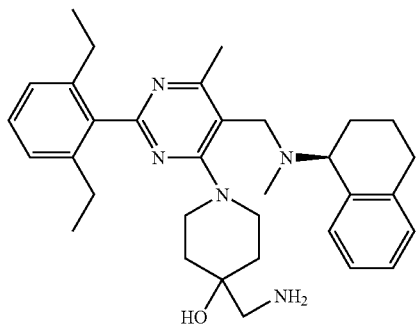

To a flask containing LAH (132 mg, 3.0 eq., 3.18 mmol) in anhydrous THF (20 mL) is added 1-(2-(2,6-diethyl-phenyl)-6-methyl-5-{[methyl-(1,2,3,4-tetrahydro-naphthalen-1-yl)-amino]-methyl}-pyrimidin-4-yl)-4-trimethylsilanyloxy-piperidine-4-carbonitrile 12 (0.63 g, 1.06 mmol) as a solution in THF (5 mL) over 10 min. The reaction is refluxed overnight. Following cooling to 0° C., water (0.132 mL) NaOH (15%, 0.132 mL) and water (0.396 mL) are added successively, followed by addition of EtOAc (100 mL) and MgSO$_4$ (100 mg). The suspension is filtered through celite and the celite bed is washed with 20:1 EtOAc:MeOH (2×100 mL). Concentration affords the title compound as an off-white solid. [mass expected (527.74); mass found (527.27)].

Example 5

Synthesis of N-({1-[2-(2,6-diethylphenyl)-6-methyl-5-({methyl[(1S)-1,2,3,4-tetrahydronaphthalen-1-yl]amino}methyl)pyrimidin-4-yl]-4-hydroxypiperidin-4-yl}methyl)acetamide

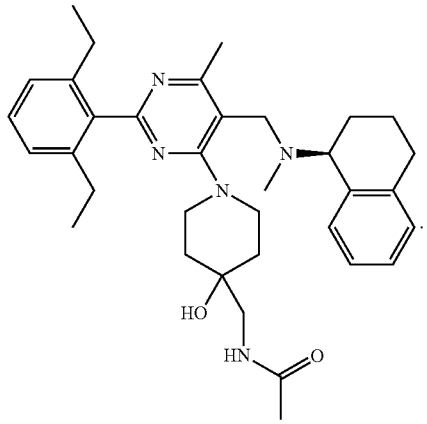

To a vial containing 4-(aminomethyl)-1-[2-(2,6-diethylphenyl)-6-methyl-5-({methyl[(1S)-1,2,3,4-tetrahydronaphthalen-1-yl]amino}methyl)pyrimidin-4-yl]piperidin-4-ol (25 mg, 0.047 mmol) in DMA (1.0 mL) is added K$_2$CO$_3$ (33 mg, 5.0 eq., 0.24 mmol) and acetic anhydride (0.023 mL, 5.0 eq., 0.24 mmol) and allowed to stir at room temperature for 16 h. EtOAc (2.0 mL) and sat NaHCO$_3$ (2.0 mL) are then added and the organic layer is transferred directly onto a SiO$_2$ plate and the product is eluted with 20:1 CHCl$_3$:MeOH affording the title compound as a white foam. [mass expected (569.78); mass found (569.30)].

Example 6

Synthesis of N-{[2-(2,6-diethylphenyl)-6-methyl-5-({methyl[(1S)-1,2,3,4-tetrahydronaphthalen-1-yl]amino}methyl)pyrimidin-4-yl]methyl}acetamide Step 1. Preparation of 2-(2,6-diethylphenyl)-6-methyl-5-({methyl[(1S)-1,2,3,4-tetrahydronaphthalen-1-yl]amino}methyl)pyrimidine-4-carbonitrile

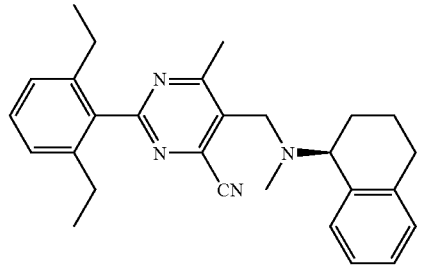

To a sealed tube containing [4-chloro-2-(2,6-diethyl-phenyl)-6-methyl-pyrimidin-5-ylmethyl]-methyl-(1S)-(1,2,3,4-tetrahydro-naphthalen-1-yl)-amine 9 (3.0 mL of a 0.2 M DMA solution, 0.6 mmol) is added KCN (780 mg, 20.0 eq., 12.0 mmol) and DMA (5 mL), sealed and allowed to stir at 130° C. for 16 h. EtOAc (50 mL) and sat. NaHCO$_3$ (50 mL) are then added and the organic layer is washed with water (100 mL), brine (100 mL) and dried over Na$_2$SO$_4$. The crude solution is filtered, concentrated and purified by SiO$_2$ flash chromatography using hexanes:Et$_2$O (5:1) affording the title compound as a yellow oil. [mass expected (424.58); mass found (424.29)].

Step 2. Preparation of (1S)—N-{[4-(aminomethyl)-2-(2,6-diethylphenyl)-6-methylpyrimidin-5-yl]methyl}-N-methyl-1,2,3,4-tetrahydronaphthalen-1-amine

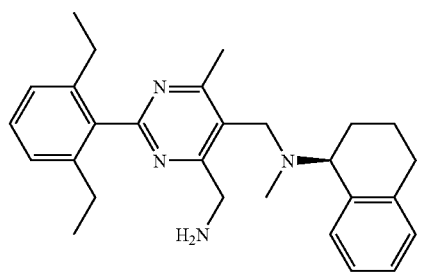

To a flask containing 2-(2,6-diethylphenyl)-6-methyl-5-({methyl[(1S)-1,2,3,4-tetrahydronaphthalen-1-yl]

amino}methyl)pyrimidine-4-carbonitrile (50 mg, 0.118 mmol) in toluene (5.0 mL) is cooled to 0° C. using an ice bath. DIBAL (0.354 mL of a 1.5 M solution in toluene, 3.0 eq., 0.53 mmol) is then added and the reaction is allowed to proceed for 3 h warming to room temperature. HCl (1.0 M 1.0 mL) is added and allowed to stir for 10 min, followed by basification with NaOH (5N). EtOAc (20 mL) is added and the organic layer is washed with NaHCO$_3$ (10%, 100 mL), brine (100 mL) and dried over Na$_2$SO$_4$. SiO$_2$ plate chromatography eluting with 20:1 CHCl$_3$:MeOH affords the title compound as a white foam. [mass expected (428.61); mass found (428.38)].

Step 3. Preparation of N-{[2-(2,6-diethylphenyl)-6-methyl-5-({methyl[(1S)-1,2,3,4-tetrahydronaphthalen-1-yl]amino}methyl)pyrimidin-4-yl]methyl}acetamide

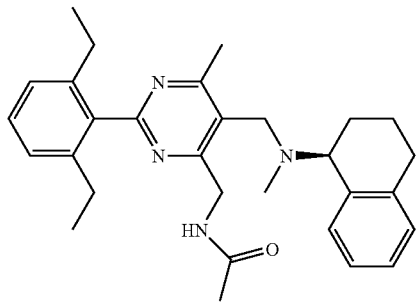

To a vial containing (1S)—N-{[4-(aminomethyl)-2-(2,6-diethylphenyl)-6-methylpyrimidin-5-yl]methyl}-N-methyl-1,2,3,4-tetrahydronaphthalen-1-amine (9 mg, 0.021 mmol) in CHCl$_3$ (2.0 mL) is added acetic anhydride (0.05 mL, 25.0 eq., 0.53 mmol) and allowed to stir at room temperature for 2 h. All solvent is then removed and excess acetic anhydride is removed azeotropically with toluene (3×2 mL). The sample is re-dissolved in CHCl$_3$ and eluted through a plug of SiO$_2$, washing with CHCl$_3$. Concentration affords the title compound as a colorless gum. [mass expected (470.65); mass found (470.34)].

Example 7

Synthesis of (1S)—N-{[2-(2,6-diethylphenyl)-4-methyl-6-phenoxypyrimidin-5-yl]methyl}-N-methyl-1,2,3,4-tetrahydronaphthalen-1-amine

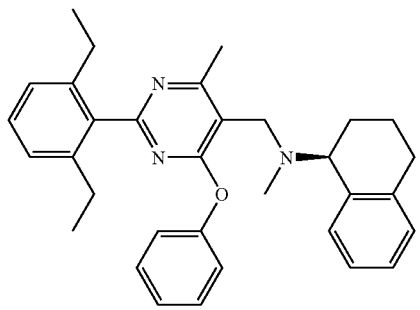

To a vial containing [4-chloro-2-(2,6-diethyl-phenyl)-6-methyl-pyrimidin-5-ylmethyl]-methyl-(1S)-(1,2,3,4-tetrahydro-naphthalen-1-yl)-amine 9 (0.1 mL of a 0.2 M DMA solution, 0.02 mmol) is added phenol (0.1 mL of a 0.3 M DMA solution, 0.03 mmol) and KOtBu (0.1 mL of a 0.3 M solution in 7:3 DMA:tBuOH, 0.03 mmol) and allowed to stir at 70° C. for 16 h. EtOAc (50 mL) and sat. NaHCO$_3$ (50 mL) are then added and the organic layer is washed with water. (100 mL), brine (100 mL) and dried over Na$_2$SO$_4$. The crude solution is filtered, concentrated and purified by SiO$_2$ flash chromatography using hexanes:Et$_2$O (5:1) affording (1S)—N-{[2-(2,6-diethylphenyl)-4-methyl-6-phenoxypyrimidin-5-yl]methyl}-N-methyl-1,2,3,4-tetrahydronaphthalen-1-amine as a colorless oil. [mass expected (491.67); mass found (491.42)].

Example 8

Synthesis of 2-(2,6-diethylphenyl)-5-[(5-isopropyl-2-methylphenoxy)methyl]-4-methyl-6-piperazin-1-ylpyrimidine Step 1. Preparation of 2,4-dichloro-5-(5-isopropyl-2-methyl-phenoxymethyl)-6-methyl-pyrimidine.

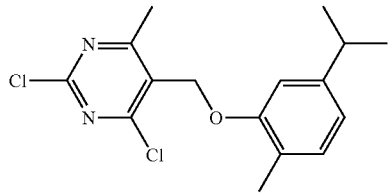

To a solution of 2,4-dichloro-5-chloromethyl-6-methyl-pyrimidine (17.4 g, 82.7 mmol) and carvacrol (6.21 g, 41.4 mmol) in DMA (166 mL) at 0° C. under nitrogen with magnetic stirring is added KOtBu (42 mL of 1 M in THF, 42 mmol) in dropwise fashion over 20 min. The resulting redish-orange colored solution is allowed to slowly warm to ambient temperature (~2 h) and stir for 18 h. The reaction mixture is re-cooled to 0° C. and another portion of carvacrol is added (6.21, 41.4 mmol) followed by dropwise addition of KOtBu (42 mL of 1 M in THF, 42 mmol). The reaction mixture is allowed to slowly warm to ambient temperature (~2 h) and stir for 18 h. The reaction mixture is partitioned between EtOAc (200 mL) and water (60 mL), the organic layer is separated, washed with water (60 mL×3), brine (60 mL), dried over sodium sulfate, filtered and evaporated at reduced pressure to obtain an orange oil. The crude product is dissolved in hexanes (300 mL), quickly extracted with Claisen's alkali (50 mL×2), dried over sodium sulfate, filtered and evaporated to obtain an orange oil. Purification by chromatography on silica gel (10 EtOAc/Hexanes) provides the title compound as a colorless oil that solidifies on standing. LC/MS (Method 3), M+H=325.2, Rt=3.03 min.; $^1$H NMR (CDCl$_3$) δ=7.09 (d, 1H), 6.82 (d, 1H), 6.81 (s, 1H), 5.17 (s, 2H), 2.90 (m, 1H), 2.68 (s, 3H), 2.14, (s, 3H), 1.26 (d, 6H).

Step 2. Preparation of 4-[2-chloro-5-(5-isopropyl-2-methyl-phenoxymethyl)-6-methyl-pyrimidin-4-yl]-piperazine-1-carboxylic acid tert-butyl ester

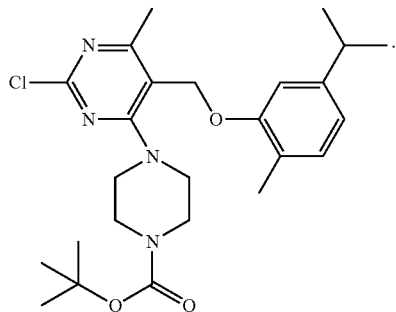

To a solution of 2,4-dichloro-5-(5-isopropyl-2-methyl-phenoxymethyl)-6-methyl-pyrimidine (978 mg, 3.01 mmol) in DMA (4 mL) is added piperazine-1-carboxylic acid tert-butyl ester (560 mg, 3.01 mmol) and potassium carbonate (832 mg, 6.02 mmol). The resulting colorless suspension is stirred at room temperature under nitrogen for 16 h. The reaction mixture is partitioned between EtOAc (60 mL) and water (20 mL), the organic layer is separated, washed with water (20 mL×2), brine (20 mL), dried over sodium sulfate, filtered and evaporated at reduced pressure to obtain a colorless oil consisting of a ~2:1 mixture of isomeric addition products. Purification on a 30 g cartridge of silica gel (10-30% EtOAc/Hexanes) affords the title compound (lower Rf material) as a colorless solid foam. $^1$H NMR (CDCl$_3$) δ=7.11 (d, 1H), 6.83 (d, 1H), 6.75 (s, 1H), 4.84 (s, 2H), 3.52 (m, 8H), 2.90 (m, 1H), 2.47, (s, 3H), 2.16, (s, 3H), 1.45, (s, 9H), 1.27 (d, 6H).

Step 3. Preparation of tert-butyl 4-{2-(2,6-diethylphenyl)-5-[(5-isopropyl-2-methylphenoxy)methyl]-6-methylpyrimidin-4-yl}piperazine-1-carboxylate

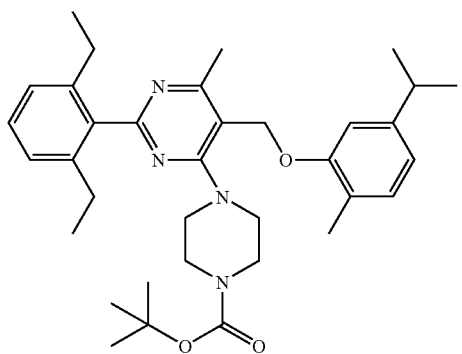

A mixture of 4-[2-chloro-5-(5-isopropyl-2-methyl-phenoxymethyl)-6-methyl-pyrimidin-4-yl]-piperazine-1-carboxylic acid tert-butyl ester (700 mg, 1.47 mmol), 2,6-diethylphenylboronic acid (394 mg, 2.21 mmol), 2 M aqueous sodium carbonate (2.21 mL, 4.42 mmol) and toluene (5 mL) is degassed with argon bubbling for 15 min. Pd(PPh$_3$)$_4$ (87 mg, 5 mol %) is added and the resulting yellow-colored mixture is heated at 90° C. under nitrogen with magnetic stirring for 40 h. The reaction mixture is partitioned between EtOAc (50 mL) and water (15 mL), the organic layer is separated, washed with water (15 mL), bring (15 mL), dried over sodium sulfate, filtered and evaporated at reduced pressure to obtain a yellow liquid. Chromatography on a 30 g silica gel cartridge (10-30% EtOAc/Hexanes) affords the title compound as a colorless oil (along with recovered 4-[2-chloro-5-(5-isopropyl-2-methyl-phenoxymethyl)-6-methyl-pyrimidin-4-yl]-piperazine-1-carboxylic acid tert-butyl ester). LC/MS (Method 3), M+H=573.2, Rt=3.18 min.; $^1$H NMR (CDCl$_3$) δ=7.26 (d, 1H), 7.12 (d, 3H), 6.83 (m, 2H), 4.99 (s, 2H), 3.51 (m, 4H), 2.90 (m, 6H), 2.55, (s, 3H), 2.42 (q, 4H) 2.24 (s, 3H), 1.28 (d, 6H), 1.10 (t, 6H).

Step 4. Preparation of 2-(2,6-diethylphenyl)-5-[(5-isopropyl-2-methylphenoxy)methyl]-4-methyl-6-piperazin-1-ylpyrimidine

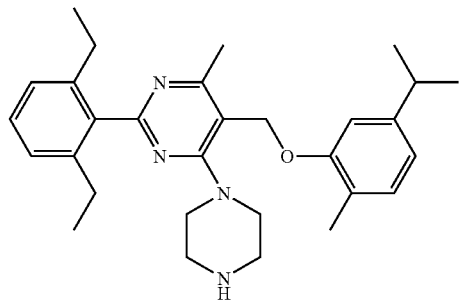

To tert-butyl 4-{2-(2,6-diethylphenyl)-5-[(5-isopropyl-2-methylphenoxy)methyl]-6-methylpyrimidin-4-yl}piperazine-1-carboxylate (228 mg, 0.40 mmol) is added trifluoroacetic acid (2 mL). Gas evolution ensues and rapidly subsides. Toluene (10 mL) is added and removed under reduced pressure. The resulting residue is dissolved in EtOAc (25 mL) and extracted with saturated potassium carbonate (10 mL) followed by brine (10 mL), dried over sodium sulfate, filtered and evaporated at reduced pressure to obtain the title compound as a colorless oil. LC/MS (Method 3), M+H=473.2, Rt=2.35 min.; $^1$H NMR (CDCl$_3$) δ=7.26 (d, 1H), 7.12 (d, 3H), 6.83 (me, 2H), 4.99 (s, 2H), 3.49 (m, 8H), 2.91 (m, 1H), 2.56, (s, 3H), 2.42 (q, 4H) 2.24 (s, 3H), 1.42 (s, 9H), 1.28 (d, 6H), 1.13 (t, 6H).

Example 9

2-(4-{2-(2,6-dimethylphenyl)-5-[(5-isopropyl-2-methylphenoxy)methyl]-6-methylpyrimidin-4-yl}piperazin-1-yl)acetamide Step 1. Preparation of 2-chloro-5-(5-isopropyl-2-methyl-phenoxymethyl)-4-methyl-6-piperazin-1-yl-pyrimidine trifluoroacetic acid salt

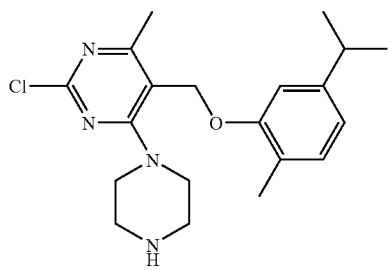

To a solution of 4-[2-chloro-5-(5-isopropyl-2-methyl-phenoxymethyl)-6-methyl-pyrimidin-4-yl]-piperazine-1-carboxylic acid tert-butyl ester (500 mg, 1.05 mmol) in DCM (5 mL) is added trifluoroacetic acid (1 mL) with magnetic stirring. Gas evolution is observed and continues for 20 min. The light yellow colored solution is evaporated at reduced pressure, diluted with DCM (20 mL) and evaporated again. Placed under high vacuum (~0.2 Torr) for 20 min to obtain the title compound as a colorless oil. LC/MS (Method 2), M+H=432.1, Rt=1.46 min.

Step 2. Preparation of 2-{4-[2-chloro-5-(5-isopropyl-2-methyl-phenoxymethyl)-6-methyl-pyrimidin-4-yl]-piperazin-1-yl}-acetamide

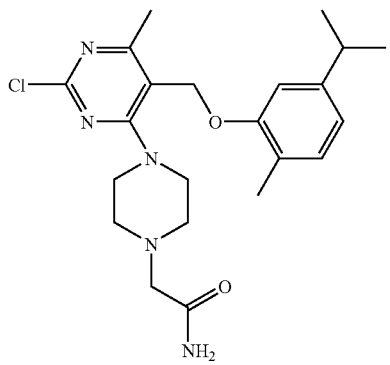

A mixture of 2-chloro-5-(5-isopropyl-2-methyl-phenoxymethyl)-4-methyl-6-piperazin-1-yl-pyrimidine trifluoroacetic acid salt (722 mg), 2-bromoacetamide (290 mg, 2.11 mmol) and potassium carbonate (871 mg, 6.30 mmol) in DMA (10 mL) is stirred at room temperature for 3 h. The reaction mixture is partitioned between EtOAc (30 mL) and water (10 mL), the organic layer is separated, washed with water (10 mL×2), brine (10 mL), dried over sodium sulfate, filtered and evaporated at reduced pressure to yield a yellow oil. Purification by chromatography on silica gel affords the title compound as a colorless oil that solidifies on standing. $^1$H NMR (CDCl$_3$) δ=7.10 (d, 1H), 6.92 (br s, 1H), 6.82 (d, 1H), 6.74 (s, 1H), 5.54 (br s, 1H), 4.83 (s, 2H), 3.61, (m, 4H), 3.04 (s, 2H) 2.90 (m, 1H), 2.63 (m, 4H), 2.47 (s, 3H), 2.14 (s, 3H), 1.27 (d, 6H).

Step 3. Preparation of 2-(4-{2-(2,6-dimethylphenyl)-5-[(5-isopropyl-2-methylphenoxy)methyl]-6-methylpyrimidin-4-yl}piperazin-1-yl)acetamide

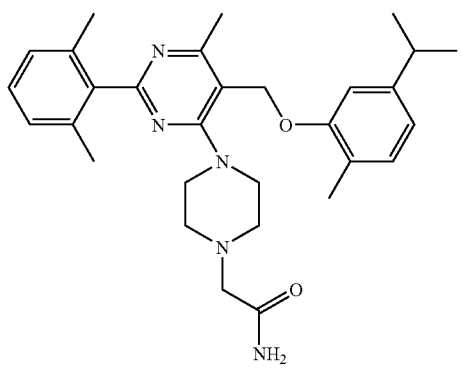

A mixture of 2-{4-[2-chloro-5-(5-isopropyl-2-methyl-phenoxymethyl)-6-methyl-pyrimidin-4-yl]-piperazin-1-yl}-acetamide (20 mg, 0.05 mmol), 2,6-dimethylphenylboronic acid (21 mg, 0.14 mmol) and 2 M sodium carbonate (0.14 mL, 0.28 mmol) in dioxane (1 mL) is degassed with bubbling argon for 20 min. Pd(PPh$_3$)$_4$ (2.9 mg, 5 mol %) is added and the reaction mixture is heated at 100° C. under nitrogen with magnetic stirring. After 18 h, the reaction mixture is partitioned between EtOAc (10 mL) and water (2 mL), the organic layer is separated, washed with brine (2 mL), dried over sodium sulfate, filtered and evaporated at reduced pressure to obtain a dark oil. Purification on silica gel (3% MeOH/CH$_2$Cl$_2$/0.1% NH$_4$OH) provides the title compound as a colorless film. LC/MS (Method 3), M+H=502.3, Rt=2.43 min.; $^1$H NMR (CDCl$_3$) δ=7.07-7.19 (m, 4H), 6.82 (m, 2H), 5.44 (br s, 1H), 4.97 (s, 2H), 3.57 (br s, 4H), 3.02 (s, 2H), 2.91 (m, 1H), 2.62 (m, 4H) 2.56 (s, 3H), 2.22 (s, 3H), 2.16 (s, 6H), 1.28 (d, 6H).

Example 10

Synthesis of 4-[2-(2,6-diethylphenyl)-4-methoxy-6-methylpyrimidin-5-yl]heptan-4-ol

Step 1. Preparation of 3-amino-2-ethoxycarbonylaminocarbonyl-but-2-enoic acid methyl ester

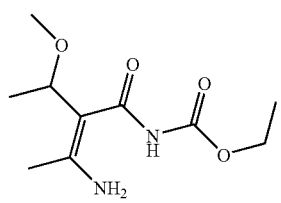

To a solution of methyl 3-aminocrotonate (39.0 g, 0.339 mol) in anhydrous diethyl ether (200 mL) under nitrogen with magnetic stirring at 0-5° C. is added in dropwise fashion a solution of ethoxycarbonyl isocyanate (0.339 mol) in diethyl ether (40 mL). The resulting pale yellow colored suspension is stirred below 5° C. for 4 h. The solid is collected by suction filtration, rinsed with 50 mL of diethyl ether and dried under vacuum at room temperature for 30 h to obtain the title compound as an off-white solid.

Step 2. Preparation of 5-carboxy-6-methyluracil methyl ester

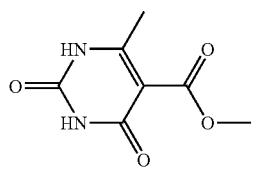

A suspension of 3-amino-2-ethoxycarbonylaminocarbonyl-but-2-enoic acid methyl ester (59 g, 0.26 mol) in 25% aqueous trimethylamine (400 mL) is stirred at 50° C. for 18 h. Another 100 mL of 25% aqueous trimethylamine is added and the reaction mixture is heated at 60° C. for 3 h to form a homogeneous yellow solution. The reaction mixture is evaporated at reduced pressure to remove most of the trimethylamine and then acidified with HOAc. The resulting white solid is collected by suction filtration and dried under vacuum at 60° C. to afford the title compound. $^1$H NMR (CDCl$_3$) δ=3.92 (br s, 2H), 3.71 (s, 3H), 2.22 (s, 3H).

Step 3. Preparation of 2,4-dichloro-6-methyl-pyrimidine-5-carboxylic acid methyl ester

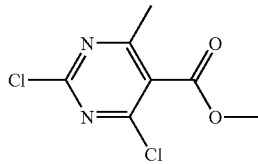

To a suspension of 5-carboxy-6-methyluracil methyl ester (25.6 g, 139 mmol) in phosphorous oxychloride (250 mL) is added slowly with magnetic stirring tri-n-butylamine (70 mL). The reaction mixture is heated at 95° C. for 3 h. The reaction mixture is cooled to room temperature, evaporated at reduced pressure and poured onto ice. The resulting residue is transferred to a separatory funnel and extracted with EtOAc (100 mL×3). The combined organic layers are washed with water (50 mL×3) and brine (50 mL), dried over magnesium sulfate, filtered through a plug of silica gel and evaporated at reduced pressure to obtain a dark brown residue. Purification by chromatography on silica gel (1:4 EtOAc/hexanes) affords the title compound. $^1$H NMR (CDCl$_3$) δ=4.00 (s, 3H), 2.59 (s, 3H).

Step 4. Preparation of 2-chloro-4-methoxy-6-methyl-pyrimidine-5-carboxylic acid methyl ester

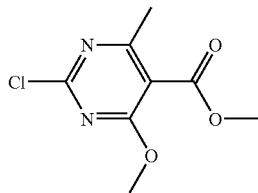

To a solution of 2,4-dichloro-6-methyl-pyrimidine-5-carboxylic acid methyl ester (15.3 g, 69.6 mmol) in methanol (150 mL) at 0° C. under nitrogen with magnetic stirring is added 0.5 M NaOMe in MeOH (139 mL, 69.6 mmol) in dropwise fashion over 1 h. HOAc (2 mL) is added and the reaction mixture is evaporated at reduced pressure. The resulting residue is treated with sat. NaHCO$_3$ (100 mL) and extracted with EtOAc (120 mL×3). The combined organic layers are washed with water (75 mL) and brine (75 mL), dried over magnesium sulfate, filtered and evaporated at reduced pressure to obtain a cream-colored solid. Purification by chromatography on silica gel (1:3 ether/hexanes) affords the title compound as a white solid (less polar of two isomeric addition products formed) and 4-chloro-2-methoxy-6-methyl-pyrimidine-5-carboxylic acid methyl ester. 2-Chloro-4-methoxy-6-methyl-pyrimidine-5-carboxylic acid methyl ester $^1$H NMR (CDCl$_3$) δ=4.03 (s, 3H), 3.92 (s, 3H), 2.48 (s, 3H). 4-Chloro-2-methoxy-6-methyl-pyrimidine-5-carboxylic acid methyl ester $^1$H NMR (CDCl$_3$) δ=4.03 (s, 3H), 3.95 (s, 3H), 2.50 (s, 3H).

Step 5. Preparation of 2-(2,6-diethyl-phenyl)-4-methoxy-6-methyl-pyrimidine-5-carboxylic acid methyl ester

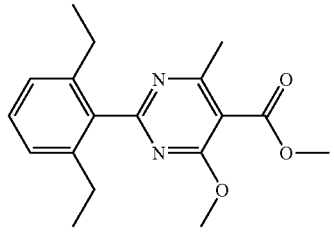

To a solution of 2-chloro-4-methoxy-6-methyl-pyrimidine-5-carboxylic acid methyl ester (4.1 g, 19.0 mmol) in DME (100 mL) is added potassium carbonate (10.5 g, 76 mmol, 4 eq) in water (40 mL) followed by 2,6-diethylphenyl-boronic acid (6.77 g, 38 mmol, 2 eq). The resulting mixture is degassed by bubbling with argon for 20 min. Pd(PPh$_3$)$_4$ (5 mol %) is added and the resulting yellow biphasic solution is heated at 95° C. in a sealed tube with magnetic stirring for 18 h. The reaction mixture is cooled to room temperature, diluted with water (100 mL) and extracted with EtOAc (75 mL×3). The combined organic layers are washed with brine (75 mL), dried over magnesium sulfate, filtered and evaporated at reduced pressure. The resulting orange oil is purified by chromatography on silica gel (1:2 ether/hexanes) to afford the title compound as a colorless oil. $^1$H NMR (CDCl$_3$) δ=7.29 (dd, 1H), 7.14 (d, 2H), 4.00 (s, 3H), 3.98 (s, 3H), 2.55 (s, 3H), 2.39 (q, 4H), 1.10 (t, 6H).

Step 6. Preparation of 4-[2-(2,6-diethylphenyl)-4-methoxy-6-methylpyrimidin-5-yl]heptan-4-ol

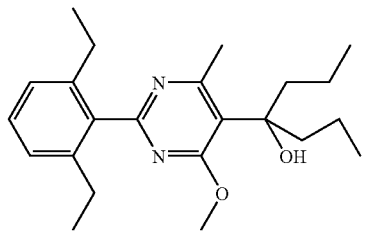

To a solution of 2-(2,6-diethyl-phenyl)-4-methoxy-6-methyl-pyrimidine-5-carboxylic acid methyl ester (3.3 g, 0.01 mol) at 0° C. in dry THF (50 mL) under nitrogen with magnetic stirring is added n-propyl magnesium chloride (26 mL, 2.0 M, 0.05 mol) in dropwise fashion. The reaction mixture is allowed to warm to room temperature and stirred for 2 h. The reaction mixture is quenched with a saturated aqueous NH$_4$Cl solution (20 mL) and extracted with DCM (100 mL). The DCM layer is dried over sodium sulfate, filtered and evaporated to obtain a residue. Purification by chromatography over silica gel eluting with 10% EtOAc-hexanes affords the title compound as a colorless oil and 1-[2-(2,6-diethylphenyl)-4-methoxy-6-methylpyrimidin-5-yl]butan-1-ol as a colorless oil. Title compound 1H NMR (300 MHz, CDCl3): δ 7.23-7.29 (m, 1H), 7.13 (d, J=9 Hz, 2H), 3.95 (s, 3H), 2.72 (s, 3H), 2.41 (q, J=7.5 Hz, 4H), 2.18-2.30 (m, 2H), 1.66-1.81 (m, 2H), 1.42-1.54 (m, 2H), 1.05-1.18 (m, 8H), 0.91 (t, J=7.2 Hz, 6H); LC-MS found 371 (MH+). 1-[2-(2,6-Diethylphenyl)-4- methoxy-6-methylpyrimidin-5-yl]butan-1-ol NMR (300 MHz, CDCl3): δ 7.23-7.28 (m, 1H), 7.1 (d, J=9 Hz, 2H), 4.81-5.11 (m, 1H), 4.01(s, 3H), 2.45 (s, 3H), 2.55 (q, J=7.5 Hz, 4H), 1.88-2.00 (m, 1H), 1.30-1.81 (m, 4H), 1.10 (q, J=7.8, 4.8 Hz, 6H), 0.91 (t, J=7.2 Hz, 6H); LC-MS found 328 (MH+).

Example 11

Synthesis of 2-(2,6-diethylphenyl)-4-methoxy-6-methyl-5-(1-propylbutyl)pyrimidine Step 1. Preparation of 2-(2,6-diethylphenyl)-4-methoxy-6-methyl-5-(1-propylbutenyl)pyrimidine

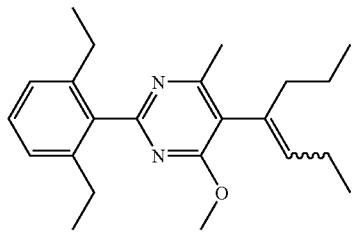

To a solution of 4-[2-(2,6-diethylphenyl)-4-methoxy-6-methylpyrimidin-5-yl]heptan-4-ol (0.6 g, 1.7 mmol) in anhydrous pyridine (10 mL) is added 1.5 mL of SOCl₂ dropwise under nitrogen. The reaction mixture is stirred at room temperature for 3 h, quenched with a saturated aqueous NaHCO₃ solution and extracted with DCM. The organic layer is washed with water, brine, dried over Na₂SO₄, and concentrated. The residue is purified by flash chromatography eluting with 10% EtOAc-hexanes to afford the title compound. ¹H NMR (300 MHz, CDCl3): δ 7.24-7.29 (m, 1H), 7.13 (d, J=9 Hz, 2H), 5.39 (t, J=7.5. Hz, 1H), 3.91 (s,3H), 2.46 (s,3H), 2.24-2.43 (m, 6H), 1.28-1.33 (m,4H), 1.10 (q, J=7.8, 4.8 Hz, 6H), 0.91 (t, j=7.2 Hz, 6H); LC-MS found 352 (MH+).

Step 2. Preparation of 2-(2,6-diethylphenyl)-4-methoxy-6-methyl-5-(1-propylbutyl)pyrimidine

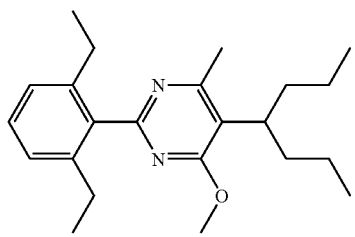

A solution of 2-(2,6-diethylphenyl)-4-methoxy-6-methyl-5-(1-propylbutenyl)pyrimidine (100 mg) in MeOH is hydrogenated over Pd—C at 50 psi for 18 h. The catalyst is removed by filtration and the filtrate is concentrated to afford the title compound. ¹H NMR (300 MHz, CDCl3): δ 7.24-7.29 (m, 1H), 7.13 (d, J=8 Hz, 2H), 3.91 (s, 3H), 2.51 (s,3H), 2.41 (q, J=7.5 Hz, 4H), 2.38-2.45 (m, 8H), 1.58-1.82 (m, 3H), 1.14-1.44 (m, 2H), 1.08 (q, J=7.5, 6.6 Hz, 6H) 0.89 (t, J=7.5 Hz, 6H); LC-MS found 355 (MH+).

Example 12

Synthesis of 2-(2,6-diethylphenyl)-5-(1-ethoxybutyl)-4-methoxy-6-methylpyrimidine and 5-[1-(4-acetylpiperazin-1-yl)butyl]-2-(2,6-diethylphenyl)-4-methoxy-6-methylpyrimidine To a solution of 1-[2-(2,6-diethylphenyl)-4-methoxy-6-methylpyrimidin-5-yl]butan-1-ol (1 g, 3 mmol) [prepared as described in Example 10] in dry DCM (20 mL) is added SOCl₂ (7 mL 0.015 mol) dropwise under nitrogen. The solution is then allowed to stir at room temperature for 1 h. The reaction mixture is concentrated and azeotroped with toluene twice to obtain 5-(1-chloro-butyl)-2-(2,6-diethyl-phenyl)-4-methoxy-6-methyl-pyrimidine which is used in standard nucleophilic displacement reactions to obtain a variety of compounds including the following:

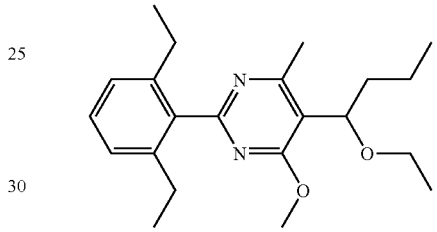

2-(2,6-Diethylphenyl)-5-(1-ethoxybutyl)-4-methoxy-6-methylpyrimidine; ¹H NMR (300 MHz, CDCl₃) δ 7.27 (t, J=7.0 Hz, 1H), 7.12 (d, J=7.5 Hz, 2H), 4.86 (t, J=5.7 Hz, 1H), 3.93 (s, 3H), 3.38 (q, J=6.9, 6.0 Hz, 2H), 2.62 (s, 3H), 2.41 (q, J=7.5, 7.5 Hz, 4H), 1.12-2.12 (m, 2H), 1.58-1.82 (m, 3H), 1.08 (q, J=7.5, 6.6 Hz, 6H) 0.89 (t, J=7.5 Hz, 6H); LC-MS found 357 (MH+).

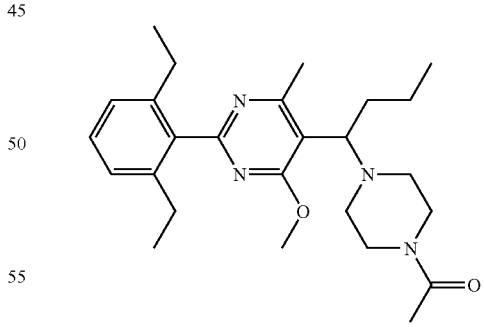

5-[1-(4-acetylpiperazin-1-yl)butyl]-2-(2,6-diethylphenyl)-4-methoxy-6-methylpyrimidine; ¹H NMR (300 MHz, CDCl₃) δ 7.28 (t, J=5.1 Hz, 1H), 7.12 (d, J=7.5 Hz, 2H), 3.91 (s, 3H), 3.40-3.80 (m, 6H), 2.66 (s, 3H), 2.42 (q, J=7.5, 7.5 Hz, 4H), 2.09 (s, 3H), 2.02-2.24 (m, 2H), 1.80-2.01 (m, 2H), 1.40-1.71 (m, 3H), 1.08 (q, J=7.5, 6.6 Hz, 3H) 0.89 (t, J=7.5 Hz, 6H); LC-MS found 439 (MH+).

Example 13

Synthesis of 2-((2R)-4-{2-(2,6-dimethylphenyl)-5-[(5-isopropyl-2-methylphenoxy)methyl]-6-methyl-4-pyrimidinyl}-2-methyl-1-piperazinyl)acetamide

Step 1. Preparation of 2-chloro-5-[(5-isopropyl-2-methylphenoxy)methyl]-4-methoxy-6-methylpyrimidine

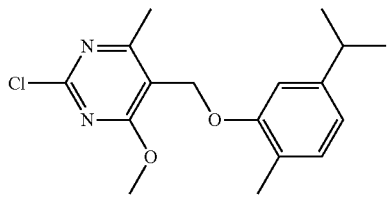

A solution of ~70% 2,4-dichloro-5-(5-isopropyl-2-methyl-phenoxymethyl)-6-methyl-pyrimidine (2.64 g, ~5.68 mmol) is cooled to −5° C. under nitrogen with magnetic stirring. A 0.5 M solution of NaOMe in MeOH (11.4 mL) is added in rapid dropwise fashion. After 1 h, reaction is complete based on LC/MS analysis. The reaction mixture is evaporated at reduced pressure, diluted with DCM (15 mL), filtered and evaporated to obtain a pale yellow oil consisting of an isomeric mixture of mono-methoxy adducts. Purification on silica gel (10-60% EtOAc/Hexanes) provides a colorless oil containing the desired isomer (first to elute) plus impurity from the starting material. $^1$H NMR (400 MHz, CDCl$_3$) δ 7.06 (d, J=8 Hz, 1H), 6.82 (s, 1H), 6.78 (d, J=8 Hz, 1H), 5.05 (s, 2H), 4.04 (s, 3H), 2.80 (m, 1H), 2.55 (s, 3H), 2.13 (s, 3H), 1.26 (d, J=6.8 Hz, 6H); LC-MS found 321.1 (MH+), rt=1.73 min, Method 2.

Step 2. Preparation of 2-(2,6-dimethylphenyl)-5-[(5-isopropyl-2-methylphenoxy)methyl]-4-methoxy-6-methylpyrimidine

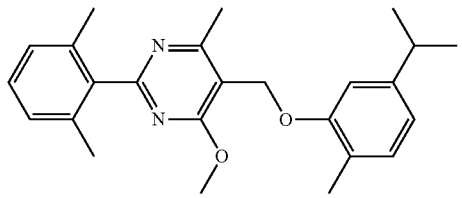

A mixture containing 2-chloro-5-[(5-isopropyl-2-methylphenoxy)methyl]-4-methoxy-6-methylpyrimidine (~3.91 mmol), 2,6-dimethylphenylboronic acid (1.17 g, 7.82 mmol), 15.6 mL of 1 M aqueous sodium carbonate and dioxane (56 mL) is degassed by bubbling with argon for 20 min. To this mixture is added Pd(PPh$_3$)$_4$ (226 mg, 0.05 mol %). The resulting yellow mixture is heated at 90° C. under nitrogen with magnetic stirring for 24 h. Another 50 mg of Pd(PPh$_3$)$_4$ is added and heating is continued for another 18 h until the reaction is complete by LC/MS analysis. The reaction mixture is allowed to cool to ambient temperature and partitioned between EtOAc (200 mL) and water (70 mL). The organic layer is separated, extracted with water (70 mL×2), brine (70 mL), dried over anhydrous sodium sulfate, filtered and evaporated to obtain a yellow oil. Purification by chromatography on silica gel (5-50% EtOAc/Hexanes) provides the title compound as a colorless solid. LC-MS found 391.4 (MH+), rt=1.93 min.

Step 3. Preparation of 2-(2,6-dimethylphenyl)-5-[(5-isopropyl-2-methylphenoxy)methyl]-6-methylpyrimidin-4-ol

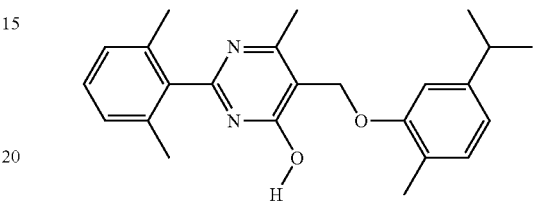

A mixture of 2-(2,6-dimethylphenyl)-5-[(5-isopropyl-2-methylphenoxy)methyl]-4-methoxy-6-methylpyrimidine (1.29 g, 3.30 mmol) and 6 N HCl is heated at 100° C. for 3 h (until starting material is consumed as determined by LC/MS analysis). The resulting mixture is adjusted to pH 6 using 10 N NaOH and extracted with EtOAc (100 mL×3). The combined extracts are washed with brine (50 mL), dried over anhydrous sodium sulfate, filtered and evaporated at reduced pressure to obtain a yellow gum. Purification by chromatography on silica gel (50-100% EtOAc/Hexanes) provides the title compound as a white solid. $^1$H NMR (400 MHz, CDCl$_3$) δ 11.4 (br s, 1H), 6.75-7.26 (m, 6H), 5.00 (s, 2H), 2.86 (m, 1H), 2.51 (s, 3H), 2.22 (s, 6H), 2.19 (s, 3H), 1.24 (d, J=6.8 Hz, 6H); LC-MS found 377.4 (MH+), rt=2.87 min, Method 3.

Step 4. Preparation of 4-chloro-2-(2,6-dimethylphenyl)-5-[(5-isopropyl-2-methylphenoxy)methyl]-6-methylpyrimidine

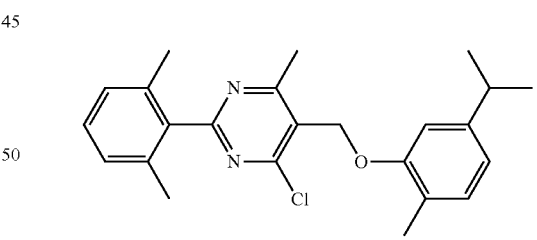

A mixture of 2-(2,6-dimethylphenyl)-5-[(5-isopropyl-2-methylphenoxy)methyl]-6-methylpyrimidin-4-ol (760 mg, 2.0 mmol) and phosphorous oxychloride (5 mL) is heated at 80° C. under nitrogen with magnetic stirring for 2 h (until starting material is consumed as determined by LC/MS analysis). The reaction mixture is evaporated at reduced pressure, diluted with DCM (50 mL), extracted with sat. NaHCO$_3$ (20 mL×3), dried over anhydrous sodium sulfate, filtered and evaporated to obtain a pale yellow oil. Purification by chromatography on silica gel (10-40% EtOAc/Hexanes) provides the title compound as a colorless oil. $^1$H NMR (400 MHz, CDCl$_3$) δ 7.08-7.25 (m, 4H), 6.88 (s, 1H), 6.82 (d, J=9 Hz, 1H), 5.28 (s, 2H), 2.91 (m, 1H), 2.74 (s, 3H), 2.21 (s, 3H), 2.14 (s, 6H), 1.28 (d, J=6.8 Hz, 6H); LC-MS found 395.4 (MH+), rt=3.33 min, Method 3.

Step 5. Preparation of 2-(2,6-dimethylphenyl)-5-[(5-isopropyl-2-methylphenoxy)methyl]-4-methyl-6-[(3R)-3-methylpiperazin-1-yl]pyrimidine

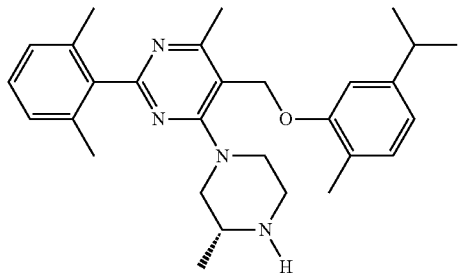

A mixture of 4-chloro-2-(2,6-dimethylphenyl)-5-[(5-isopropyl-2-methylphenoxy)methyl]-6-methylpyrimidine (0.1 mmol in 0.5 mL DMA), (R)-2-methyl-piperazine (40 mg) and sodium carbonate (85 mg) is heated at 100° C. with agitation for 18 h. The reaction mixture is allowed to cool and partitioned between EtOAc (6 mL) and water (2 mL). The organic layer is separated, washed with water (2 mL×2), brine (2 mL), dried over anhydrous sodium sulfate, filtered and evaporated to obtain a colorless oil. Purification by chromatography on silica gel (2% MeOH/DCM/0.1% Ammonium hydroxide) provides the title compound as a colorless oil. $^1$H NMR (300 MHz, CDCl$_3$) δ 7.06-7.26 (m, 4H), 6.79-6.82 (m, 2H), 4.97 (dd, 2H), 3.89-3.96 (m, 2H), 2.87-3.05 (m, 5H), 2.62-2.69 (m, 1H), 2.56 (s, 3H), 2.23 (s, 3H), 2.16 (s, 6H), 1.27 (d, J=6.8 Hz, 6H), 0.93 (d, J=6.6 Hz, 3H).

Step 6. Preparation of 2-((2R)-4-{2-(2,6-dimethylphenyl)-5-[(5-isopropyl-2-methylphenoxy)methyl]-6-methyl-4-pyrimidinyl}-2-methyl-1-piperazinyl)acetamide

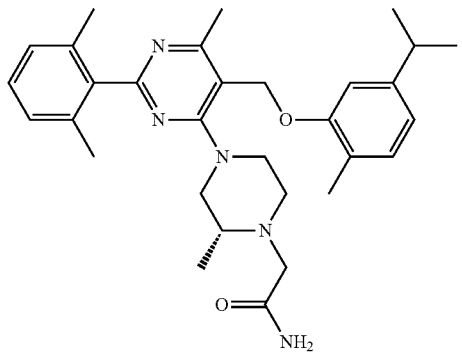

A mixture of 2-(2,6-dimethylphenyl)-5-[(5-isopropyl-2-methylphenoxy)methyl]-4-methyl-6-[(3R)-3-methylpiperazin-1-yl]pyrimidine (32 mg, 0.07 mmol), 2-bromoacetamide (29 mg, 0.21 mmol), sodium carbonate (44 mg) and DMA (1 mL) is heated at 60° C. under nitrogen with magnetic stirring for 18 h. The reaction mixture is allowed to cool and partitioned between EtOAc (8 mL) and water (2 mL). The organic layer is separated, washed with water (2 mL), brine (2 mL), dried over anhydrous sodium sulfate, filtered and evaporated to obtain a colorless oil. Purification by chromatography on silica gel (2% MeOH/DCM/0.1% Ammonium hydroxide) provides the title compound as a colorless oil. $^1$H NMR (300 MHz, CDCl$_3$) δ 7.06-7.26 (m, 5H), 6.81-6.83 (m, 2H), 5.58 (br d, J=6.3 Hz, 1H), 4.97 (dd, 2H), 3.77-3.86 (m, 2H), 3.25-3.33 (m, 2H), 2.80-3.00 (m, 4H), 2.45-2.62 (m, 5H), 2.22 (s, 3H), 2.16 (s, 6H), 1.27 (d, J=6.8 Hz, 6H), 0.93 (d, J=6.6 Hz, 3H).

Example 14

Synthesis of 2-(4-(2-(2,6-diethylphenyl)-5-((5-isopropyl-2-methylphenoxy)methyl)-6-methylpyrimidin-4-yl-5,6-dihydropyridin-1(2H)-yl)acetamide Step 1. Preparation of tert-butyl 4-(2-(2,6-diethylphenyl)-5-((5-isopropyl-2-methylphenoxy)methyl)-6-methylpyrimidin-4-yl)-5,6-dihydropyridine-1(2H)-carboxylate

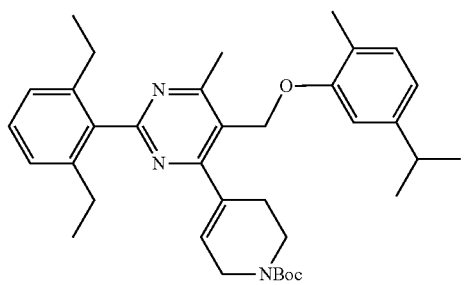

To a solution of 4-chloro-2-(2,6-diethylphenyl)-5-((5-isopropyl-2-methylphenoxy)methyl)-6-methylpyrimidine (423 mg, 1 mmol) and tert-butyl 4-(4,4,5,5-tetramethyl-1,3,2-dioxaborolan-2-yl)-5,6-dihydropyridine-1(2H)-carboxylate (Wustrow and Wise, *Synthesis,* 1991, 993) (371 mg, 1.2 mmol) in anhydrous DMF (5 mL) is added K$_2$CO$_3$ (414 mg, 3 mmol). The mixture is bubbled with N$_2$ for 15 min and PdCl$_2$dppf (28 mg) is added. The mixture is then heated under N$_2$ at 80° C. for 16 h. After cooling to room temperature, the mixture is diluted with ether, washed with water and brine. The organic layer is dried over anhydrous MgSO$_4$, concentrated and purified by silica gel column chromatography to provide the title product. [mass expected (569.8); mass found (M+1: 570.6)].

Step 2. Preparation of 2-(2,6-diethylphenyl)-5-((5-isopropyl-2-methylphenoxy)methyl)-4-methyl-6-(1,2,3,6-tetrahydropyridin-4-yl)pyrimidine

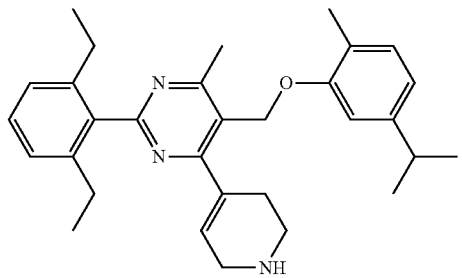

To a solution of tert-butyl 4-(2-(2,6-diethylphenyl)-5-((5-isopropyl-2-methylphenoxy)methyl)-6-methylpyrimidin-4-yl)-5,6-dihydropyridine-1 (2H)-carboxylate (741 mg, 1.3 mmol) in anhydrous $CH_2Cl_2$ (2 mL) at 0° C. is added TFA (2 mL). The mixture is then stirred a room temperature for 16 h. After removal of the solvent and excess of TFA under reduced pressure, the residue is neutralized with sat. $NaHCO_3$, and extracted with $CH_2Cl_2$. The extracts are dried over anhydrous $MgSO_4$, concentrated and purified by silica gel column chromatography to provide the desired product. [mass expected (469.7); mass found (M+1: 470.6)].

Step 3. Preparation of 2-(4-(2-(2,6-diethylphenyl)-5-((5-isopropyl-2-methylphenoxy)methyl)-6-methylpyrimidin-4-yl)-5,6-dihydropyridin-1 (2H)-yl)acetamide

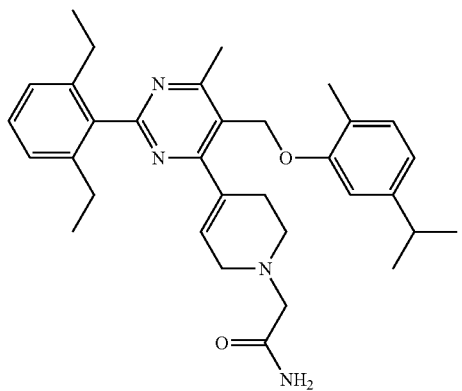

This compound is prepared in the similar manner as described in Example 13 (step 6) using 2-(2,6-diethylphenyl)-5-((5-isopropyl-2-methylphenoxy)methyl)-4-methyl-6-(1,2,3,6-tetrahydropyridin-4-yl)pyrimidine as the starting material. [mass expected (526.7); mass found (M+1: 527.4)].

Step 4. Preparation of 2-(4-(2-(2,6-diethylphenyl)-5-((5-isopropyl-2-methylphenoxy)methyl)-6-methylpyrimidin-4-yl)piperidin-1-yl)acetamide

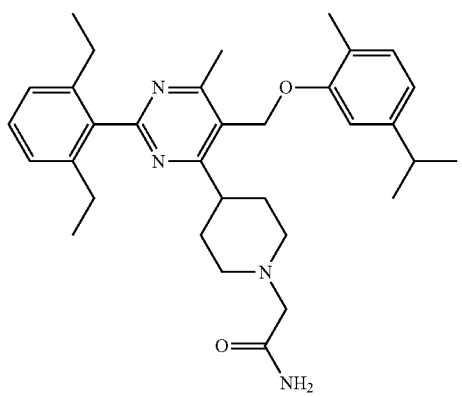

To a solution of 2-(4-(2-(2,6-diethylphenyl)-5-((5-isopropyl-2-methylphenoxy)methyl)-6-methylpyrimidin-4-yl)-5,6-dihydropyridin-1(2H)-yl)acetamide (131 mg, 0.25 mmol) in EtOAc (5 mL) is added 5% Pd/C (100 mg). The mixture is hydrogenated at room temperature and atmosphere pressure for 16 h. After filtered though celite, the solution is concentrated and purified by silica gel column chromatography to provide the title product. [mass expected (528.7); mass found (M+1: 529.4)].

Example 15

Additional 4,5-disubstituted-2-aryl Pyrimidines

The compounds shown in Tables I-V are prepared according to the procedures given in the above Schemes and further illustrated in the above Examples. All compounds in Tables I-IV and in Examples 1-14 exhibit an $IC_{50}$ of 2 micromolar or less in the calcium mobilization assay provided in Example 25, herein.

LC/MS data is provided in the tables, along with retention time in minutes and a number (1, 2 or 3) indicating the method used. For Table III, all LC/MS data was obtained by method 1. The LC/MS methods are as follows:

Method 1:
  Analytical HPLC/MS instrumentation: Analyses are performed using a Waters 600 series pump (Waters Corporation, Milford, Mass.), a Waters 996 Diode Array Detector and a Gilson 215 auto-sampler (Gilson Inc, Middleton, Wis.), Micromass® LCT time-of-flight electrospray ionization mass analyzer. Data are acquired using MassLynx™ 4.0 software, with OpenLynx Global Server™, OpenLynx™, and AutoLynx™ processing.
  Analytical HPLC conditions: 4.6×50 mm, Chromolith™ SpeedROD RP-18e column (Merck KGaA, Darmstadt, Germany); UV 10 spectra/sec, 220-340 nm summed; flow rate 6.0 mL/min; injection volume 1 µl;
    Gradient conditions—mobile phase A is 95% water, 5% methanol with 0.05% TFA; mobile phase B is 95% methanol, 5% water with 0.025% TFA, and the gradient is 0-0.5 min 10-100% B, hold at 100% B to 1.2 min, return to 10% B at 1.21 min inject-to-inject cycle time is 2.15 min.
  Analytical MS conditions: capillary voltage 3.5 kV; cone voltage 30V; desolvation and source temperature are 350° C. and 120° C., respectively; mass range 181-750 with a scan time of 0.22 seconds and an inter scan delay of 0.05 min.
Method 2:
  HPLC instrumentation: Analyses are performed using a Waters 600 series pump (Waters Corporation, Milford, Mass.), a Waters 996 Diode Array Detector and a Gilson 215 autosampler (Gilson Inc, Middleton, Wis.). Data are acquired using MassLynx 4.0 software, with OpenLynx processing.
  HPLC conditions: 4.6×50 mm, Chromolith SpeedRod column (Merck AEG); UV 5 spectra/sec, 220, 254 nm; flow rate 6.0 mL/min; injection volume 1-10 µl ;
    Gradient conditions—Mobile phase A 95% Water, 5% Methanol with 0.05% Formic acid;
      Mobile phase B 95% Methanol, 5% Water with 0.025% Formic acid;

| Gradient: | |
|---|---|
| Time (min) | % B |
| 0 | 5 |
| 0.01 | 5 |

-continued

Gradient:

| Time (min) | % B |
|---|---|
| 1.0 | 100 |
| 2 | 100 |
| 2.1 | 5 |

MS instrumentation: LC-MS experiments are performed using a Waters ZMD II Mass Spectrometer.

MS conditions: Electrospray positive ionization; capillary voltage 3.5 kV; cone voltage 30V; desolvation and source temperature 250° C. and 100° C. respectively; mass range 120-800 with a scan time of 0.5 seconds and an inter scan delay of 0.1 min.

Method 3:

HPLC instrumentation: Analyses are performed using a Waters 600 series pump (Waters Corp.), a Waters 996 Diode Array Detector and a Gilson 215 autosampler (Gilson Inc.). Data are acquired using MassLynx 4.0 software, with OpenLynx processing.

HPLC conditions: 4.6×50 mm, XTerra MS C18, 5 μm column (Waters Corp.); UV 10 spectra/sec, 220, 254 nm; flow rate 4.0 mL/min; injection volume 1-10 μl;

Gradient conditions—Mobile phase A 95% Water, 5% Methanol with 0.05% Formic acid;

Mobile phase B 95% Methanol, 5% Water with 0.025% Formic acid;

Gradient:

| Time (min) | % B |
|---|---|
| 0 | 5 |
| 0.01 | 5 |
| 2.0 | 100 |
| 3.50 | 100 |
| 3.51 | 5 |

MS instrumentation: LC-MS experiments are performed using a Waters ZMD II Mass Spectrometer.

MS conditions: Electrospray positive ionization; capillary voltage 3.5 kV; cone voltage 30V; desolvation and source temperature 250° C. and 100° C. respectively; mass range 120-800 with a scan time of 0.5 seconds and an inter scan delay of 0.1 min.

TABLE I

| Cpd # | Structure | Name | LCMS Retention Time | LCMS Mass (amu) | LCMS M + H (amu) | LCMS Method |
|---|---|---|---|---|---|---|
| 1 | 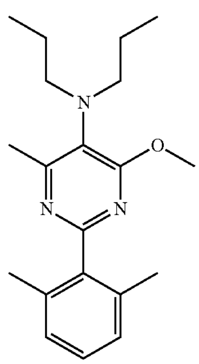 | 2-(2,6-dimethylphenyl)-4-methoxy-6-methyl-N,N-dipropylpyrimidin-5-amine | 1.29 | 327.2 | 328.3 | 1 |
| 2 | 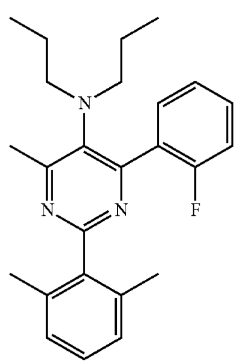 | 2-(2,6-dimethylphenyl)-4-(2-fluorophenyl)-6-methyl-N,N-dipropylpyrimidin-5-amine | 1.33 | 391.2 | 392.3 | 1 |

TABLE I-continued

| Cpd # | Structure | Name | LCMS Retention Time | LCMS Mass (amu) | LCMS M + H (amu) | LCMS Method |
|---|---|---|---|---|---|---|
| 3 | 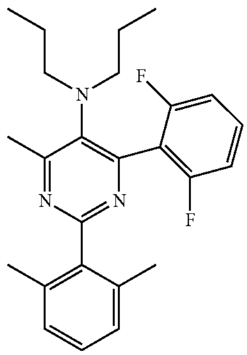 | 4-(2,6-difluorophenyl)-2-(2,6-dimethylphenyl)-6-methyl-N,N-dipropylpyrimidin-5-amine | | | | |
| 4 | 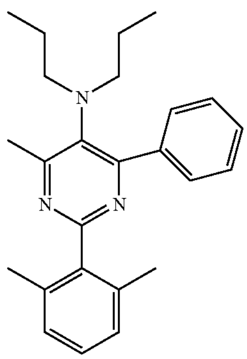 | 2-(2,6-dimethylphenyl)-4-methyl-6-phenyl-N,N-dipropylpyrimidin-5-amine | 1.34 | 373.3 | 374.3 | 1 |
| 5 | 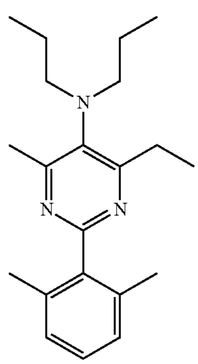 | 2-(2,6-dimethylphenyl)-4-ethyl-6-methyl-N,N-dipropylpyrimidin-5-amine | 1.33 | 325.3 | 326.1 | 1 |
| 6 | 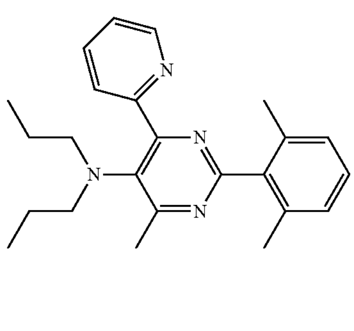 | 2-(2,6-dimethylphenyl)-4-methyl-N,N-dipropyl-6-pyridin-2-ylpyrimidin-5-amine | 1.21 | 374.2 | 375.3 | 1 |

TABLE I-continued

| Cpd # | Structure | Name | LCMS Retention Time | LCMS Mass (amu) | LCMS M + H (amu) | LCMS Method |
|---|---|---|---|---|---|---|
| 7 | 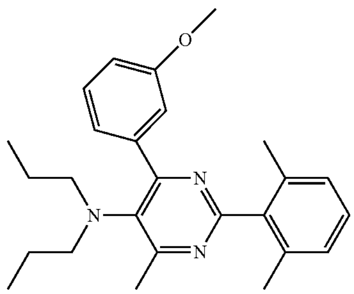 | 2-(2,6-dimethylphenyl)-4-(3-methoxyphenyl)-6-methyl-N,N-dipropylpyrimidin-5-amine | 1.35 | 403.3 | 404.3 | 1 |
| 8 | 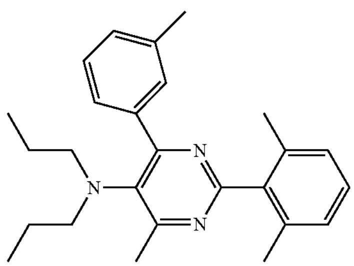 | 2-(2,6-dimethylphenyl)-4-methyl-6-(3-methylphenyl)-N,N-dipropylpyrimidin-5-amine | 1.37 | 387.3 | 388.3 | 1 |
| 9 | 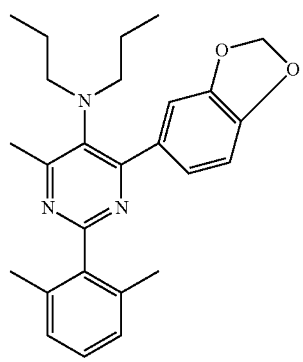 | 4-(1,3-benzodioxol-5-yl)-2-(2,6-dimethylphenyl)-6-methyl-N,N-dipropylpyrimidin-5-amine | 1.34 | 417.2 | 418.1 | 1 |
| 10 | 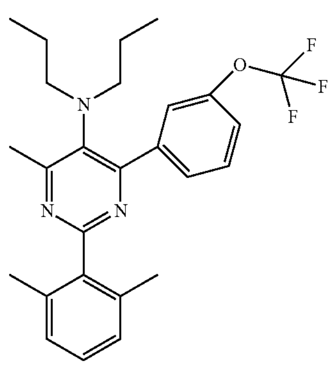 | 2-(2,6-dimethylphenyl)-4-methyl-N,N-dipropyl-6-[3-(trifluoromethoxy)phenyl]dipropylpyrimidin-5-amine | 1.39 | 457.2 | 458.2 | 1 |

TABLE I-continued

| Cpd # | Structure | Name | LCMS Retention Time | LCMS Mass (amu) | LCMS M + H (amu) | LCMS Method |
|---|---|---|---|---|---|---|
| 11 | 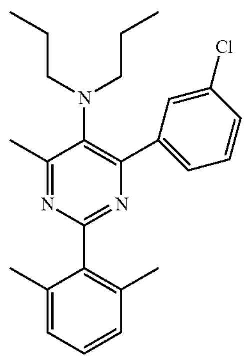 | 4-(3-chlorophenyl)-2-(2,6-dimethylphenyl)-6-methyl-N,N-dipropylpyrimidin-5-amine | 1.39 | 407.2 | 408.1 | 1 |
| 12 | 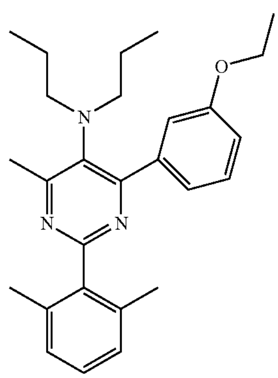 | 2-(2,6-dimethylphenyl)-4-(3-ethoxyphenyl)-6-methyl-N,N-dipropylpyrimidin-5-amine | 1.36 | 417.3 | 418.2 | 2 |
| 13 | 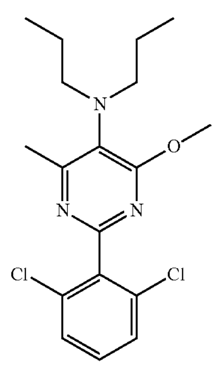 | 2-(2,6-dichlorophenyl)-4-methyl-6-methyl-N,N-dipropylpyrimidin-5-amine | 1.35 | 367.1 | 368.3 | 1 |
| 14 | 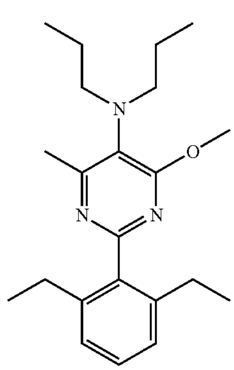 | 2-(2,6-diethylphenyl)-4-methoxy-6-methyl-N,N-dipropylpyrimidin-5-amine | 1.33 | 355.3 | 356.4 | 1 |

| Cpd # | Structure | Name | LCMS Retention Time | LCMS Mass (amu) | LCMS M + H (amu) | LCMS Method |
|---|---|---|---|---|---|---|
| 15 | 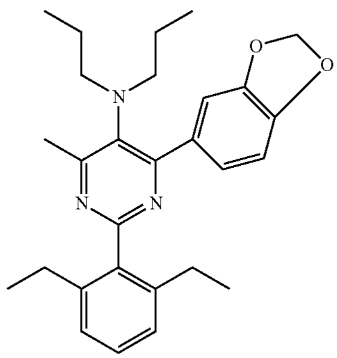 | 4-(1,3-benzodioxol-5-yl)-2-(2,6-diethylphenyl)-6-methyl-N,N-dipropylpyrimidin-5-amine | 1.37 | 445.3 | 446.3 | 1 |
| 16 | 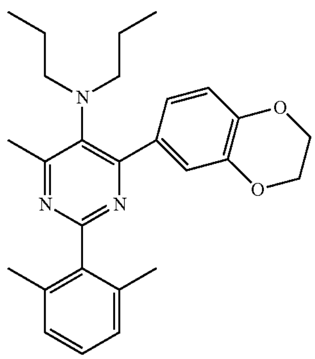 | 4-(2,3-dihydro-1,4-benzodioxin-6-yl)-2-(2,6-dimethylphenyl)-6-methyl-N,N-dipropylpyrimidin-5-amine | 1.33 | 431.3 | 432.3 | 1 |
| 17 | 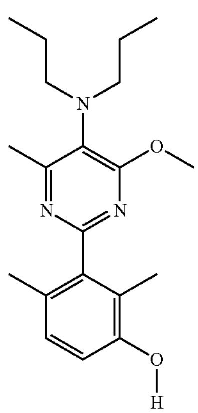 | 3-[5-(dipropylamino)-4-methoxy-6-methylpyrimidin-2-yl]-2,4-dimethylphenol | 1.23 | 343.2 | 344.3 | 1 |
| 18 | 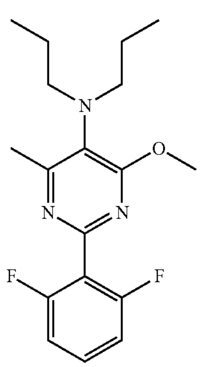 | 2-(2,6-difluorophenyl)-4-methoxy-6-methyl-N,N-dipropylpyrimidin-5-amine | 1.32 | 335.2 | 336.2 | 1 |

TABLE I-continued

| Cpd # | Structure | Name | LCMS Retention Time | LCMS Mass (amu) | LCMS M + H (amu) | LCMS Method |
|---|---|---|---|---|---|---|
| 19 | 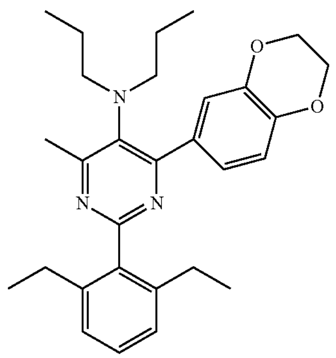 | 2-(2,6-diethylphenyl)-4-(2,3-dihydro-1,4-benzodioxin-6-yl)-6-methyl-N,N-dipropylpyrimidin-5-amine | 1.37 | 459.3 | 460.3 | 1 |
| 20 | 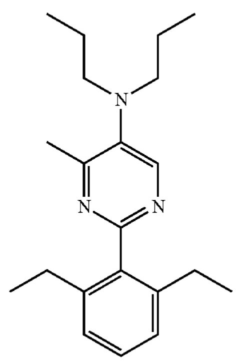 | 2-(2,6-diethylphenyl)-4-methyl-N,N-dipropylpyrimidin-5-amine | 1.31 | 325.3 | 326.4 | 2 |
| 21 | 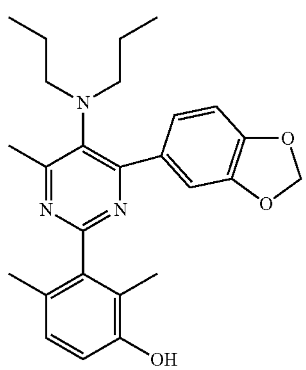 | 3-[4-(1,3-benzodioxol-5-yl)-5-(dipropylamino)-6-methylpyrimidin-2-yl]-2,4-dimethylphenyl | 1.29 | 433.2 | 434.3 | 1 |
| 22 | 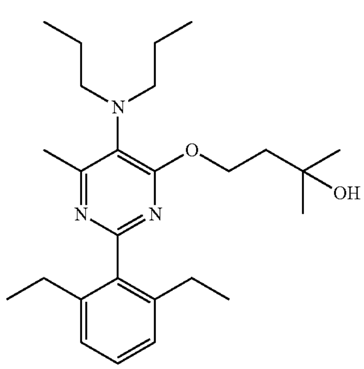 | 4-{[2-(2,6-diethylphenyl)-5-(dipropylamino)-6-methylpyrimidin-4-yl]oxy}-2-methylbutan-2-ol | 1.29 | 427.3 | 428.2 | 1 |

TABLE I-continued

| Cpd # | Structure | Name | LCMS Retention Time | LCMS Mass (amu) | LCMS M + H (amu) | LCMS Method |
|---|---|---|---|---|---|---|
| 23 | 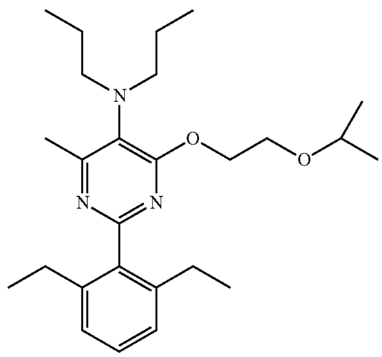 | 2-(2,6-diethylphenyl)-4-(2-isopropoxyethoxy)-6-methyl-N,N-dipropylpyrimidin-5-amine | 1.39 | 427.3 | 428.2 | 1 |
| 24 | 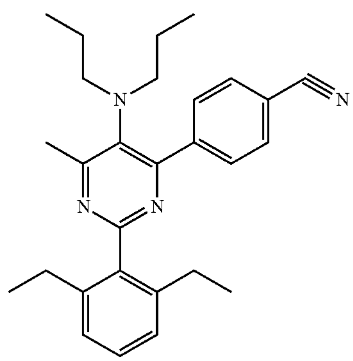 | 4-[2-(2,6-diethylphenyl)-5-(dipropylamino)-6-methylpyrimidin-4-yl]benzonitrile | 1.35 | 426.3 | 427.2 | 1 |
| 25 | 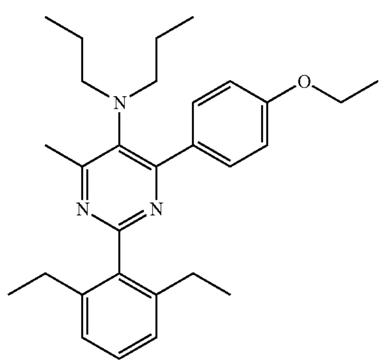 | 2-(2,6-diethylphenyl)-4-(4-ethoxyphenyl)-6-methyl-N,N-dipropylpyrimidin-5-amine | 1.41 | 445.3 | 446.2 | 1 |
| 26 | 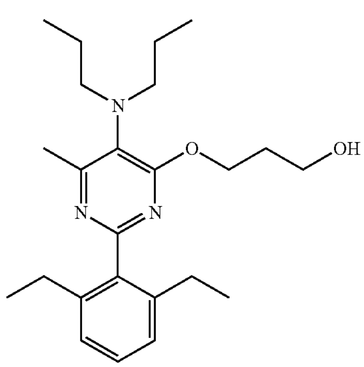 | 3-{[2-(2,6-diethylphenyl)-5-(dipropylamino)-6-methylpyrimidin-4-yl]oxy}propan-1-ol | | | | |

TABLE I-continued

| Cpd # | Structure | Name | LCMS Retention Time | LCMS Mass (amu) | LCMS M + H (amu) | LCMS Method |
|---|---|---|---|---|---|---|
| 27 | 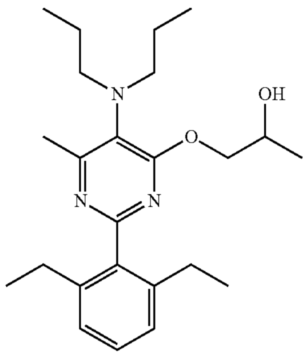 | 1-{[2-(2,6-diethylphenyl)-5-(dipropylamino)-6-methylpyrimidin-4-yl]oxy}propan-2-ol | | | | |
| 28 | 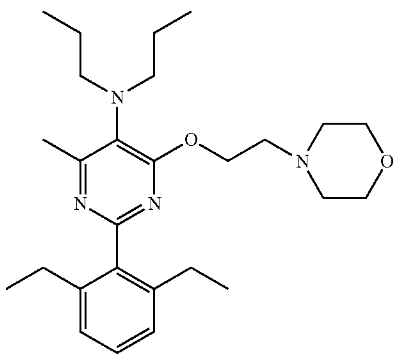 | 2-(2,6-diethylphenyl)-4-methyl-6-(2-morpholin-4-ylethoxy)-N,N-dipropylpyrimidin-5-amine | 1.17 | 454.3 | 455.3 | 1 |
| 29 | 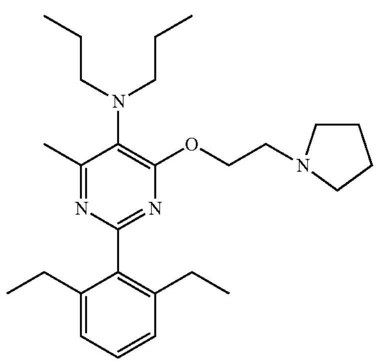 | 2-(2,6-diethylphenyl)-4-methyl-N,N-dipropyl-6-(2-pyrrolidin-1-ylethoxy)pyrimidin-5-amine | 1.16 | 438.3 | 439.3 | 1 |
| 30 | 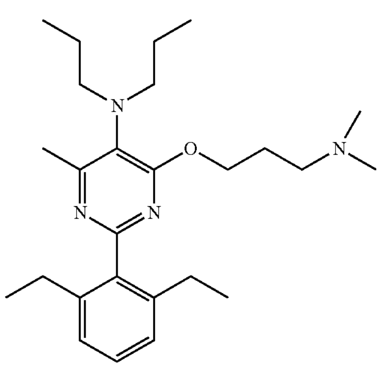 | 2-(2,6-diethylphenyl)-4-[3-(dimethylamino)propoxy]-6-methyl-N,N-dipropylpyrimidin-5-amine | 1.16 | 426.3 | 427.3 | 1 |

TABLE I-continued

| Cpd # | Structure | Name | LCMS Retention Time | LCMS Mass (amu) | LCMS M + H (amu) | LCMS Method |
|---|---|---|---|---|---|---|
| 31 | 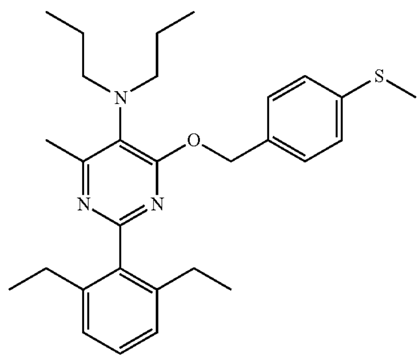 | 2-(2,6-diethylphenyl)-4-methyl-6-{[4-(methylthio)benzyl]oxy}-N,N-dipropylpyrimidin-5-amine | 1.41 | 477.3 | 478.4 | 1 |
| 32 | 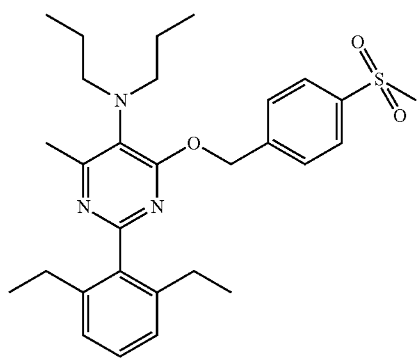 | 2-(2,6-diethylphenyl)-4-methyl-6-{[4-(methylsulfonyl)benzyl]oxy}-N,N-dipropylpyrimidin-5-amine | 1.29 | 509.3 | 510.4 | 1 |
| 33 | 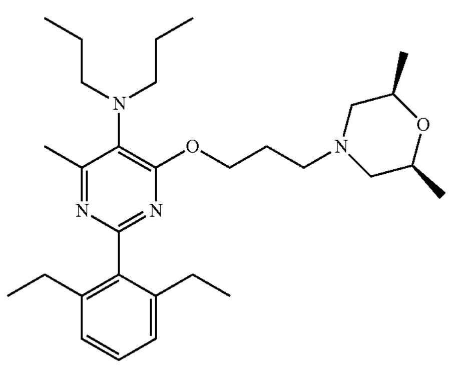 | 2-(2,6-diethylphenyl)-4-{3-[(2R,6S)-2,6-dimethylmorpholin-4-yl]propoxy}-6-methyl-N,N-dipropylpyrimidin-5-amine | 1.19 | 496.4 | 497.3 | 1 |
| 34 | 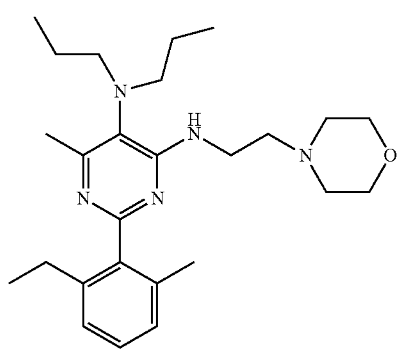 | 2-(2,6-diethylphenyl)-6-methyl-N~4~-(2-morpholin-4-ylethyl)-N~5~, N~5~-dipropylpyrimidine-4,5-diamine | 1.07 | 453.3 | 454.4 | 1 |

TABLE I-continued

| Cpd # | Structure | Name | LCMS Retention Time | LCMS Mass (amu) | LCMS M + H (amu) | LCMS Method |
|---|---|---|---|---|---|---|
| 35 | 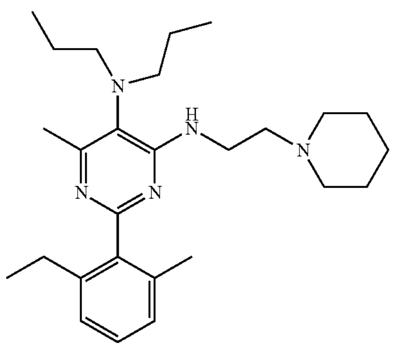 | 2-(2,6-diethylphenyl)-6-methyl-N~4~-(2-piperidin-1-ylethyl)-N~5~,N~5~-dipropylpyrimidine-4,5-diamine | 1.07 | 451.4 | 452.4 | 1 |
| 36 | 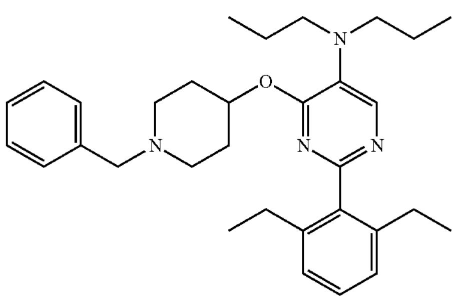 | 4-[(1-benzylpiperidin-4-yl)oxy]-2-(2,6-diethylphenyl)-N,N-dipropylpyrimidin-5-amine | | | | |
| 37 | 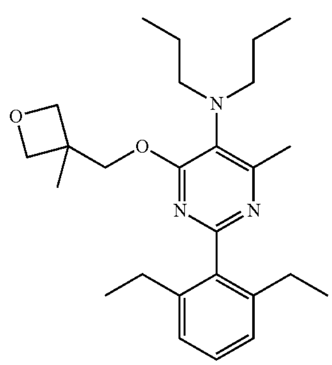 | 2-(2,6-diethylphenyl)-4-methyl-6-[(3-methyloxetan-3-yl)methoxy]-N,N-dipropylpyrimidin-5-amine | 1.33 | 425.3 | 426.2 | 1 |
| 38 | 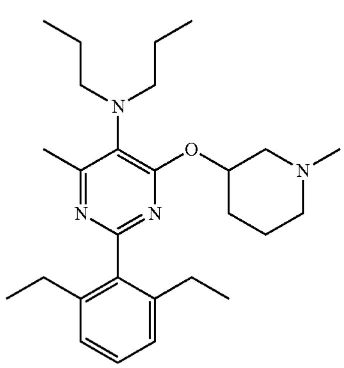 | 2-(2,6-diethylphenyl)-4-methyl-6-[(1-methylpiperidin-3-yl)oxy]-N,N-dipropylpyrimidin-5-amine | | | | |

TABLE I-continued

| Cpd # | Structure | Name | LCMS Retention Time | LCMS Mass (amu) | LCMS M + H (amu) | LCMS Method |
|---|---|---|---|---|---|---|
| 39 | 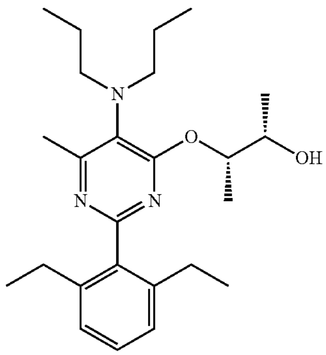 | (2S,3S)-3-{[2-(2,6-diethylphenyl)-5-(dipropylamino)-6-methylpyrimidin-4-yl]oxy}butan-2-ol | | | | |
| 40 | 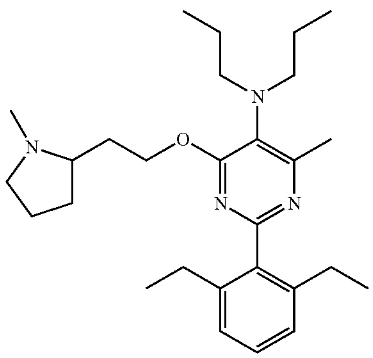 | 2-(2,6-diethylphenyl)-4-methyl-6-[2-(1-methylpyrrolidin-2-yl)ethoxy]-N,N-dipropylpyrimidin-5-amine | 1.22 | 452.4 | 453.4 | 1 |
| 41 | 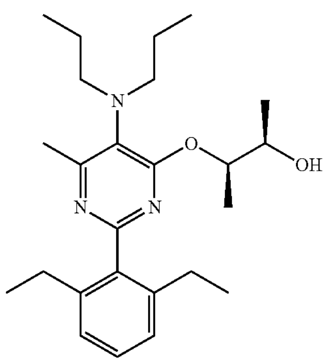 | (2R,3R)-3-{[2-(2,6-diethylphenyl)-5-(dipropylamino)-6-methylpyrimidin-4-yl]oxy}butan-2-ol | 1.31 | 413.3 | 415.4 | 1 |
| 42 | 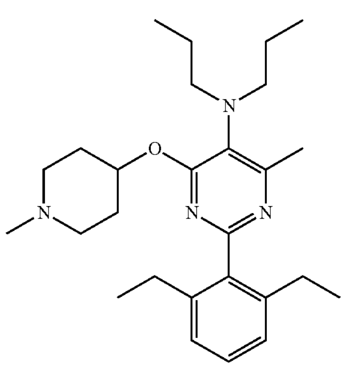 | 2-(2,6-diethylphenyl)-4-methyl-6-[(1-methylpiperidin-4-yl)oxy]-N,N-dipropylpyrimidin-5-amine | 1.22 | 438.3 | 439.4 | 1 |

TABLE I-continued

| Cpd # | Structure | Name | LCMS Retention Time | LCMS Mass (amu) | LCMS M + H (amu) | LCMS Method |
|---|---|---|---|---|---|---|
| 43 | 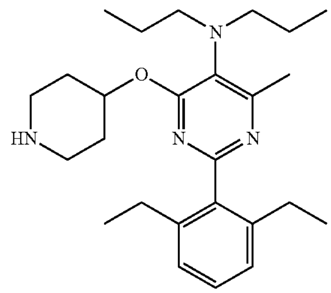 | 2-(2,6-diethylphenyl)-4-methyl-6-(piperidin-4-yloxy)-N,N-dipropylpyrimidin-5-amine | | | | |
| 44 | 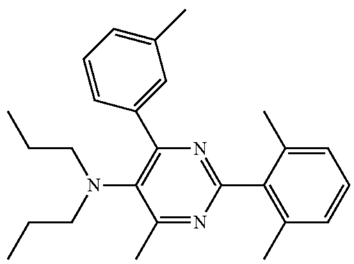 | 1-[2-(2,6-diethylphenyl)-5-(dipropylamino)-6-methylpyrimidin-4-yl]piperidin-4-ol | | | | |
| 45 | 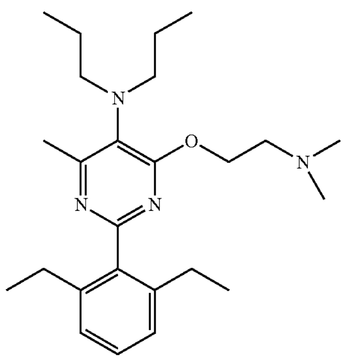 | 2-(2,6-diethylphenyl)-4-[2-(dimethylamino)ethoxy]-6-methyl-N,N-dipropylpyrimidin-5-amine | 2.63 | 412.6 | 413.7 | 3 |
| 46 | 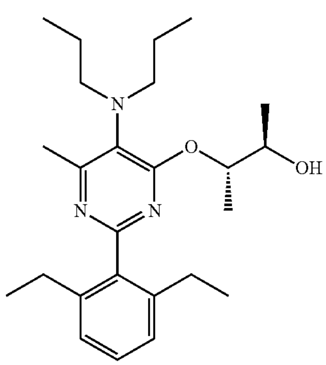 | (2R,3S)-3-{[2-(2,6-diethylphenyl)-5-(dipropylamino)-6-methylpyrimidin-4-yl]oxy}butan-2-ol | | | | |

TABLE I-continued

| Cpd # | Structure | Name | LCMS Retention Time | LCMS Mass (amu) | LCMS M + H (amu) | LCMS Method |
|---|---|---|---|---|---|---|
| 47 | 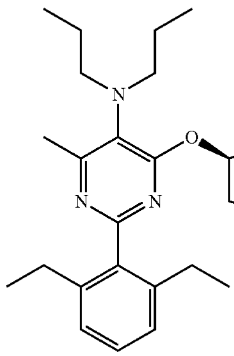 | (1S,2R)-2-{[2-(2,6-diethylphenyl)-5-(dipropylamino)-6-methylpyrimidin-4-yl]oxy}cyclopentanol | 1.27 | 425.3 | 426.3 | 1 |
| 48 | 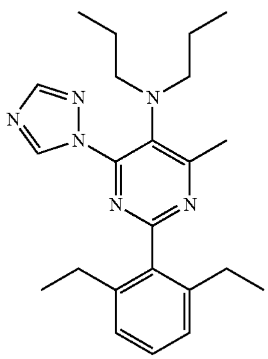 | 2-(2,6-diethylphenyl)-4-methyl-N,N-dipropyl-6-(1H-1,2,4-triazol-1-yl)pyrimidin-5-amine | 1.32 | 392.3 | 393.4 | 1 |
| 49 | 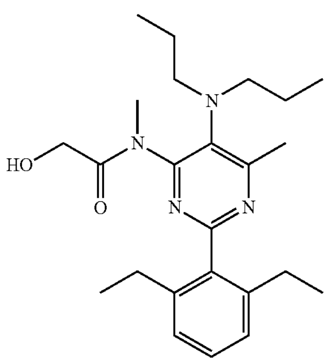 | N-[2-(2,6-diethylphenyl)-5-(dipropylamino)-6-methylpyrimidin-4-yl]-2-hydroxy-N-methylacetamide | 1.24 | 412.3 | 413.4 | 1 |
| 50 | 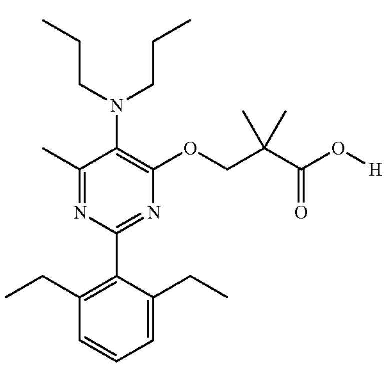 | 3-{[2-(2,6-diethylphenyl)-5-(dipropylamino)-6-methylpyrimidin-4-yl]oxy}-2,2-dimethylpropanoic acid | 2.9 | 441.6 | 442.6 | 3 |

TABLE I-continued

| Cpd # | Name | LCMS Retention Time | LCMS Mass (amu) | LCMS M + H (amu) | LCMS Method |
|---|---|---|---|---|---|
| 51 | 2-(2,6-diethylphenyl)-4-methyl-N,N-dipropyl-6-(1H-pyrazol-1-yl)pyrimidin-5-amine | | | | |
| 52 | 2-(2,6-diethylphenyl)-4-methyl-6-[(1-methylpyrrolidin-3-yl)oxy]-N,N-dipropylpyrimidin-5-amine | 1.18 | 424.3 | 425.4 | 1 |
| 53 | 2-(2,6-diethylphenyl)-4-methyl-N,N-dipropyl-6-(pyridin-3-yloxy)pyrimidin-5-amine | | | | |
| 54 | 2-(2,6-diethylphenyl)-4-methyl-6-[2-(4-oxidomorpholin-4-yl)ethoxy]-N,N-dipropylpyrimidin-5-amine | 1.17 | 471.3 | 471.5 | 1 |

TABLE I-continued

| Cpd # | Structure | Name | LCMS Retention Time | LCMS Mass (amu) | LCMS M + H (amu) | LCMS Method |
|---|---|---|---|---|---|---|
| 55 | 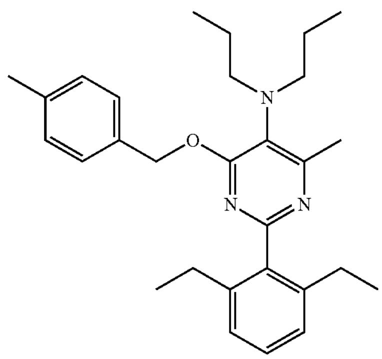 | 2-(2,6-diethylphenyl)-4-methyl-6-[(4-methylbenzyl)oxy]-N,N-dipropylpyrimidin-5-amine | 1.52 | 445.3 | 446.3 | 1 |
| 56 | 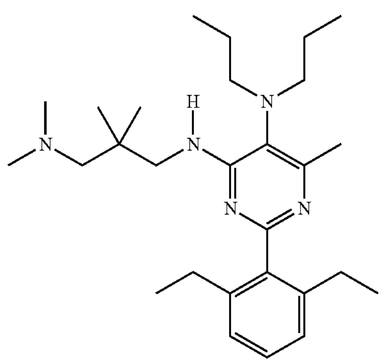 | 2-(2,6-diethylphenyl)-N~4~-[3-(dimethylamino)-2,2-dimethylpropyl]-6-methyl-N~5~, N~5~-dipropylpyrimidine-4,5-diamine | 1.1 | 453.4 | 454.4 | 1 |

TABLE II

| Cpd # | Structure | Name | LCMS Retention Time | LCMS Mass (amu) | LCMS M + H (amu) | LCMS Method |
|---|---|---|---|---|---|---|
| 57 | 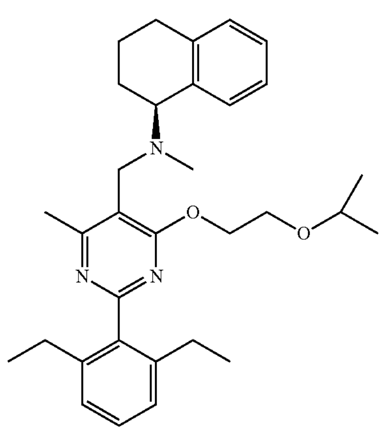 | (1S)-N-{[2-(2,6-diethylphenyl)-4-(2-isopropoxyethoxy)-6-methylpyrimidin-5-yl]methyl}-N-methyl-1,2,3,4-tetrahydronaphthalen-1-amine | 1.19 | 501.3 | 502.2 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 58 | 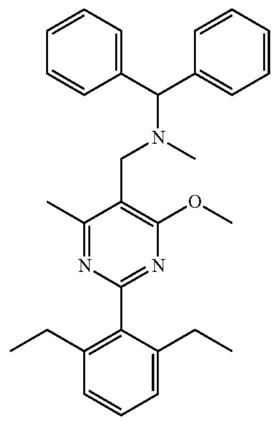 | N-{[2-(2,6-diethylphenyl)-4-methoxy-6-methylpyrimidin-5-yl]methyl}-N-methyl-1,1-diphenylmethanamine | 1.17 | 465.3 | 466.4 | 1 |
| 59 | 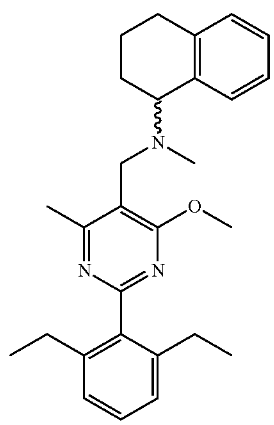 | N-{[2-(2,6-diethylphenyl)-4-methoxy-6-methylpyrimidin-5-yl]methyl}-N-methyl-1,2,3,4-tetrahydronaphthalen-1-amine | 1.16 | 429.3 | 430.4 | 1 |
| 60 | 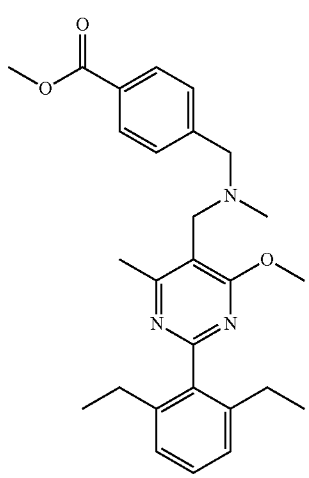 | methyl 4-{[{[2-(2,6-diethylphenyl)-4-methoxy-6-methylpyrimidin-5-yl]methyl}(methyl)amino]methyl}benzoate | 1.13 | 447.3 | 448.2 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 61 | 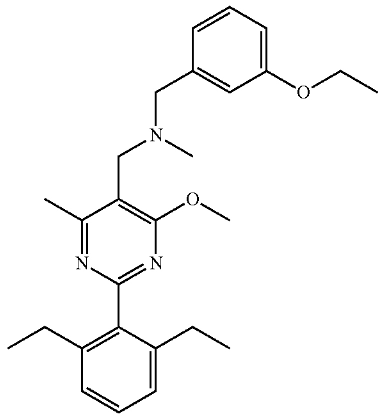 | 1-[2-(2,6-diethylphenyl)-4-methoxy-6-methylpyrimidin-5-yl]-N-(3-ethoxybenzyl)-N-methylmethanamine | 1.17 | 433.3 | 434.2 | 1 |
| 62 | 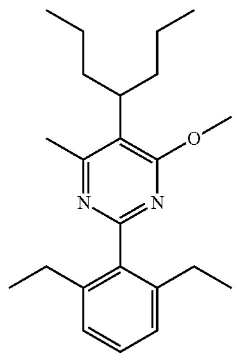 | 2-(2,6-diethylphenyl)-4-methoxy-6-methyl-5-(1-propylbutyl)pyrimidine | 1.34 | 354.3 | 355.2 | 1 |
| 63 | 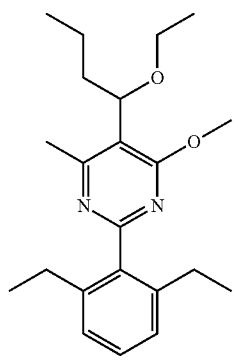 | 2-(2,6-diethylphenyl)-5-(1-ethoxybutyl)-4-methoxy-6-methylpyrimidine | 1.31 | 356.2 | 357.2 | 1 |
| 64 | 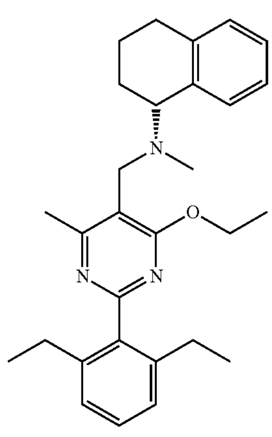 | (1S)-N-{[2-(2,6-diethylphenyl)-4-ethoxy-6-methylpyrimidin-5-yl]methyl}-N-methyl-1,2,3,4-tetrahydronaphthalen-1-amine | 1.16 | 443.3 | 444.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 65 | 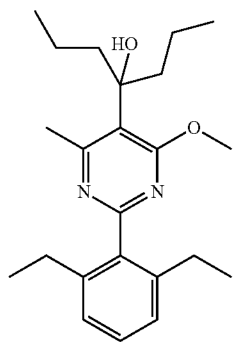 | 4-[2-(2,6-diethylphenyl)-4-methoxy-6-methylpyrimidin-5-yl]heptan-4-ol | 2.94 | 370.5 | 371.4 | 3 |
| 66 | 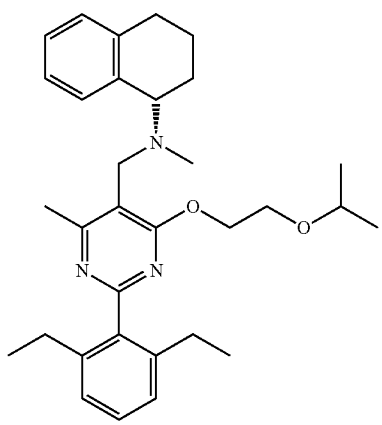 | (1R)-N-{[2-(2,6-diethylphenyl)-4-(2-isopropoxyethoxy)-6-methylpyrimidin-5-yl]methyl}-N-methyl-1,2,3,4-tetrahydronaphthalen-1-amine | 1.22 | 501.3 | 502.2 | 1 |
| 67 | 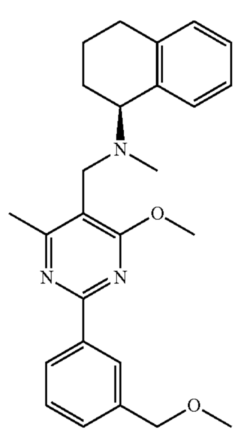 | (1S)-N-({4-methoxy-2-[3-(methoxymethyl)phenyl]-6-methylpyrimidin-5-yl}methyl)-N-methyl-1,2,3,4-tetrahydronaphthalen-1-amine | 1.17 | 417.2 | 418.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 68 | 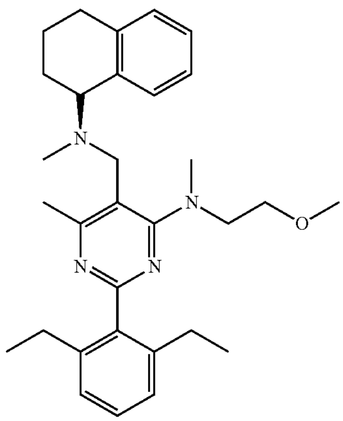 | 2-(2,6-diethylphenyl)-N-(2-methoxyethyl)-N,6-dimethyl-5-({methyl[(1R)-1,2,3,4-tetrahydronaphthalen-1-yl]amino}methyl)pyrimidin-4-amine | 1.23 | 486.3 | 487.4 | 1 |
| 69 | 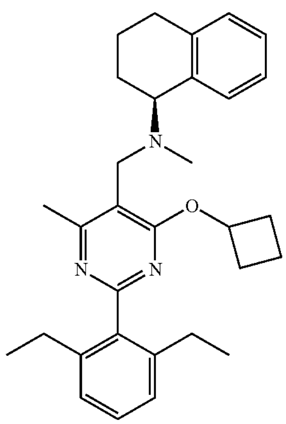 | (1S)-N-{[4-(cyclobutyloxy)-2-(2,6-diethylphenyl)-6-methylpyrimidin-5-yl]methyl}-N-methyl-1,2,3,4-tetrahydronaphthalen-1-amine | 1.25 | 469.3 | 471.4 | 1 |
| 70 | 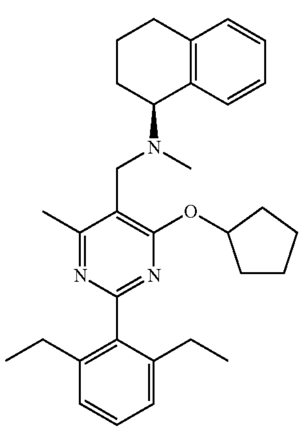 | (1S)-N-{[4-(cyclopentyloxy)-2-(2,6-diethylphenyl)-6-methylpyrimidin-5-yl]methyl}-N-methyl-1,2,3,4-tetrahydronaphthalen-1-amine | 1.25 | 483.3 | 484.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 71 | 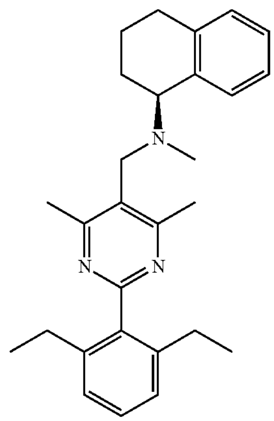 | (1S)-N-{[2-(2,6-diethylphenyl)-4,6-dimethylpyrimidin-5-yl]methyl}-N-methyl-1,2,3,4-tetrahydronaphthalen-1-amine | 1.15 | 41.33 | 414.3 | 1 |
| 72 | 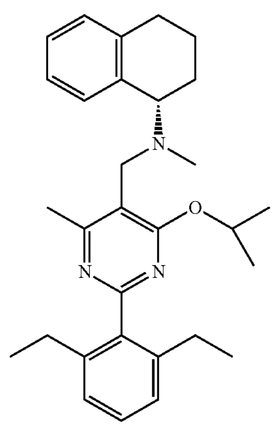 | (1S)-N-{[2-(2,6-diethylphenyl)-4-isopropoxy-6-methylpyrimidin-5-yl]methyl}-N-methyl-1,2,3,4-tetrahydronaphthalen-1-amine | 1.19 | 457.3 | 458.4 | 1 |
| 73 | 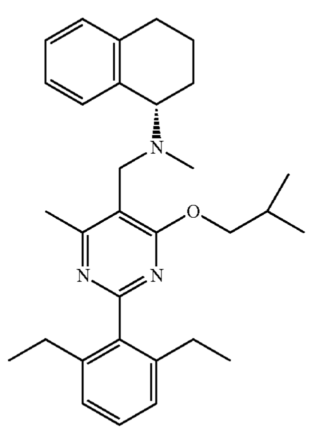 | (1S)-N-{[2-(2,6-diethylphenyl)-4-isobutoxy-6-methylpyrimidin-5-yl]methyl}-N-methyl-1,2,3,4-tetrahydronaphthalen-1-amine | 1.22 | 471.3 | 472.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 74 | 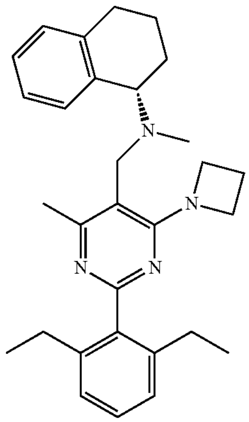 | (1S)-N-{[4-azetidin-1-yl-2-(2,6-diethylphenyl)-6-methylpyrimidin-5-yl]methyl}-N-methyl-1,2,3,4-tetrahydronaphthalen-1-amine | 1.18 | 454.3 | 455.4 | 1 |
| 75 | 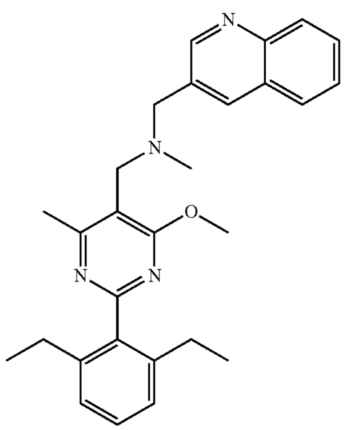 | 1-[2-(2,6-diethylphenyl)-4-methoxy-6-methylpyrimidin-5-yl]-N-methyl-N-(quinolin-3-ylmethyl)methanamine | 1.14 | 440.3 | 441.3 | 1 |
| 76 | 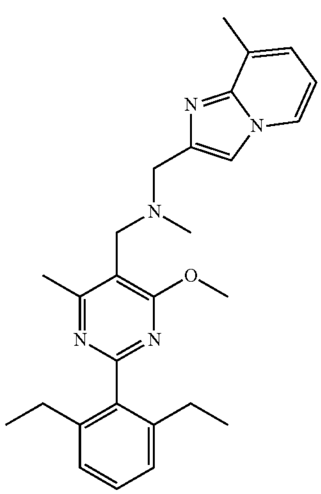 | 1-[2-(2,6-diethylphenyl)-4-methoxy-6-methylpyrimidin-5-yl]-N-methyl-N-[(8-methylimidazo[1,2-a]pyridin-2-yl)methyl]methanamine | 1.13 | 443.3 | 444.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 77 | 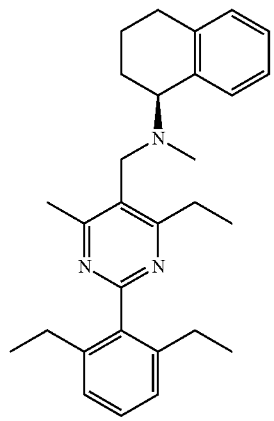 | (1S)-N-{[2-(2,6-diethylphenyl)-4-ethyl-6-methylpyrimidin-5-yl]methyl}-N-methyl-1,2,3,4-tetrahydronaphthalen-1-amine | 1.2 | 427.3 | 428.3 | 1 |
| 78 | 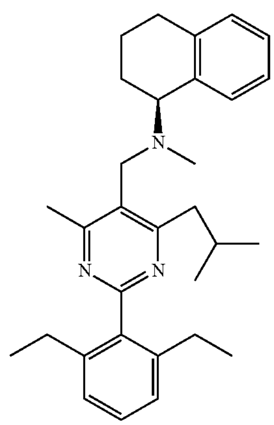 | (1S)-N-{[2-(2,6-diethylphenyl)-4-isobutyl-6-methylpyrimidin-5-yl]methyl}-N-methyl-1,2,3,4-tetrahydronaphthalen-1-amine | 1.24 | 455.3 | 456.4 | 1 |
| 79 | 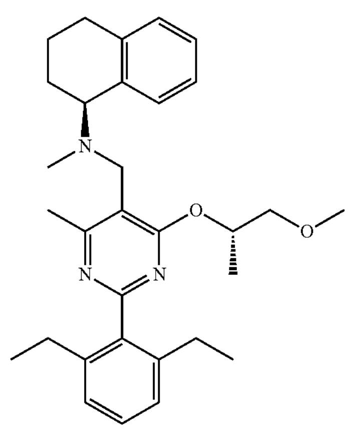 | (1S)-N-({2-(2,6-diethylphenyl)-4-[(1S)-2-methoxy-1-methylethoxy]-6-methylpyrimidin-5-yl}methyl)-N-methyl-1,2,3,4-tetrahydronaphthalen-1-amine | 2.34 | 487.7 | 488.4 | 3 |

TABLE II-continued

| Cpd # | Structure | Name | LCMS Retention Time | LCMS Mass (amu) | LCMS M + H (amu) | LCMS Method |
|---|---|---|---|---|---|---|
| 80 | 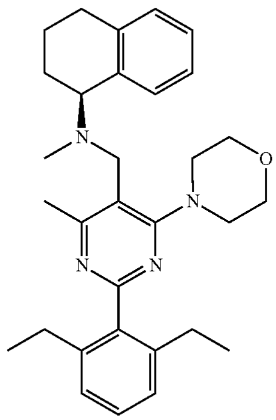 | (1S)-N-{[2-(2,6-diethylphenyl)-4-methyl-6-morpholin-4-ylpyrimidin-5-yl]methyl}-N-methyl-1,2,3,4-tetrahydronaphthalen-1-amine | 1.17 | 484.3 | 485.4 | 1 |
| 81 | 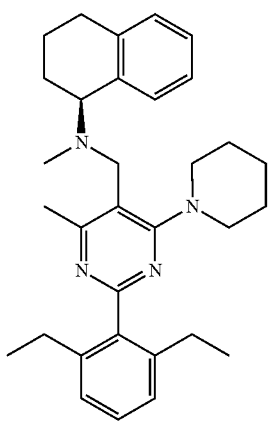 | (1S)-N-{[2-(2,6-diethylphenyl)-4-methyl-6-piperidin-1-ylpyrimidin-5-yl]methyl}-N-methyl-1,2,3,4-tetrahydronaphthalen-1-amine | 1.24 | 482.3 | 483.4 | 1 |
| 82 | 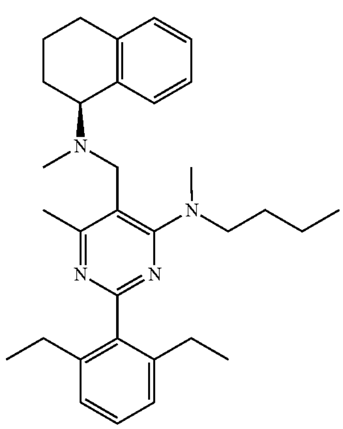 | N-butyl-2-(2,6-diethylphenyl)-N,6-dimethyl-5-({methyl[(1S)-1,2,3,4-tetrahydronaphthalen-1-yl]amino}methyl)pyrimidin-4-amine | 1.25 | 484.4 | 485.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 83 | 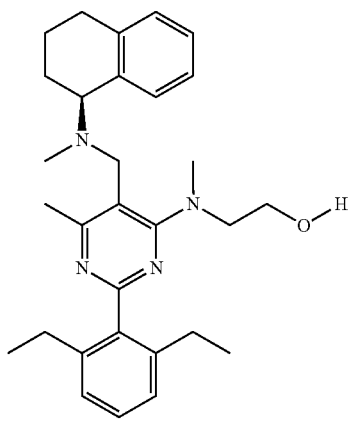 | 2-[[2-(2,6-diethylphenyl)-6-methyl-5-({methyl[(1S)-1,2,3,4-tetrahydronaphthalen-1-yl]amino}methyl)pyrimidin-4-yl](methyl)amino]ethanol | 1.15 | 472.3 | 473.4 | 1 |
| 84 | 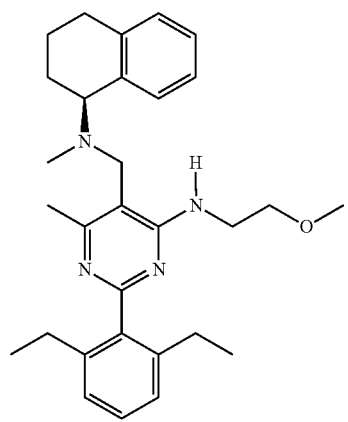 | 2-(2,6-diethylphenyl)-N-(2-methoxyethyl)-6-methyl-5-({methyl[(1S)-1,2,3,4-tetrahydronaphthalen-1-yl]amino}methyl)pyrimidin-4-amine | 1.21 | 472.3 | 473.4 | 1 |
| 85 | 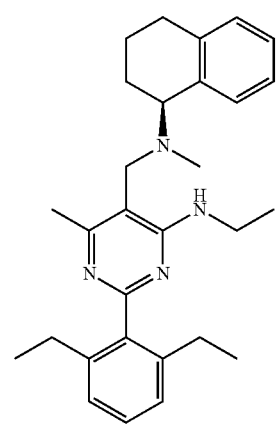 | 2-(2,6-diethylphenyl)-6-methyl-5-({methyl[(1S)-1,2,3,4-tetrahydronaphthalen-1-yl]amino}methyl)-N-propylpyrimidin-4-amine | 1.23 | 456.3 | 457.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 86 | 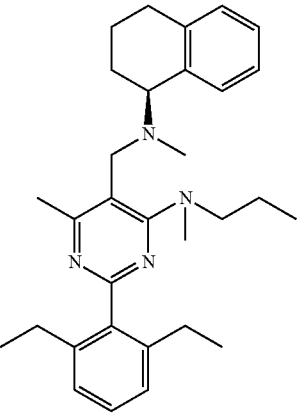 | 2-(2,6-diethylphenyl)-N,6-dimethyl-5-({methyl[(1S)-1,2,3,4-tetrahydronaphthalen-1-yl]amino}methyl)-N-propylpyrimidin-4-amine | 1.23 | 470.3 | 471.4 | 1 |
| 87 | 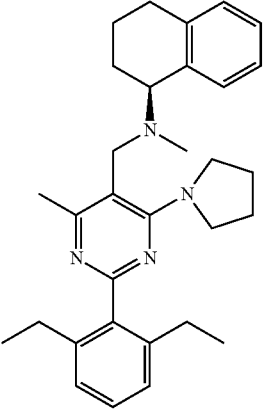 | (1S)-N-{[2-(2,6-diethylphenyl)-4-methyl-6-pyrrolidin-1-ylpyrimidin-5-yl]methyl}-N-methyl-1,2,3,4-tetrahydronaphthalen-1-amine | 1.2 | 468.3 | 469.5 | 1 |
| 88 | 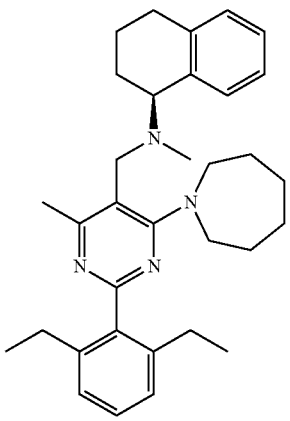 | (1S)-N-{[4-azepan-1-yl-2-(2,6-diethylphenyl)-6-methylpyrimidin-5-yl]methyl}-N-methyl-1,2,3,4-tetrahydronaphthalen-1-amine | 1.23 | 496.4 | 497.6 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 89 | 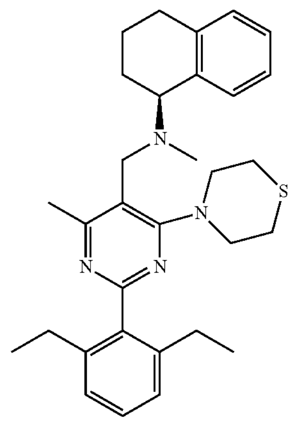 | (1S)-N-{[2-(2,6-diethylphenyl)-4-methyl-6-thiomorpholin-4-ylpyrimidin-5-yl]methyl}-N-methyl-1,2,3,4-tetrahydronaphthalen-1-amine | 1.22 | 500.3 | 501.6 | 1 |
| 90 | 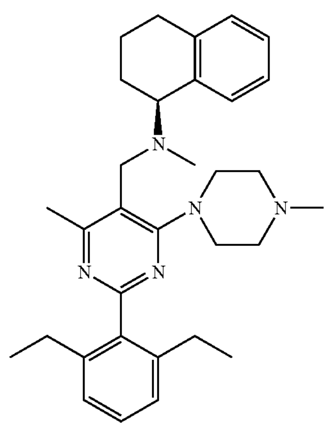 | (1S)-N-{[2-(2,6-diethylphenyl)-4-methyl-6-(4-methylpiperazin-1-yl)pyrimidin-5-yl]methyl}-N-methyl-1,2,3,4-tetrahydronaphthalen-1-amine | | | | |
| 91 | 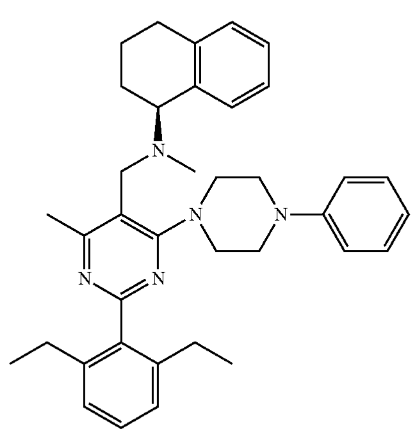 | (1S)-N-{[2-(2,6-diethylphenyl)-4-methyl-6-(4-phenylpiperazin-1-yl)pyrimidin-5-yl]methyl}-N-methyl-1,2,3,4-tetrahydronaphthalen-1-amine | 1.26 | 559.4 | 560.7 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 92 | 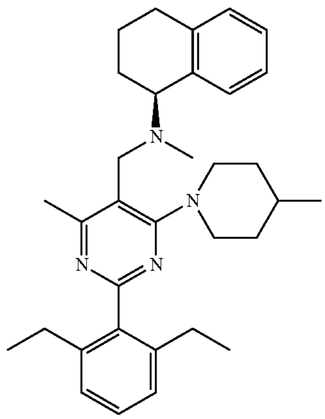 | (1S)-N-{[2-(2,6-diethylphenyl)-4-methyl-6-(4-methylpiperidin-1-yl)pyrimidin-5-yl]methyl}-N-methyl-1,2,3,4-tetrahydronaphthalen-1-amine | 1.25 | 496.4 | 497.6 | 1 |
| 93 | 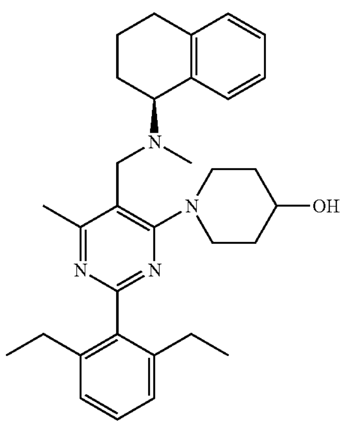 | 1-[2-(2,6-diethylphenyl)-6-methyl-5-({methyl[(1S)-1,2,3,4-tetrahydronaphthalen-1-yl]amino}methyl)pyrimidin-4-yl]piperidin-4-ol | 1.17 | 498.3 | 499.6 | 1 |
| 94 | 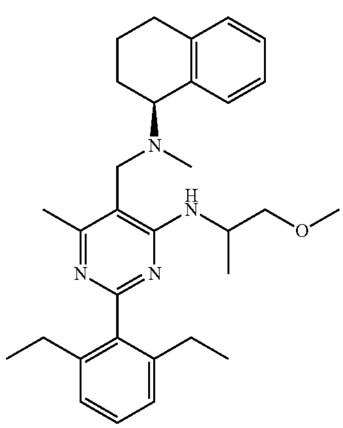 | 2-(2,6-diethylphenyl)-N-(2-methoxy-1-methylethyl)-6-methyl-5-({methyl[(1S)-1,2,3,4-tetrahydronaphthalen-1-yl]amino}methyl)pyrimidin-4-amine | 2.35 | 486.7 | 487.3 | 3 |

TABLE II-continued

| Cpd # | Structure | Name | LCMS Retention Time | LCMS Mass (amu) | LCMS M + H (amu) | LCMS Method |
|---|---|---|---|---|---|---|
| 95 | 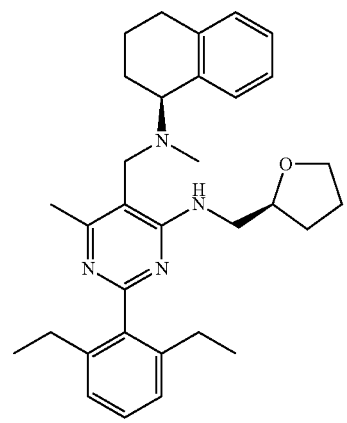 | 2-(2,6-diethylphenyl)-6-methyl-5-({methyl[(1S)-1,2,3,4-tetrahydronaphthalen-1-yl]amino}methyl)-N-[(2S)-tetrahydrofuran-2-ylmethyl]pyrimidin-4-amine | 1.22 | 498.3 | 499.6 | 1 |
| 96 | 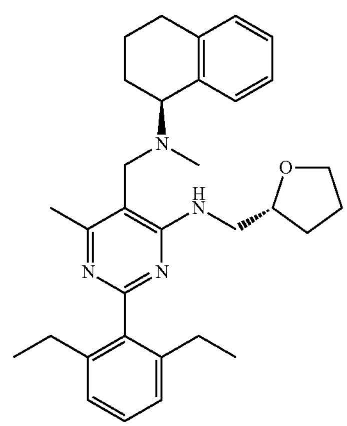 | 2-(2,6-diethylphenyl)-6-methyl-5-({methyl[(1S)-1,2,3,4-tetrahydronaphthalen-1-yl]amino}methyl)-N-[(2R)-tetrahydrofuran-2-ylmethyl]pyrimidin-4-amine | 1.21 | 498.3 | 499.6 | 1 |
| 97 | 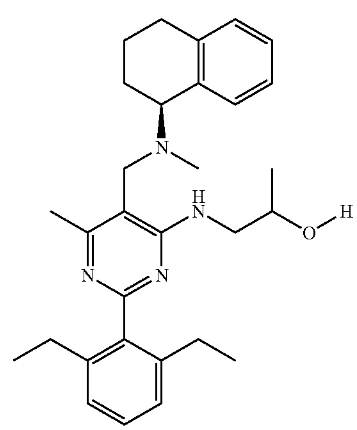 | 1-{[2-(2,6-diethylphenyl)-6-methyl-5-({methyl[(1S)-1,2,3,4-tetrahydronaphthalen-1-yl]amino}methyl)pyrimidin-4-yl]amino}propan-2-ol | 1.16 | 472.3 | 473.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 98 | 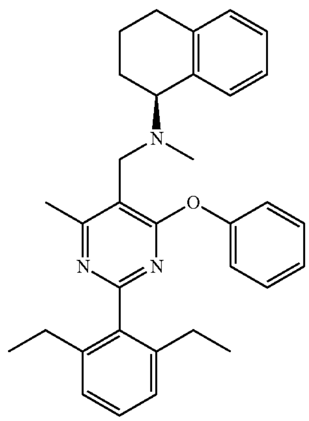 | (1S)-N-{[2-(2,6-diethylphenyl)-4-methyl-6-phenoxypyrimidin-5-yl]methyl}-N-methyl-1,2,3,4-tetrahydronaphthalen-1-amine | 2.58 | 491.7 | 492.4 | 3 |
| 99 | 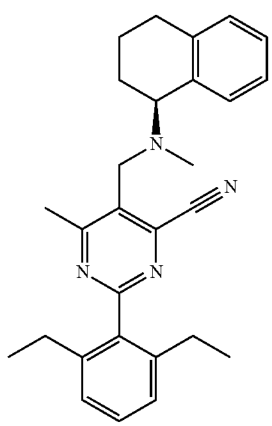 | 2-(2,6-diethylphenyl)-6-methyl-5-({methyl[(1S)-1,2,3,4-tetrahydronaphthalen-1-yl]amino}methyl)pyrimidine-4-carbonitrile | 1.37 | 424.6 | 425.3 | 2 |
| 100 | 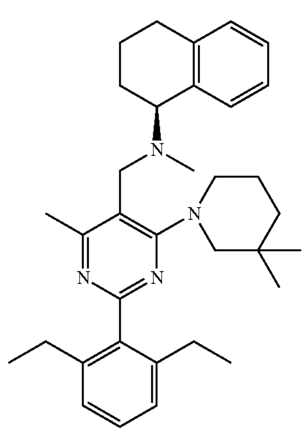 | (1S)-N-{[2-(2,6-diethylphenyl)-4-(3,3-dimethylpiperidin-1-yl)-6-methylpyrimidin-5-yl]methyl}-N-methyl-1,2,3,4-tetrahydronaphthalen-1-amine | 1.26 | 510.4 | 511.6 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 101 | 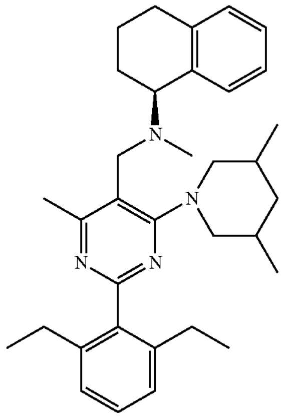 | (1S)-N-{[2-(2,6-diethylphenyl)-4-(3,5-dimethylpiperidin-1-yl)-6-methylpyrimidin-5-yl]methyl}-N-methyl-1,2,3,4-tetrahydronaphthalen-1-amine | 1.27 | 510.4 | 511.6 | 1 |
| 102 | 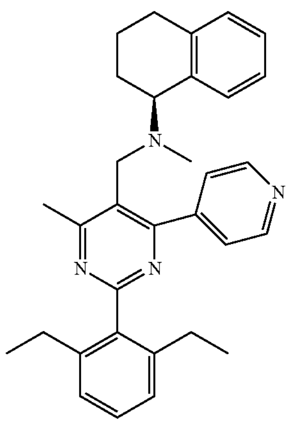 | (1S)-N-{[2-(2,6-diethylphenyl)-4-methyl-6-pyridin-4-ylpyrimidin-5-yl]methyl}-N-methyl-1,2,3,4-tetrahydronaphthalen-1-amine | | | | |
| 103 | 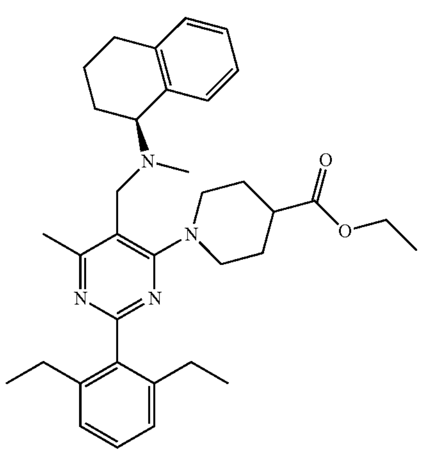 | ethyl 1-[2-(2,6-diethylphenyl)-6-methyl-5-({methyl[(1S)-1,2,3,4-tetrahydronaphthalen-1-yl]amino}methyl)pyrimidin-4-yl]piperidine-4-carboxylate | 1.23 | 554.4 | 555.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 104 | 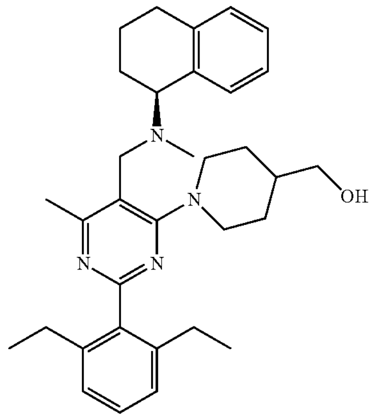 | {1-[2-(2,6-diethylphenyl)-6-methyl-5-({methyl[(1S)-1,2,3,4-tetrahydronaphthalen-1-yl]amino}methyl)pyrimidin-4-yl]piperidin-4-yl}methanol | 1.18 | 512.4 | 513.5 | 1 |
| 105 | 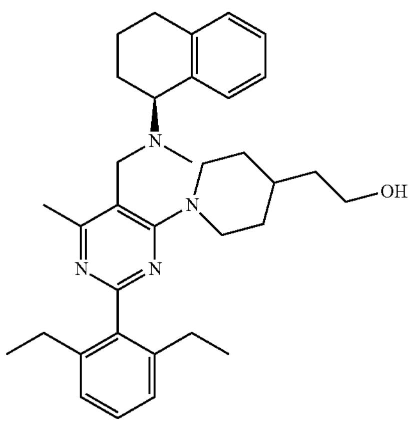 | 2-{1-[2-(2,6-diethylphenyl)-6-methyl-5-({methyl[(1S)-1,2,3,4-tetrahydronaphthalen-1-yl]amino}methyl)pyrimidin-4-yl]piperidin-4-yl}ethanol | 1.2 | 526.4 | 527.5 | 1 |
| 106 | 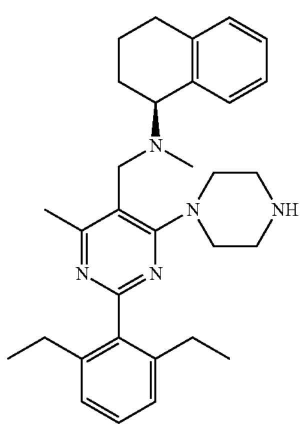 | (1S)-N-{[2-(2,6-diethylphenyl)-4-methyl-6-piperazin-1-ylpyrimidin-5-yl]methyl}-N-methyl-1,2,3,4-tetrahydronaphthalen-1-amine | 1.06 | 483.3 | 484.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 107 | 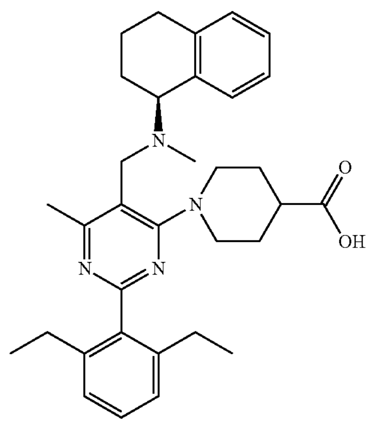 | 1-[2-(2,6-diethylphenyl)-6-methyl-5-({methyl[(1S)-1,2,3,4-tetrahydronaphthalen-1-yl]amino}methyl)pyrimidin-4-yl]piperidine-4-carboxylic acid | 1.18 | 526.3 | 527.6 | 1 |
| 108 | 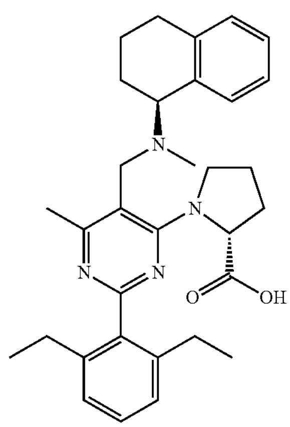 | 1-[2-(2,6-diethylphenyl)-6-methyl-5-({methyl[(1S)-1,2,3,4-tetrahydronaphthalen-1-yl]amino}methyl)pyrimidin-4-yl]-D-proline | 1.14 | 512.3 | 513.5 | 1 |
| 109 | 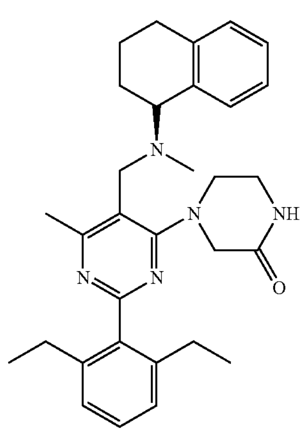 | 4-[2-(2,6-diethylphenyl)-6-methyl-5-({methyl[(1R)-1,2,3,4-tetrahydronaphthalen-1-yl]amino}methyl)pyrimidin-4-yl]piperazin-2-one | 1.11 | 497.7 | 498.3 | 2 |

TABLE II-continued

| Cpd # | Structure | Name | LCMS Retention Time | LCMS Mass (amu) | LCMS M + H (amu) | LCMS Method |
|---|---|---|---|---|---|---|
| 110 | 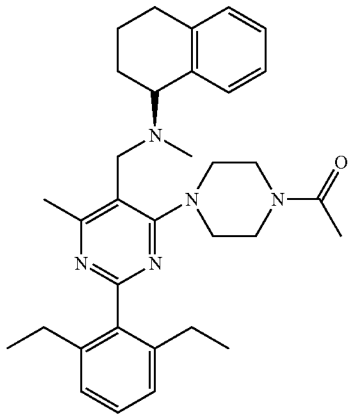 | (1R)-N-{[4-(4-acetylpiperazin-1-yl)-2-(2,6-diethylphenyl)-6-methylpyrimidin-5-yl]methyl}-N-methyl-1,2,3,4-tetrahydronaphthalen-1-amine | 1.14 | 525.3 | 526.6 | 1 |
| 111 | 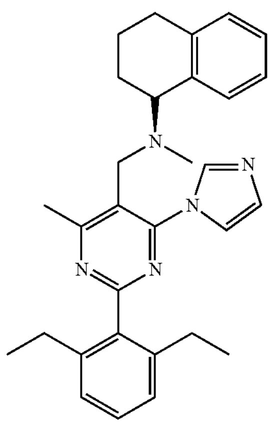 | (1R)-N-{[2-(2,6-diethylphenyl)-4-(1H-imidazo-1-yl)-6-methylpyrimidin-5-yl]methyl}-N-methyl-1,2,3,4-tetrahydronaphthalen-1-amine | 1.24 | 465.3 | 466.5 | 1 |
| 112 | 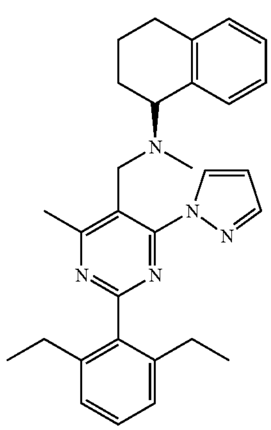 | (1R)-N-{[2-(2,6-diethylphenyl)-4-methyl-6-(1H-pyrazol-1-yl)pyrimidin-5-yl]methyl}-N-methyl-1,2,3,4-tetrahydronaphthalen-1-amine | 1.15 | 465.3 | 466.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 113 | 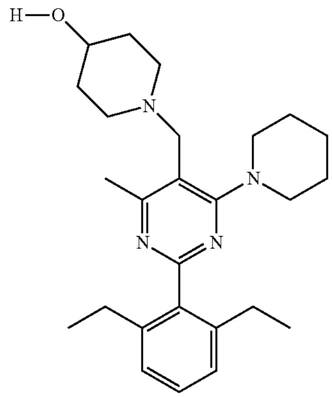 | 1-{[2-(2,6-diethylphenyl)-4-methyl-6-piperidin-1-ylpyrimidin-5-yl]methyl}piperidin-4-ol | 1.08 | 422.3 | 423.5 | 1 |
| 114 | 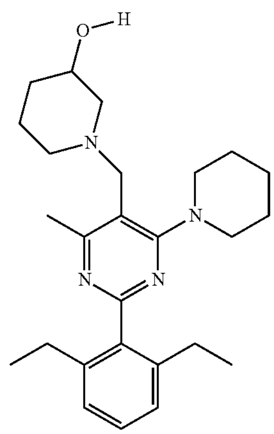 | 1-{[2-(2,6-diethylphenyl)-4-methyl-6-piperidin-1-ylpyrimidin-5-yl]methyl}piperidin-3-ol | 1.11 | 422.3 | 423.5 | 1 |
| 115 | 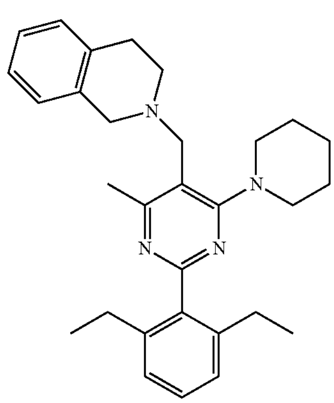 | 2-{[2-(2,6-diethylphenyl)-4-methyl-6-piperidin-1-ylpyrimidin-5-yl]methyl}-1,2,3,4-tetrahydroisoquinoline | 1.19 | 454.3 | 455.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 116 | 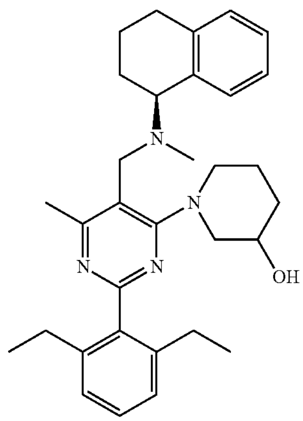 | 1-[2-(2,6-diethylphenyl)-6-methyl-5-({methyl[(1S)-1,2,3,4-tetrahydronaphthalen-1-yl]amino}methyl)pyrimidin-4-yl]piperidin-3-ol | 1.18 | 498.3 | 499.6 | 1 |
| 117 | 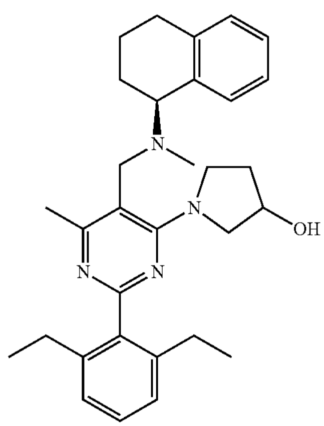 | 1-[2-(2,6-diethylphenyl)-6-methyl-5-({methyl[(1S)-1,2,3,4-tetrahydronaphthalen-1-yl]amino}methyl)pyrimidin-4-yl]pyrrolidin-3-ol | 1.15 | 484.3 | 485.5 | 1 |
| 118 | 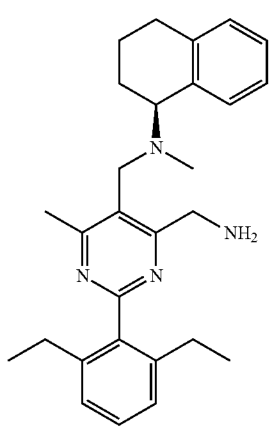 | (1S)-N-{[4-(aminomethyl)-2-(2,6-diethylphenyl)-6-methylpyrimidin-5-yl]methyl}-N-methyl-1,2,3,4-tetrahydronaphthalen-1-amine | 1.15 | 428.3 | 429.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 119 | 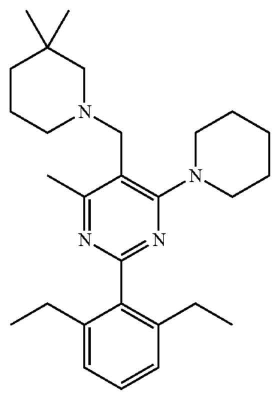 | 2-(2,6-diethylphenyl)-5-[(3,3-dimethylpiperidin-1-yl)methyl]-4-methyl-6-piperidin-1-ylpyrimidine | 1.2 | 434.3 | 435.5 | 1 |
| 120 | 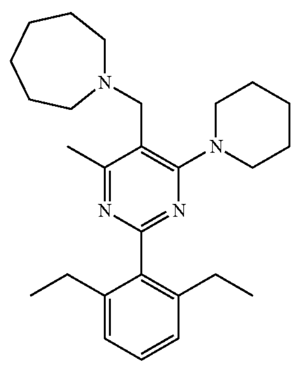 | 1-{[2-(2,6-diethylphenyl)-4-methyl-6-piperidin-1-ylpyrimidin-5-yl]methyl}azepane | 1.12 | 420.3 | 421.5 | 1 |
| 121 | 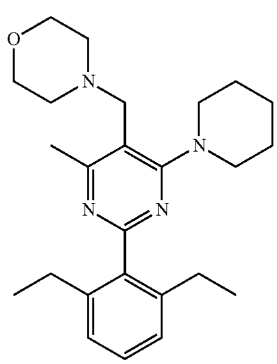 | 4-{[2-(2,6-diethylphenyl)-4-methyl-6-piperidin-1-ylpyrimidin-5-yl]methyl}morpholine | 1.14 | 408.3 | 409.4 | 1 |
| 122 | 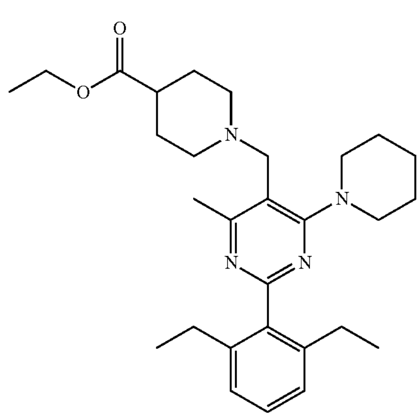 | ethyl 1-{[2-(2,6-diethylphenyl)-4-methyl-6-piperidin-1-ylpyrimidin-5-yl]methyl}piperidine-4-carboxylate | 1.15 | 478.3 | 479.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 123 | 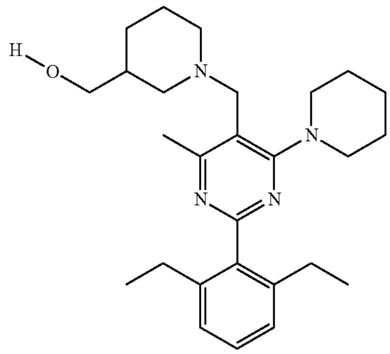 | (1-{[2-(2,6-diethylphenyl)-4-methyl-6-piperidin-1-ylpyrimidin-5-yl]methyl}piperidin-3-yl)methanol | 1.08 | 436.3 | 437.5 | 1 |
| 124 | 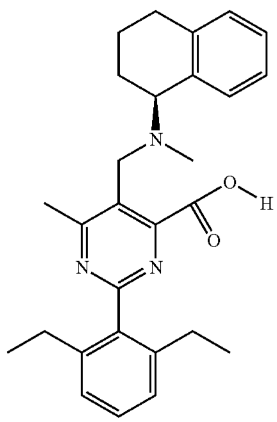 | 2-(2,6-diethylphenyl)-6-methyl-5-({methyl[(1S)-1,2,3,4-tetrahydronaphthalen-1-yl]amino}methyl)pyrimidine-4-carboxylic acid | 2.33 | 443.5 | 444.6 | 3 |
| 125 | 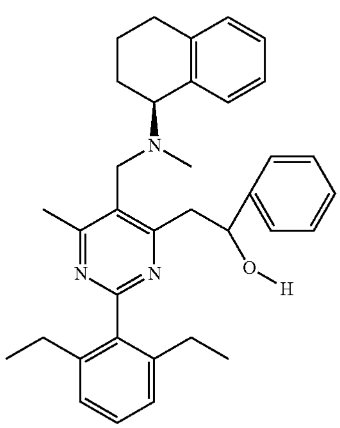 | 2-[2-(2,6-diethylphenyl)-6-methyl-5-({methyl[(1S)-1,2,3,4-tetrahydronaphthalen-1-yl]amino}methyl)pyrimidin-4-yl]-1-phenylethanol | 1.18 | 519.3 | 520.6 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 126 | 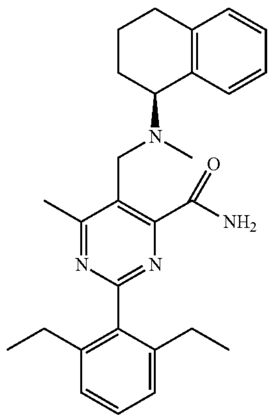 | 2-(2,6-diethylphenyl)-6-methyl-5-({methyl[(1S)-yl]amino}methyl)pyrimidine-4-carboxamide | 1.12 | 442.3 | 443.5 | 1 |
| 127 | 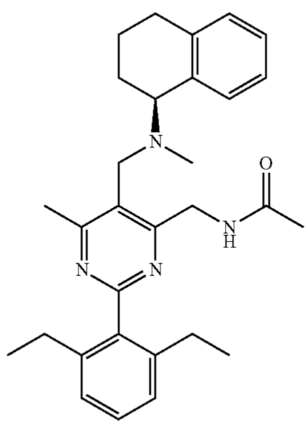 | N-{[2-(2,6-diethylphenyl)-6-methyl-5-({methyl[(1S)-1,2,3,4-tetrahydronaphthalen-1-yl]amino}methyl)pyrimidin-4-yl]methyl}acetamide | 1.1 | 470.3 | 471.5 | 1 |
| 128 | 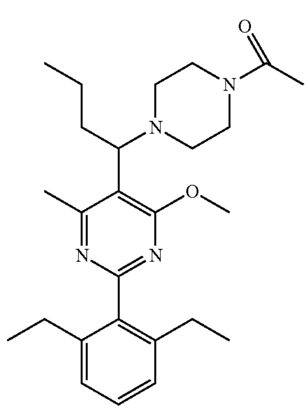 | 5-[1-(4-acetylpiperazin-1-yl)butyl]-2-(2,6-diethylphenyl)-4-methoxy-6-methylpyrimidine | 2.07 | 438.6 | 439.4 | 3 |

TABLE II-continued

| Cpd # | Structure | Name | LCMS Retention Time | LCMS Mass (amu) | LCMS M + H (amu) | LCMS Method |
|---|---|---|---|---|---|---|
| 129 | 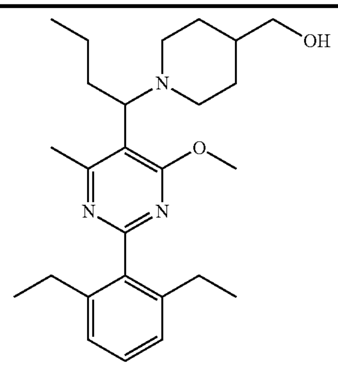 | (1-{1-[2-(2,6-diethylphenyl)-4-methoxy-6-methylpyrimidin-5-yl]butyl}piperidin-4-yl)methanol | | | | |
| 130 | 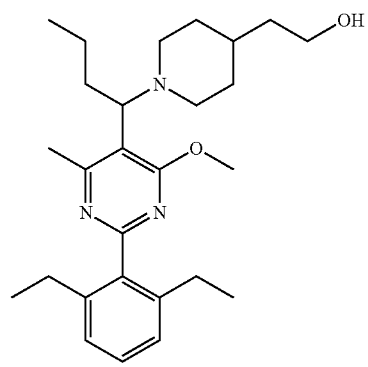 | 2-(1-{1-[2-(2,6-diethylphenyl)-4-methoxy-6-methylpyrimidin-5-yl]butyl}piperidin-4-yl)ethanol | 1.97 | 439.6 | 440.4 | 3 |
| 131 | 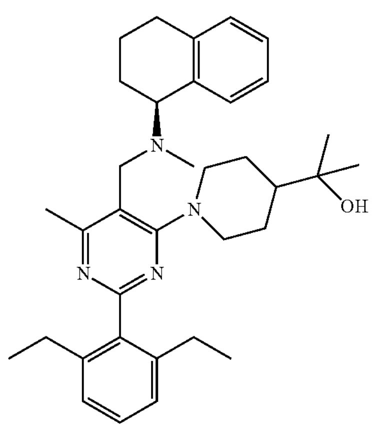 | 2-{1-[2-(2,6-diethylphenyl)-6-methyl-5-({methyl[(1S)-1,2,3,4-tetrahydronaphthalen-1-yl]amino}methyl)pyrimidin-4-yl]piperidin-4-yl}propan-2-ol | 1.26 | 540.4 | 541.4 | 1 |
| 132 | 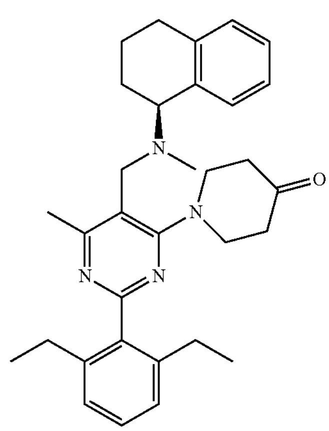 | 1-[2-(2,6-diethylphenyl)-6-methyl-5-({methyl[(1S)-1,2,3,4-tetrahydronaphthalen-1-yl]amino}methyl)pyrimidin-4-yl]piperidin-4-one | 1.22 | 496.3 | 497.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 133 | 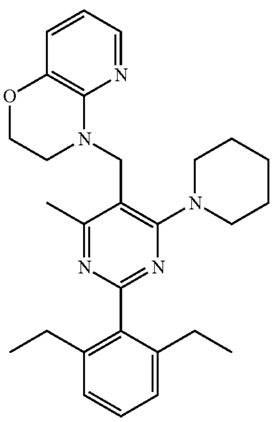 | 4-{[2-(2,6-diethylphenyl)-4-methyl-6-piperidin-1-ylpyrimidin-5-yl]methyl}-3,4-dihydro-2H-pyrido[3,2-b][1,4]oxazine | 1.23 | 457.3 | 458.3 | 1 |
| 134 | 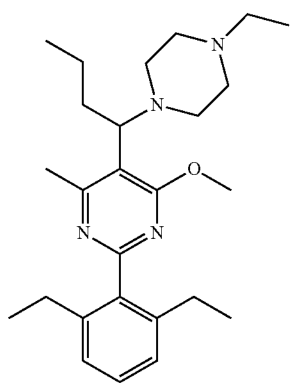 | 2-(2,6-diethylphenyl)-5-[1-(4-ethylpiperazin-1-yl)butyl]-methylpyrimidine | 1.2 | 424.3 | 425.3 | 1 |
| 135 | 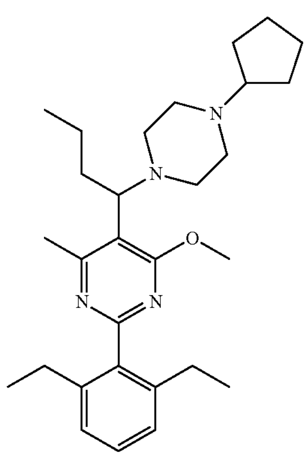 | 5-[1-(4-cyclopentylpiperazin-1-yl)butyl]-2-(2,6-diethylphenyl)-4-methoxy-6-methylpyrimidine | 1.21 | 464.4 | 465.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 136 | 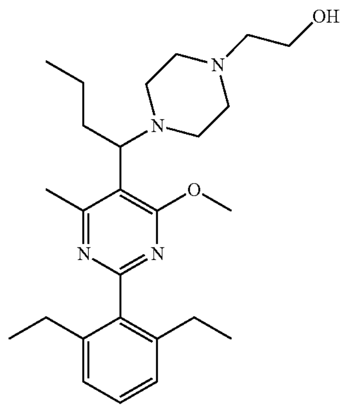 | 2-(4-{1-[2-(2,6-diethylphenyl)-4-methoxy-6-methylpyrimidin-5-yl]butyl}piperazin-1-yl)ethanol | 2.1 | 440.6 | 441.4 | 3 |
| 137 | 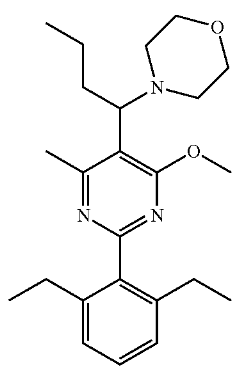 | 4-{1-[2-(2,6-diethylphenyl)-4-methoxy-6-methylpyrimidin-5-yl]butyl}morpholine | 1.99 | 397.6 | 398.3 | 3 |
| 138 | 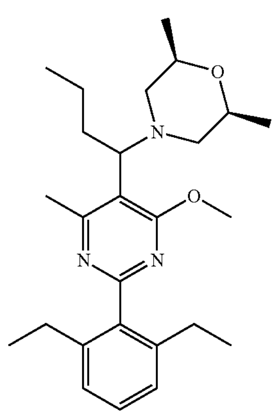 | (2R,6S)-4-{1-[2-(2,6-diethylphenyl)-4-methoxy-6-methylpyrimidin-5-yl]butyl}-2,6-dimethylmorpholine | 2.25 | 425.6 | 426.3 | 3 |

TABLE II-continued

| Cpd # | Structure | Name | LCMS Retention Time | LCMS Mass (amu) | LCMS M + H (amu) | LCMS Method |
|---|---|---|---|---|---|---|
| 139 | 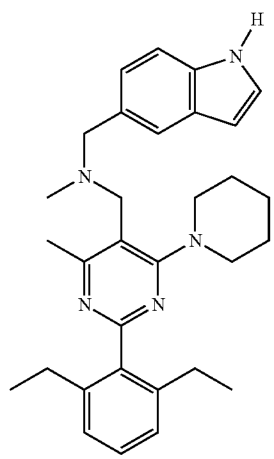 | 1-[2-(2,6-diethylphenyl)-4-methyl-6-piperidin-1-ylpyrimidin-5-yl]-N-(1H-indol-5-ylmethyl)-N-methylmethanamine | 1.11 | 481.3 | 482.3 | 1 |
| 140 | 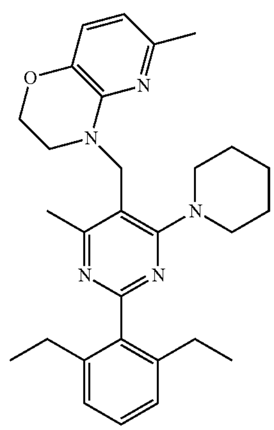 | 4-{[2-(2,6-diethylphenyl)-4-methyl-6-piperidin-1-ylpyrimidin-5-yl]methyl}-6-methyl-3,4-dihydro-2H-pyrido[3,2-b][1,4]oxazine | 1.22 | 471.3 | 472.3 | 1 |
| 141 | 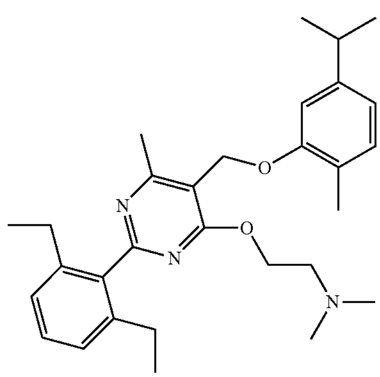 | 2-({2-(2,6-diethylphenyl)-5-[(5-isopropyl-2-methylphenoxy)methyl]-6-methylpyrimidin-4-yl}oxy)-N,N-dimethylethanamine | 1.21 | 475.3 | 476.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 142 | 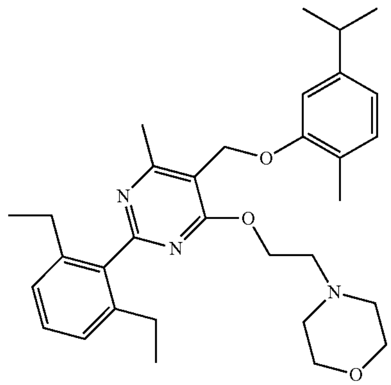 | 4-[2-({2-(2,6-diethylphenyl)-5-[(5-isopropyl-2-methylphenoxy)methyl]-6-methylpyrimidin-4-yl}oxy)ethyl]morpholine | 2.56 | 517.7 | 518.4 | 3 |
| 143 | 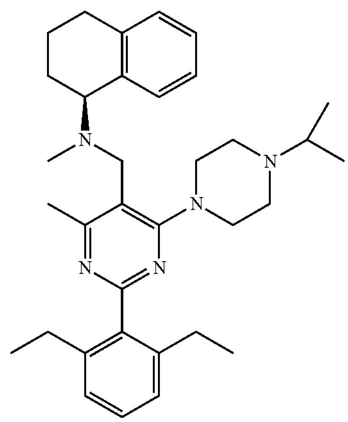 | (1S)-N-{[2-(2,6-diethylphenyl)-4-(4-isopropylpiperazin-1-yl)-6-methylpyrimidin-5-yl]methyl}-N-methyl-1,2,3,4-tetrahydronaphthalen-1-amine | 1.11 | 525.4 | 526.3 | 1 |
| 144 | 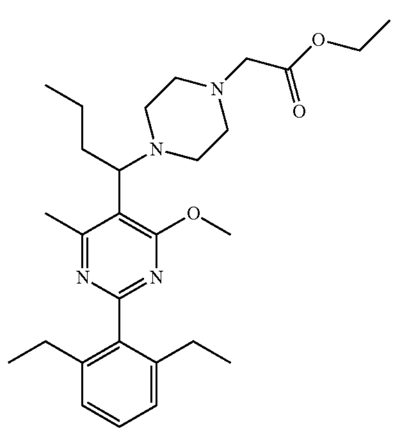 | ethyl (4-{1-[2-(2,6-diethylphenyl)-4-methoxy-6-methylpyrimidin-5-yl]butyl}piperazin-1-yl)acetate | 1.19 | 482.3 | 483.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 145 | 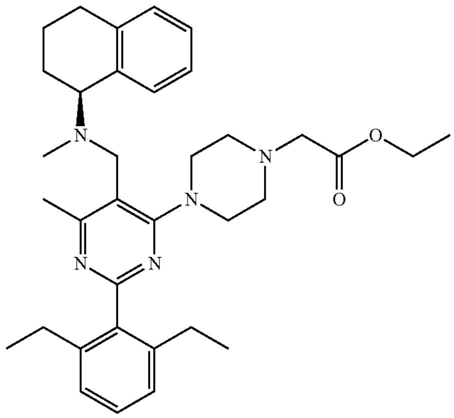 | ethyl {4-[2-(2,6-diethylphenyl)-6-methyl-5-({methyl[(1S)-1,2,3,4-tetrahydronaphthalen-1-yl]amino}methyl)pyrimidin-4-yl]piperazin-1-yl}acetate | 2.66 | 569.8 | 570.4 | 3 |
| 146 | 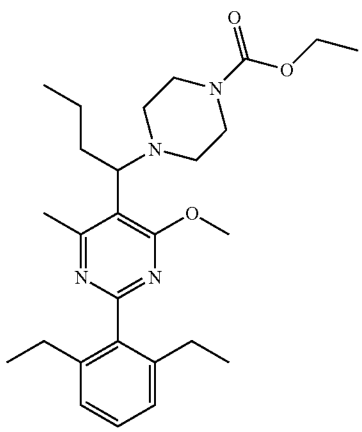 | ethyl 4-{1-[2-(2,6-diethylphenyl)-4-methoxy-6-methylpyrimidin-5-yl]butyl}piperazine-1-carboxylate | 1.17 | 468.3 | 469.3 | 1 |
| 147 | 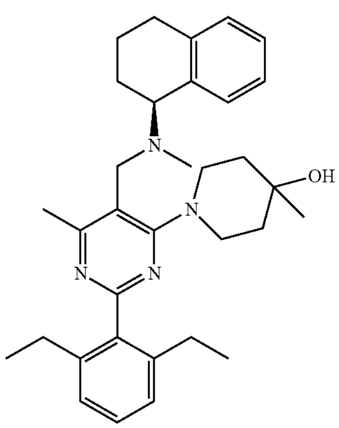 | 1-[2-(2,6-diethylphenyl)-6-methyl-5-({methyl[(1S)-1,2,3,4-tetrahydronaphthalen-1-yl]amino}methyl)pyrimidin-4-yl]-4-methylpiperidin-4-ol | 1.2 | 512.4 | 513.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 148 | 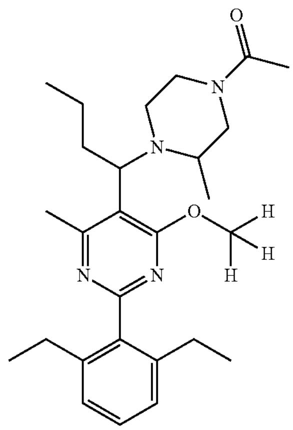 | 5-[1-(4-acetyl-2-methylpiperazin-1-yl)butyl]-2-(2,6-diethylphenyl)-4-methoxy-6-methylpyrimidine | 2.81 | 452.6 | 453.3 | 3 |
| 149 | 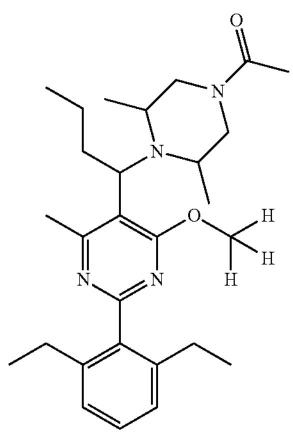 | 5-[1-(4-acetyl-2,6-dimethylpiperazin-1-yl)butyl]-2-(2,6-diethylphenyl)-4-methoxy-6-methylpyrimidine | 1.25 | 466.3 | 467.3 | 1 |
| 150 | 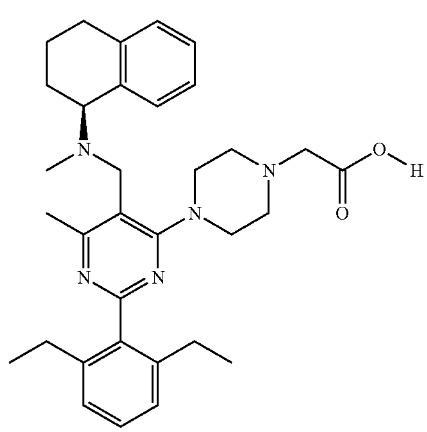 | {4-[2-(2,6-diethylphenyl)-6-methyl-5-({methyl[(1S)-1,2,3,4-tetrahydronaphthalen-1-yl]amino}methyl)pyrimidin-4-yl]piperazin-1-yl}acetic acid | 1.09 | 541.3 | 542.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 151 | 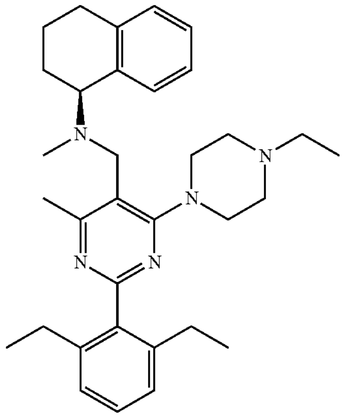 | (1S)-N-{[2-(2,6-diethylphenyl)-4-(4-ethylpiperazin-1-yl)-6-methylpyrimidin-5-yl]methyl}-N-methyl-1,2,3,4-tetrahydronaphthalen-1-amine | 1.06 | 511.4 | 512.4 | 1 |
| 152 | 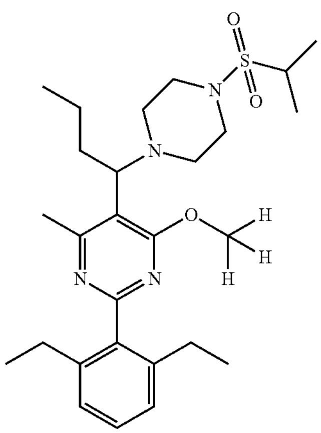 | 2-(2,6-diethylphenyl)-5-{1-[4-(isopropylsulfonyl)piperazin-1-yl]butyl}-4-methoxy-6-methylpyrimidine | 1.14 | 502.3 | 503.3 | 1 |
| 153 | 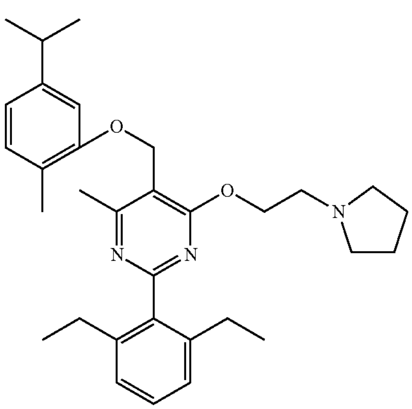 | 2-(2,6-diethylphenyl)-5-[(5-isopropyl-2-methylphenoxy)methyl]-4-methyl-6-(2-pyrrolidin-1-ylethoxy)pyrimidine | 1.21 | 501.3 | 502.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 154 | 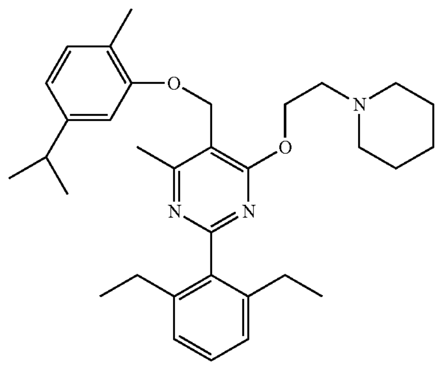 | 2-(2,6-diethylphenyl)-5-[(5-isopropyl-2-methylphenoxy)methyl]-4-methyl-6-(2-piperidin-1-ylethoxy)pyrimidine | 1.22 | 515.4 | 516.4 | 1 |
| 155 | 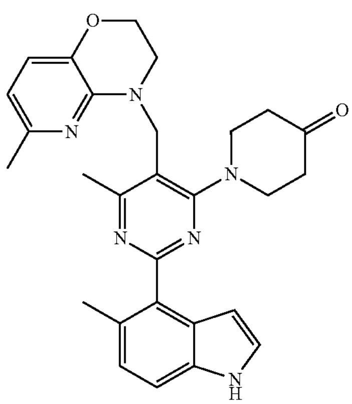 | 1-[6-methyl-5-[(6-methyl-2,3-dihydro-4H-pyrido[3,2-b][1,4]oxazin-4-yl)methyl]-2-(5-methyl-1H-indol-4-yl)pyrimidin-4-yl]piperidin-4-one | 1.14 | 482.2 | 483.2 | 1 |
| 156 | 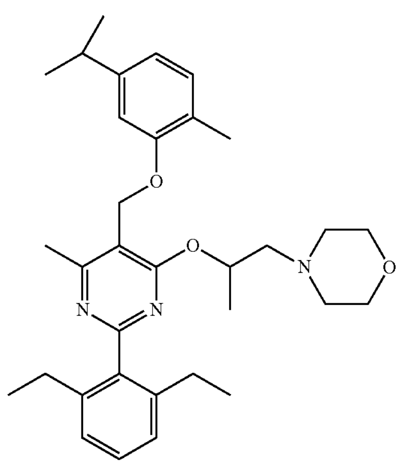 | 4-[2-({2-(2,6-diethylphenyl)-5-[(5-isopropyl-2-methylphenoxy)methyl]-6-methylpyrimidin-4-yl}oxy)propyl]morpholine | 1.28 | 531.3 | 532.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 157 | 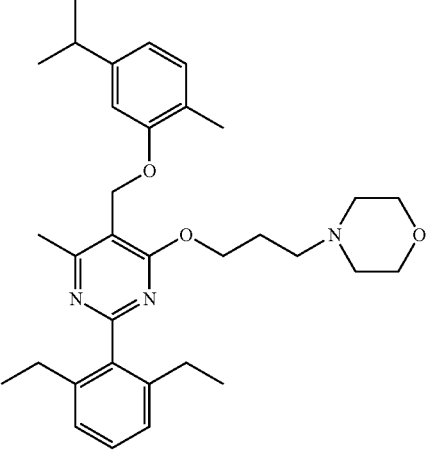 | 4-[3-({2-(2,6-diethylphenyl)-5-[(5-isopropyl-2-methylphenoxy)methyl]-6-methylpyrimidin-4-yl}oxy)propyl]morpholine | 1.27 | 531.3 | 532.3 | 1 |
| 158 | 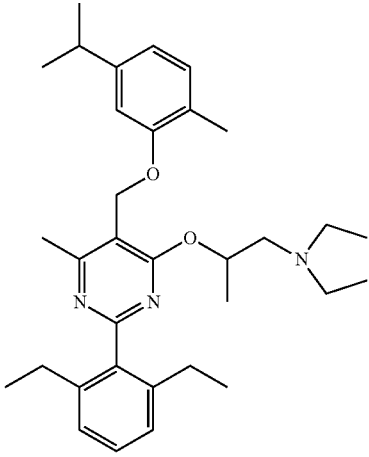 | 2-({2-(2,6-diethylphenyl)-5-[(5-isopropyl-2-methylphenoxy)methyl]-6-methylpyrimidin-4-yl}oxy)-N,N-diethylpropan-1-amine | 2.39 | 517.8 | 518.3 | 3 |
| 159 | 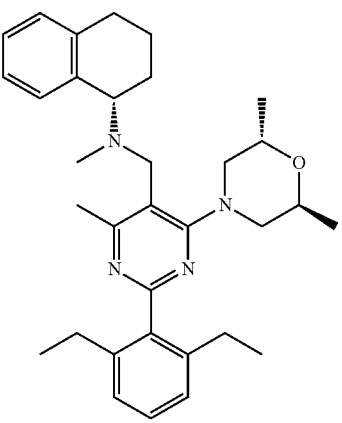 | (1S)-N-({2-(2,6-diethylphenyl)-4-[(2S,6S)-2,6-dimethylmorpholin-4-yl]-6-methylpyrimidin-5-yl}methyl)-N-methyl-1,2,3,4-tetrahydronaphthalen-1-amine | 1.27 | 512.4 | 513.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 160 | 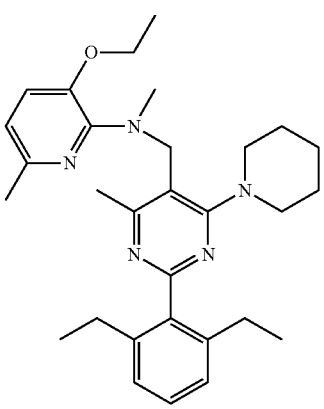 | N-{[2-(2,6-diethylphenyl)-4-methyl-6-piperidin-1-ylpyrimidin-5-yl]methyl}-3-ethoxy-N,6-dimethylpyridin-2-amine | 1.26 | 487.3 | 488.3 | 1 |
| 161 | 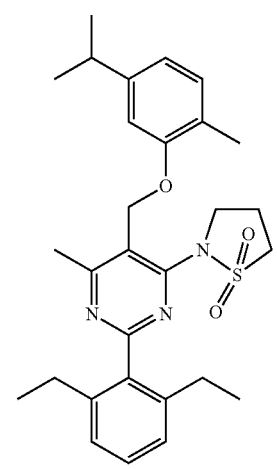 | 2-(2,6-diethylphenyl)-4-(1,1-dioxidoisothiazolidin-2-yl)-5-[(5-isopropyl-2-methylphenoxy)methyl]-6-methylpyrimidine | 3.11 | 507.7 | 508.2 | 3 |
| 162 | 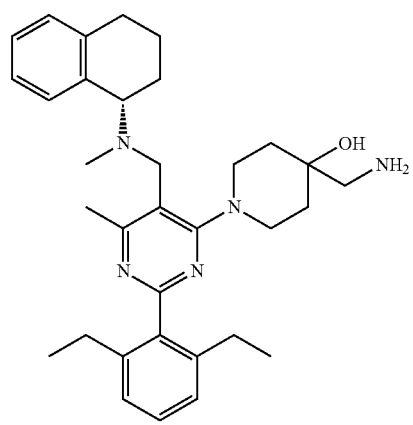 | 4-(aminomethyl)-1-[2-(2,6-diethylphenyl)-6-methyl-5-({methyl[(1S)-1,2,3,4-tetrahydronaphthalen-1-yl]amino}methyl)pyrimidin-4-yl]piperidin-4-ol | 1.08 | 527.4 | 528.6 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 163 | 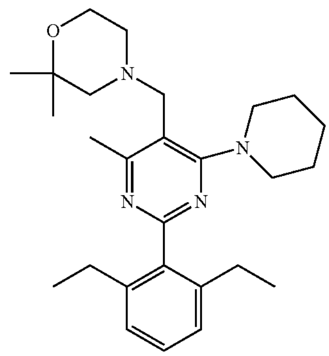 | 4-{[2-(2,6-diethylphenyl)-4-methyl-6-piperidin-1-ylpyrimidin-5-yl]methyl}-2,2-dimethylmorpholine | 2.33 | 436.6 | 437.4 | 3 |
| 164 | 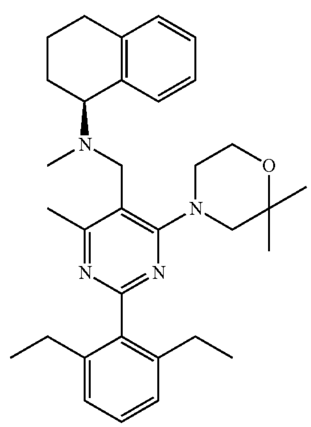 | (1S)-N-{[2-(2,6-diethylphenyl)-4-(2,2-dimethylmorpholin-4-yl)-6-methylpyrimidin-5-yl]methyl}-N-methyl-1,2,3,4-tetrahydronaphthalen-1-amine | | | | |
| 165 | 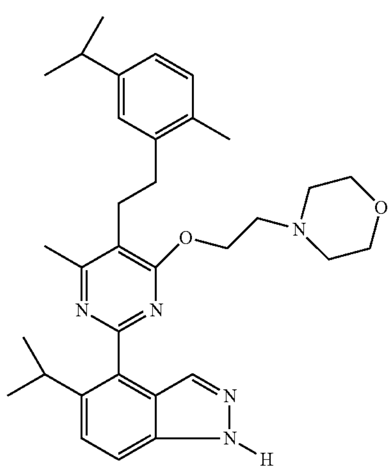 | 5-isopropyl-4-[5-[(5-isopropyl-2-methylphenoxy)methyl]-4-methyl-6-(2-morpholin-4-ylethoxy)pyrimidin-2-yl]-1H-indazole | 2.46 | 543.7 | 544.2 | 3 |

TABLE II-continued

| Cpd # | Structure | Name | LCMS Retention Time | LCMS Mass (amu) | LCMS M + H (amu) | LCMS Method |
|---|---|---|---|---|---|---|
| 166 | 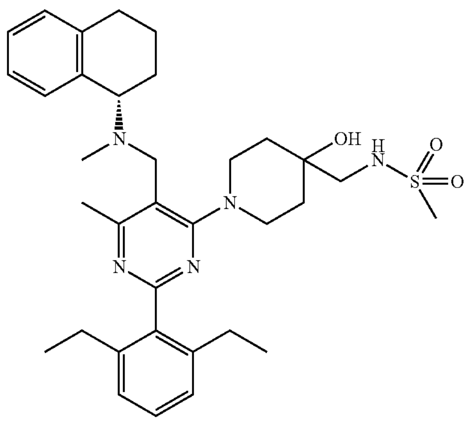 | N-({1-[2-(2,6-diethylphenyl)-6-methyl-5-({methyl[(1S)-1,2,3,4-tetrahydronaphthalen-1-yl]amino}methyl)pyrimidin-4-yl]-4-hydroxypiperidin-4-yl}methyl)methanesulfonamide | | | | |
| 167 | 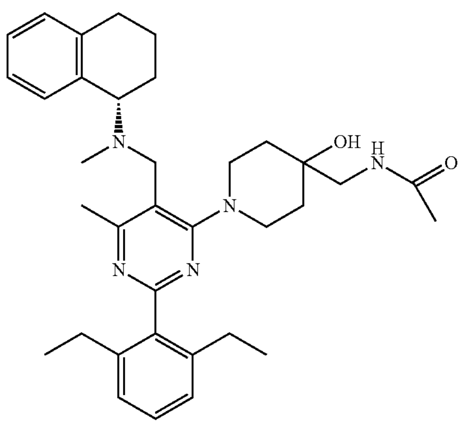 | N-({1-[2-(2,6-diethylphenyl)-6-methyl-5-({methyl[(1S)-1,2,3,4-tetrahydronaphthalen-1-yl]amino}methyl)pyrimidin-4-yl]-4-hydroxypiperidin-4-yl}methyl)acetamide | 1.14 | 569.4 | 570.6 | 1 |
| 168 | 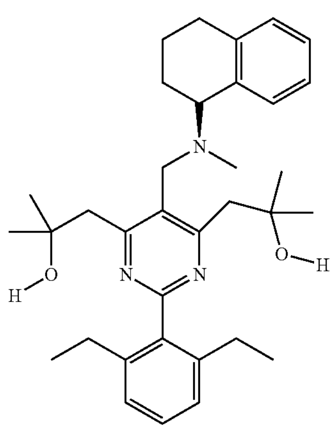 | 1,1'-[2-(2,6-diethylphenyl)-5-({methyl[(1S)-1,2,3,4-tetrahydronaphthalen-1-yl]amino}methyl)pyrimidine-4,6-diyl]bis(2-methylpropan-2-ol | 1.14 | 529.4 | 530.6 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 169 | 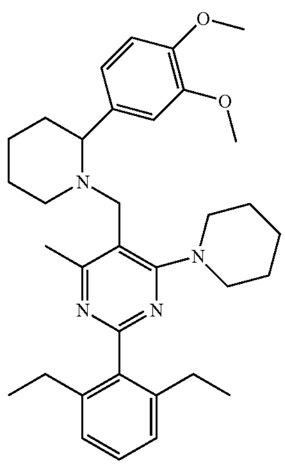 | 2-(2,6-diethylphenyl)-5-{[2-(3,4-dimethoxyphenyl)piperidin-1-yl]methyl}-4-methyl-6-piperidin-1-ylpyrimidine | 1.12 | 542.4 | 543.6 | 1 |
| 170 | 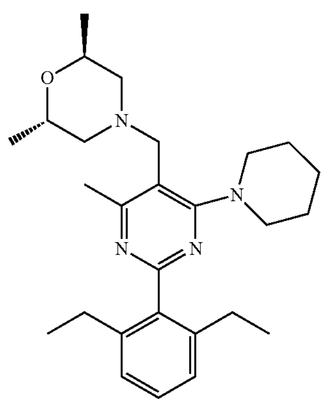 | (2S,6S)-4-{[2-(2,6-diethylphenyl)-4-methyl-6-piperidin-1-ylpyrimidin-5-yl]methyl}-2,6-dimethylmorpholine | 1.17 | 436.3 | 437.5 | 1 |
| 171 | 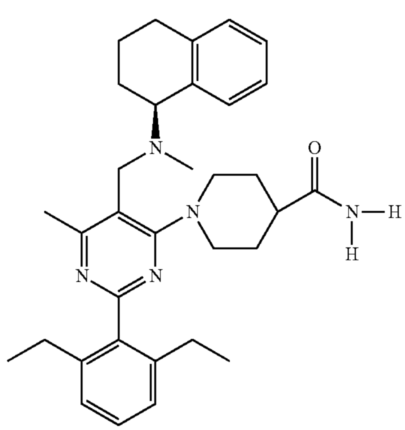 | 1-[2-(2,6-diethylphenyl)-6-methyl-5-({methyl[(1S)-1,2,3,4-tetrahydronaphthalen-1-yl]amino}methyl)pyrimidin-4-yl]piperidine-4-carboxamide | 1.2 | 525.3 | 526.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 172 | 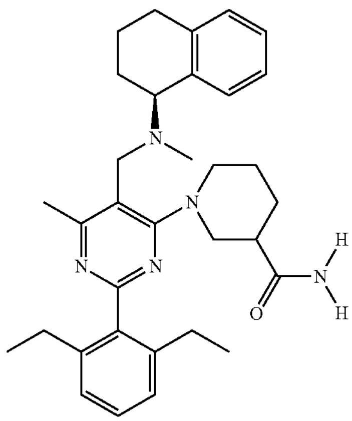 | 1-[2-(2,6-diethylphenyl)-6-methyl-5-({methyl[(1S)-1,2,3,4-tetrahydronaphthalen-1-yl]amino}methyl)pyrimidin-4-yl]piperidine-3-carboxamide | 1.15 | 525.3 | 526.6 | 1 |
| 173 | 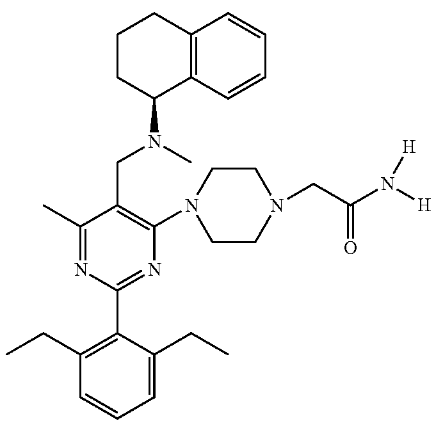 | 2-{4-[2-(2,6-diethylphenyl)-6-methyl-5-({methyl[(1S)-1,2,3,4-tetrahydronaphthalen-1-yl]amino}methyl)pyrimidin-4-yl]piperazin-1-yl}acetamide | 1.07 | 540.4 | 541.6 | 1 |
| 174 | 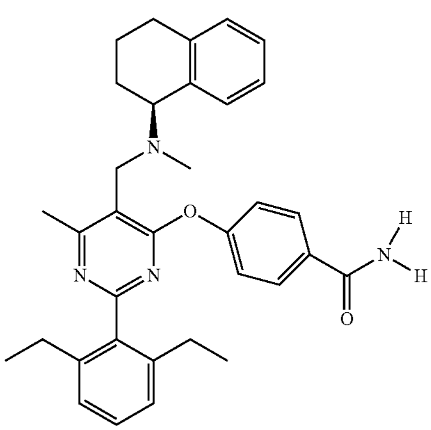 | 4-{[2-(2,6-diethylphenyl)-6-methyl-5-({methyl[(1S)-1,2,3,4-tetrahydronaphthalen-1-yl]amino}methyl)pyrimidin-4-yl]oxy}benzamide | 1.09 | 534.3 | 535.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 175 | 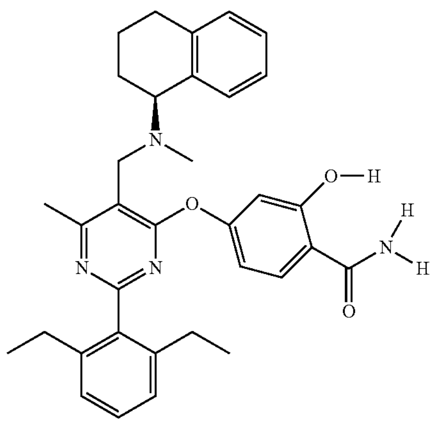 | 4-{[2-(2,6-diethylphenyl)-6-methyl-5-({methyl[(1S)-1,2,3,4-tetrahydronaphthalen-1-yl]amino}methyl)pyrimidin-4-yl]oxy}-2-hydroxybenzamide | 1.12 | 550.3 | 551.6 | 1 |
| 176 | 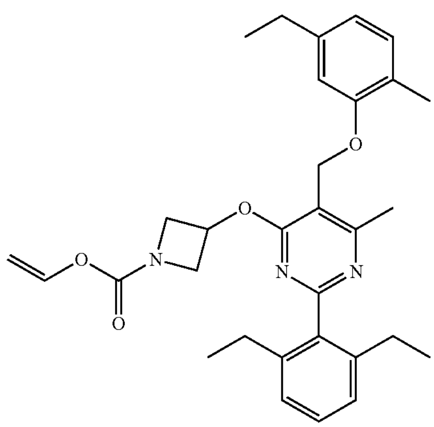 | vinyl 3-({2-(2,6-diethylphenyl)-5-[(5-isopropyl-2-methylphenoxy)methyl]-6-methylpyrimidin-4-yl}oxy)azetidine-1-carboxylate | 1.37 | 529.3 | 530.5 | 1 |
| 177 | 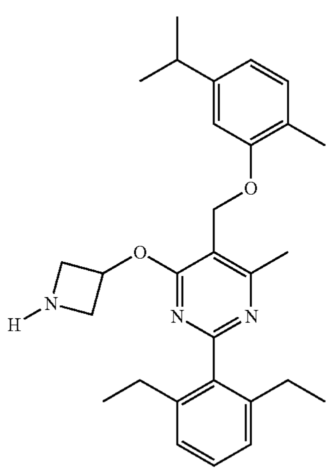 | 4-(acetidin-3-yloxy)-2-(2,6-diethylphenyl)-5-[(5-isopropyl-2-methylphenoxy)methyl]-6-methylpyrimidine | 2.36 | 459.3 | 460.2 | 3 |

TABLE II-continued

| Cpd # | Structure | Name | LCMS Retention Time | LCMS Mass (amu) | LCMS M + H (amu) | LCMS Method |
|---|---|---|---|---|---|---|
| 178 | 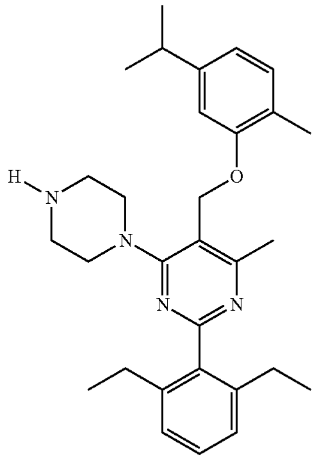 | 2-(2,6-diethylphenyl)-5-[(5-isopropyl-2-methylphenoxy)methyl]-4-methyl-6-piperazin-1-ylpyrimidine | 1.16 | 472.3 | 473.5 | 1 |
| 179 | 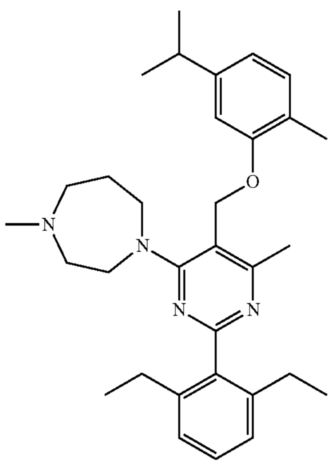 | 1-{2-(2,6-diethylphenyl)-5-[(5-isopropyl-2-methylphenoxy)methyl]-6-methylpyrimidin-4-yl}-4-methyl-1,4-diazepane | 1.12 | 500.4 | 502.6 | 1 |
| 180 | 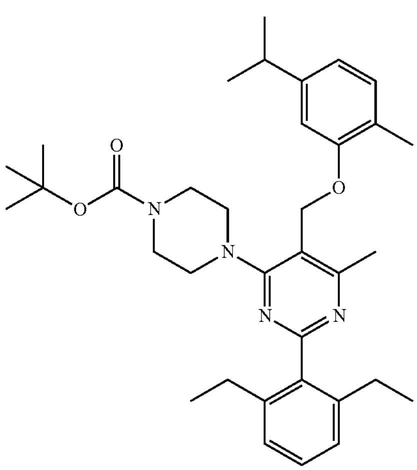 | tert-butyl 4-{2-(2,6-diethylphenyl)-5-[(5-isopropyl-2-methylphenoxy)methyl]-6-methylpyrimidin-4-yl}piperazine-1-carboxylate | 1.32 | 572.4 | 573.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 181 | 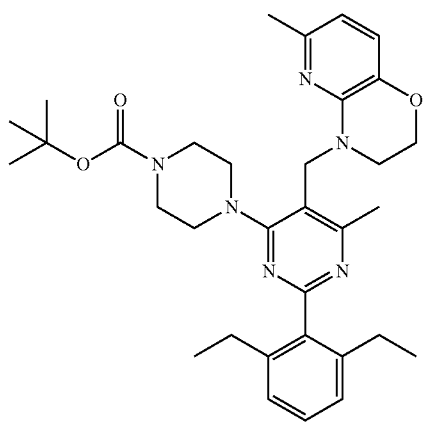 | tert-butyl 4-{2-(2,6-diethylphenyl)-6-methyl-5-[(6-methyl-2,3-dihydro-4H-pyrido[3,2-b][1,4]oxazin-4-yl)methyl]pyrimidin-4-yl}piperazine-1-carboxylate | 1.28 | 572.3 | 573.4 | 1 |
| 182 | 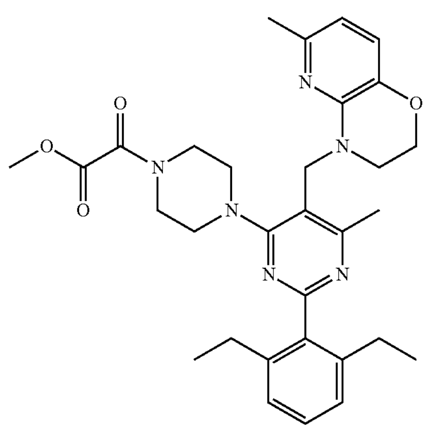 | methyl (4-{2-(2,6-diethylphenyl)-6-methyl-5-[(6-methyl-2,3-dihydro-4H-pyrido[3,2-b][1,4]oxazin-4-yl)methyl]pyrimidin-4-yl}piperazin-1-yl)(oxo)acetate | 1.19 | 558.3 | 559.3 | 1 |
| 183 | 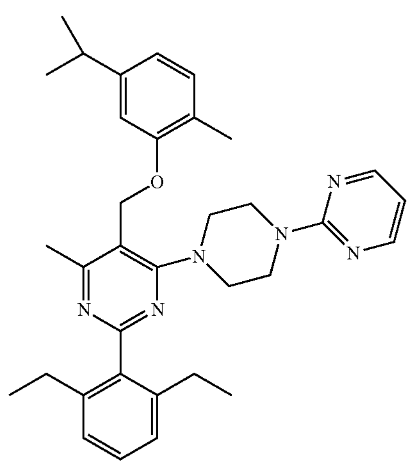 | 2-(2,6-diethylphenyl)-5-[(5-isopropyl-2-methylphenoxy)methyl]-4-methyl-6-(4-pyrimidin-2-ylpiperazin-1-yl)pyrimidine | 1.31 | 550.3 | 551.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 184 | 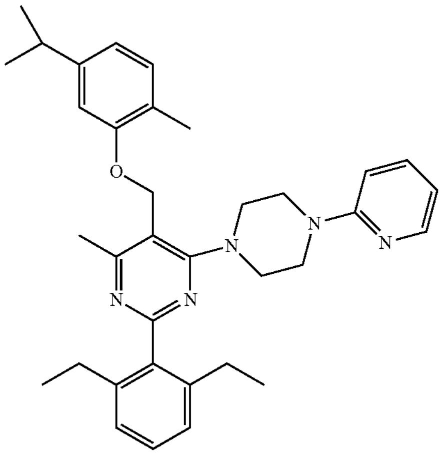 | 2-(2,6-diethylphenyl)-5-[(5-isopropyl-2-methylphenoxy)methyl]-4-methyl-6-(4-pyridin-2-ylpiperazin-1-yl)pyrimidine | 1.22 | 549.3 | 550.4 | 1 |
| 185 | 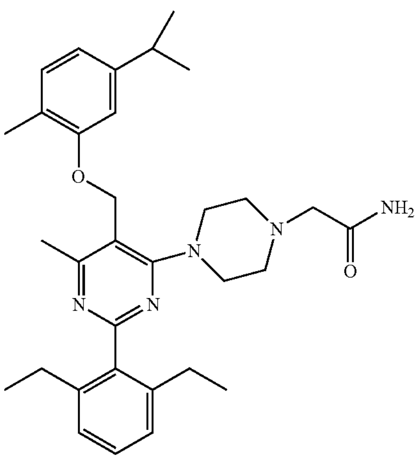 | 2-(4-{2-(2,6-diethylphenyl)-5-[(5-isopropyl-2-methylphenoxy)methyl]-6-methylpyrimidin-4-yl}piperazin-1-yl)acetamide | 1.22 | 529.3 | 530.4 | 1 |
| 186 | 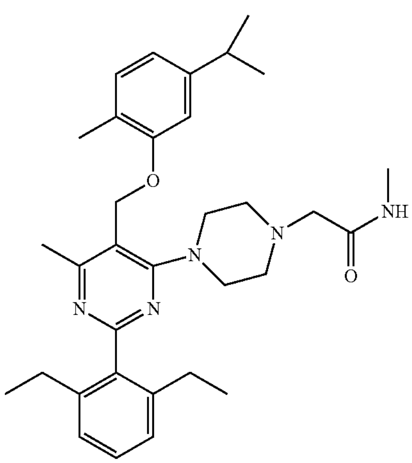 | 2-(4-{2-(2,6-diethylphenyl)-5-[(5-isopropyl-2-methylphenoxy)methyl]-6-methylpyrimidin-4-yl}piperazin-1-yl)-N-methylacetamide | 1.23 | 543.4 | 544.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 187 | 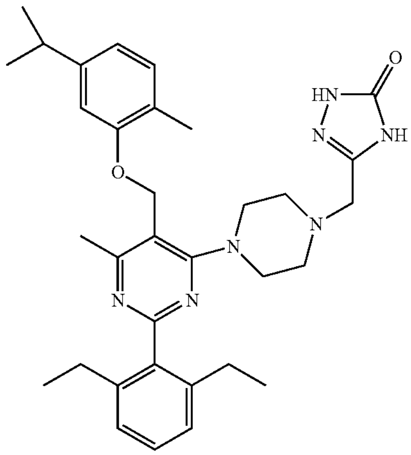 | 5-[(4-{2-(2,6-diethylphenyl)-5-[(5-isopropyl-2-methylphenoxy)methyl]-6-methylpyrimidin-4-yl}piperazin-1-yl)methyl]-2,4-dihydro-3H-1,2,4-triazol-3-one | 1.22 | 569.3 | 570.4 | 1 |
| 188 | 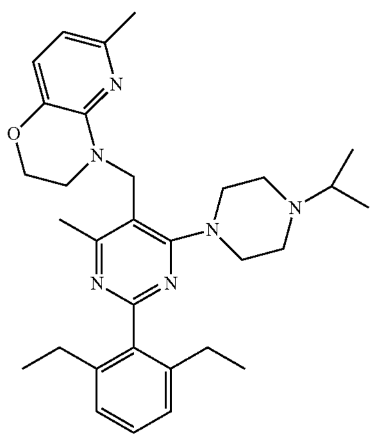 | 4-{[2-(2,6-diethylphenyl)-4-(4-isopropylpiperazin-1-yl)-6-methylpyrimidin-5-yl]methyl}-6-methyl-3,4-dihydro-2H-pyrido[3,2-b][1,4]oxazine | 1.12 | 514.3 | 515.4 | 1 |
| 189 | 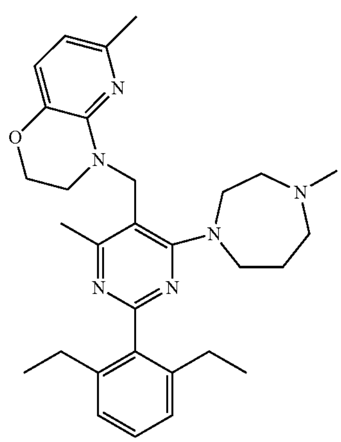 | 4-{[2-(2,6-diethylphenyl)-4-methyl-6-(4-methyl-1,4-diazepan-1-yl)pyrimidin-5-yl]methyl}-6-methyl-3,4-dihydro-2H-pyrido[3,2-b][1,4]oxazine | 1.64 | 500.6 | 501.2 | 3 |

TABLE II-continued

| Cpd # | Structure | Name | LCMS Retention Time | LCMS Mass (amu) | LCMS M + H (amu) | LCMS Method |
|---|---|---|---|---|---|---|
| 190 | 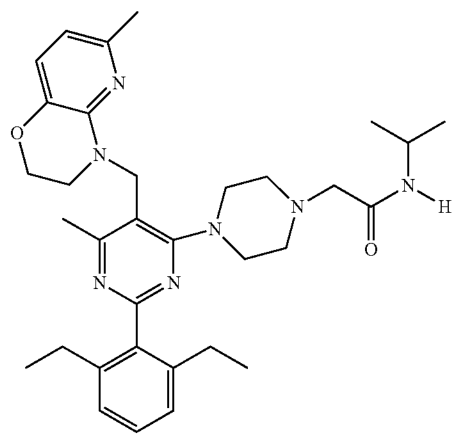 | 2-(4-{2-(2,6-diethylphenyl)-6-methyl-5-[(6-methyl-2,3-dihydro-4H-pyrido[3,2-b][1,4]oxazin-4-yl)methyl]pyrimidin-4-yl}piperazin-1-yl)-N-isopropylacetamide | 1.18 | 571.4 | 572.4 | 1 |
| 191 | 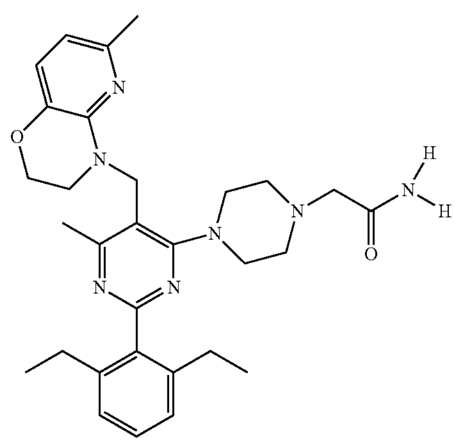 | 2-(4-{2-(2,6-diethylphenyl)-6-methyl-5-[(6-methyl-2,3-dihydro-4H-pyrido[3,2-b][1,4]oxazin-4-yl)methyl]pyrimidin-4-yl}piperazin-1-yl)acetamide | 1.14 | 529.3 | 530.3 | 1 |
| 192 | 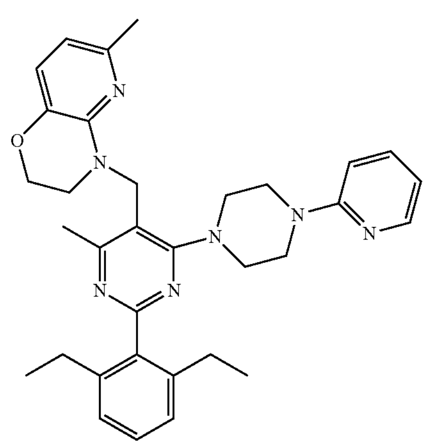 | 4-{[2-(2,6-diethylphenyl)-4-methyl-6-(4-pyridin-2-ylpiperazin-1-yl)pyrimidin-5-yl]methyl}-6-methyl-3,4-dihydro-2H-pyrido[3,2-b][1,4]oxazine | 2.36 | 549.7 | 550.2 | 3 |

TABLE II-continued

| Cpd # | Structure | Name | LCMS Retention Time | LCMS Mass (amu) | LCMS M + H (amu) | LCMS Method |
|---|---|---|---|---|---|---|
| 193 | 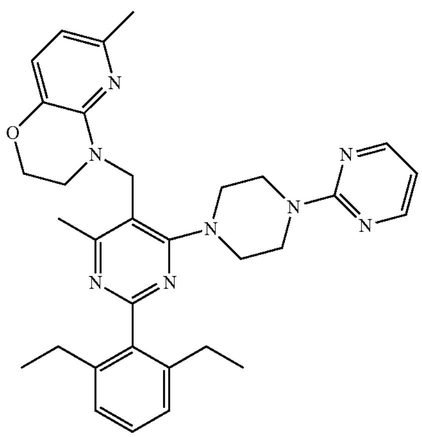 | 4-{[2-(2,6-diethylphenyl)-4-methyl-6-(4-pyrimidin-2-ylpiperazin-1-yl)pyrimidin-5-yl]methyl}-6-methyl-3,4-dihydro-2H-pyrido[3,2-b][1,4]oxazine | 1.25 | 550.3 | 551.3 | 1 |
| 194 | 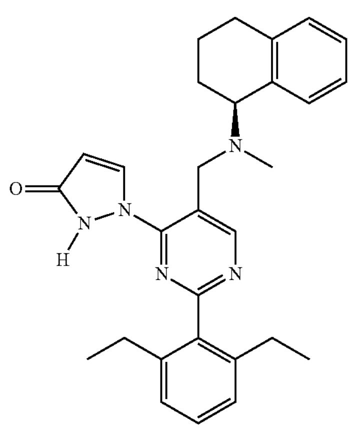 | 1-[2-(2,6-diethylphenyl)-6-methyl-5-({methyl[(1S)-1,2,3,4-tetrahydronaphthalen-1-yl]amino}methyl)pyrimidin-4-yl]-1,2-dihydro-3H-pyrazol-3-one | 2.18 | 481.3 | 482.2 | 3 |
| 195 | 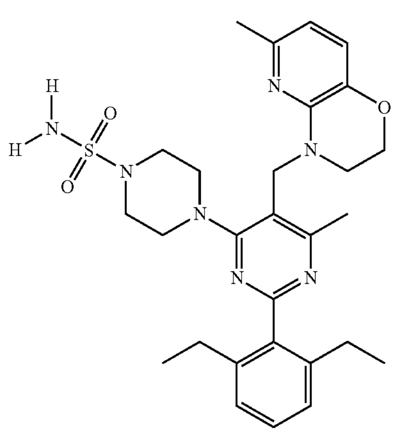 | 4-{2-(2,6-diethylphenyl)-6-methyl-5-[(6-methyl-2,3-dihydro-4H-pyrido[3,2-b][1,4]oxazin-4-yl)methyl]pyrimidin-4-yl}piperazine-1-sulfonamide | 1.16 | 551.3 | 552.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 196 | 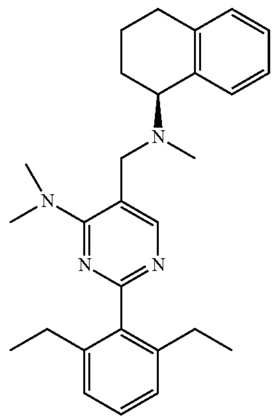 | 2-(2,6-diethylphenyl)-N,N,6-trimethyl-5-({methyl[(1S)-1,2,3,4-tetrahydronaphthalen-1-yl]amino}methyl)pyrimidin-4-amine | 1.22 | 442.3 | 443.5 | 1 |
| 197 | 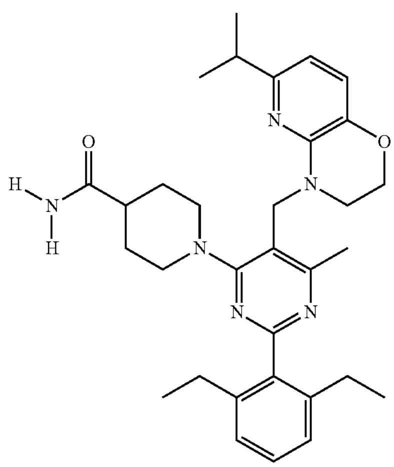 | 1-{2-(2,6-diethylphenyl)-6-methyl-5-[(6-methyl-2,3-dihydro-4H-pyrido[3,2-b][1,4]oxazin-4-yl)methyl]pyrimidin-4-yl}piperidine-4-carboxamide | 1.17 | 514.3 | 515.5 | 1 |
| 198 | 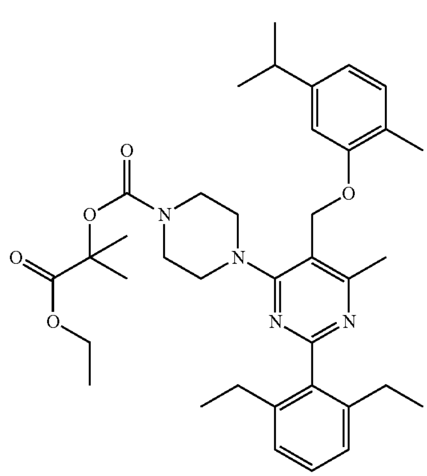 | 2-ethoxy-1,1-dimethyl-2-oxoethyl 4-{2-(2,6-diethylphenyl)-5-[(5-isopropyl-2-methylphenoxy)methyl]-6-methylpyrimidin-4-yl}piperazine-1-carboxylate | 1.3 | 630.4 | 631.7 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 199 | 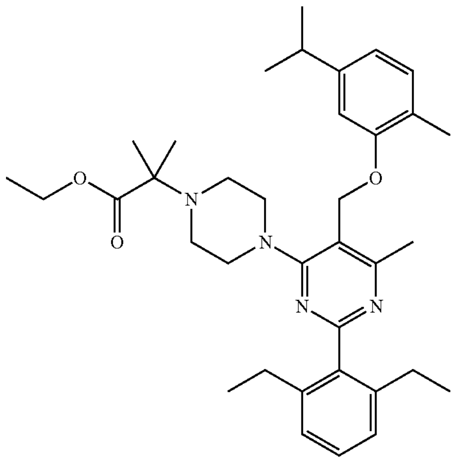 | ethyl 2-(4-{2-(2,6-diethylphenyl)-5-[(5-isopropyl-2-methylphenoxy)methyl]-6-methylpyrimidin-4-yl}piperazin-1-yl)-2-methylpropanoate | 1.31 | 586.4 | 588.7 | 1 |
| 200 | 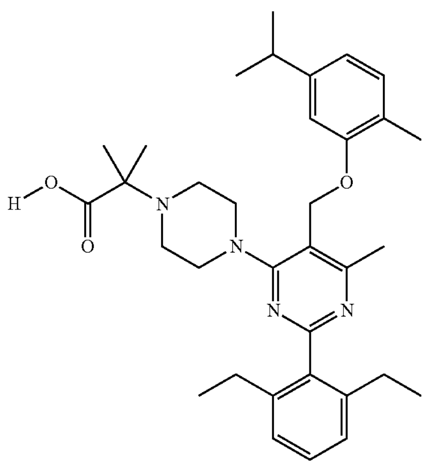 | 2-(4-{2-(2,6-diethylphenyl)-5-[(5-isopropyl-2-methylphenoxy)methyl]-6-methylpyrimidin-4-yl}piperazin-1-yl)-2-methylpropanoic acid | 1.25 | 558.4 | 559.6 | 1 |
| 201 | 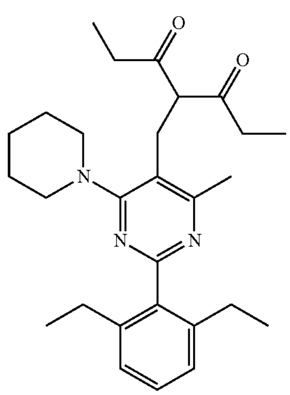 | 4-{[2-(2,6-diethylphenyl)-4-methyl-6-piperidin-1-ylpyrimidin-5-yl]methyl}heptane-3,5-dione | 1.2 | 449.3 | 450.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 202 | 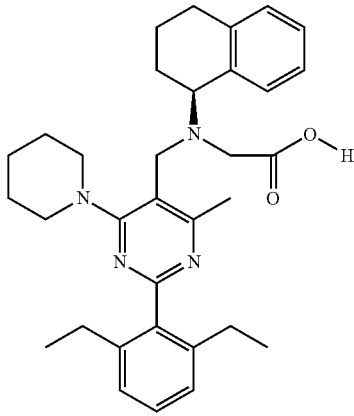 | N-{[2-(2,6-diethylphenyl)-4-methyl-6-piperidin-1-ylpyrimidin-5-yl]methyl}-N-[(1S)-1,2,3,4-tetrahydronaphthalen-1-yl]glycine | 1.26 | 526.3 | 527.5 | 1 |
| 203 | 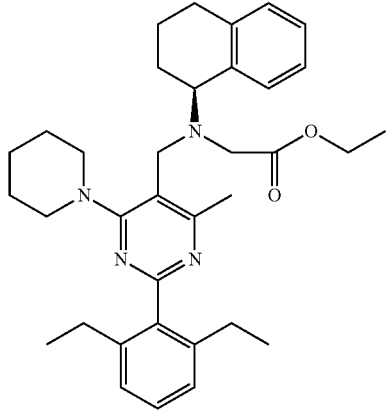 | ethyl N-{[2-(2,6-diethylphenyl)-4-methyl-6-piperidin-1-ylpyrimidin-5-yl]methyl}-N-[(1S)-1,2,3,4-tetrahydronaphthalen-1-yl]glycinate | 1.29 | 554.4 | 556.6 | 1 |
| 204 | 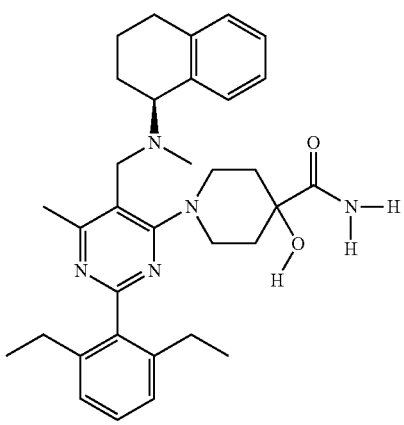 | 1-[2-(2,6-diethylphenyl)-6-methyl-5-({methyl[(1S)-1,2,3,4-tetrahydronaphthalen-1-yl]amino}methyl)pyrimidin-4-yl]-4-hydroxypiperidine-4-carboxamide | 1.21 | 541.3 | 542.5 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 205 | 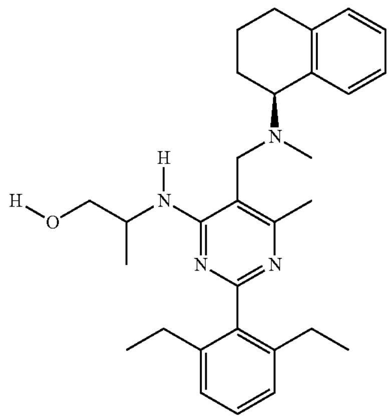 | 2-{[2-(2,6-diethylphenyl)-6-methyl-5-({methyl[(1S)-1,2,3,4-tetrahydronaphthalen-1-yl]amino}methyl)pyrimidin-4-yl]amino}propan-1-ol | 1.23 | 472.3 | 473.3 | 1 |
| 206 | 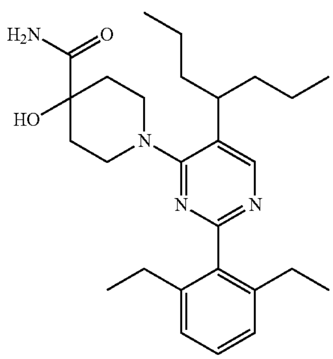 | 1-[2-(2,6-diethylphenyl)-5-(1-propylbutyl)pyrimidin-4-yl]-4-hydroxypiperidine-4-carboxamide | | | | |
| 207 | 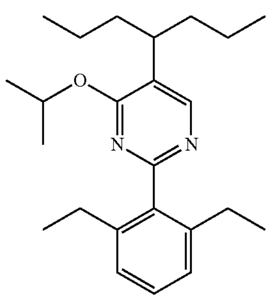 | 2-(2,6-diethylphenyl)-4-isopropoxy-5-(1-propylbutyl)pyrimidine | | | | |
| 208 | 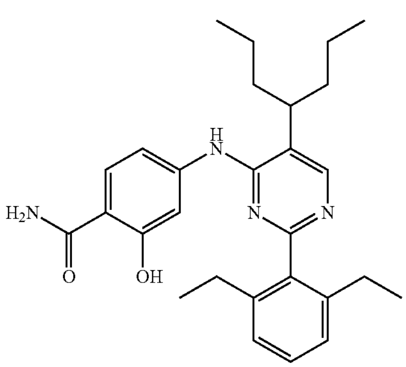 | 4-{[2-(2,6-diethylphenyl)-5-(1-propylbutyl)pyrimidin-4-yl]amino}-2-hydroxybenzamide | | | | |

TABLE II-continued

| Cpd # | Structure | Name | LCMS Retention Time | LCMS Mass (amu) | LCMS M + H (amu) | LCMS Method |
|---|---|---|---|---|---|---|
| 209 | 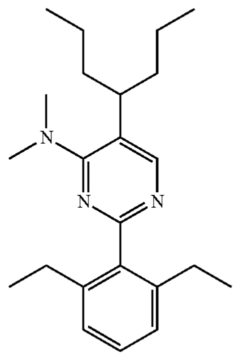 | 2-(2,6-diethylphenyl)-N,N-dimethyl-5-(1-propylbutyl)pyrimidin-4-amine | 1.21 | 353.3 | 354.3 | 1 |
| 210 | 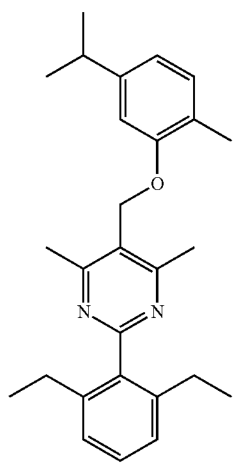 | 2-(2,6-diethylphenyl)-5-[(5-isopropyl-2-methylphenoxy)methyl]-4,6-dimethylpyrimidine | 1.45 | 402.3 | 403.3 | 1 |
| 211 | 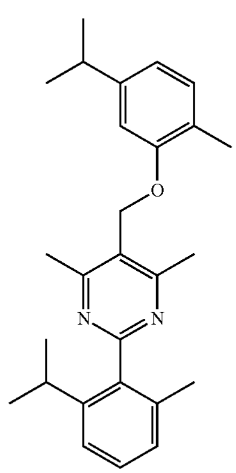 | 5-[(5-isopropyl-2-methylphenoxy)methyl]-2-(2-isopropyl-6-methylphenyl)-4,6-dimethylpyrimidine | 1.45 | 402.3 | 403.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 212 | 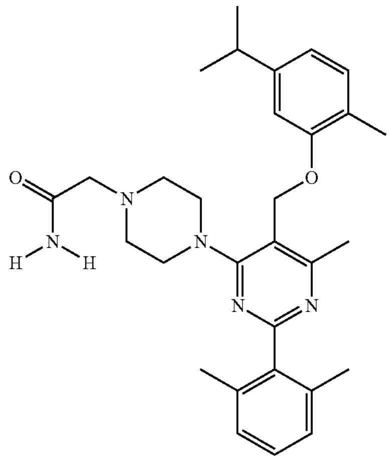 | 2-(4-{2-(2,6-dimethylphenyl)-5-[(5-isopropyl-2-methylphenoxy)methyl]-6-methylpyrimidin-4-yl}piperazin-1-yl)acetamide | 2.43 | 501.6 | 502.3 | 3 |
| 213 | 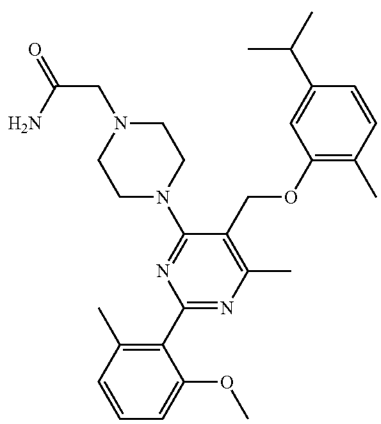 | 2-{4-[5-[(5-isopropyl-2-methylphenoxy)methyl]-2-(2-methoxy-6-methylphenyl)-6-methylpyrimidin-4-yl]piperazin-1-yl}acetamide | 1.17 | 517.3 | 518.3 | 1 |
| 214 | 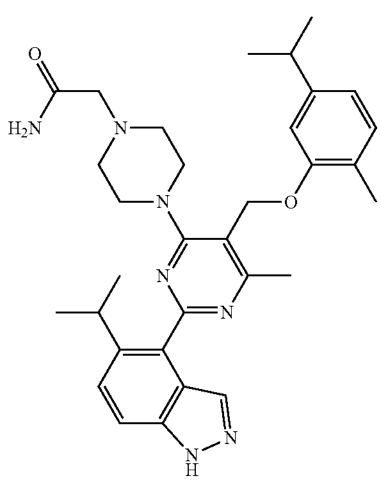 | 2-(4-{2-(5-isopropyl-1H-indazol-4-yl)-5-[(5-isopropyl-2-methylphenoxy)methyl]-6-methylpyrimidin-4-yl}piperazin-1-yl)acetamide | 1.2 | 555.3 | 556.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 215 | 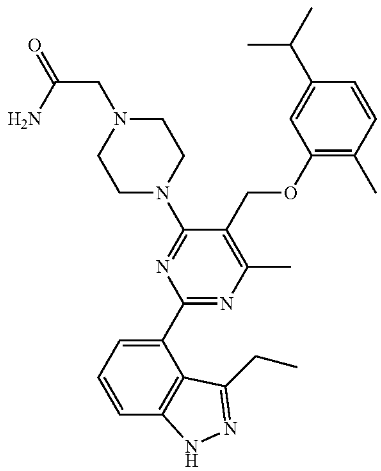 | 2-(4-{2-(3-ethyl-1H-indazol-4-yl)-5-[(5-isopropyl-2-methylphenoxy)methyl]-6-methylpyrimidin-4-yl}piperazin-1-yl)acetamide | 1.21 | 541.3 | 542.4 | 1 |
| 216 | 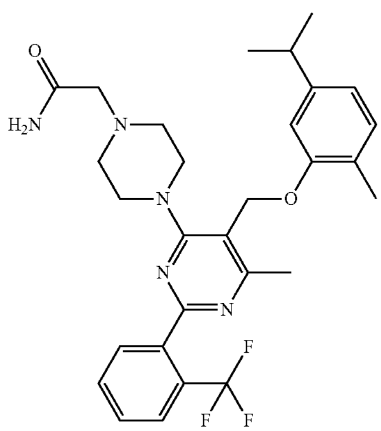 | 2-(4-{5-[(5-isopropyl-2-methylphenxoy)methyl]-6-methyl-2-[2-(trifluoromethyl)phenyl]pyrimidin-4-yl}piperazin-1-yl)acetamide | 1.25 | 541.3 | 542.3 | 1 |
| 217 | 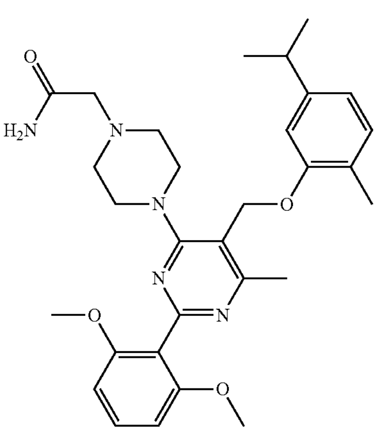 | 2-(4-{2-(2,6-dimethoxyphenyl)-5-[(5-isopropyl-2-methylphenoxy)methyl]-6-methylpyrimidin-4-yl}piperazin-1-yl)acetamide | 1.15 | 533.3 | 534.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 218 | 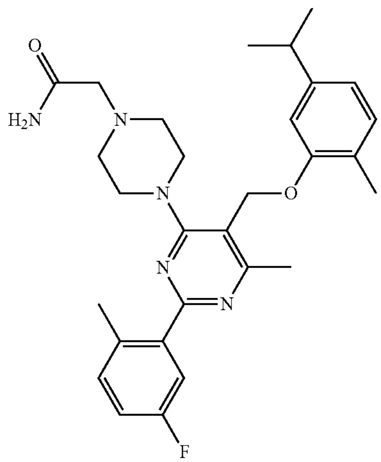 | 2-(4-{2-(5-fluoro-2-methylphenyl)-5-[(5-isopropyl-2-methylphenoxy)methyl]-6-methylpyrimidin-4-yl}piperazin-1-yl)acetamide | 1.27 | 505.3 | 506.3 | 1 |
| 219 | 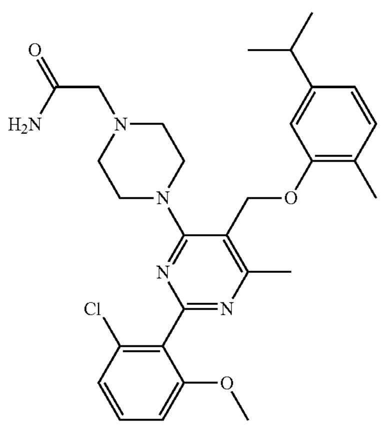 | 2-(4-{2-(2-chloro-6-methoxyphenyl)-5-[(5-isopropyl-2-methylphenoxy)methyl]-6-methylpyrimidin-4-yl}piperazin-1-yl)acetamide | 1.21 | 537.3 | 538.3 | 1 |
| 220 | 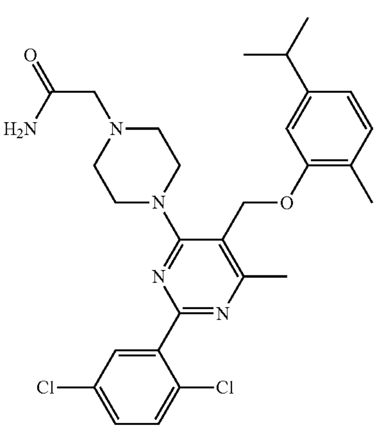 | 2-(4-{2-(2,5-dichlorophenyl)-5-[(5-isopropyl-2-methylphenoxy)methyl]-6-methylpyrimidin-4-yl}piperazin-1-yl)acetamide | 1.21 | 537.3 | 538.3 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 221 | 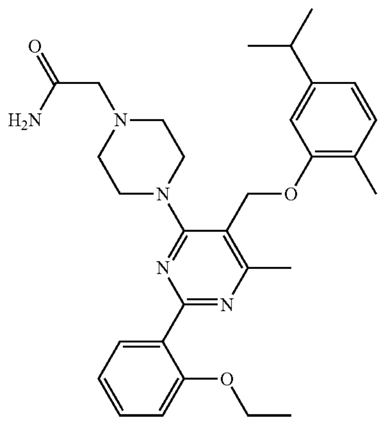 | 2-(4-{2-(2-ethoxyphenyl)-5-[(5-isopropyl-2-methylphenoxy)methyl]-6-methylpyrimidin-4-yl}piperazin-1-yl)acetamide | 1.21 | 537.3 | 538.3 | 1 |
| 222 | 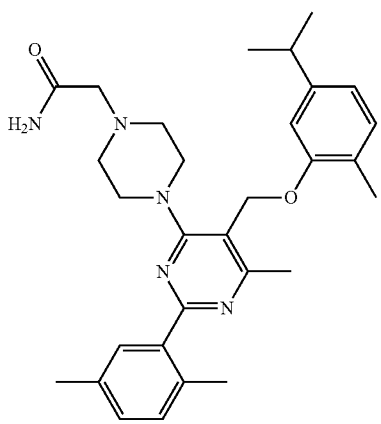 | 2-(4-{2-(2,5-dimethylphenyl)-5-[(5-isopropyl-2-methylphenoxy)methyl]-6-methylpyrimidin-4-yl}piperazin-1-yl)acetamide | 1.23 | 501.3 | 279.1 | 1 |
| 223 | 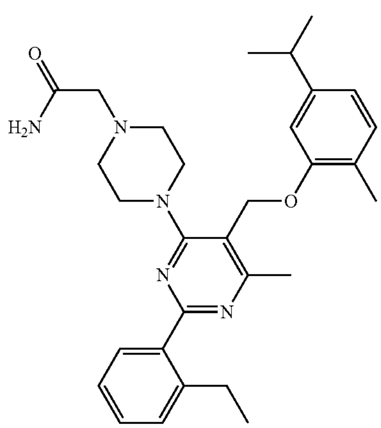 | 2-(4-{2-(2-ethylphenyl)-5-[(5-isopropyl-2-methylphenoxy)methyl]-6-methylpyrimidin-4-yl}piperazin-1-yl)acetamide | 1.23 | 501.3 | 502.4 | 1 |

TABLE II-continued

| Cpd # | Name | LCMS Retention Time | LCMS Mass (amu) | LCMS M + H (amu) | LCMS Method |
|---|---|---|---|---|---|
| 224 | 2-{4-[(5-isopropyl-2-methylphenoxy)methyl]-2-(2-methoxy-5-methylphenyl)-6-methylpyrimidin-4-yl]piperazin-1-yl}acetamide | 1.17 | 517.3 | 518.4 | 1 |
| 225 | 2-(4-{2-(5-chloro-2-methoxyphenyl)-5-[(5-isopropyl-2-methylphenoxy)methyl]-6-methylpyrimidin-4-yl}piperazin-1-yl)acetamide | 1.2 | 537.3 | 538.3 | 1 |
| 226 | 2-(4-{2-(5-fluoro-2-methoxyphenyl)-5-[(5-isopropyl-2-methylphenoxy)methyl]-6-methylpyrimidin-4-yl}piperazin-1-yl)acetamide | 1.18 | 521.3 | 522.4 | 1 |

TABLE II-continued

| Cpd # | Structure | Name | LCMS Retention Time | LCMS Mass (amu) | LCMS M + H (amu) | LCMS Method |
|---|---|---|---|---|---|---|
| 227 | 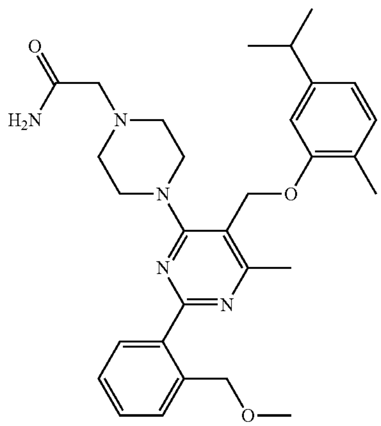 | 2-(4-{5-[(5-isopropyl-2-methylphenoxy)methyl]-2-[2-(methoxymethyl)phenyl]-6-methylpyrimidin-4-yl}piperazin-1-yl)acetamide | 1.35 | 517.3 | 501.0 | 1 |

TABLE III

| Cpd # | Structure | Name | LCMS Ret Time (min) | LCMS Mass (amu) | LCMS M + H (amu) | LCMS Method |
|---|---|---|---|---|---|---|
| 228 | 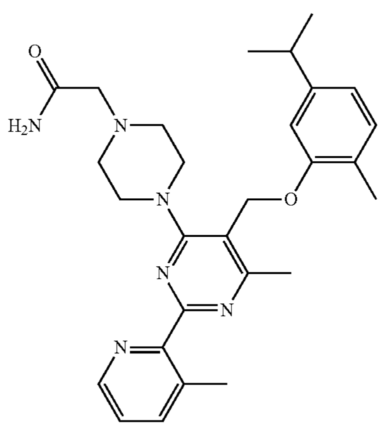 | 2-{4-[5-[(5-isopropyl-2-methylphenoxy)methyl]-6-methyl-2-(3-methylpyridin-2-yl) pyrimidin-4-yl]piperazin-1-yl}acetamide | 1.17 | 488.3 | 489.3 | 1 |
| 229 | 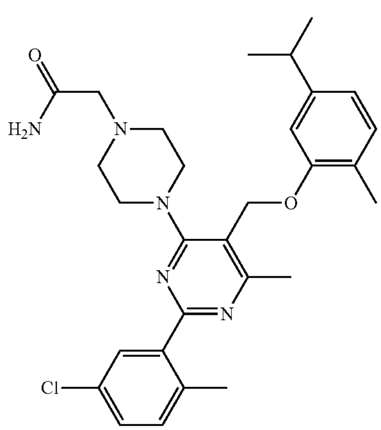 | 2-(4-{2-(5-chloro-2-methylphenyl)-5-[(5-isopropyl-2-methylphenoxy)methyl]-6-methylpyrimidin-4-yl}piperazin-1-yl)acetamide | 1.31 | 521.3 | 522.3 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 230 | 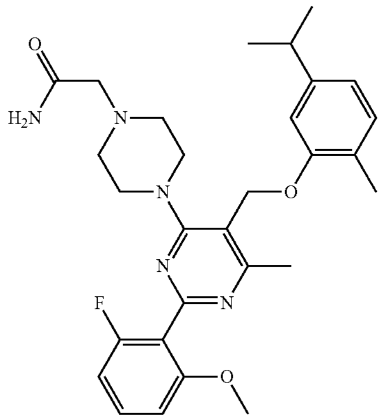 | 2-(4-{2-(2-fluoro-6-methoxyphenyl)-5-[(5-isopropyl-2-methylphenoxy)methyl]-6-methylpyrimidin-4-yl}piperazin-1-yl)acetamide | | | | |
| 231 | 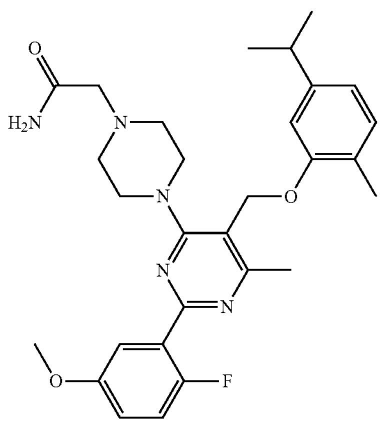 | 2-(4-{2-(2-fluoro-5-methoxyphenyl)-5-[(5-isopropyl-2-methylphenoxy)methyl]-6-methylpyrimidin-4-yl}piperazin-1-yl)acetamide | 1.26 | 521.3 | 522.3 | 1 |
| 232 | 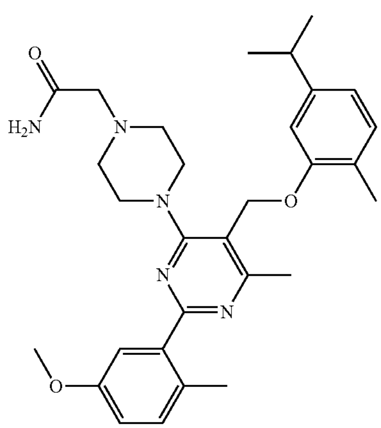 | 2-{4-[5-isopropyl-2-methylphenoxy)methyl]-2-(5-methoxy-2-methylphenyl)-6-methylpyrimidin-4-yl]piperazin-1-yl}acetamide | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 233 | 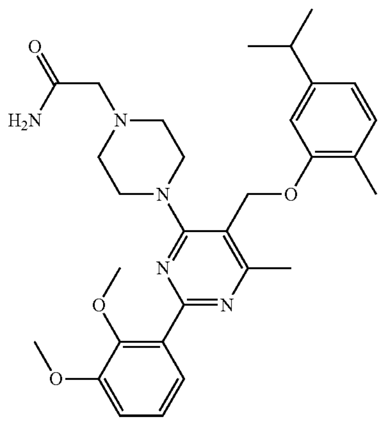 | 2-(4-{2-(2,3-dimethoxyphenyl)-5-[(5-isopropyl-2-methylphenoxy)methyl]-6-methylpyrimidin-4-yl}piperazin-1-yl)acetamide | | | | |
| 234 | 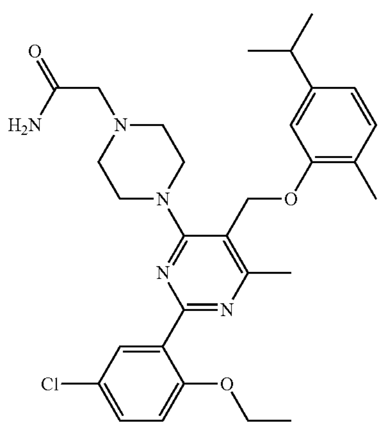 | 2-(4-{2-(5-chloro-2-ethoxyphenyl)-5-[(5-isopropyl-2-methylphenoxy)methyl]-6-methylpyrimidin-4-yl}piperazin-1-yl)acetamide | 1.22 | 551.3 | 552.3 | 1 |
| 235 | 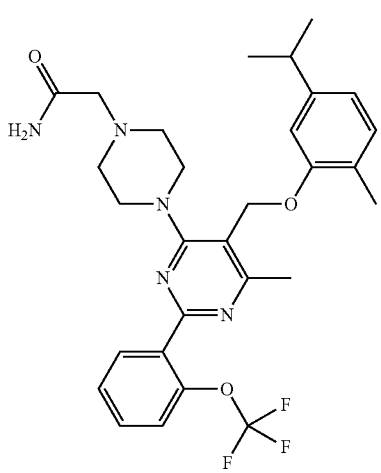 | 2-(4-{5-[(5-isopropyl-2-methylphenoxy)methyl]-6-methyl-2-[2-(trifluoromethoxy)phenyl]pyrimidin-4-yl}piperazin-1-yl)acetamide | 1.29 | 557.3 | 558.3 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 236 | 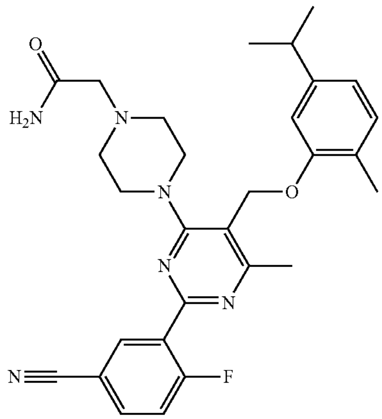 | 2-(4-{2-(5-cyano-2-fluorophenyl)-5-[(5-isopropyl-2-methylphenoxy) methyl]-6-methylpyrimidin-4-yl}piperazin-1-yl)acetamide | | | | |
| 237 | 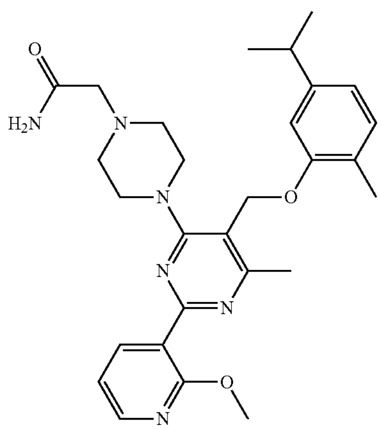 | 2-{4-[5-[(5-isopropyl-2-methylphenoxy)methyl]-2-(2-methoxypyridin-3-yl)-6-methylpyrimidin-4-yl]piperazin-1-yl}acetamide | 1.19 | 504.3 | 505.3 | 1 |
| 238 | 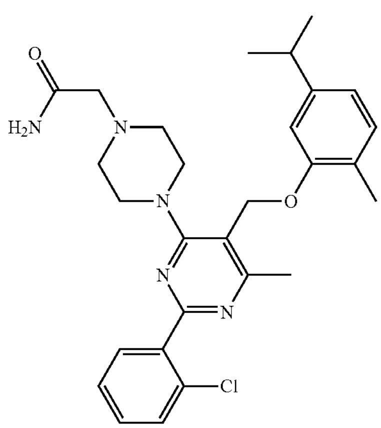 | 2-(4-{2-(2-chlorophenyl)-5-[(5-isopropyl-2-methylphenoxy) methyl]-6-methylpyrimidin-4-yl}piperazin-1-yl)acetamide | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 239 | 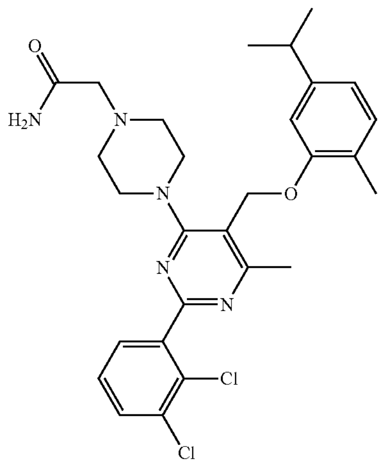 | 2-(4-{2-(2,3-dichlorophenyl)-5-[(5-isopropyl-2-methylphenoxy) methyl]-6-methylpyrimidin-4-yl}piperazin-1-yl)acetamide | | | | |
| 240 | 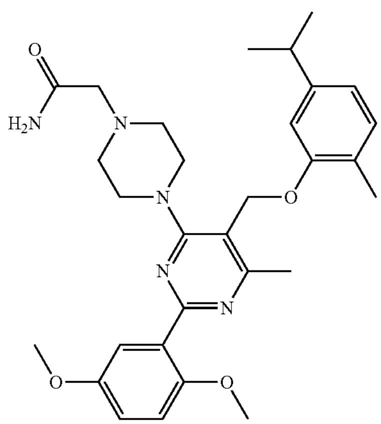 | 2-(4-{2-(2,5-dimethoxyphenyl)-5-[(5-isopropyl-2-methylphenoxy) methyl]-6-methylpyrimidin-4-yl}piperazin-1-yl)acetamide | | | | |
| 241 | 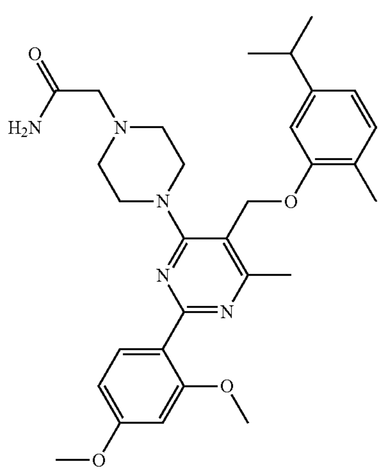 | 2-(4-{2-(2,4-dimethoxyphenyl)-5-[(5-isopropyl-2-methylphenoxy) methyl]-6-methylpyrimidn-4-yl}piperazin-1-yl)acetamide | 1.18 | 533.3 | 534.3 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 242 | 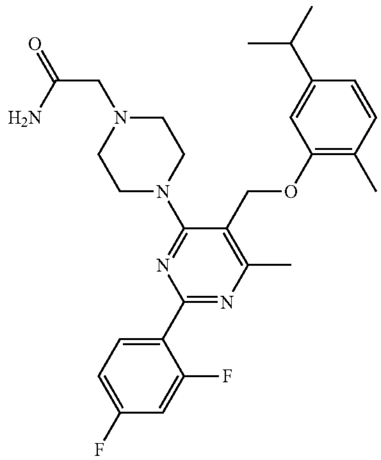 | 2-(4-{2-(2,4-difluorophenyl)-5-[(5-isopropyl-2-methylphenoxy) methyl]-6-methylpyrimidin-4-yl}piperazin-1-yl)acetamide | 1.28 | 509.3 | 510.3 | 1 |
| 243 | 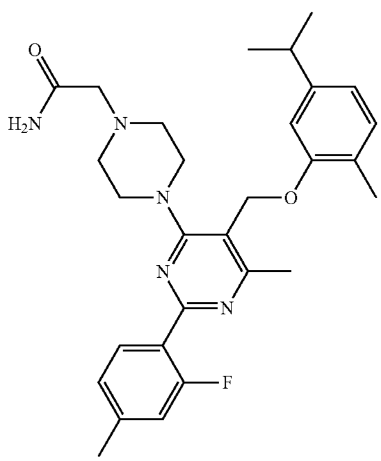 | 2-(4-{2-(2-fluoro-4-methylphenyl)-5-[(5-isopropyl-2-methylphenoxy) methyl]-6-methylpyrimidin-4-yl}piperazin-1-yl)acetamide | 1.26 | 505.3 | 506.3 | 1 |
| 244 | 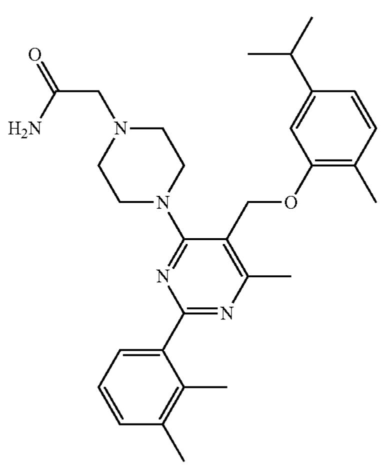 | 2-(4-{2-(2,3-dimethylphenyl)-5-[(5-isopropyl-2-methylphenoxy) methyl]-6-methylpyrimidin-4-yl}piperazin-1-yl)acetamide | 1.23 | 501.3 | 502.4 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 245 | 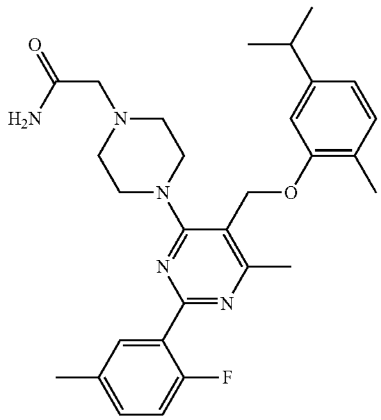 | 2-(4-{2-(2-fluoro-5-methylphenyl)-5-[(5-isopropyl-2-methylphenoxy)methyl]-6-methylpyrimidin-4-yl}piperazin-1-yl)acetamide | 1.27 | 505.3 | 506.3 | 1 |
| 246 | 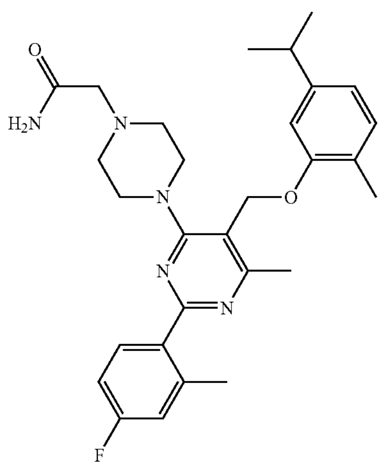 | 2-(4-{2-(4-fluoro-2-methylphenyl)-5-[(5-isopropyl-2-methylphenoxy)methyl]-6-methylpyrimidin-4-yl}piperazin-1-yl)acetamide | 1.25 | 505.3 | 506.3 | 1 |
| 247 | 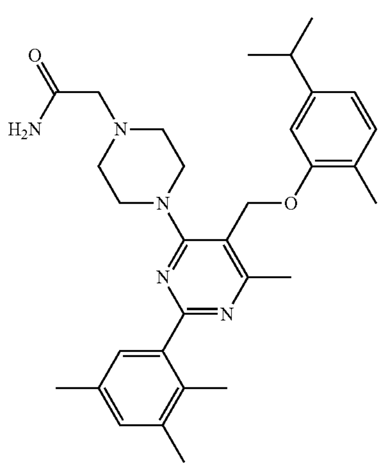 | 2-{4-[5-[(5-isopropyl-2-methylphenoxy)methyl]-6-methyl-2-(2,3,5-trimethylphenyl)pyrimidin-4-yl]piperazin-1-yl}acetamide | 1.26 | 515.3 | 516.4 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 248 | 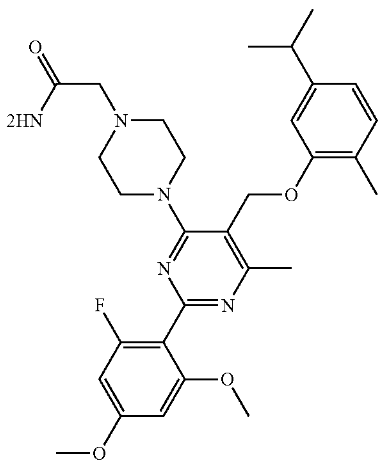 | 2-(4-{2-(2-fluoro-4,6-dimethoxyphenyl)-5-[(5-isopropyl-2-methylphenoxy)methyl]-6-methylpyrimidin-4-yl}piperazin-1-yl)acetamide | 1.2 | 551.3 | 552.3 | 1 |
| 249 | 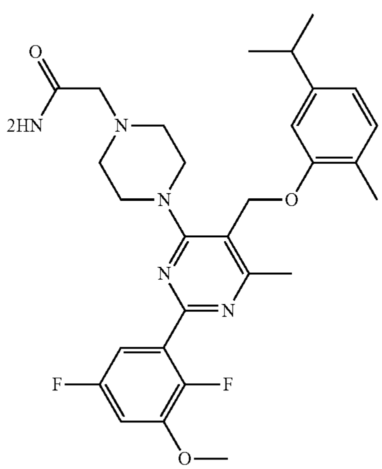 | 2-(4-{2-(2,5-difluoro-3-methoxyphenyl)-5-[(5-isopropyl-2-methylphenoxy)methyl]-6-methylpyrimidin-4-yl}piperazin-1-yl)acetamide | 1.28 | 539.3 | 540.3 | 1 |
| 250 | 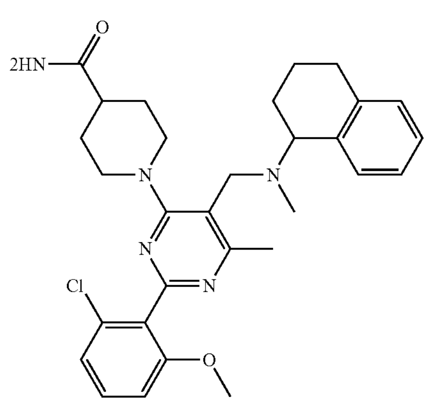 | 1-(2-(2-chloro-6-methoxyphenyl)-6-methyl-5-{[methyl(1,2,3,4-tetrahydronaphthalen-1-yl)amino]methyl}pyrimidin-4-yl)piperidine-4-carboxamide | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 251 | 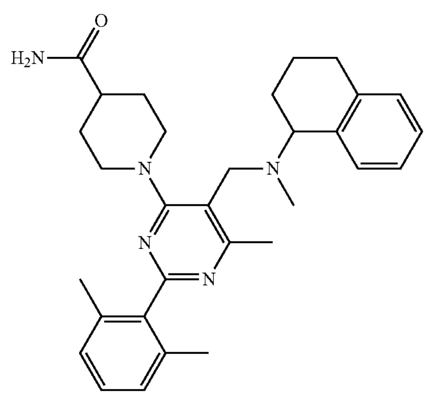 | 1-(2-(2,6-dimethylphenyl)-6-methyl-5-{[methyl(1,2,3,4-tetrahydronaphthalen-1-yl)amino]methyl}pyrimidin-4-yl)piperidine-4-carboxamide | 1.19 | 497.3 | 498.4 | 1 |
| 252 | 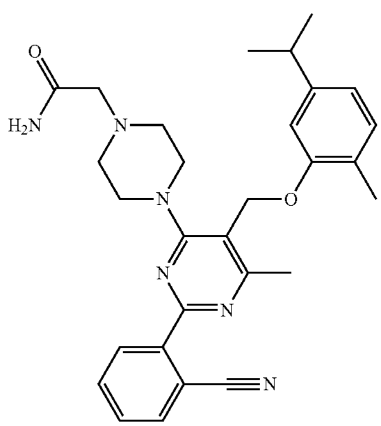 | 2-(4-{2-(2-cyanophenyl)-5-[(5-isopropyl-2-methylphenoxy) methyl]-6-methylpyrimidin-4-yl}piperazin-1-yl)acetamide | | | | |
| 253 | 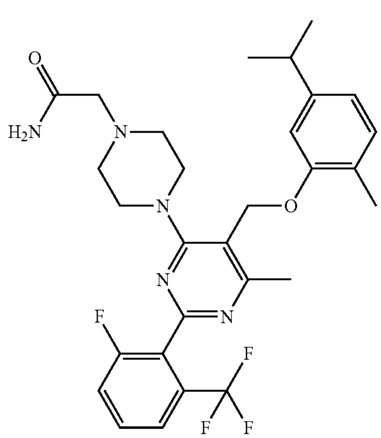 | 2-(4-{2-[2-fluoro-6-(trifluoromethyl)phenyl]-5-[(5-isopropyl-2-methylphenoxy) methyl]-6-methylpyrimidin-4-yl}piperazin-1-yl)acetamide | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 254 | 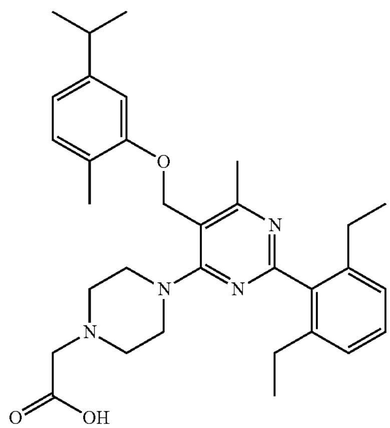 | (4-{2-(2,6-diethylphenyl)-5-[(5-isopropyl-2-methylphenoxy)methyl]-6-methylpyrimidin-4-yl}piperazin-1-yl)acetic acid | | | | |
| 255 | 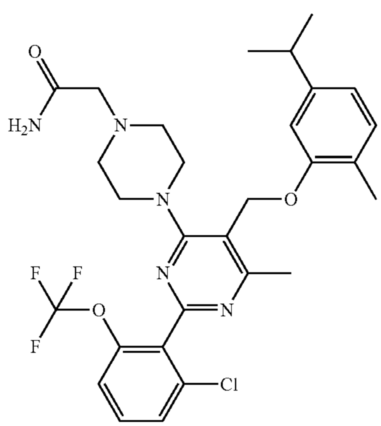 | 2-(4-{2-[2-chloro-6-(trifluoromethoxy)phenyl]-5-[(5-isopropyl-2-methylphenoxy) methyl]-6-methylpyrimidin-4-yl}piperazin-1-yl)acetamide | | | | |
| 256 | 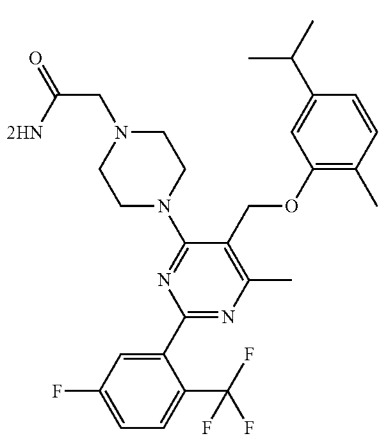 | 2-(4-{2-[5-fluoro-2-(trifluoromethyl)phenyl]-5-[(5-isopropyl-2-methylphenoxy) methyl]-6-methylpyrimidin-4-yl}piperazin-1-yl)acetamide | 1.3 | 559.3 | 560.3 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 257 | 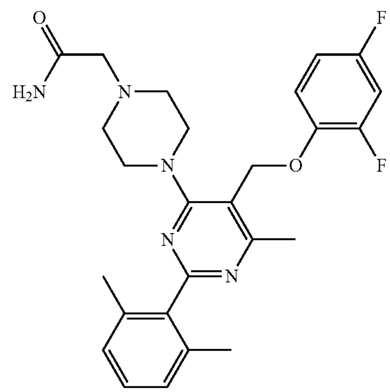 | 2-{4-[5-[(2,4-difluorophenoxy)methyl]-2-(2,6-dimethylphenyl)-6-methylpyrimidin-4-yl]piperazin-1-yl}acetamide | | | | |
| 258 | 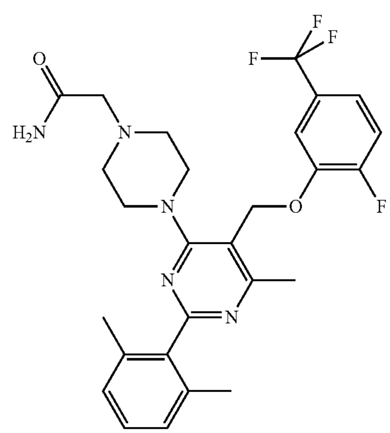 | 2-[4-(2-(2,6-dimethylphenyl)-5-{[2-fluoro-5-(trifluoromethyl)phenoxy]methyl}-6-methylpyrimidin-4-yl)piperazin-1-yl]acetamide | | | | |
| 259 | 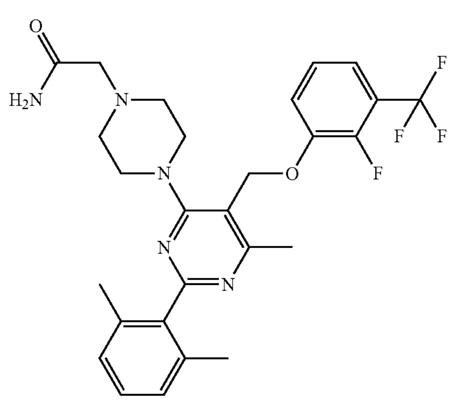 | 2-[4-(2-(2,6-dimethylphenyl)-5-{[2-fluoro-3-(trifluoromethyl)phenoxy]methyl}-6-methylpyrimidin-4-yl)piperazin-1-yl]acetamide | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 260 | 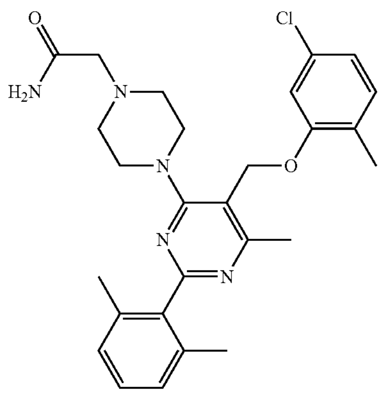 | 2-{4-[5-[(5-chloro-2-methylphenoxy)methyl]-2-(2,6-dimethylphenyl)-6-methylpyrimidin-4-yl]piperazin-1-yl}acetamide | | | | |
| 261 | 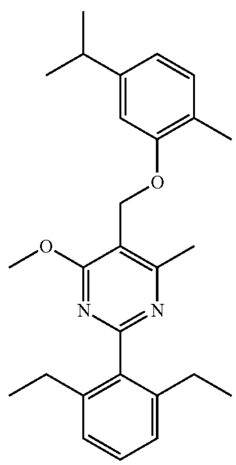 | 2-(2,6-diethylphenyl)-5-[(5-isopropyl-2-methylphenoxy)methyl]-4-methoxy-6-methylpyrimidine | 1.56 | 418.3 | 419.3 | 1 |
| 262 | 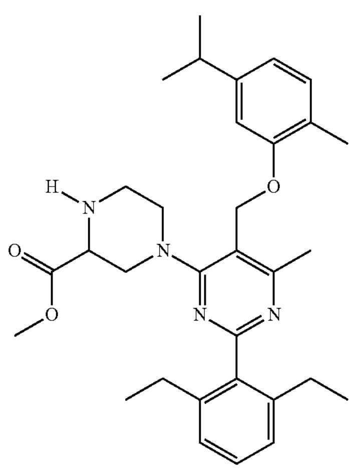 | methyl 4-{2-(2,6-diethylphenyl)-5-[(5-isopropyl-2-methylphenoxy)methyl]-6-methylpyrimidin-4-yl}piperazine-2-carboxylate | 1.3 | 530.3 | 531.4 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 263 | 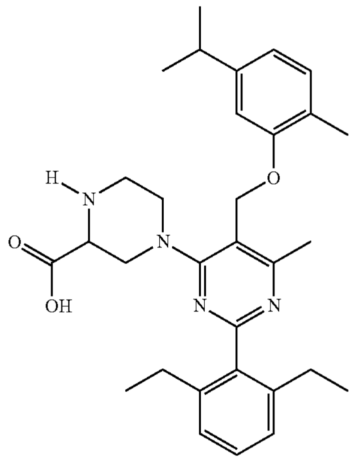 | 4-{2-(2,6-diethylphenyl)-5-[(5-isopropyl-2-methylphenoxy)methyl]-6-methylpyrimidin-4-yl}piperazine-2-carboxylic acid | 1.29 | 516.3 | 517.4 | 1 |
| 264 | 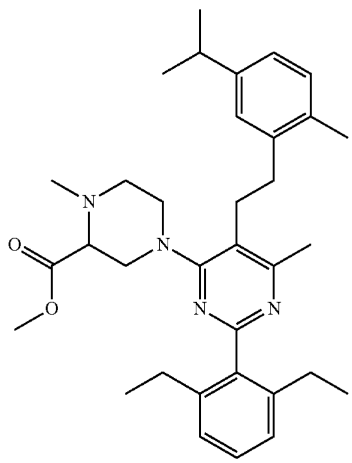 | methyl 4-{2-(2,6-diethylphenyl)-5-[(5-isopropyl-2-methylphenoxy)methyl]-6-methylpyrimidin-4-yl}-1-methylpiperazine-2-carboxylate | 1.32 | 544.3 | 545.4 | 1 |
| 265 | 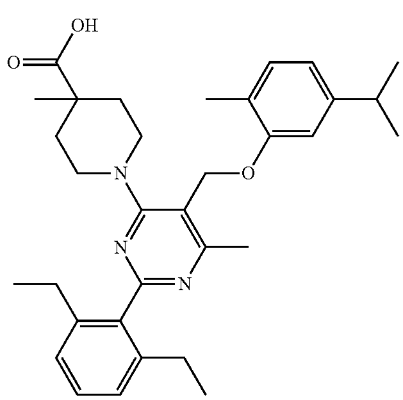 | 1-{2-(2,6-diethylphenyl)-5-[(5-isopropyl-2-methylphenoxy)methyl]-6-methylpyrimidin-4-yl}-4-methylpiperidine-4-carboxylic acid | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 266 | 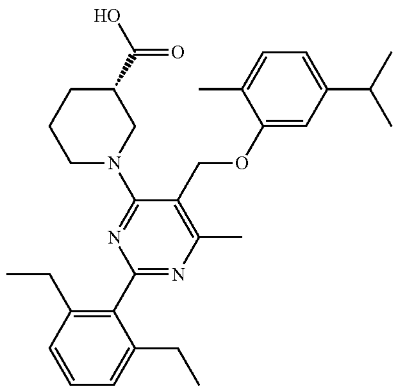 | (3S)-1-{2-(2,6-diethylphenyl)-5-[(5-isopropyl-2-methylphenoxy) methyl]-6-methylpyrimidin-4-yl}piperidine-3-carboxylic acid | 1.31 | 515.3 | 516.4 | 1 |
| 267 | 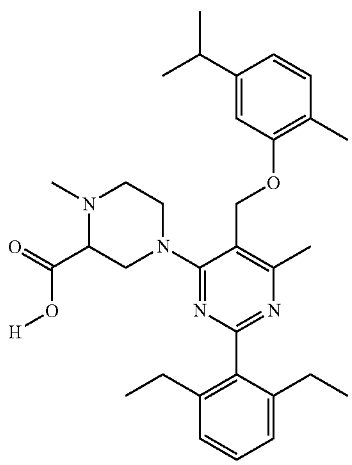 | 4-{2-(2,6-diethylphenyl)-5-[(5-isopropyl-2-methylphenoxy) methyl]-6-methylpyrimidin-4-yl}-1-methylpiperazine-2-carboxylic acid | 1.29 | 530.3 | 531.4 | 1 |
| 268 | 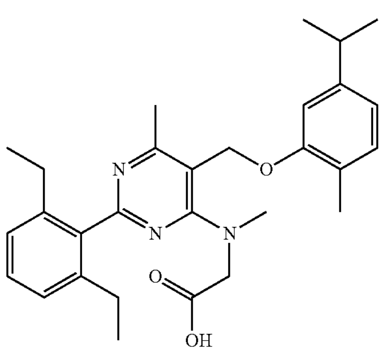 | N-{2-(2,6-diethylphenyl)-5-[(5-isopropyl-2-methylphenoxy) methyl]-6-methylpyrimidin-4-yl}-N-methylglycine | 1.29 | 475.3 | 476.4 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 269 | 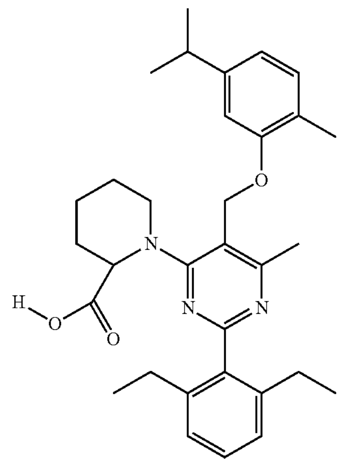 | 1-{2-(2,6-diethylphenyl)-5-[(5-isopropyl-2-methylphenoxy) methyl]-6-methylpyrimidin-4-yl}piperidine-2-carboxylic acid | 1.34 | 515.3 | 516.4 | 1 |
| 270 | 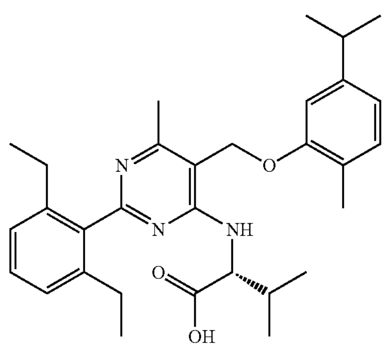 | N-{2-(2,6-diethylphenyl)-5-[(5-isopropyl-2-methylphenoxy) methyl]-6-methylpyrimidin-4-yl}-D-valine | 1.33 | 503.3 | 504.4 | 1 |
| 271 | 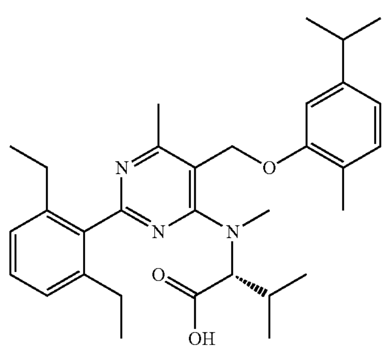 | N-{2-(2,6-diethylphenyl)-5-[(5-isopropyl-2-methylphenoxy) methyl]-6-methylpyrimidin-4-yl}-N-methyl-D-valine | 1.34 | 517.3 | 518.4 | 1 |
| 272 | 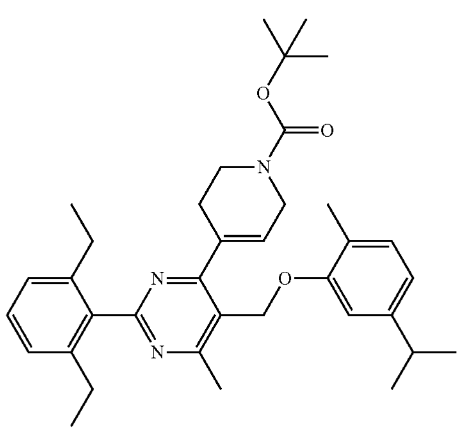 | tert-butyl 4-{2-(2,6-diethylphenyl)-5-[(5-isopropyl-2-methylphenoxy) methyl]-6-methylpyrimidin-4-yl}-3,6-dihydropyridine-1(2H)-carboxylate | 1.59 | 569.4 | 570.5 | 1 |

| Cpd # | Structure | Name | LCMS Ret Time (min) | LCMS Mass (amu) | LCMS M + H (amu) | LCMS Method |
|---|---|---|---|---|---|---|
| 273 | 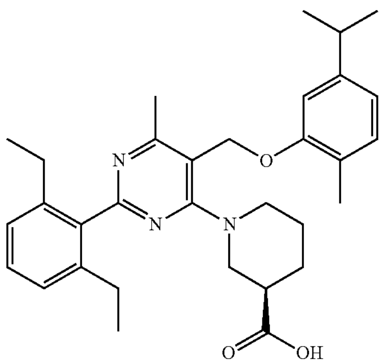 | (3R)-1-{2-(2,6-diethylphenyl)-5-[(5-isopropyl-2-methylphenoxy) methyl]-6-methylpyrimidin-4-yl}piperidine-3-carboxylic acid | | | | |
| 274 | 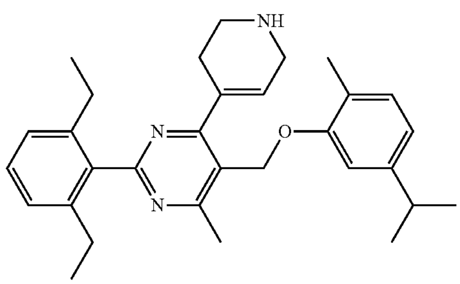 | 2-(2,6-diethylphenyl)-5-[(5-isopropyl-2-methylphenoxy)methyl]-4-methyl-6-(1,2,3,6-tetrahydropyridin-4-yl)pyrimidine | 1.34 | 469.3 | 470.4 | 1 |
| 275 | 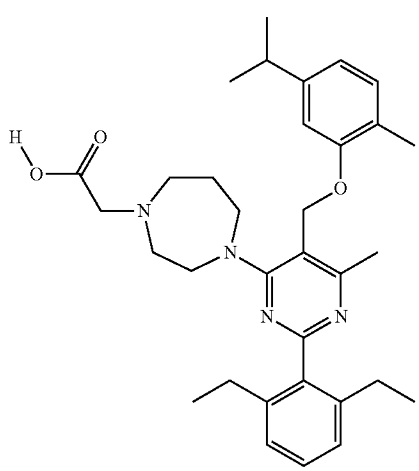 | (4-{2-(2,6-diethylphenyl)-5-[(5-isopropyl-2-methylphenoxy) methyl]-6-methylpyrimidin-4-yl}-1,4-diazepan-1-yl)acetic acid | 1.25 | 544.3 | 545.5 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 276 | 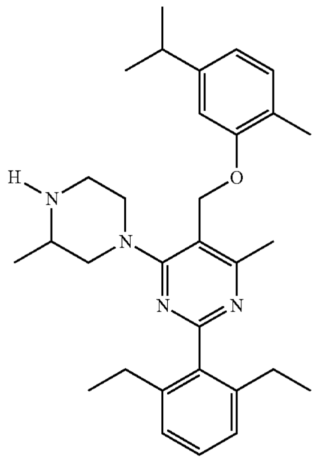 | 2-(2,6-diethylphenyl)-5-[(5-isopropyl-2-methylphenoxy)methyl]-4-methyl-6-(3-methylpiperazin-1-yl)pyrimidine | | | | |
| 277 | 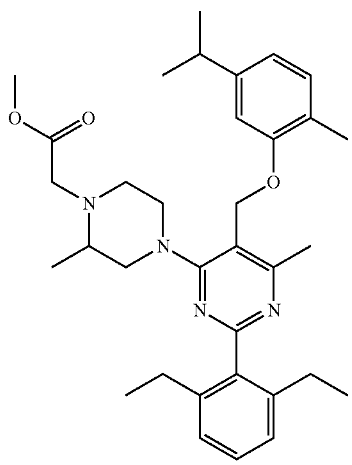 | methyl (4-{2-(2,6-diethylphenyl)-5-[(5-isopropyl-2-methylphenoxy)methyl]-6-methylpyrimidin-4-yl}-2-methylpiperazin-1-yl)acetate | 1.29 | 558.4 | 559.4 | 1 |
| 278 | 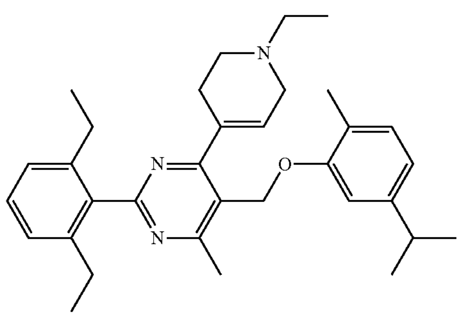 | 2-(2,6-diethylphenyl)-4-(1-ethyl)-1,2,3,6-tetrahydropyridin-4-yl)-5-[(5-isopropyl-2-methylphenoxy)methyl]-6-methylpyrimidine | 1.29 | 497.3 | 498.4 | 1 |
| 279 | 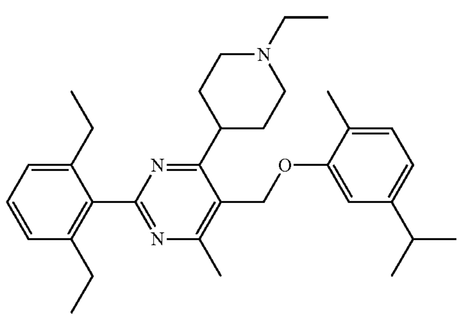 | 2-(2,6-diethylphenyl)-4-(1-ethylpiperidin-4-yl)-5-[(5-isopropyl-2-methylphenoxy)methyl]-6-methylpyrimidine | 1.3 | 499.4 | 500.4 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 280 | 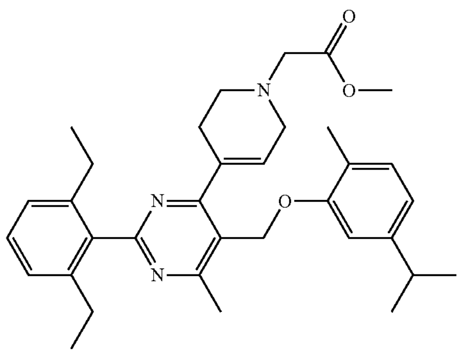 | methyl [4-{2-(2,6-diethylphenyl)-5-[(5-isopropyl-2-methylphenoxy)methyl]-6-methylpyrimidin-4-yl}-3,6-dihydropyridin-1(2H)-yl]acetate | 1.3 | 541.3 | 542.4 | 1 |
| 281 | 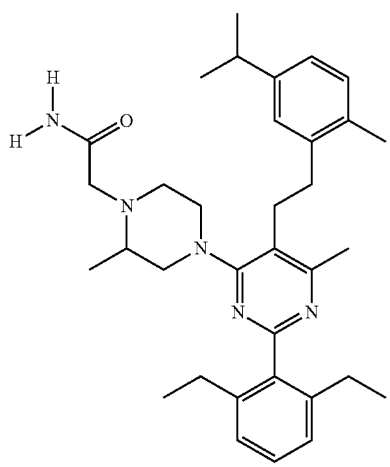 | 2-(4-{2-(2,6-diethylphenyl)-5-[(5-isopropyl-2-methylphenoxy) methyl]-6-methylpyrimidin-4-yl}-2-methylpiperazin-1-yl)acetamide | 1.25 | 543.4 | 544.4 | 1 |
| 282 | 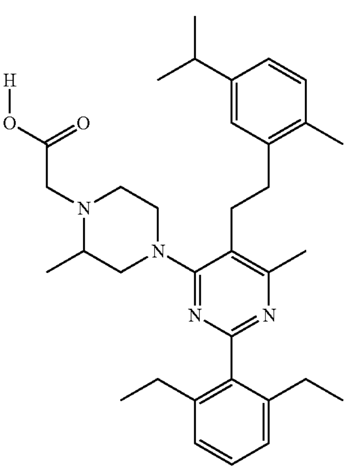 | (4-{2-(2,6-diethylphenyl)-5-[(5-isopropyl-2-methylphenoxy) methyl]-6-methylpyrimidin-4-yl}-2-methylpiperazin-1-yl)acetic acid | 1.26 | 544.3 | 545.4 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 283 | 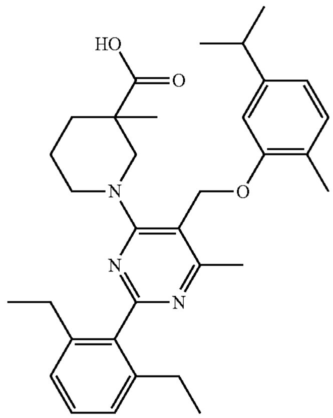 | 1-{2-(2,6-diethylphenyl)-5-[(5-isopropyl-2-methylphenoxy)methyl]-6-methylpyrimidin-4-yl}-3-methylpiperidine-3-carboxylic acid | 1.29 | 529.3 | 530.4 | 1 |
| 284 | 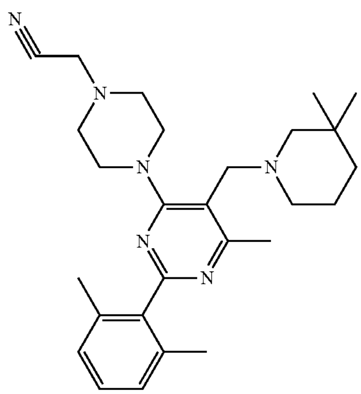 | (4-{2-(2,6-dimethylphenyl)-5-[(3,3-dimethylpiperidin-1-yl)methyl]-6-methylpyrimidin-4-yl}piperazin-1-yl)acetonitrile | | | | |
| 285 | 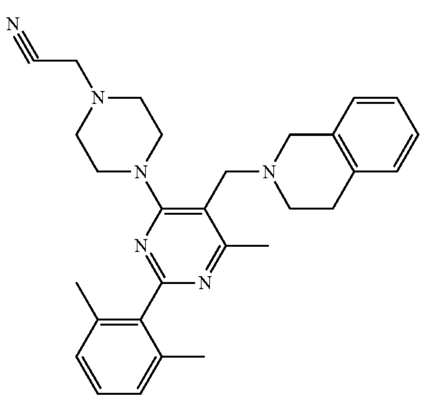 | {4-[5-(3,4-dihydroisoquinolin-2(1H)-ylmethyl)-2-(2,6-dimethylphenyl)-6-methylpyrimidin-4-yl]piperazin-1-yl} acetonitrile | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 286 | 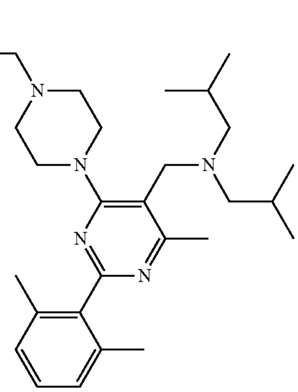 | {4-[5-[(diisobutylamino)methyl]-2-(2,6-dimethylphenyl)-6-methylpyrimidin-4-yl]piperazin-1-yl} acetonitrile | | | | |
| 287 | 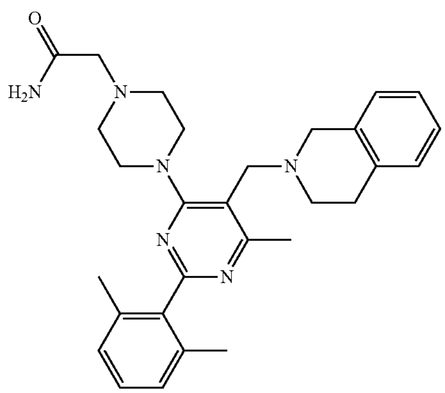 | 2-{4-[5-(3,4-dihydroisoquinolin-2(1H)-ylmethyl)-2-(2,6-dimethylphenyl)-6-methylpyrimidin-4-yl]piperazin-1-yl} acetamide | | | | |
| 288 | 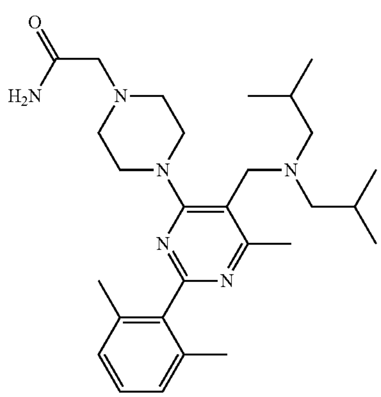 | 2-{4-[5-[(dissobutylamino)methyl]-2-(2,6-dimethylphenyl)-6-methylpyrimidin-4-yl]piperazin-1-yl} acetamide | | | | |
| 289 | 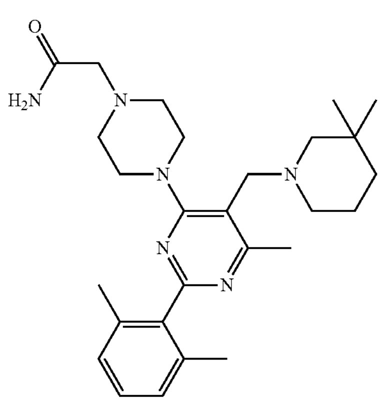 | 2-(4-{2-(2,6-dimethylphenyl)-5-[(3,3-dimethylpiperidin-1-yl)methyl]-6-methylpyrimidin-4-yl}piperazin-1-yl) acetamide | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 290 | 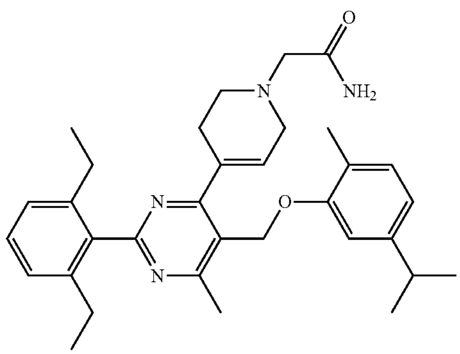 | 2-[4-{2-(2,6-diethylphenyl)-5-[(5-isopropyl-2-methylphenoxy) methyl]-6-methylpyrimidin-4-yl}-3,6-dihydropyridin-1(2H)-yl] acetamide | 1.29 | 526.3 | 527.4 | 1 |
| 291 | 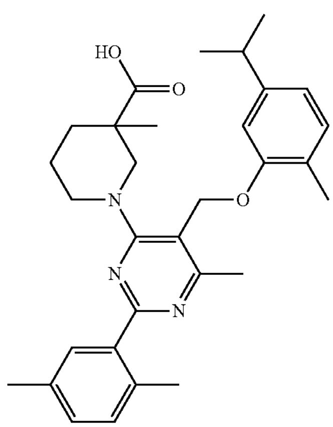 | 1-{2-(2,5-dimethylphenyl)-5-[(5-isopropyl-2-methylphenoxy) methyl]-6-methylpyrimidin-4-yl}-3-methylpiperidine-3-carboxylic acid | | | | |
| 292 | 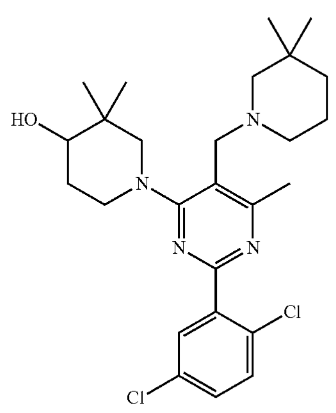 | 1-{2-(2,5-dichlorophenyl)-5-[(3,3-dimethylpiperidin-1-yl)methyl]-6-methylpyrimidin-4-yl}-3,3-dimethylpiperidin-4-ol | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 293 | 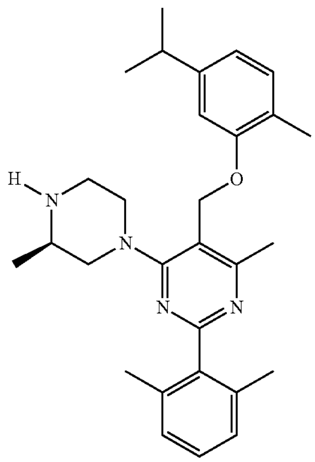 | 2-(2,6-dimethylphenyl)-5-[(5-isopropyl-2-methylphenoxy) methyl]-4-methyl-6-[(3R)-3-methylpiperazin-1-yl] pyrimidine | 1.18 | 458.3 | 459.4 | 1 |
| 294 | 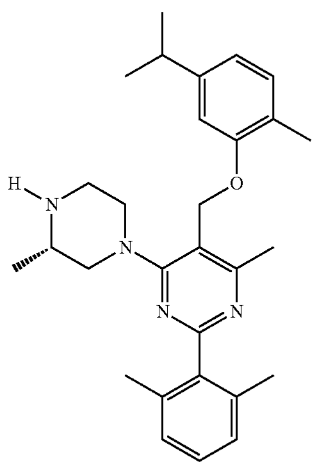 | 2-(2,6-dimethylphenyl)-5-[(5-isopropyl-2-methylphenoxy) methyl]-4-methyl-6-[(3S)-3-methylpiperazin-1-yl] pyrimidine | 1.18 | 458.3 | 459.4 | 1 |
| 295 | 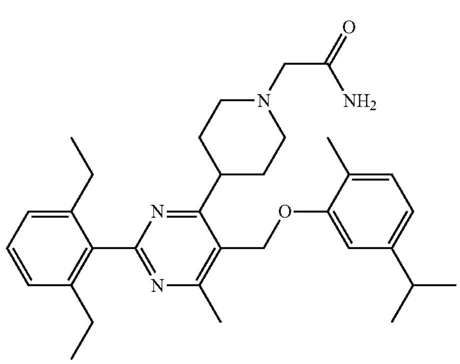 | 2-(4-{2-(2,6-diethylphenyl)-5-[(5-isopropyl-2-methylphenoxy) methyl]-6-methylpyrimidin-4-yl}piperidin-1-yl)acetamide | 1.26 | 528.3 | 529.5 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 296 | 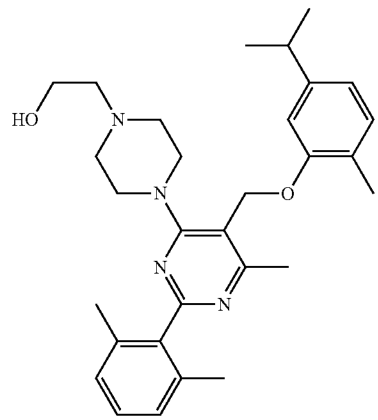 | 2-(4-{2-(2,6-dimethylphenyl)-5-[(5-isopropyl-2-methylphenoxy) methyl]-6-methylpyrimidin-4-yl} piperazin-1-yl)ethanol | 1.17 | 488.3 | 489.4 | 1 |
| 297 | 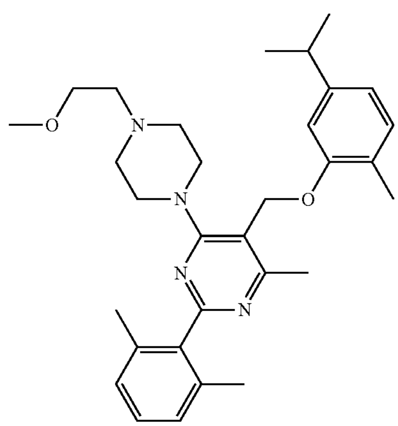 | 2-(2,6-dimethylphenyl)-5-[(5-isopropyl-2-methylphenoxy) methyl]-4-[4-(2-methoxyethyl) piperazin-1-yl]-6-methylpyrimidine | 1.18 | 502.3 | 503.4 | 1 |
| 298 | 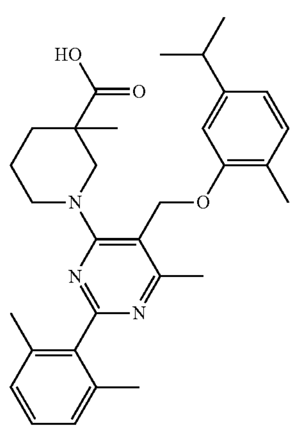 | 1-{2-(2,6-dimethylphenyl)-5-[(5-isopropyl-2-methylphenoxy) methyl]-6-methylpyrimidin-4-yl}-3-methylpiperidine-3-carboxylic acid | 1.24 | 501.3 | 502.4 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 299 | 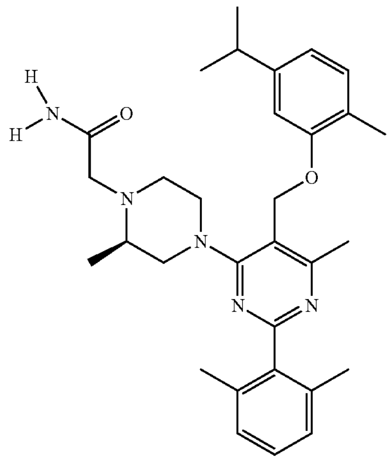 | 2-((2R)-4-{2-(2,6-dimethylphenyl)-5-[(5-isopropyl-2-methylphenoxy)methyl]-6-methylpyrimidin-4-yl}-2-methylpiperazin-1-yl)acetamide | 1.19 | 515.3 | 516.4 | 1 |
| 300 | 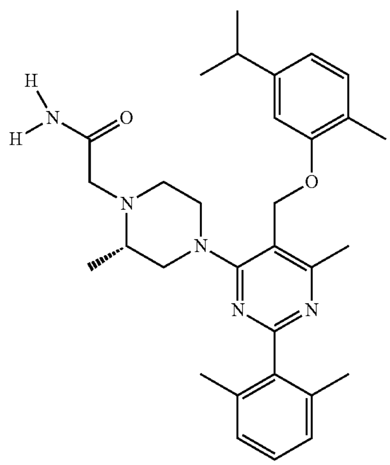 | 2-((2S)-4-{2-(2,6-dimethylphenyl)-5-[(5-isopropyl-2-methylphenoxy)methyl]-6-methylpyrimidin-4-yl}-2-methylpiperazin-1-yl)acetamide | 1.18 | 515.3 | 516.4 | 1 |
| 301 | 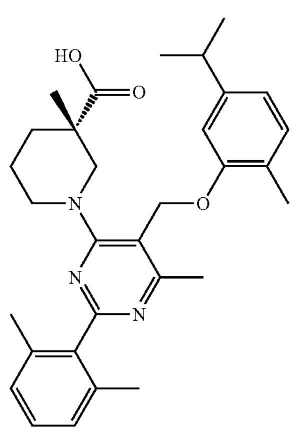 | (3S)-1-{2-(2,6-dimethylphenyl)-5-[(5-isopropyl-2-methylphenoxy)methyl]-6-methylpyrimidin-4-yl}-3-methylpiperidine-3-carboxylic acid | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 302 | 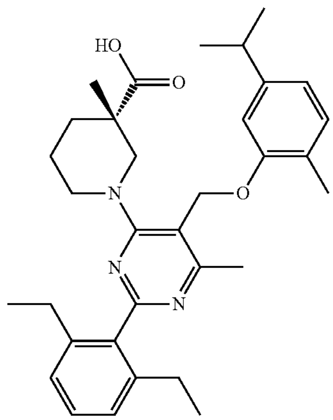 | (3S)-1-{2-(2,6-diethylphenyl)-5-[(5-isopropyl-2-methylphenoxy) methyl]-6-methylpyrimidin-4-yl}-3-methylpiperidine-3-carboxylic acid | 1.35 | 529.3 | 530.3 | 1 |
| 303 | 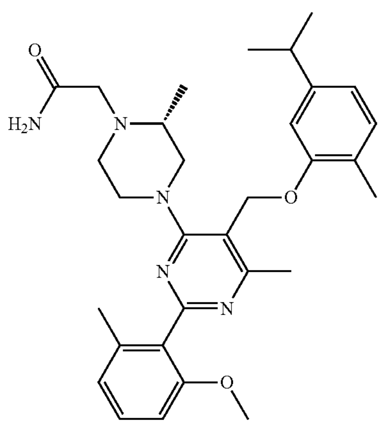 | 2-{(2R)-4-[5-[5-isopropyl-2-methylphenoxy)methyl]-2-(2-methoxy-6-methylphenyl)-6-methylpyrimidin-4-yl]-2-methylpiperazin-1-yl} acetamide | 1.23 | 531.3 | 532.3 | 1 |
| 304 | 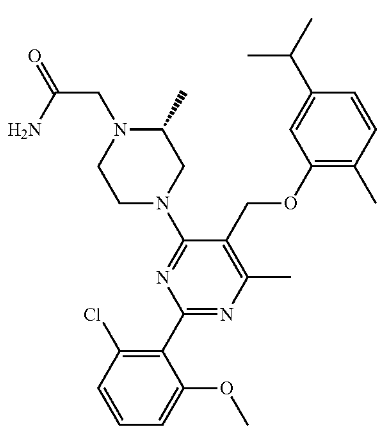 | 2-((2R)-4-{2-(2-chloro-6-methoxyphenyl)-5-[(5-isopropyl-2-methylphenoxy)methyl]-6-methylpyrimidin-4-yl}-2-methylpiperazin-1-yl) acetamide | 1.26 | 551.3 | 552.2 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 305 | 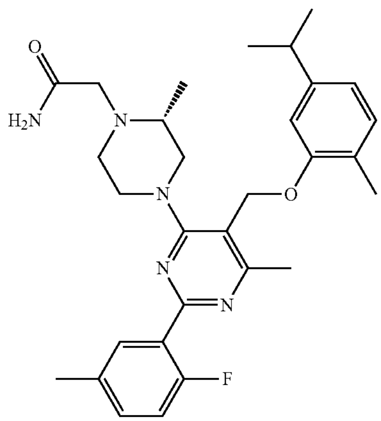 | 2-((2R)-4-{2-(2-fluoro-5-methylphenyl)-5-[(5-isopropyl-2-methylphenoxy)methyl]-6-methylpyrimidin-4-yl}-2-methylpiperazin-1-yl)acetamide | 1.32 | 519.3 | 520.3 | 1 |
| 306 | 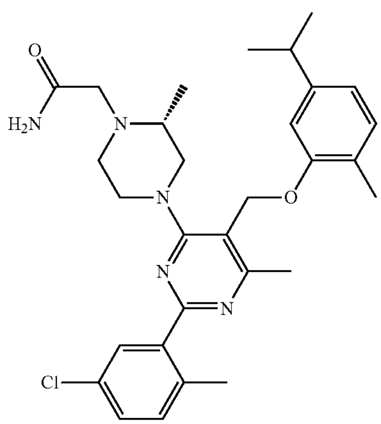 | 2-((2R)-4-{2-(5-chloro-2-methylphenyl)-5-[(5-isopropyl-2-methylphenoxy)methyl]-6-methylpyrimidin-4-yl}-2-methylpiperazin-1-yl)acetamide | 1.35 | 535.3 | 536.2 | 1 |
| 307 | 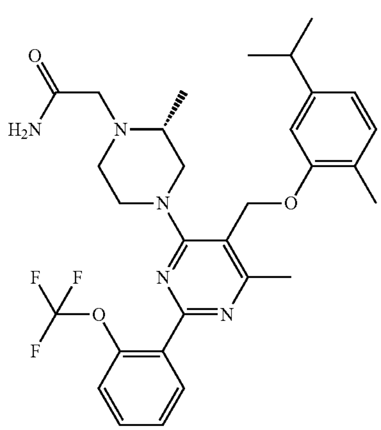 | 2-((2R)-4-{5-[(5-isopropyl-2-methylphenoxy)methyl]-6-methyl-2-[2-(trifluoromethoxy)phenyl]pyrimidin-4-yl}-2-methylpiperazin-1-yl)acetamide | 1.33 | 571.3 | 572.2 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 308 | 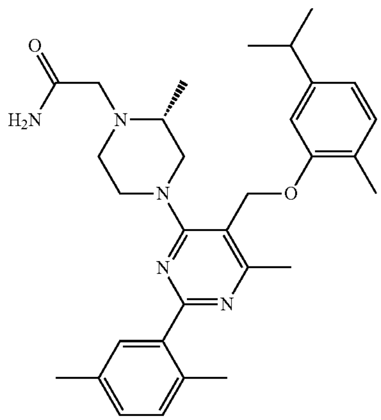 | 2-((2R)-4-{2-(2,5-dimethylphenyl)-5-[(5-isopropyl-2-methylphenoxy)methyl]-6-methylpyrimidin-4-yl}-2-methylpiperazin-1-yl)acetamide | 1.28 | 515.3 | 516.3 | 1 |
| 309 | 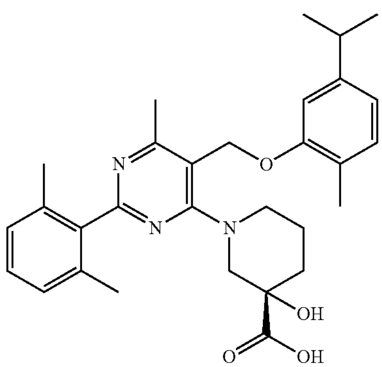 | 1-{2-(2,6-dimethylphenyl)-5-[(5-isopropyl-2-methylphenoxy) methyl]-6-methylpyrimidin-4-yl}-3-hydroxypiperidine-3-carboxylic acid | | | | |
| 310 | 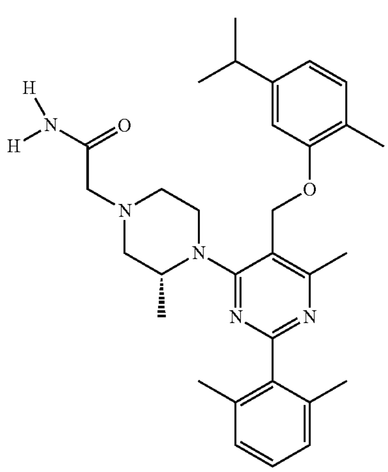 | 2-((3R)-4-{2-(2,6-dimethylphenyl)-5-[(5-isopropyl-2-methylphenoxy)methyl]-6-methylpyrimidin-4-yl}-3-methylpiperazin-1-yl)acetamide | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 311 | 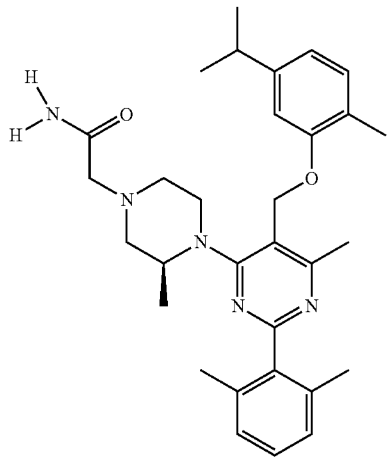 | 2-((3S)-4-{2-(2,6-dimethylphenyl)-5-[(5-isopropyl-2-methylphenoxy)methyl]-6-methylpyrimidin-4-yl}-3-methylpiperazin-1-yl) acetamide | | | | |
| 312 | 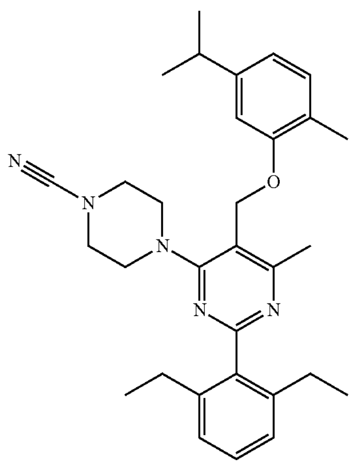 | 4-{2-(2,6-diethylphenyl)-5-[(5-isopropyl-2-methylphenoxy)methyl]-6-methylpyrimidin-4-yl}piperazine-1-carbonitrile | | | | |
| 313 | 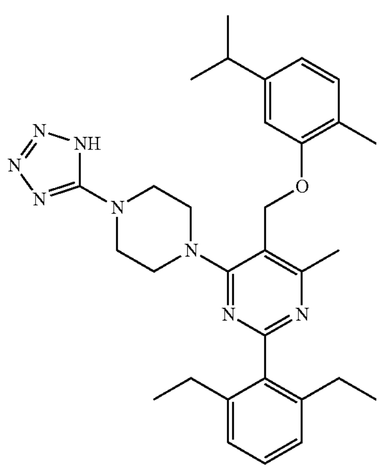 | 2-(2,6-diethylphenyl)-5-[(5-isopropyl-2-methylphenoxy) methyl]-4-methyl-6-[4-(1H-tetrazol-5-yl)piperazin-1-yl] pyrimidine | 1.23 | 540.3 | 541.5 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 314 | 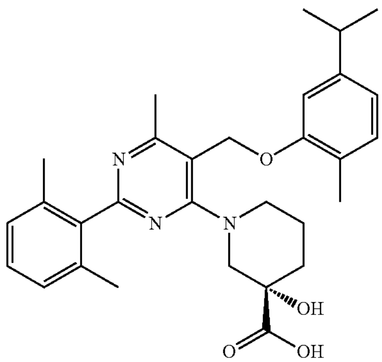 | (3R)-1-{2-(2,6-dimethylphenyl)-5-[(5-isopropyl-2-methylphenoxy)methyl]-6-methylpyrimidin-4-yl}-3-methylpiperidine-3-carboxylic acid | | | | |
| 315 | 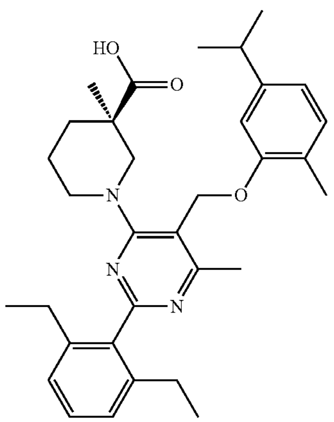 | (3R)-1-{2-(2,6-diethylphenyl)-5-[(5-isopropyl-2-methylphenoxy) methyl]-6-methylpyrimidin-4-yl}-3-methylpiperidine-3-carboxylic acid | 1.27 | 529.3 | 530.5 | 1 |
| 316 | 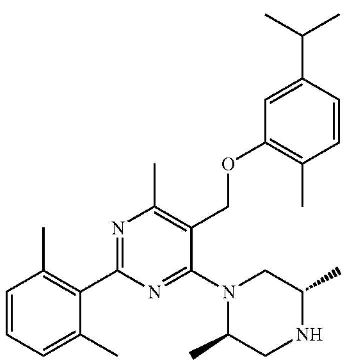 | rel-2-(2,6-dimethylphenyl)-4-[(2R,5S)-2,5-dimethylpiperazin-1-yl]-5-[(5-isopropyl-2-methylphenoxy)methyl]-6-methylpyrimidine | 1.24 | 472.3 | 473.5 | 1 |
| 317 | 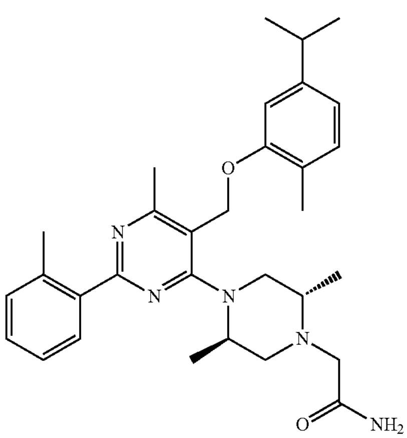 | rel-2-{(2R,5S)-4-[5-[(5-isopropyl-2-methylphenoxy)methyl]-6-methyl-2-(2-methylphenyl)pyrimidin-4-yl]-2,5-dimethylpiperazin-1-yl}acetamide | 1.23 | 515.3 | 516.5 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 318 | 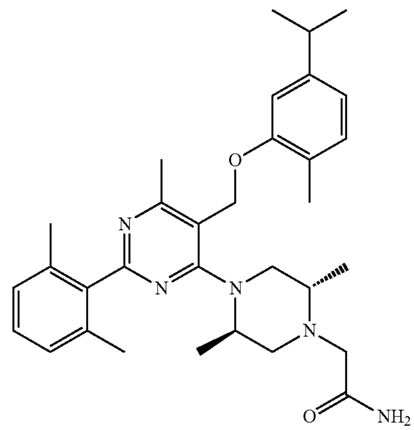 | rel-2-((2R,5S)-4-{2-(2,6-dimethylphenyl)-5-[(5-isopropyl-2-methylphenoxy)methyl]-6-methylpyrimidin-4-yl}-2,5-dimethylpiperazin-1-yl)acetamide | 1.29 | 529.3 | 530.3 | 1 |
| 319 | 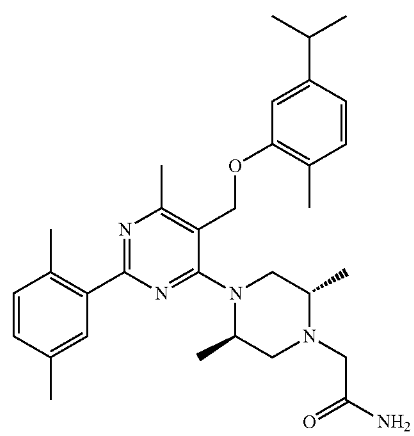 | rel-2-((2R,5S)-4-{2-(2,5-dimethylphenyl)-5-[(5-isopropyl-2-methylphenoxy)methyl]-6-methylpyrimidin-4-yl}-2,5-dimethylpiperazin-1-yl)acetamide | | | | |
| 320 | 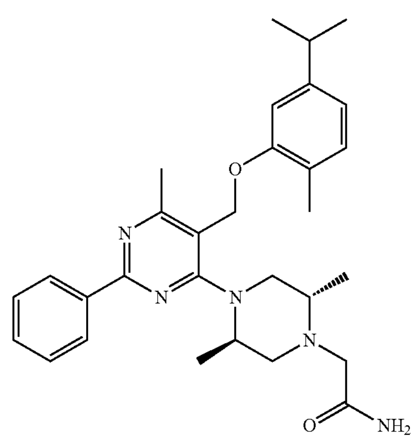 | rel-2-((2R,5S)-4-{5-[(5-isopropyl-2-methylphenoxy)methyl]-6-methyl-2-phenylpyrimidin-4-yl}-2,5-dimethylpiperazin-1-yl)acetamide | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 321 | 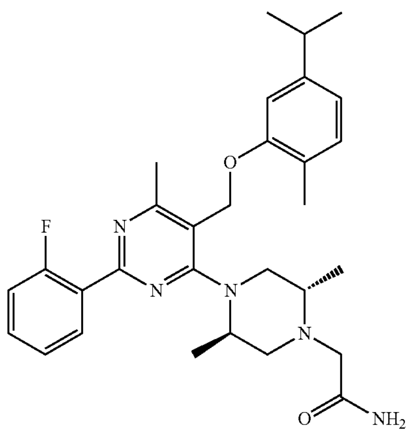 | rel-2-((2R,5S)-4-{2-(2-fluorophenyl)-5-[(5-isopropyl-2-methylphenoxy)methyl]-6-methylpyrimidin-4-yl}-2,5-dimethylpiperazin-1-yl)acetamide | | | | |
| 322 | 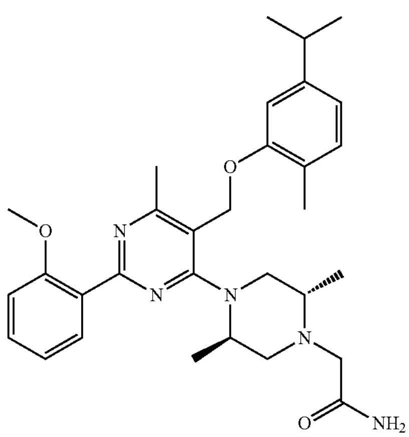 | rel-2-{(2R,5S)-4-[5-[(5-isopropyl-2-methylphenoxy)methyl]-2-(2-methoxyphenyl)-6-methylpyrimidin-4-yl]-2,5-dimethylpiperazin-1-yl}acetamide | 1.23 | 531.3 | 532.3 | 1 |
| 323 | 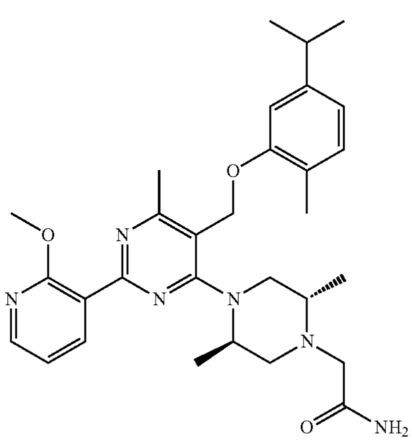 | rel-2-{(2R,5S)-4-[5-[(5-isopropyl-2-methylphenoxy)methyl]-2-(2-methoxypyridin-3-yl)-6-methylpyrimidin-4-yl]-2,5-dimethylpiperazin-1-yl}acetamide | 1.27 | 532.3 | 533.3 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 324 | 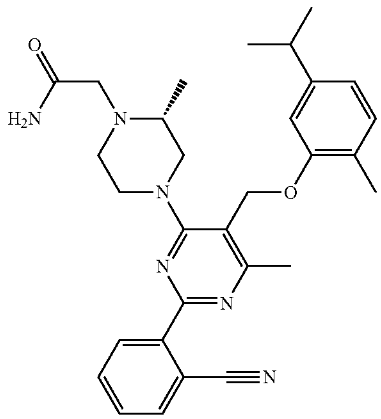 | 2-((2R)-4-{2-(2-cyanophenyl)-5-[(5-isopropyl-2-methylphenoxy) methyl]-6-methylpyrimidin-4-yl}-2-methylpiperazin-1-yl) acetamide | | | | |
| 325 | 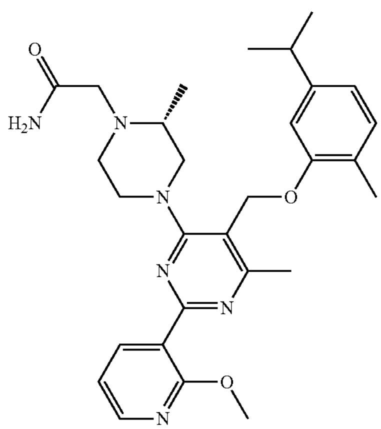 | 2-{(2R)-4-[5-[(5-isopropyl-2-methylphenoxy)methyl]-2-(2-methoxypyridin-3-yl)-6-methylpyrimidin-4-yl]-2-methylpiperazin-1-yl}acetamide | | | | |
| 326 | 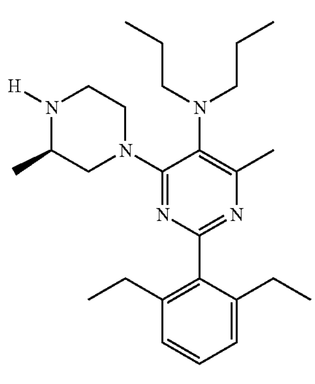 | 2-(2,6-diethylphenyl)-4-methyl-6-(3-methylpiperazin-1-yl)-N,N-dipropylpyrimidin-5-amine | 1.16 | 423.3 | 424.3 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 327 | 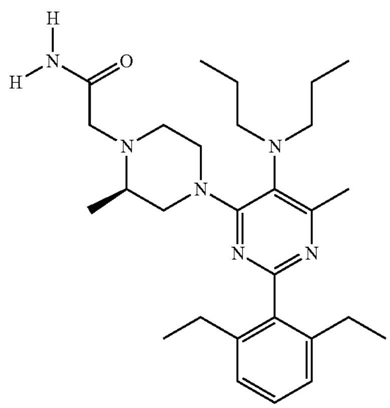 | 2-{4-[2-(2,6-diethylphenyl)-5-(dipropylamino)-6-methylpyrimidin-4-yl]-2-methylpiperazin-1-yl}acetamide | 1.18 | 480.4 | 481.3 | 1 |
| 328 | 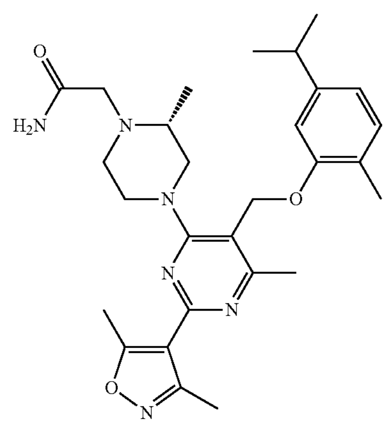 | 2-((2R)-4-{2-(3,5-dimethylisoxazol-4-yl)-5-[(5-isopropyl-2-methylphenoxy)methyl]-6-methylpyrimidin-4-yl}-2-methylpiperazin-1-yl)acetamide | | | | |
| 329 | 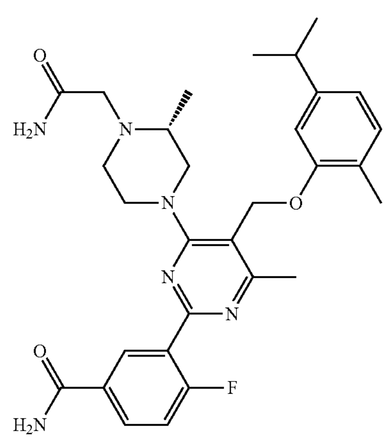 | 3-{4-[(3R)-4-(2-amino-2-oxoethyl)-3-methylpiperazin-1-yl]-5-[(5-isopropyl-2-methylphenoxy)methyl]-6-methylpyrimidin-2-yl}-4-fluorobenzamide | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 330 | 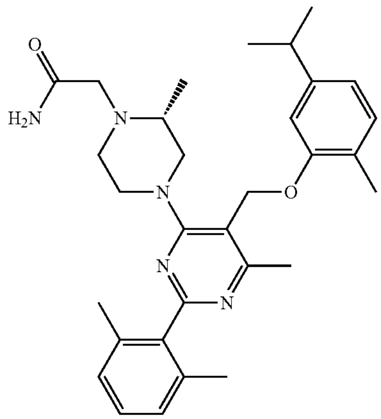 | 2-((2R)-4-{2-(2,6-dimethylphenyl)-5-[(5-isopropyl-2-methylphenoxy)methyl]pyrimidin-4-yl}-2-methylpiperazin-1-yl)acetamide | | | | |
| 331 | 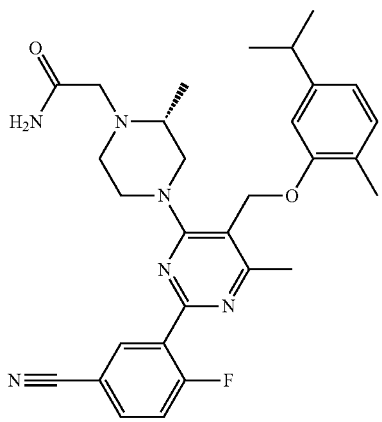 | 2-((2R)-4-{2-(5-cyano-2-fluorophenyl)-5-[(5-isopropyl-2-methylphenoxy)methyl]-6-methylpyrimidin-4-yl}-2-methylpiperazin-1-yl)acetamide | | | | |
| 332 | 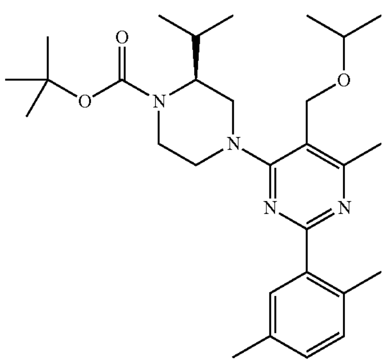 | tert-butyl (2S)-4-[2-(2,5-dimethylphenyl)-5-(isopropoxymethyl)-6-methylpyrimidin-4-yl]-2-isopropylpiperazine-1-carboxylate | | | | |
| 333 | 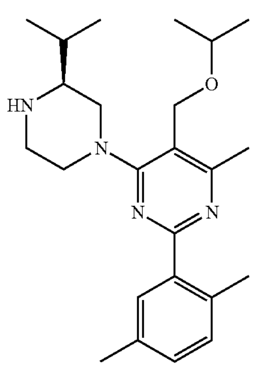 | 2-(2,5-dimethylphenyl)-5-(isopropoxymethyl)-4-[(3S)-3-isopropylpiperazin-1-yl]-6-methylpyrimidine | | | | |

TABLE III-continued

| Cpd # | Structure | Name | LCMS Ret Time (min) | LCMS Mass (amu) | LCMS M + H (amu) | LCMS Method |
|---|---|---|---|---|---|---|
| 334 | 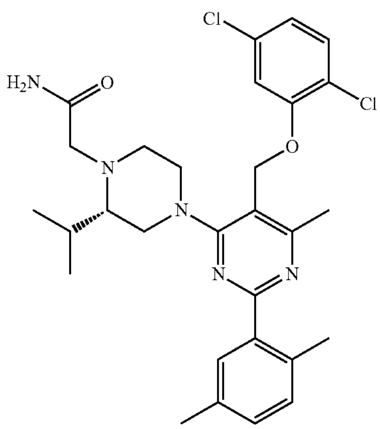 | 2-{(2S)-4-[5-[(2,5-dichlorophenoxy)methyl]-2-(2,5-dimethylphenyl)-6-methylpyrimidin-4-yl]-2-isopropylpiperazin-1-yl}acetamide | 1.29 | 555.2 | 556.2 | 1 |
| 335 | 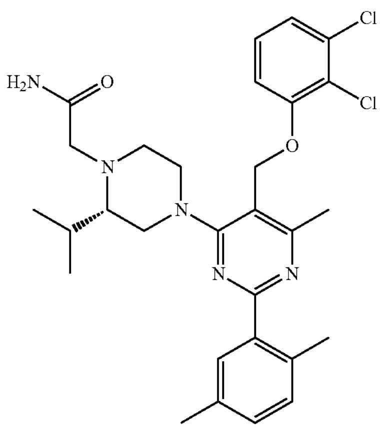 | 2-{(2S)-4-[5-[(2,3-dichlorophenoxy)methyl]-2-(2,5-dimethylphenyl)-6-methylpyrimidin-4-yl]-2-isopropylpiperazin-1-yl} acetamide | 1.29 | 555.2 | 556.2 | 1 |
| 336 | 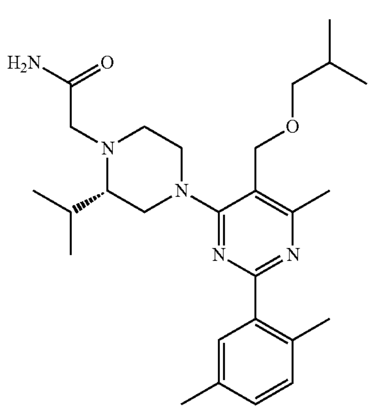 | 2-{(2S)-4-[2-(2,5-dimethylphenyl)-5-(isobutoxymethyl)-6-methylpyrimidin-4-yl]-2-isopropylpiperazin-1-yl} acetamide | 1.22 | 467.3 | 468.3 | 1 |

TABLE III-continued

| Cpd # | Structure | Name | LCMS Ret Time (min) | LCMS Mass (amu) | LCMS M + H (amu) | LCMS Method |
|---|---|---|---|---|---|---|
| 337 | 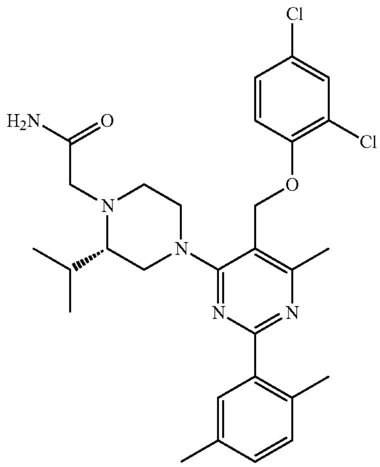 | 2-{(2S)-4-[5-[(2,4-dichlorophenoxy)methyl]-2-(2,5-dimethylphenyl)-6-methylpyrimidin-4-yl]-2-isopropylpiperazin-1-yl} acetamide | 1.3 | 555.2 | 556.2 | 1 |
| 338 | 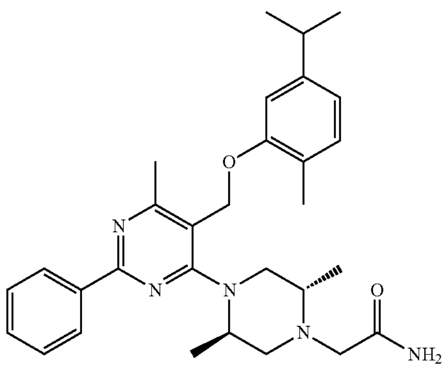 | 2-((2S,5R)-4-{5-[(5-isopropyl-2-methylphenoxy)methyl]-6-methyl-2-phenylpyrimidin-4-yl}-2,5-dimethylpiperazin-1-yl) acetamide | 1.35 | 501.3 | 502.3 | 1 |

TABLE IV

| Cpd # | Structure | Name | MW |
|---|---|---|---|
| 339 | 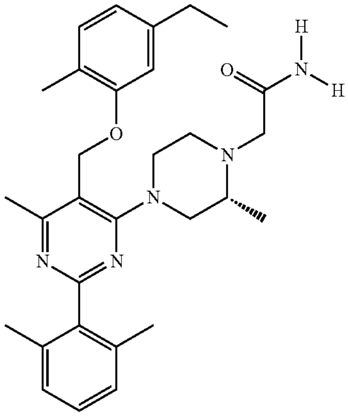 | 2-((2R)-4-{2-(2,6-dimethylphenyl)-5-[(5-ethyl-2-methylphenoxy)methyl]-6-methylpyrimidin-4-yl}-2-methylpiperazin-1-yl)acetamide | 501.7 |

TABLE IV-continued

| Cpd # | Structure | Name | MW |
|---|---|---|---|
| 340 | 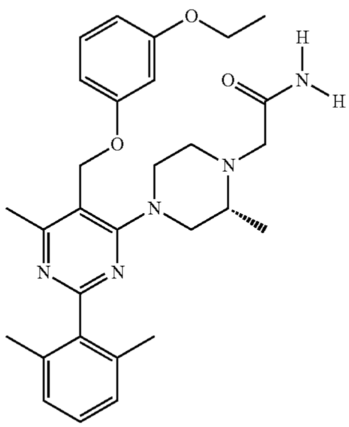 | 2-((2R)-4-{2-(2,6-dimethylphenyl)-5-[(3-ethoxyphenoxy)methyl]-6-methylpyrimidin-4-yl}-2-methylpiperazin-1-yl)acetamide | 503.6 |
| 341 | 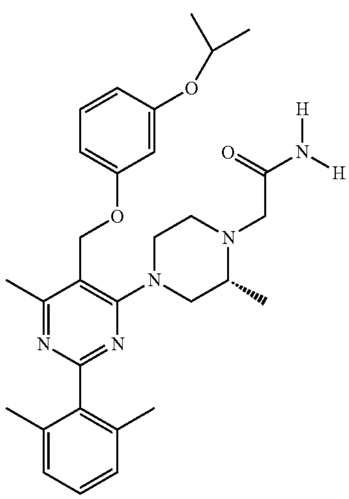 | 2-((2R)-4-{2-(2,6-dimethylphenyl)-5-[(3-isopropoxyphenoxy)methyl]-6-methylpyrimidin-4-yl}-2-methylpiperazin-1-yl)acetamide | 517.7 |
| 342 | 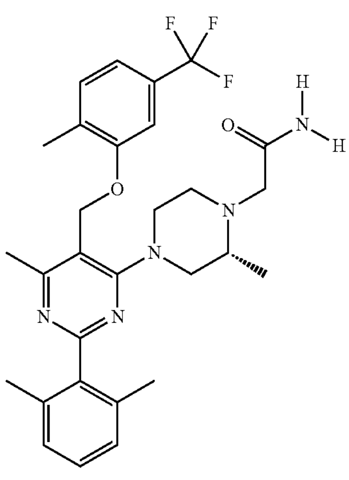 | 2-[(2R)-4-(2-(2,6-dimethylphenyl)-6-methyl-5-{[2-methyl-5-(trifluoromethyl)phenoxy]methyl}pyrimidin-4-yl)-2-methylpiperazin-1-yl]acetamide | 541.6 |

TABLE IV-continued

| Cpd # | Structure | Name | MW |
|---|---|---|---|
| 343 | 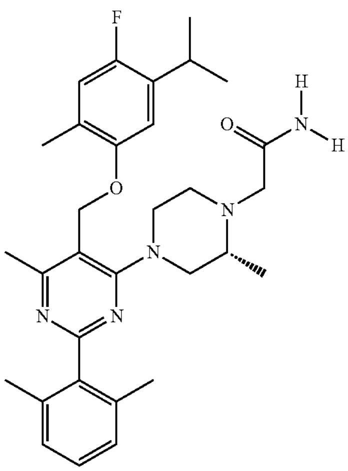 | 2-((2R)-4-{2-(2,6-dimethylphenyl)-5-[(4-fluoro-5-isopropyl-2-methylphenoxy)methyl]-6-methylpyrimidin-4-yl}-2-methylpiperazin-1-yl)acetamide | 533.7 |
| 344 | 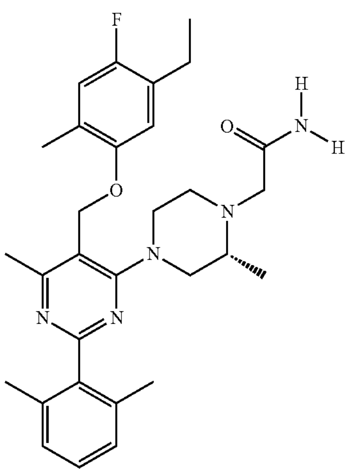 | 2-((2R)-4-{2-(2,6-dimethylphenyl)-5-[(5-ethyl-4-fluoro-2-methylphenoxy)methyl]-6-methylpyrimidin-4-yl}-2-methylpiperazin-1-yl)acetamide | 519.7 |
| 345 | 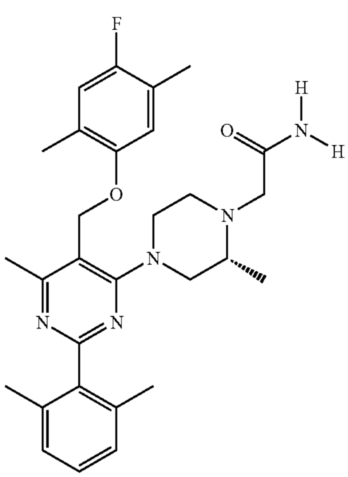 | 2-((2R)-4-{2-(2,6-dimethylphenyl)-5-[(4-fluoro-2,5-dimethylphenoxy)methyl]-6-methylpyrimidin-4-yl}-2-methylpiperazin-1-yl)acetamide | 505.6 |

TABLE IV-continued

| Cpd # | Structure | Name | MW |
|---|---|---|---|
| 346 | 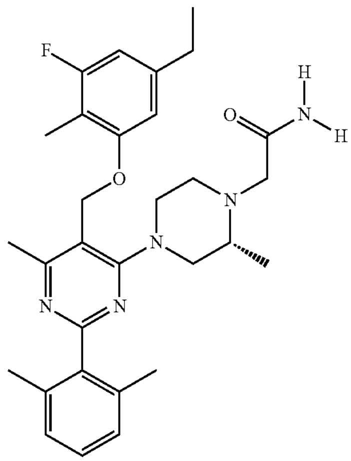 | 2-((2R)-4-{2-(2,6-dimethylphenyl)-5-[(5-ethyl-3-fluoro-2-methylphenoxy)methyl]-6-methylpyrimidin-4-yl}-2-methylpiperazin-1-yl)acetamide | 519.7 |
| 347 | 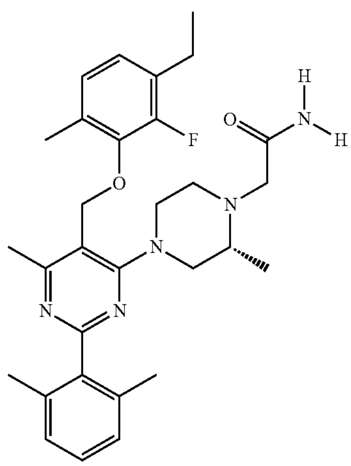 | 2-((2R)-4-{2-(2,6-dimethylphenyl)-5-[(3-ethyl-2-fluoro-6-methylphenoxy)methyl]-6-methylpyrimidin-4-yl}-2-methylpiperazin-1-yl)acetamide | 519.7 |
| 348 | 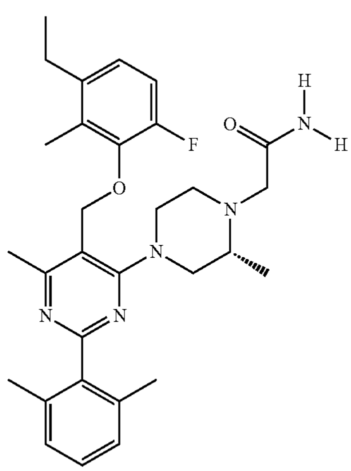 | 2-((2R)-4-{2-(2,6-dimethylphenyl)-5-[(3-ethyl-6-fluoro-2-methylphenoxy)methyl]-6-methylpyrimidin-4-yl}-2-methylpiperazin-1-yl)acetamide | 519.7 |

TABLE IV-continued

| Cpd # | Structure | Name | MW |
|---|---|---|---|
| 349 | 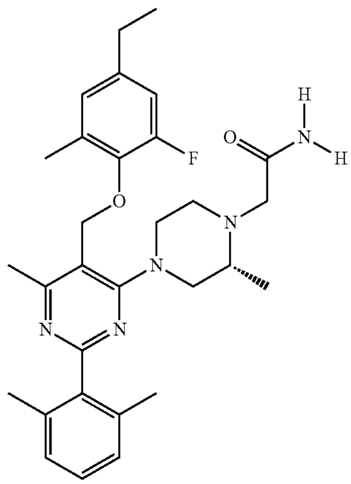 | 2-((2R)-4-{2-(2,6-dimethylphenyl)-5-[(4-ethyl-2-fluoro-6-methylphenoxy)methyl]-6-methylpyrimidin-4-yl}-2-methylpiperazin-1-yl)acetamide | 519.7 |
| 350 | 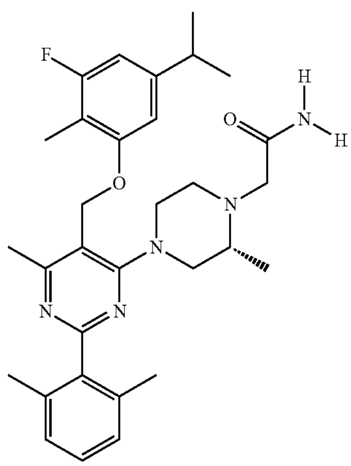 | 2-((2R)-4-{2-(2,6-dimethylphenyl)-5-[(3-fluoro-5-isopropyl-2-methylphenoxy)methyl]-6-methylpyrimidin-4-yl}-2-methylpiperazin-1-yl)acetamide | 533.7 |
| 351 | 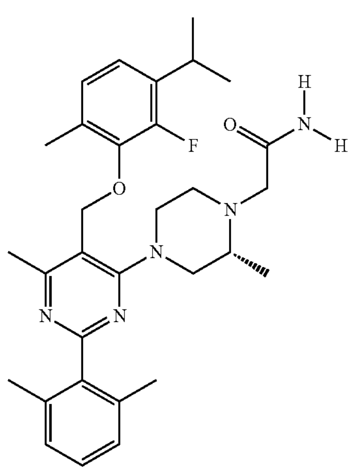 | 2-((2R)-4-{2-(2,6-dimethylphenyl)-5-[(2-fluoro-3-isopropyl-6-methylphenoxy)methyl]-6-methylpyrimidin-4-yl}-2-methylpiperazin-1-yl)acetamide | 533.7 |

TABLE IV-continued

| Cpd # | Structure | Name | MW |
|---|---|---|---|
| 352 | 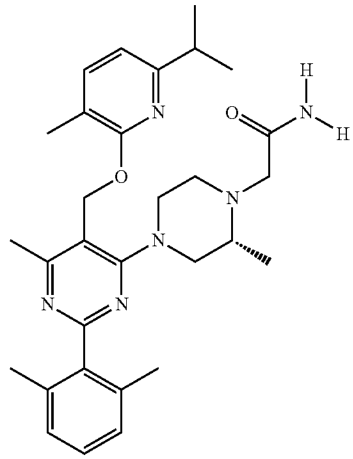 | 2-[(2R)-4-(2-(2,6-dimethylphenyl)-5-{[(6-isopropyl-3-methylpyridin-2-yl)oxy]methyl}-6-methylpyrimidin-4-yl)-2-methylpiperazin-1-yl]acetamide | 516.7 |
| 353 | 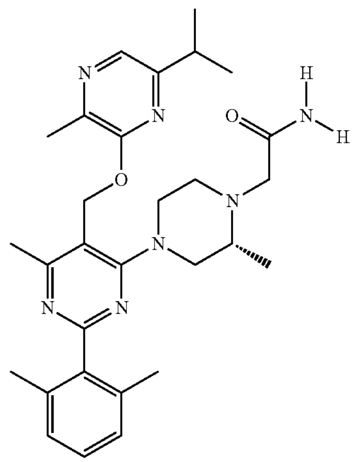 | 2-[(2R)-4-(2-(2,6-dimethylphenyl)-5-{[(6-isopropyl-3-methylpyrazin-2-yl)oxy]methyl}-6-methylpyrimidin-4-yl)-2-methylpiperazin-1-yl]acetamide | 517.7 |
| 354 | 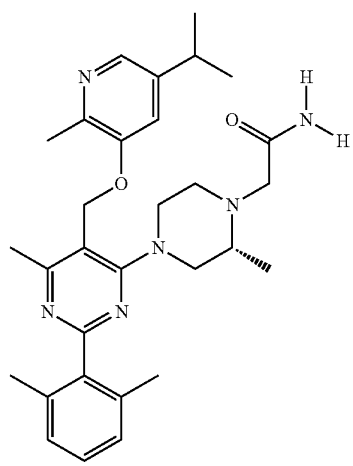 | 2-[(2R)-4-(2-(2,6-dimethylphenyl)-5-{[(5-isopropyl-2-methylpyridin-3-yl)oxy]methyl}-6-methylpyrimidin-4-yl)-2-methylpiperazin-1-yl]acetamide | 516.7 |

TABLE IV-continued

| Cpd # | Structure | Name | MW |
|---|---|---|---|
| 355 | 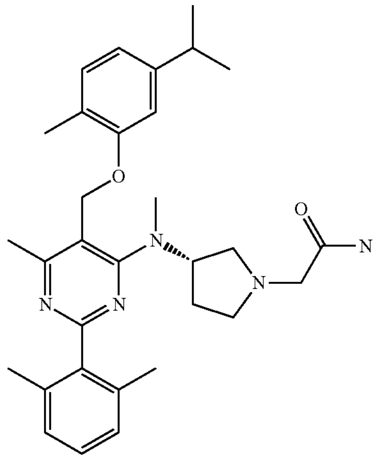 | 2-((S)-3-{[2-(2,6-Dimethyl-phenyl)-5-(5-isopropyl-2-methyl-phenoxymethyl)-6-methyl-pyrimidin-4-yl]-methyl-amino}-pyrrolidin-1-yl)-acetamide | 515.7 |
| 356 | 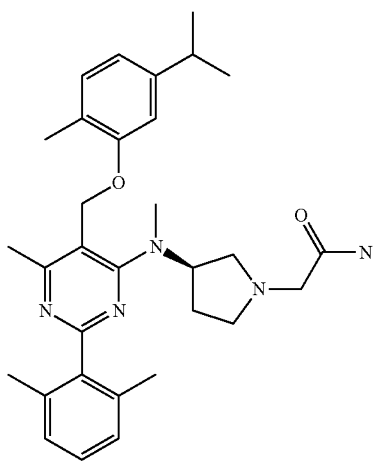 | 2-((R)-3-{[2-(2,6-Dimethyl-phenyl)-5-(5-isopropyl-2-methyl-phenoxymethyl)-6-methyl-pyrimidin-4-yl]-methyl-amino}-pyrrolidin-1-yl)-acetamide | 515.7 |
| 357 | 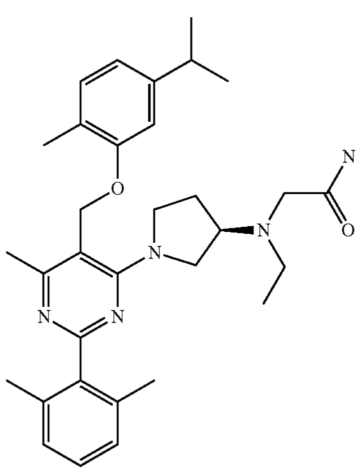 | 2-({(R)-1-[2-(2,6-Dimethyl-phenyl)-5-(5-isopropyl-2-methyl-phenoxymethyl)-6-methyl-pyrimidin-4-yl]-pyrrolidin-3-yl}-ethyl-amino)-acetamide | 529.7 |

TABLE IV-continued

| Cpd # | Structure | Name | MW |
|---|---|---|---|
| 358 | 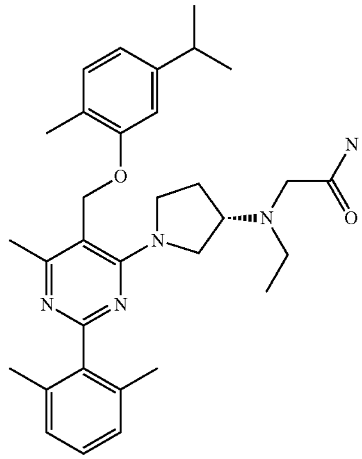 | 2-({(S)-1-[2-(2,6-Dimethyl-phenyl)-5-(5-isopropyl-2-methyl-phenoxymethyl)-6-methyl-pyrimidin-4-yl]-pyrrolidin-3-yl}-ethyl-amino)-acetamide | 529.7 |
| 359 | 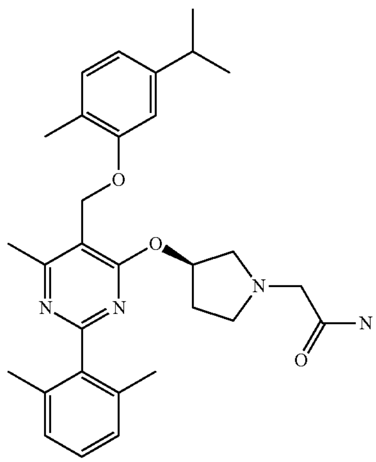 | 2-{(R)-3-[2-(2,6-Dimethyl-phenyl)-5-(5-isopropyl-2-methyl-phenoxymethyl)-6-methyl-pyrimidin-4-yloxy]-pyrrolidin-1-yl}-acetamide | 502.7 |
| 360 | 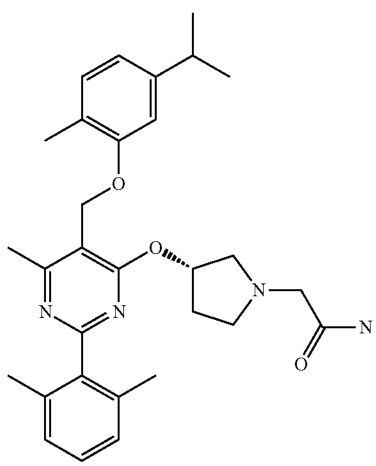 | 2-{(S)-3-[2-(2,6-Dimethyl-phenyl)-5-(5-isopropyl-2-methyl-phenoxymethyl)-6-methyl-pyrimidin-4-yloxy]-pyrrolidin-1-yl}-acetamide | 502.7 |

TABLE IV-continued

| Cpd # | Structure | Name | MW |
|---|---|---|---|
| 361 | 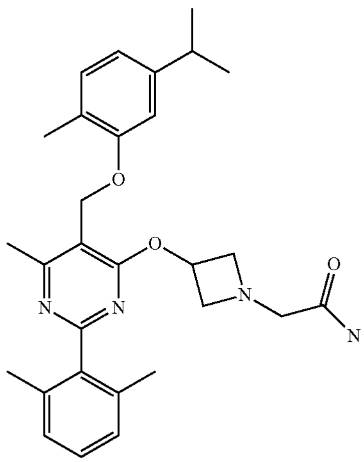 | 2-{3-[2-(2,6-Dimethyl-phenyl)-5-(5-isopropyl-2-methyl-phenoxymethyl)-6-methyl-pyrimidin-4-yloxy]-azetidin-1-yl}-acetamide | 488.6 |

Example 16

Pharmaceutical Preparations of Oral and Intravenous Administration

A. Tablets containing a C5a antagonist and an anti-arthritic agent that is not a C5a receptor antagonist can be prepared as illustrated below:

| Ingredient | Amount |
|---|---|
| C5a receptor antagonist | 5 mg-500 mg |
| C5a receptor-inactive therapeutic agent | 1 mg-500 mg |
| diluent, binder, disintigrant, lubricant, excipients | q.s. 200-400 mg. |

B. Tablets containing a C5a receptor antagonist as the only active ingredient can be prepared as illustrated below:

| Ingredient | mg | mg |
|---|---|---|
| C5a receptor antagonist | 10 | 50 |
| Microcrystalline Cellulose | 70.4 | 352 |
| Granular Mannitol | 15.1 | 75.5 |
| Croscarmellose Sodium | 3.0 | 15.0 |
| Colloidal Silicon Dioxide | 0.5 | 2.5 |
| Magnesium Stearate (Impalpable Powder) | 1.0 | 5.0 |
| Total (mg) | 100 | 500 |

C. Tablets containing a C5a receptor antagonist and a C5a receptor inactive agent may be prepared as follows:

| Ingredient | mg | mg |
|---|---|---|
| C5a receptor antagonist | 10 | 25 |
| C5a receptor inactive therapeutic agent | 10 | 25 |
| Microcrystalline Cellulose | 40 | 100 |
| Modified food corn starch | 1.05 | 4.25 |
| Magnesium stearate | 1.25 | 0.5 |

D. Intravenous formulations containing a C5a receptor antagonist and a C5a receptor inactive agent may be prepared as follows:

| Ingredient | Amount |
|---|---|
| C5a receptor antagonist | 0.5-10 mg |
| C5a receptor inactive therapeutic agent | 0.5-10 mg |
| Sodium Citrate | 5-50 mg |
| Citric Acid | 1-15 mg |
| Sodium Chloride | 1-8 mg |
| Water for Injection | to 1.0 liter |

E. Oral suspensions containing a C5a receptor antagonist and a C5a receptor inactive agent may be prepared as follows:

| Ingredient | Amount per 5 mL dose |
|---|---|
| C5a receptor antagonist | 5-100 mg |
| C5a receptor inactive therapeutic agent | 5-100 mg |
| Polyvinylpyrrolidone | 150 mg |
| Poly oxyethylene sorbitan monolaurate | 25 mg |
| Benzoic Acid | 10 mg to 5 mL with sorbitol solution (70%) |

Example 17

Preparation of Radiolabeled Probes

Compounds provided herein are prepared as radiolabeled probes by carrying out their synthesis using precursors comprising at least one atom that is a radioisotope. The radioisotope is preferably at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.;

American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using a compound provided herein as substrate. In addition, certain precursors may be subjected to tritium-halogen exchange with tritium gas, tritium gas reduction of unsaturated bonds, or reduction using sodium borotritide, as appropriate.

Example 18

Assay for C5A Receptor Mediated Chemotaxis

This Example provides a standard assay of C5a receptor-mediated chemotaxis.

Human promonocytic U937 cells (or purified human or non-human neutrophils) are treated with dibutyryl cAMP for 48 hours prior to performing the assay. Human neutrophils or those from another mammalian species are used directly after isolation. The cells are pelleted and resuspended in culture media containing 0.1% fetal bovine serum (FBS) and 10 µg/mL calcein AM (a fluorescent dye). This suspension is then incubated at 37° C. for 30 minutes such that the cells take up the fluorescent dye. The suspension is then centrifuged briefly to pellet the cells, which are then resuspended in culture media containing 0.1% FBS at a concentration of approximately $3\times10^6$ cells/mL. Aliquots of this cell suspension are transferred to clean test tubes, which contain vehicle (1% DMSO in culture media containing 0.1% FBS) or varying concentrations of a compound of interest, and are incubated at room temperature for at least 30 minutes. The chemotaxis assay is performed in CHEMO TX 101-8, 96 well plates (Neuro Probe, Inc.; Gaithersburg, Md.). The bottom wells of the plate are filled with medium containing 0-10 nM of C5a, preferably derived from the same species of mammal as are the neutrophils or other cells (e.g., human C5a for human U937 cells). The top wells of the plate are filled with cell suspensions (compound- or vehicle-treated). The plate is then placed in a tissue culture incubator for 60 minutes. The top surface of the plate is washed with PBS to remove excess cell suspension. The number of cells that have migrated into the bottom well is then determined using a fluorescence reader. Chemotaxis index (the ratio of migrated cells to total number of cells loaded) is then calculated for each compound concentration to determine an $EC_{50}$ value.

As a control to ensure that cells retain chemotactic ability in the presence of the compound of interest, the bottom wells of the plate may be filled with varying concentrations chemoattractants that do not mediate chemotaxis via the C5a receptor, such as zymosan-activated serum (ZAS), N-formylmethionyl-leucyl-phenylalanine (FMLP) or leukotriene B4 (LTBt), rather than C5a, under which conditions compounds provided herein preferably do not detectably inhibit chemotaxis. Preferred C5a receptor modulators exhibit $EC_{50}$ values of less than 1 µM in the above assay for C5a mediated chemotaxis.

Example 19

Expression of a C5A Receptor

A human C5a receptor cDNA is obtained by PCR using 1) a forward primer adding a Kozak ribosome binding site and 2) a reverse primer that adds no additional sequence, and 3) an aliquot of a Stratagene Human Fetal Brain cDNA library as template. The sequence of the resulting PCR product is described in PCT International Application WO 02/49993 as SEQ ID NO: 1. The PCR product is subcloned into the cloning vector pCR-Script AMP (STRATAGENE, La Jolla, Calif.) at the Srf I site. It is then excised using the restriction enzymes EcoRI and NotI and subcloned in the appropriate orientation for expression into the baculoviral expression vector pBacPAK 9 (CLONTECH, Palo Alto, Calif.) that has been digested with EcoRI and NotI.

Example 20

Baculoviral Preparations for C5A Expression

The human C5a (hC5a) receptor baculoviral expression vector is co-transfected along with BACULOGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Kansas City) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 mL of insect medium for amplification. Each 1 mL volume of recombinant baculovirus (at passage 0) is used to infect a separate T25 flask containing $2\times10^6$ Sf9 cells in 5 mL of insect medium. After five days of incubation at 27° C., supernatant medium is harvested from each of the T25 infections for use as passage 1 inoculum.

Two of seven recombinant baculoviral clones are then chosen for a second round of amplification, using 1 mL of passage 1 stock to infect $1\times10^8$ cells in 100 mL of insect medium divided into 2 T175 flasks. Forty-eight hours post infection, passage 2 medium from each 100 mL prep is harvested and plaque assayed for titer. The cell pellets from the second round of amplification are assayed by affinity binding as described below to verify recombinant receptor expression. A third round of amplification is then initiated using a multiplicity of infection of 0.1 to infect a liter of Sf9 cells. Forty hours post-infection the supernatant medium is harvested to yield passage 3 baculoviral stock.

The remaining cell pellet is assayed for affinity binding using the protocol of DeMartino et al. (1994) *J. Biol. Chem.* 269(20):14446-14450 (which is incorporated herein by reference for its teaching of binding assays at page 14447), adapted as follows. Radioligand is 0.005-0.500 nM [$^{125}$I]C5a (human recombinant) (New England Nuclear Corp., Boston, Mass.); the hC5a receptor-expressing baculoviral cells are used instead of 293 cells; the assay buffer contains 50 mM Hepes pH. 7.6, 1 mM $CaCl_2$, 5 mM $MgCl_2$, 0.1% BSA, pH 7.4, 0.1 mM bacitracin, and 100 KIU/mL aprotinin; filtration is carried out using GF/C WHATMAN filters (presoaked in 1.0% polyethyeneimine for 2 hours prior to use); and the filters are washed twice with 5 mL cold binding buffer without BSA, bacitracin, or aprotinin.

Titer of the passage 3 baculoviral stock is determined by plaque assay and a multiplicity of infection, incubation time course, binding assay experiment is carried out to determine conditions for optimal receptor expression.

A multiplicity of infection of 0.1 and a 72-hour incubation period were the best infection parameters found for hC5a receptor expression in up to 1-liter Sf9 cell infection cultures.

Example 21

Baculoviral Infections

Log-phase Sf9 cells (INVITROGEN Corp., Carlsbad Calif.), are infected with one or more stocks of recombinant baculovirus followed by culturing in insect medium at 27° C. Infections are carried out either only with virus directing the expression of the hC5a receptor or with this virus in combination with three G-protein subunit-expression virus stocks: 1) rat $Ga_{i2}$ G-protein-encoding virus stock (BIOSIGNAL #V5J008), 2) bovine b1 G-protein-encoding virus stock (BIOSIGNAL #V5H012), and 3) human g2 G-protein-encoding virus stock (BIOSIGNAL #V6B003), which may be obtained from BIOSIGNAL Inc., Montreal.

The infections are conveniently carried out at a multiplicity of infection of 0.1:1.0:0.5:0.5. At 72 hours post-infection, a sample of cell suspension is analyzed for viability by trypan blue dye exclusion, and the remaining Sf9 cells are harvested via centrifugation (3000 rpm/10 minutes/4° C.).

Example 22

Purified Recombinant Insect Cell Membranes

Sf9 cell pellets are resuspended in homogenization buffer (10 mM HEPES, 250 mM sucrose, 0.5 µg/mL leupeptin, 2 µg/mL Aprotinin, 200 µM PMSF, and 2.5 mM EDTA, pH 7.4) and homogenized using a POLYTRON homogenizer (setting 5 for 30 seconds). The homogenate is centrifuged (536 ×g/10 minutes/4° C.) to pellet the nuclei. The supernatant containing isolated membranes is decanted to a clean centrifuge tube, centrifuged (48,000 ×g/30 minutes, 4° C.) and the resulting pellet resuspended in 30 mL homogenization buffer. This centrifugation and resuspension step is repeated twice. The final pellet is resuspended in ice cold Dulbecco's PBS containing 5 mM EDTA and stored in frozen aliquots at −80° C. until needed. The protein concentration of the resulting membrane preparation (hereinafter "P2 membranes") is conveniently measured using a Bradford protein assay (Bio-Rad Laboratories, Hercules, Calif.). By this measure, a 1-liter culture of cells typically yields 100-150 mg of total membrane protein.

Example 23

Radioligand Binding Assays

Purified P2 membranes, prepared by the method given above, are resuspended by Dounce homogenization (tight pestle) in binding buffer (50 mM Hepes pH. 7.6, 120 mM NaCl, 1 mM $CaCl_2$, 5 mM $MgCl_2$, 0.1% BSA, pH 7.4, 0.1 mM bacitracin, 100 KIU/mL aprotinin).

For saturation binding analysis, membranes (5-50 µg) are added to polypropylene tubes containing 0.005-0.500 nM [$^{125}$I]C5a (human (recombinant), New England Nuclear Corp., Boston, Mass.) with a final assay volume of 0.25 ml. Nonspecific binding is determined in the presence of 300 nM hC5a (Sigma Chemical Co., St Louis, Mo.) and accounted for less than 10% of total binding. For evaluation of guanine nucleotide effects on receptor affinity, GTPγS is added to duplicate tubes at the final concentration of 50 µM.

For competition analysis, membranes (5-50 µg) are added to polypropylene tubes containing 0.030 nM [$^{125}$I]C5a (human). Non-radiolabeled displacers are added to separate assays at concentrations ranging from $10^{-10}$ M to $10^{-5}$ M to yield a final volume of 0.250 mL. Nonspecific binding is determined in the presence of 300 nM hC5a (Sigma Chemical Co., St. Louis, Mo.) and accounted for less than 10% of total binding. Following a 2-hour incubation at room temperature, the reaction is terminated by rapid vacuum filtration. Samples are filtered over presoaked (in 1.0% polyethyleneimine for 2 hours prior to use) GF/C WHATMAN filters and rinsed 2 times with 5 mL cold binding buffer without BSA, bacitracin, or aprotinin. Remaining bound radioactivity is quantified by gamma counting. $K_I$ and Hill coefficient ("nH") are determined by fitting the Hill equation to the measured values with the aid of SIGMAPLOT software.

Example 24

Agonist-Induced GTP Binding

Agonist-stimulated GTP-gamma$^{35}$S binding ("GTP binding") activity can be used to identify agonist and antagonist compounds and to differentiate neutral antagonist compounds from those that possess inverse agonist activity. This activity can also be used to detect partial agonism mediated by antagonist compounds. A compound being analyzed in this assay is referred to herein as a "test compound." Agonist-stimulated GTP binding activity is measured as follows: Four independent baculoviral stocks (one directing the expression of the hC5a receptor and three directing the expression of each of the three subunits of a heterotrimeric G-protein) are used to infect a culture of Sf9 cells as described above.

Agonist-stimulated GTP binding on purified membranes (prepared as described above) is assessed using hC5a (Sigma Chemical Co., St Louis, Mo., USA) as agonist in order to ascertain that the receptor/G-protein-alpha-beta-gamma combination(s) yield a functional response as measured by GTP binding.

P2 membranes are resuspended by Dounce homogenization (tight pestle) in GTP binding assay buffer (50 mM Tris pH 7.0, 120 mM NaCl, 2 mM MgCl2, 2 mM EGTA, 0.1% BSA, 0.1 mM bacitracin, 100 KIU/mL aprotinin, 5 µM GDP) and added to reaction tubes at a concentration of 30 µg protein/reaction tube. After adding increasing doses of the agonist hC5a at concentrations ranging from $10^{-12}$ M to $10^{-6}$ M, reactions are initiated by the addition of 100 pM GTPgamma$^{35}$S with a final assay volume of 0.25 ml. In competition experiments, non-radiolabeled test compounds (e.g., compounds of Formula I) are added to separate assays at concentrations ranging from $10^{-10}$ M to $10^{-5}$ M along with 10 nM hC5a to yield a final volume of 0.25 mL.

Neutral antagonists are those test compounds that reduce the C5a-stimulated GTP binding activity towards, but not below, baseline (the level of GTh bound by membranes in this assay in the absence of added C5a or other agonist and in the further absence of any test compound).

In contrast, in the absence of added C5a, certain preferred compounds reduce the GTh binding activity of the receptor-containing membranes below baseline, and are thus characterized as inverse agonists. If a test compound that displays antagonist activity does not reduce the GTP binding activity below baseline in the absence of the C5a agonist, it is characterized as a neutral antagonist.

An antagonist test compound that elevates GTP binding activity above baseline in the absence of added hC5a in this assay is characterized as having partial agonist activity. Preferred antagonist compounds provided herein do not elevate GTP binding activity under such conditions more than 10% above baseline, preferably not more than 5% above baseline, and most preferably not more than 2% above baseline.

Following a 60-minute incubation at room temperature, the reactions are terminated by vacuum filtration over GF/C filters (pre-soaked in wash buffer, 0.1% BSA) followed by washing with ice-cold wash buffer (50 mM Tris pH 7.0, 120 mM NaCl). The amount of receptor-bound (and thereby membrane-bound) GTPgamma$^{35}$S is determined by measuring the bound radioactivity, preferably by liquid scintillation spectrometry of the washed filters. Non-specific binding is determined using 10 mM GTPgammaS and typically represents less than 5 percent of total binding. Data is expressed as percent above basal (baseline). The results of these GTP binding experiments is analyzed using SIGMAPLOT software (SPSS Inc., Chicago, Ill.).

Example 25

Calcium Mobilization Assays

A. Response to C5a

U937 cells are grown in differentiation media (1 mM dibutyryl cAMP in RPMI 1640 medium containing 10% fetal bovine serum) for 48 hours at 37° C. then reseeded onto 96-well plates suitable for use in a FLIPR™ Plate Reader (Molecular Devices Corp., Sunnyvale Calif.). Cells are grown an additional 24 hours (to 70-90% confluence) before the assay. The cells are then washed once with Krebs Ringer solution. FLUO-3 calcium sensitive dye (Molecular Probes, Inc. Eugene, Oreg.) is added to 10 µg/mL and incubated with the cells in Krebs Ringer solution at room temperature for 1 to 2 hours. The 96 well plates are then washed to remove excess dye. Fluorescence responses, measured by excitation at 480 nM and emission at 530 nM, are monitored upon the addition of human C5a to the cells to a final concentration of 0.01-30.0 nM, using the FLIPR™ device (Molecular Devices). Differentiated U937 cells typically exhibit signals of 5,000-50,000 Arbitrary Fluorescent Light Units in response to agonist stimulation.

B. Assays for Determination of ATP Responses

Differentiated U937 cells (prepared and tested as described above under "A. Response to C5a") are stimulated by the addition of ATP (rather than C5a) to a final concentration of 0.01 to 30 µM. This stimulation typically triggers a signal of 1,000 to 12,000 arbitrary fluorescence light units. Certain preferred compounds produce less than a 10%, preferably less than a 5%, and most preferably less than a 2% alteration of this calcium mobilization signal when this control assay is carried out in the presence or absence of the compounds.

C. Assays for the Identification of Receptor Modulatory Agents: Antagonists and Agonists Those of skill in the art will recognize that the calcium mobilization assay described above may be readily adapted for identifying test compounds as having agonist or antagonist activity at the human C5a receptor.

For example, in order to identify antagonist compounds, differentiated U937 cells are washed and incubated with Fluo-3 dye as described above. One hour prior to measuring the fluorescence signal, a subset of the cells is incubated with a 1 µM concentration of at least one compound to be tested. The fluorescence response upon the subsequent addition of 0.3 nM (final concentration) human recombinant C5a is monitored using the FLIPR™ plate reader. Antagonist compounds elicit at least a 2-fold decrease in the fluorescence response relative to that measured in the presence of human C5a alone. Preferred antagonist compounds elicit at least a 5-fold, preferably at least a 10-fold, and more preferably at least a 20-fold decrease in the fluorescence response relative to that measured in the presence of human C5a alone. Agonist compounds elicit an increase in fluorescence without the addition of C5a, which increase will be at least partially blocked by a known C5a receptor antagonist.

If multiple concentrations of antagonist compound are examined as described in the preceding paragraph, the concentration required to provide a 50% inhibition of the 0.3 nM C5a response (hereafter referred to as IC$_{50}$) can be determined. The IC$_{50}$ value is calculated by fitting the percent inhibition calculated from the relative fluorescence units (RFU) obtained at the FLIPR against the concentration of antagonist compound to the following equation:

$$y=m_1*(1/(1+(m_2/m_0)^{m3})),$$

where y=% Inhibition of C5a-induced signal, $m_0$=antagonist compound concentration, $m_1$=maximum inhibition of C5a-induced signal by highest concentration of antagonist compound, $m_2$=IC$_{50}$, and $m_3$=Hill slope. The data are fit to this equation using a least squares regression to determine IC$_{50}$ and Hill slope. The Ki is calculated using the Cheng-Prusoff equation:

$$Ki=IC_{50}/(1+[L]/K_d),$$

where IC$_{50}$ is determined as described above, [L] is the C5a concentration used to test antagonist compound activity, and $K_d$ is the dissociation constant of recombinant human C5a.

Example 26

Assays to Evaluate Agonist Activity of Small Molecule C5A Receptor Antagonists

Certain preferred compounds of Formula I are C5a receptor antagonists that do not possess significant (e.g., greater than 5%) agonist activity in any of the C5a mediated functional assays discussed herein. Such agonist activity can be evaluated, for example, in the assay of C5a induced GTP binding given above, by measuring small molecule mediated GTP binding in the absence of the natural agonist, C5a. Similarly, in a calcium mobilization assay such as the assay described above a small molecule compound can be directly assayed for the ability of the compound to stimulate calcium levels in the absence of the natural agonist, C5a The preferred extent of C5a agonist activity exhibited by certain compounds provided herein is less than 10%, more preferably less than 5% and most preferably less than 2% of the response elicited by the natural agonist, C5a.

Example 27

MDCK Toxicity Assay

This Example illustrates the evaluation of compound toxicity using a Madin Darby canine kidney (MDCK) cell cytotoxicity assay.

1 µL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of 0.1×10$^6$ cells/ml with warm (37° C.) medium (VITACELL Minimum Essential Medium Eagle, ATCC catalog #30-2003). 100 µL of diluted cells is added to each well, except for five standard curve control wells that contain 100 µL of warm medium without cells. The plate is then incubated at 37° C. under 95% $O_2$, 5% $CO_2$ for 2 hours with constant shaking. After incubation, 50 µL of mammalian cell lysis solution" (available as a component of the PACKARD (Meriden, Conn.) ATP-LITE-M Luminescent ATP detection kit) is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD ATP-LITE-M Luminescent ATP detection kit, product no. 6016941, is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 µL of serially diluted PACKARD standard is added to each of the standard curve control wells to yield a final concentration in each subsequent well of 200 nM, 100 nM, 50 nM, 25 nM and 12.5 nM. PACKARD substrate solution (50 µL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 µM of a preferred test compound exhibit ATP levels that are at least 80%, preferably at least 90%, of the untreated cells. When a 100 µM concentration of the test compound is used, cells treated with preferred test compounds exhibit ATP levels that are at least 50%, preferably at least 80%, of the ATP levels detected in untreated cells.

What is claimed is:
1. A compound according to Formula II:

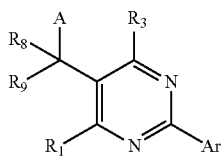

(II)

or a pharmaceutically acceptable salt thereof, wherein:
Ar is mono-, di-, or tri-substituted phenyl, optionally substituted naphthyl, or optionally substituted heteroaryl having from 1 to 3 rings and 5 to 7 ring members in each ring;
A is $OR_4$, $NR_4R_5$, or $CR_4(XR_y)_2$;
$R_1$ is selected from hydrogen, optionally substituted alkyl, optionally substituted alkenyl, optionally substituted alkynyl, optionally substituted cycloalkyl, optionally substituted cycloalkenyl, optionally substituted alkoxy, optionally substituted cycloalkoxy, optionally substituted (cycloalkyl)alkoxy, and optionally substituted heterocycloalkyl;

$R_3$ is pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, triazolyl, piperidinyl, pyrrolidinyl, azetidinyl, azepanyl, or diazepanyl, each of which may be optionally substituted;

$R_4$ is:
(i) $C_2$-$C_8$alkyl, $C_2$-$C_8$alkenyl, $C_2$-$C_8$alkynyl, ($C_3$-$C_7$cycloalkyl)$C_0$-$C_4$alkyl, mono- or di-($C_1$-$C_4$alkyl)amino$C_2$-$C_4$alkyl, (3- to 7-membered heterocycloalkyl)$C_0$-$C_4$alkyl, aryl$C_0$-$C_4$alkyl, or heteroaryl$C_{0-4}$alkyl, each of which is substituted with from 0 to 4 substituents independently chosen from $R_x$, $C_2$-$C_4$alkanoyl, mono- and di-($C_1$-$C_4$alkyl)amino$C_1$-$C_4$alkyl, mono- and di-($C_1$-$C_4$alkyl)amino$C_1$-$C_4$alkoxy, (3- to 7-membered heterocycloalkyl)$C_0$-$C_4$alkyl and $XR_y$; or
(ii) joined to $R_5$ to form, with the nitrogen to which $R_4$ and $R_5$ are bound, a heterocycle having from 1 to 3 rings, 5 to 7 ring members in each ring, wherein the heterocycle is substituted with from 0 to 4 substituents independently chosen from $R_x$, oxo and W—Z;

$R_5$ is:
(i) hydrogen;
(ii) $C_1$-$C_6$alkyl, $C_2$-$C_6$alkenyl, $C_2$-$C_6$alkynyl, ($C_3$-$C_7$carbocycle)$C_0$-$C_4$alkyl, each of which is substituted with from 0 to 3 substituents independently chosen from halogen, hydroxy, amino, cyano, $C_1$-$C_4$alkyl, $C_1$-$C_4$alkoxy, methylamino, dimethylamino, trifluoromethyl and trifluoromethoxy; or
(iii) joined to $R_4$ to form an optionally substituted heterocycle;

$R_8$ and $R_9$ are independently selected from hydrogen, halogen, hydroxy, $C_1$-$C_6$alkyl, $C_2$-$C_6$alkenyl, $C_2$-$C_6$alkynyl, $C_1$-$C_6$alkoxy, $C_1$-$C_6$alkylamino and ($C_3$-$C_7$cycloalkyl)$C_0$-$C_4$alkyl;

E is a single covalent bond, oxygen, or $NR_A$;
X is a single covalent bond, —$CR_AR_B$—, —O—, —C(=O)—, —C(=O)O—, —S(O)$_n$— or —$NR_B$—; and $R_y$ is:
(i) hydrogen; or
(ii) $C_1$-$C_{10}$alkyl, $C_2$-$C_{10}$alkenyl, $C_2$-$C_{10}$alkynyl, ($C_3$-$C_{10}$carbocycle)$C_0$-$C_4$alkyl or (3- to 10-membered heterocycle)$C_0$-$C_4$alkyl, each of which is substituted with from 0 to 6 substituents independently selected from $R_x$, oxo, —NH($C_1$-$C_6$alkanoyl), —N($C_1$-$C_6$alkyl)($C_1$-$C_6$alkanoyl), —NHS(O$_n$)$C_1$-$C_6$alkyl, —N(S(O$_n$)($C_1$-$C_6$alkyl)$_2$, —S(O$_n$)NHC$_1$-$C_6$alkyl and —S(O$_n$)N($C_1$-$C_6$alkyl)$_2$;

W is a single covalent bond, —$CR_AR_B$—, —$NR_B$— or —O—;

Z is independently selected at each occurrence from 3- to 7-membered carbocycles and heterocycles, each of which is substituted with from 0 to 4 substituents independently selected from halogen, oxo, —COOH, C(O)NH$_2$, —CH$_2$COOH, —CH$_2$C(O)NH$_2$, hydroxy, amino, cyano, cyanomethyl, $C_1$-$C_6$alkyl, $C_1$-$C_6$alkoxy, $C_1$-$C_6$haloalkyl, $C_1$-$C_6$haloalkoxy, $C_1$-$C_6$alkoxycarbonyl, —CH$_2$COO($C_1$-$C_6$alkyl), mono- and di-($C_1$-$C_6$alkyl)amino, ($C_1$-$C_6$alkyl)(2-acetamide)amino, and —S(O$_n$)$C_1$-$C_6$alkyl;

$R_A$ and $R_B$ are independently selected at each occurrence from:
(i) hydrogen; and
(ii) $C_1$-$C_{10}$alkyl, $C_2$-$C_{10}$alkenyl, $C_2$-$C_{10}$alkynyl, saturated or partially saturated ($C_3$-$C_{10}$carbocycle)$C_0$-$C_4$alkyl and saturated or partially saturated (3- to 10-membered heterocycle)$C_0$-$C_4$alkyl, each of which is substituted with from 0 to 6 substituents independently selected from oxo, hydroxy, halogen, cyano, amino, $C_1$-$C_6$alkoxy, mono- and di-($C_1$-$C_4$alkyl) amino, —COOH, —C(=O)$NH_2$, —NHC(=O)($C_1$-$C_6$alkyl), —N($C_1$-$C_6$alkyl)C(=O)($C_1$-$C_6$alkyl), —NHS($O_n$)$C_1$-$C_6$alkyl, $SO_3H$, —$SO_2NH_2$, —S($O_n$)$C_1$-$C_6$alkyl, —S($O_n$)NH$C_1$-$C_6$alkyl, —S($O_n$)N($C_1$-$C_6$alkyl)$C_1$-$C_6$alkyl and Z;

$R_C$ and $R_D$ are independently selected from $R_A$, hydroxy, $C_{1-6}$alkoxy, and oxo;

$R_x$ is independently chosen at each occurrence from halogen, hydroxy, amino, cyano, nitro, —COOH, —C(=O)$NH_2$, $C_1$-$C_6$alkoxycarbonyl, mono- and di-($C_{1-6}$alkyl) aminocarbonyl, $C_1$-$C_6$alkyl, $C_2$-$C_6$alkenyl, $C_2$-$C_6$alkynyl, mono- and di-($C_1$-$C_6$alkyl)amino, $C_1$-$C_6$alkoxy, $C_1$-$C_2$hydroxyalkyl, $C_1$-$C_2$haloalkyl, $C_1$-$C_2$haloalkoxy, ($C_3$-$C_7$cycloalkyl)$C_0$-$C_4$alkyl, and —S($O_n$)$C_1$-$C_6$alkyl;

m is independently selected at each occurrence from integers ranging from 0 to 8; and n is an integer independently selected at each occurrence from 0, 1 and 2.

2. A compound or salt according to claim 1, wherein A is $NR_4R_5$.

3. A compound or salt according to claim 2, wherein the compound is according to Formula III:

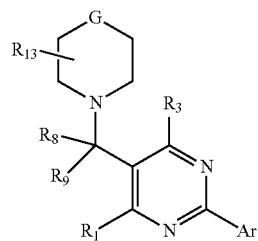

(III)

wherein:

$R_{13}$ represents from 0 to 3 substituents independently chosen from:
(i) $R_x$; and
(ii) phenyl and pyridyl, each of which is substituted with from 0 to 4 substituents independently chosen from halogen, hydroxy, amino, cyano, $C_1$-$C_4$alkyl, $C_1$-$C_4$alkoxy, ($C_3$-$C_7$cycloalkyl)$C_0$-$C_4$alkyl, $C_1$-$C_2$haloalkyl, $C_1$-$C_2$haloalkoxy and mono- and di-($C_1$-$C_4$alkyl)amino; and G is $CH_2$, sulfur, oxygen or $NR_E$; wherein $R_E$ is:
(i) hydrogen; or
(ii) $C_1$-$C_6$alkyl, ($C_3$-$C_7$cycloalkyl)$C_0$-$C_4$alkyl, phenyl or a 5- or 6-membered heteroaryl ring, each of which is substituted with from 0 to 3 substituents independently chosen from $R_x$.

4. A pharmaceutical composition comprising at least one compound or salt according to claim 1, in combination with a physiologically acceptable carrier or excipient.

5. A compound of claim 1 chosen from:
(1S)-N-{[4-azetidin-1-yl-2-(2,6-diethylphenyl)-6-methylpyrimidin-5-yl]methyl}-N-methyl-1,2,3,4-tetrahydronaphthalen-1-amine;
(1S)-N-{[2-(2,6-diethylphenyl)-4-methyl-6-morpholin-4-ylpyrimidin-5-yl]methyl}-N-methyl-1,2,3,4-tetrahydronaphthalen-1-amine;
(1S)-N-{[2-(2,6-diethylphenyl)-4-methyl-6-piperidin-1-ylpyrimidin-5-yl]methyl}-N-methyl-1,2,3,4-tetrahydronaphthalen-1-amine;
(1S)-N-{[2-(2,6-diethylphenyl)-4-methyl-6-pyrrolidin-1-ylpyrimidin-5-yl]methyl}-N-methyl-1,2,3,4-tetrahydronaphthalen-1-amine;
(1S)-N-{[4-azepan-1-yl-2-(2,6-diethylphenyl)-6-methylpyrimidin-5-yl]methyl}-N-methyl-1,2,3,4-tetrahydronaphthalen-1-amine;
(1S)-N-{[2-(2,6-diethylphenyl)-4-methyl-6-thiomorpholin-4-ylpyrimidin-5-yl]methyl}-N-methyl-1,2,3,4-tetrahydronaphthalen-1-amine;
(1S)-N-{[2-(2,6-diethylphenyl)-4-methyl-6-(4-methylpiperidin-1-yl)pyrimidin-5-yl]methyl}-N-methyl-1,2,3,4-tetrahydronaphthalen-1-amine;
1-[2-(2,6-diethylphenyl)-6-methyl-5-({methyl[(1S)-1,2,3,4-tetrahydronaphthalen-1-yl]amino}methyl)pyrimidin-4-yl]piperidin-4-ol;
(1S)-N-{[2-(2,6-diethylphenyl)-4-(3,3-dimethylpiperidin-1-yl)-6-methylpyrimidin-5-yl]methyl}-N-methyl-1,2,3,4-tetrahydronaphthalen-1-amine;
(1S)-N-{[2-(2,6-diethylphenyl)-4-(3,5-dimethylpiperidin-1-yl)-6-methylpyrimidin-5-yl]methyl}-N-methyl-1,2,3,4-tetrahydronaphthalen-1-amine;
(1S)-N-{[2-(2,6-diethylphenyl)-4-methyl-6-pyridin-4-ylpyrimidin-5-yl]methyl}-N-methyl-1,2,3,4-tetrahydronaphthalen-1-amine;
ethyl 1-[2-(2,6-diethylphenyl)-6-methyl-5-({methyl[(1S)-1,2,3,4-tetrahydronaphthalen-1-yl]amino}methyl)pyrimidin-4-yl]piperidine-4-carboxylate;
{1-[2-(2,6-diethylphenyl)-6-methyl-5-({methyl[(1S)-1,2,3,4-tetrahydronaphthalen-1-yl]amino}methyl)pyrimidin-4-yl]piperidin-4-yl}methanol;
2-{1-[2-(2,6-diethylphenyl)-6-methyl-5-({methyl[(1S)-1,2,3,4-tetrahydronaphthalen-1-yl]amino}methyl)pyrimidin-4-yl]piperidin-4-yl}ethanol;
1-[2-(2,6-diethylphenyl)-6-methyl-5-({methyl[(1S)-1,2,3,4-tetrahydronaphthalen-1-yl]amino}methyl)pyrimidin-4-yl]piperidine-4-carboxylic acid;
1-[2-(2,6-diethylphenyl)-6-methyl-5-({methyl[(1S)-1,2,3,4-tetrahydronaphthalen-1-yl]amino}methyl)pyrimidin-4-yl]-D-proline;
(1R)-N-{[2-(2,6-diethylphenyl)-4-(1H-imidazol-1-yl)-6-methylpyrimidin-5-yl]methyl}-N-methyl-1,2,3,4-tetrahydronaphthalen-1-amine;
(1R)-N-{[2-(2,6-diethylphenyl)-4-methyl-6-(1H-pyrazol-1-yl)pyrimidin-5-yl]methyl}-N-methyl-1,2,3,4-tetrahydronaphthalen-1-amine;
1-{[2-(2,6-diethylphenyl)-4-methyl-6-piperidin-1-ylpyrimidin-5-yl]methyl}piperidin-4-ol;
1-{[2-(2,6-diethylphenyl)-4-methyl-6-piperidin-1-ylpyrimidin-5-yl]methyl}piperidin-3-ol;
2-{[2-(2,6-diethylphenyl)-4-methyl-6-piperidin-1-ylpyrimidin-5-yl]methyl}-1,2,3,4-tetrahydroisoquinoline;
1-[2-(2,6-diethylphenyl)-6-methyl-5-({methyl[(1S)-1,2,3,4-tetrahydronaphthalen-1-yl]amino}methyl)pyrimidin-4-yl]piperidin-3-ol;
1-[2-(2,6-diethylphenyl)-6-methyl-5-({methyl[(1S)-1,2,3,4-tetrahydronaphthalen-1-yl]amino}methyl)pyrimidin-4-yl]pyrrolidin-3-ol;
2-(2,6-diethylphenyl)-5-[(3,3-dimethylpiperidin-1-yl)methyl]-4-methyl-6-piperidin-1-ylpyrimidine;
1-{[2-(2,6-diethylphenyl)-4-methyl-6-piperidin-1-ylpyrimidin-5-yl]methyl}azepane;
4-{[2-(2,6-diethylphenyl)-4-methyl-6-piperidin-1-ylpyrimidin-5-yl]methyl}morpholine;

ethyl 1-{[2-(2,6-diethylphenyl)-4-methyl-6-piperidin-1-ylpyrimidin-5-yl]methyl}piperidine-4-carboxylate;

(1-{[2-(2,6-diethylphenyl)-4-methyl-6-piperidin-1-ylpyrimidin-5-yl]methyl}piperidin-3-yl)methanol;

2-{1-[2-(2,6-diethylphenyl)-6-methyl-5-({methyl[(1S)-1,2,3,4-tetrahydronaphthalen-1-yl]amino}methyl)pyrimidin-4-yl]piperidin-4-yl}propan-2-ol;

1-[2-(2,6-diethylphenyl)-6-methyl-5-({methyl[(1S)-1,2,3,4-tetrahydronaphthalen-1-yl]amino}methyl)pyrimidin-4-yl]piperidin-4-one;

4-{[2-(2,6-diethylphenyl)-4-methyl-6-piperidin-1-ylpyrimidin-5-yl]methyl}-3,4-dihydro-2H-pyrido[3,2-b][1,4]oxazine;

1-[2-(2,6-diethylphenyl)-4-methyl-6-piperidin-1-ylpyrimidin-5-yl]-N-(1H-indol-5-ylmethyl)-N-methylmethanamine;

4-{[2-(2,6-diethylphenyl)-4-methyl-6-piperidin-1-ylpyrimidin-5-yl]methyl}-6-methyl-3,4-dihydro-2H-pyrido[3,2-b][1,4]oxazine;

1-[2-(2,6-diethylphenyl)-6-methyl-5-({methyl[(1S)-1,2,3,4-tetrahydronaphthalen-1-yl]amino}methyl)pyrimidin-4-yl]-4-methylpiperidin-4-ol;

1-[6-methyl-5-[(6-methyl-2,3-dihydro-4H-pyrido[3,2-b][1,4]oxazin-4-yl)methyl]-2-(5-methyl-1H-indol-4-yl)pyrimidin-4-yl]piperidin-4-one;

(1S)-N-({2-(2,6-diethylphenyl)-4-[(2S,6S)-2,6-dimethylmorpholin-4-yl]-6-methylpyrimidin-5-yl}methyl)-N-methyl-1,2,3,4-tetrahydronaphthalen-1-amine;

N-{[2-(2,6-diethylphenyl)-4-methyl-6-piperidin-1-ylpyrimidin-5-yl]methyl}-3-ethoxy-N,6-dimethylpyridin-2-amine;

4-(aminomethyl)-1-[2-(2,6-diethylphenyl)-6-methyl-5-({methyl[(1S)-1,2,3,4-tetrahydronaphthalen-1-yl]amino}methyl)pyrimidin-4-yl]piperidin-4-ol;

4-{[2-(2,6-diethylphenyl)-4-methyl-6-piperidin-1-ylpyrimidin-5-yl]methyl}-2,2-dimethylmorpholine;

(1S)-N-{[2-(2,6-diethylphenyl)-4-(2,2-dimethylmorpholin-4-yl)-6-methylpyrimidin-5-yl]methyl}-N-methyl-1,2,3,4-tetrahydronaphthalen-1-amine;

N-({1-[2-(2,6-diethylphenyl)-6-methyl-5-({methyl[(1S)-1,2,3,4-tetrahydronaphthalen-1-yl]amino}methyl)pyrimidin-4-yl]-4-hydroxypiperidin-4-yl}methyl)methanesulfonamide;

N-({1-[2-(2,6-diethylphenyl)-6-methyl-5-({methyl[(1S)-1,2,3,4-tetrahydronaphthalen-1-yl]amino}methyl)pyrimidin-4-yl]-4-hydroxypiperidin-4-yl}methyl)acetamide;

2-(2,6-diethylphenyl)-5-{[2-(3,4-dimethoxyphenyl)piperidin-1-yl]methyl}-4-methyl-6-piperidin-1-ylpyrimidine;

(2S,6S)-4-{[2-(2,6-diethylphenyl)-4-methyl-6-piperidin-1-ylpyrimidin-5-yl]methyl}-2,6-dimethylmorpholine;

1-[2-(2,6-diethylphenyl)-6-methyl-5-({methyl[(1S)-1,2,3,4-tetrahydronaphthalen-1-yl]amino}methyl)pyrimidin-4-yl]piperidine-4-carboxamide;

1-[2-(2,6-diethylphenyl)-6-methyl-5-({methyl[(1S)-1,2,3,4-tetrahydronaphthalen-1-yl]amino}methyl)pyrimidin-4-yl]piperidine-3-carboxamide;

4-{[2-(2,6-diethylphenyl)-4-methyl-6-(4-methyl-1,4-diazepan-1-yl)pyrimidin-5-yl]methyl}-6-methyl-3,4-dihydro-2H-pyrido[3,2-b][1,4]oxazine;

1-[2-(2,6-diethylphenyl)-6-methyl-5-({methyl[(1S)-1,2,3,4-tetrahydronaphthalen-1-yl]amino}methyl)pyrimidin-4-yl]-1,2-dihydro-3H-pyrazol-3-one;

1-{2-(2,6-diethylphenyl)-6-methyl-5-[(6-methyl-2,3-dihydro-4H-pyrido[3,2-b][1,4]oxazin-4-yl)methyl]pyrimidin-4-yl}piperidine-4-carboxamide;

N-{[2-(2,6-diethylphenyl)-4-methyl-6-piperidin-1-ylpyrimidin-5-yl]methyl}-N-[(1S)-1,2,3,4-tetrahydronaphthalen-1-yl]glycine;

ethyl N-{[2-(2,6-diethylphenyl)-4-methyl-6-piperidin-1-ylpyrimidin-5-yl]methyl}-N-[(1S)-1,2,3,4-tetrahydronaphthalen-1-yl]glycinate;

1-[2-(2,6-diethylphenyl)-6-methyl-5-({methyl[(1S)-1,2,3,4-tetrahydronaphthalen-1-yl]amino}methyl)pyrimidin-4-yl]-4-hydroxypiperidine-4-carboxamide;

1-(2-(2-chloro-6-methoxyphenyl)-6-methyl-5-{[methyl(1,2,3,4-tetrahydronaphthalen-1-yl)amino]methyl}pyrimidin-4-yl)piperidine-4-carboxamide;

1-(2-(2,6-dimethylphenyl)-6-methyl-5-{[methyl(1,2,3,4-tetrahydronaphthalen-1-yl)amino]methyl}pyrimidin-4-yl)piperidine-4-carboxamide; and 1-{2-(2,5-dichlorophenyl)-5-[(3,3-dimethylpiperidin-1-yl)methyl]-6-methylpyrimidin-4-yl}-3,3-dimethylpiperidin-4-ol.

* * * * *